(12) United States Patent
Whitton

(10) Patent No.: US 11,696,846 B2
(45) Date of Patent: Jul. 11, 2023

(54) AURAL HEMATOMA SPLINT SYSTEM AND METHOD

(71) Applicant: Daniel Francis Whitton, Justin, TX (US)

(72) Inventor: Daniel Francis Whitton, Justin, TX (US)

(*) Notice: Subject to any disclaimer, the term of this patent is extended or adjusted under 35 U.S.C. 154(b) by 227 days.

(21) Appl. No.: 17/343,238

(22) Filed: Jun. 9, 2021

(65) Prior Publication Data
US 2022/0331137 A1    Oct. 20, 2022

Related U.S. Application Data

(60) Provisional application No. 63/175,862, filed on Apr. 16, 2021.

(51) Int. Cl.
*A61F 5/058* (2006.01)
*A61D 9/00* (2006.01)
*A61F 5/30* (2006.01)

(52) U.S. Cl.
CPC ............ *A61F 5/05891* (2013.01); *A61D 9/00* (2013.01); *A61F 5/30* (2013.01)

(58) Field of Classification Search
CPC ........ A61F 5/01; A61F 5/0102; A61F 5/0104; A61F 5/04; A61F 5/05; A61F 5/058; A61F 5/05825; A61F 5/05883; A61F 5/05891; A61F 5/37; A61F 5/3707; A61F 5/30; A61F 2013/00089; A61F 13/00; A61F 13/04; A61F 13/12; A61F 11/00; A61F 11/06; A61F 11/14; A61D 9/00; A61H 1/00; A61H 1/08; A01K 13/00; A01K 15/04; A01K 27/00; A01K 27/001; A01K 27/002; A01K 13/06; A61B 17/08; A61B 17/00; A61B 17/122

See application file for complete search history.

(56) References Cited

U.S. PATENT DOCUMENTS

| | | | |
|---|---|---|---|
| 5,295,950 A | 3/1994 | Godley | |
| 5,827,212 A | 10/1998 | Gaskill | |
| 7,153,313 B2 | 12/2006 | Whitton | |
| 9,522,015 B2 | 12/2016 | Tan | |
| 9,931,190 B2 | 4/2018 | Haught | |
| 10,154,935 B1 | 12/2018 | Ales | |
| 2004/0059353 A1* | 3/2004 | Whitton | ........ A61B 17/08 606/151 |

* cited by examiner

*Primary Examiner* — Ophelia A Hawthorne
*Assistant Examiner* — Gina McCarthy
(74) *Attorney, Agent, or Firm* — Kevin Mark Klughart

(57) ABSTRACT

An aural hematoma splint (AHS) system/method providing for animal ear pinna (AEP) suspension and/or compression allowing non-surgical treatment of AEP auricular hematoma is disclosed. The AHS promotes healing performance by including a conical primary plate (CPP) and angular secondary plate (ASP) that are used in conjunction with non-elastic fabric tape (NFT) to hold the AEP in suspension during treatment. The NFT includes a long strap collar (LSC) and cross support strips (CSS) for preparatory taping and application of the CPP/ASP to the AEP. This sandwich configuration of the CPP/ASP surrounding the AEP creates equilibrium in hematoma fluid pressures within the damaged area of the AEP, promotes a uniform thin layer of blood to clot in the entirety of the hematoma region, and allows regeneration of damaged tissues in a controlled environment while limiting structural and aesthetic damage to the healed AEP post treatment.

10 Claims, 112 Drawing Sheets

FIG. 32 Merged LSC

3200

6800

8500

9000

9300

AURAL HEMATOMA SPLINT SYSTEM AND METHOD

CROSS REFERENCE TO RELATED APPLICATIONS

Provisional Patent Applications

This application claims benefit under 35 U.S.C. § 119 and incorporates by reference United States Provisional patent application for AURAL HEMATOMA SPLINT SYSTEM AND METHOD by inventor Daniel Francis Whitton, filed electronically with the USPTO on 2021 Apr. 16, with Ser. No. 63/175,862, EFS ID 42477307, confirmation number 4869.

UNITED STATES UTILITY PATENT INCLUDED REFERENCES

This application includes by reference the following United States patents:
U.S. Pat. No. 5,295,950 (application Ser. No. 07/964,420) for EAR PRESSURE DRESSING issued on Mar. 22, 1994 to Frederick A. Godley;
U.S. Pat. No. 5,827,212 (application Ser. No. 08/955,775) for SPLINTING DEVICE FOR AURICULAR HEMATOMA issued on Oct. 27, 1998 to J. Richard Gaskill;
U.S. Pat. No. 7,153,313 (application Ser. No. 10/246,346) for AURICULAR HEMATOMA CLAMP issued on Dec. 26, 2006 to Daniel F. Whitton;
U.S. Pat. No. 9,522,015 (application Ser. No. 14/071,177) for FIXING DEVICE FOR AURAL HEMATOMA TREATMENT issued on Dec. 20, 2016 to Ta-Lun Tan;
U.S. Pat. No. 9,931,190 (application Ser. No. 14/722,457) for PROTECTIVE DEVICE FOR THE HEAD AND EARS OF AN ANIMAL issued on Apr. 3, 2018 to Julie Anne Haught; and
U.S. Pat. No. 10,154,935 (application Ser. No. 14/120,490) for PRESSURE BEARING AURICULAR HEMATOMA APPLIANCE issued on Dec. 18, 2018 to Bryan L. Ales.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to an auricular suspension device in the field of veterinary medicine for use in the treatment of an aural hematoma occurring in canines or other animals. Without limitation, the present invention describes an aural hematoma splint (AHS) system and method that may be used to treat aural hematomas in canines and other animals.

An aural hematoma is a collection of blood within the cartilage of the ear and the skin. It usually arises as a self-inflicted injury from scratching and/or head shaking. The underlying causes include all conditions that result in otitis externa (infection of the external ear canal).

BACKGROUND AND PRIOR ART

This invention contains improvements to the prior utility U.S. Pat. No. 7,153,313 for AURICULAR HEMATOMA CLAMP by Whitton, for the treatment of auricular hematoma in canine and other animals, or other conditions where needs of a medical compression device to support the ear flap while healing occurs.

As presented in U.S. Pat. No. 10,154,935, issued to Ales in December 2018, the pressure bearing auricular hematoma appliance uses magnetic discs to attract opposite shells for the purpose of compressing the auricle. The entirety of the device would be subject to the amount of attraction by said magnets, those being of a larger size for greater attraction, as well larger for more compressed materials between said plates. This would inhibit performance as it relates to the need for a small thin layer of blood clot to form in the aural hematoma splint where the preparatory taping of any relative compressed materials are present between plate and ear, thus providing the least amount of materials between ear and plate. In addition, the active forces of attraction present in Ales could overly continue to compress without regulation. The active forces in the aural hematoma splint are set at time of installation and no further compression is occurring due to device and method. Additional compression forces are present until equalization as hematoma refills into pocket area contained and suspended to limit the ability to form any other than a thin layer of blood and subsequent clot.

As presented in U.S. Pat. No. 9,931,190, issued to Haught in April 2018, protective device for the head and ears of an animal is used as a subsequent covering after any or no medical procedure for aural hematoma or other affliction. The device may be comfortable and effective for restricting access to an ear of the animal, but limitation of the different ear orientations under the device make it non-purposeful for an animal with erect standing ears. To put an ear with displaced cartilage or a medically sutured ear under the device would force the healing of the ear in its present position and makes no allowance for having the erect ear to be healed in the erect position.

As presented in U.S. Pat. No. 9,522,015, issued to Tan in December 2016, fixing device for aural hematoma treatment is a harming device where constant impaling of the auricle is required by a puncturing element. Any such element penetrating the skin of the auricle and in a fixed position lies dangerous as to movement of the device and apparatus causing relocation of puncturing element now causing tearing of the skin.

As presented in U.S. Pat. No. 5,827,212, issued to Gaskill in October 1998, splinting device for auricular hematoma imparts wounding to the animal with through penetrations where the need for considerable post application care is required. The open wounds caused by penetrations are subject to the elements and possible infection from environment infiltration.

As presented in U.S. Pat. No. 5,295,950, issued to Godley in March 1994, ear pressure dressing uses ductile materials subject to reformation during treatment, and sponge type of compression materials beneath exterior elements to provide compression against ear cartilage.

BRIEF SUMMARY OF THE INVENTION

The present invention pertains to a system and method that implement an aural hematoma splint (AHS). The AHS contains improvements over prior art and continues to perform as a whole treatment modality where an aural hematoma affected ear is healed using a non-surgical compression device to suspend and limit the affliction to an area defined by use of rigid plastic plates held in place by a specific taping regimen. The aural hematoma splint makes improvements over prior art with advances in both taping and plate(s) shape and performance characteristics.

To increase efficiency of preparatory taping, the initial outward length strips are not lessened by folding tape, but instead are whole taped either side of pinna with only a small portion or tape protruding beyond ear edge allowing for contact with opposing ear side similar lengths, and pressed against each other glue sides, for strict adhesion of the two pieces. The greater tape area against ear surfaces allows for greater attraction of tape to ear. A central tape apparatus contained in aural hematoma splint taping procedural improves the securing of treatment plates in place and holding the treatment together in position for the duration of the treatment.

The need for a better tape securing apparatus is by making use of a long strap collar, with continuous length of tape starting beyond ear tip, secured on underside of ear, folded over ear tip without folding ear tissue, extending down back side of ear onto head of animal, continuing over the head behind opposite ear, down around behind jaw line, up and around treatment side continuing to location, repeating on top of initial loop, and perform a second loop to secure making a collar. Loops around neck of animal use care to not inhibit animal's ability to function eating and breathing, but be tight enough as to not allow rising from animal. The process of long strapping the ear is combined in conjunction with the use of a cross strip to solidify long strap to ear base at back of ear.

The cross strip specifically prevents the long strap from lifting, therefore making improvement to condition, holding aural hematoma splint primary and secondary plates in position for duration of treatment schedule by preparing ear with a more substantial foundation for treatment application. By removal of a second full sized ear shaped plate, the lessened weight is an advantage to comfort and ability to use a smaller secondary stabilizing plate attached in similar fashion to back of ear using the long strap and cross strip taping procedure.

Thus the initial preparatory taping and installation taping of primary plate performs the desired function for prevention of expansion of the hematoma and protection to auricle. The function of the smaller secondary plate stabilizer is achieved by using a narrower folded ridged plastic strip situated on top of head of animal with vertical portion extending upward behind auricle, a bend at ear base, and a horizontal portion extending onto and over head of animal.

A cross strip is used to locate the stabilizer, with afore described subsequent long strap collar and cross strips to secure. The bracing action of the ridged fold in stabilizer plate, and the taping procedure, assists in keeping auricle in erect position, and allows for healing to occur in natural position with improved final outcome for both erect and pendent eared animals.

With regard to conditions while treatment is in location, the use of perforations and/or access ports in the primary plate allows for migration of moisture, through primary plate and taping, outward away from ear. The specifically shaped and located perforations on primary plate retain plate rigidity, and allow plate to migrate moisture outward, thereby improving environment. Perforations are not used as locations for attachment by through fasteners because this would cause wounding to ear and promote chances of infection.

By covering the inner surface of the primary plate with a suitable fabric, an advance in moisture control is achieved. In addition, an open area of primary plate could be included, not large enough to reduce structural rigidity, to allow access to an existing area or wound on ear, for monitoring or additional treatment attention to said area or wound. By keeping the principle of rigidity of primary plate, and introducing ability to flex along the vertical axis, an articulating plate fills the need to treat overly large pendent ears while in the pendent position and kept against side of head by a taped collar.

The ribbed primary plate and matching ribbed secondary plate of same size and form are installed in similar fashion, with the preparatory taping, locating of primary and secondary plates using the cross strip location, long strap collar and taught cross strips for securing. These aural hematoma splints provide a healing solution for aural hematoma in canines, are non-surgical, protect the ear during healing, and perform at a greater capacity than its predecessors.

The need for a better environment under the aural hematoma splint primary plate is improved by perforating the primary plate for the expressed reason for environment moisture mitigation. The unneeded accumulation of moisture under the plates is in need of escape, where the use of non-elastic fabric tape such as cloth surgical tape, allows for this moisture to migrate through tape and escape.

BRIEF DESCRIPTION OF THE DRAWINGS

For a fuller understanding of the advantages provided by the invention, reference should be made to the following detailed description together with the accompanying drawings wherein.

DESCRIPTION OF THE PRESENTLY PREFERRED EXEMPLARY EMBODIMENTS

Figure 1:
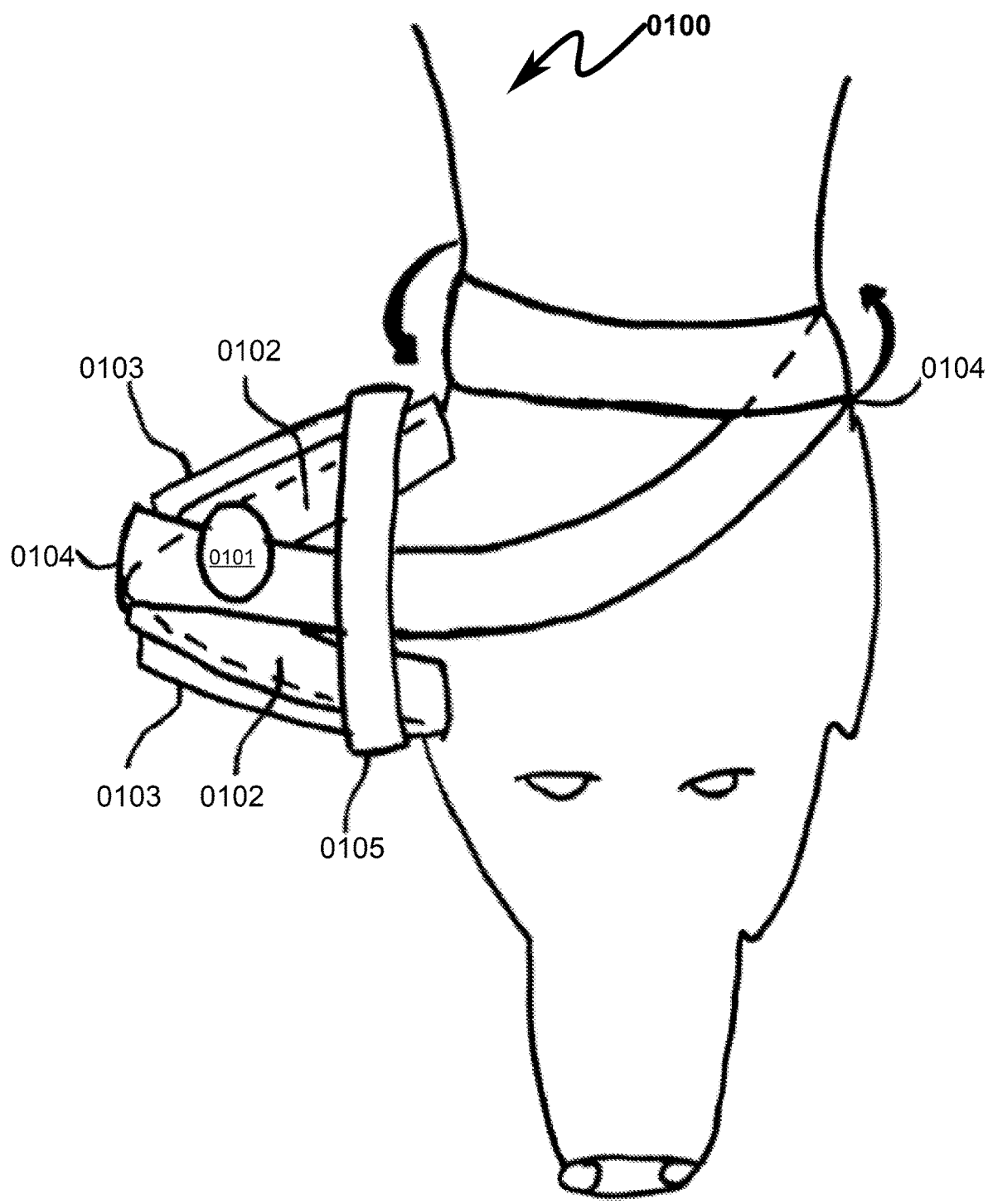
FIG. 1 exhibits preparatory taping including initial lengths tape sections applied to underside and outside of ear pinna. These sections extend beyond ear edge slightly to be able to connect from both sides of ear and provide substantial surface area for adhesive attachment. The long strap collar is drawn starting on underside of ear, extending outward past tip, folded over at tip, without any flesh of ear folded upon itself, running down back of ear, onto head and neck, and around neck near jaw line, tight to animal without impairing functions of breathing or eating, and making two rotations around securing onto previous taped location, in collar capacity.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of an AURAL HEMATOMA SPLINT SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

AEP Nomenclature

Within this document the AEP will be referred to as having an "inside" and "outside" areas of primary concern. The "inside" area is generally related to the bottom-side portion of the AEP in which the aural canal is located, with the "outside" area being the top-side portion of the AEP.

CPP/ASP/RPP/RSP Materials not Limitive

While the present invention as described herein depicts the conical primary plate (CPP), angular secondary plate (ASP), ribbed primary plate (RPP), and ribbed secondary plate (RSP) as typically comprising rigid plastic construction, the present invention is not limited to these materials and other materials may be utilized in their construction with no loss of generality in the scope of the claimed invention.

Rigid Construction not Limitive

While the present invention as described herein depicts the conical primary plate (CPP), angular secondary plate (ASP), ribbed primary plate (RPP), and ribbed secondary plate (RSP) as typically comprising a rigid material, the term "rigid" should be broadly construed as to include materials that may exhibit some flexion under torsion or bending, but nonetheless return to a non-flexed state when the torque or bending force is removed. Thus, the present invention is not limited to perfectly rigid materials and other semi-rigid materials may be utilized in their construction with no loss of generality in the scope of the claimed invention.

Curvature in Drawings not Limitive

The drawings presented herein are rendered with dot surface patterns in order to illustrate the curvature of the various elements of preferred exemplary embodiments of the present invention. The dot surface patterns as illustrated are not necessarily functional and may not be present in many preferred embodiments. Some preferred embodiments may incorporate holes or other recesses in the CPP and/or ASP and/or RPP and/or RSP to facilitate hematoma healing or address varying thicknesses of the animal ear under treatment. Neither the dot surface patterns nor specific curvatures of the elements depicted herein limit the scope of the present invention. In many circumstances the specific curvatures of the CPP and/or ASP and/or RPP and/or RSP may be application specific.

Curvature in CPP/ASP/RPP/RSP

The curvatures depicted in the conical primary plate (CPP), angular secondary plate (ASP), ribbed primary plate (RPP), and ribbed secondary plate (RSP) as typically discussed herein may vary widely and need not be constant along their overall length. Some embodiments of the CPP and/or ASP may incorporate lofted curvatures that vary over the length of the particular CPP/ASP/RPP/RSP element. Additionally, one or more of the curvatures depicted in the ASP shown herein may be omitted in some preferred embodiments.

Peripheral Form of CPP/ASP/RPP/RSP

The peripheral form depicted in the conical primary plate (CPP), angular secondary plate (ASP), ribbed primary plate (RPP), and ribbed secondary plate (RSP) discussed herein may vary widely based on application context and AEP dimensions of the animal treated. The forms depicted herein are only exemplary of many possible peripheral forms of the CPP and ASP. While not explicitly shown in the drawings, one or more peripheral edges of the CPP and/or ASP may be molded to have a cylindrical and/or filleted form so as to ensure that the peripheral edge does not present an abrasion hazard for the skin of the patient for which the AEP hematoma is to be treated.

Internal Surface Form of CPP/ASP/RPP/RSP

The internal surface form depicted in the conical primary plate (CPP), angular secondary plate (ASP), ribbed primary plate (RPP), and ribbed secondary plate (RSP) discussed herein may vary widely based on application context and AEP dimensions of the animal treated. The forms depicted herein are only exemplary of many possible internal surface forms of the CPP/ASP/RPP/RSP. Many preferred embodiments may utilize internal surface forms constructed of plastic, covered with fabric (that may include anti-bacterial, anti-microbial, and/or anti-fungal treatment), perforated (in many different possible patterns), and/or having internal regions removed (to allow exposure/treatment/viewing of hematoma areas). Not all of these configurations are depicted in the drawings provided herein, but are well within the scope of knowledge of one skilled in the art given the disclosure presented herein.

Mirrored Images not Shown

The present invention as illustrated herein may be applied to a canine or other animal hematoma present on a particular left or right ear. The present invention anticipates that elements of the AHS shown herein may be mirrored about a symmetric vertical plane at the middle of the head of the animal between the ears of the animal. Thus, the drawings shown herein may only depict one half of the potential mirrored AHS as it may be applied to the other ear of the animal. One skilled in the art will recognize that this mirroring operation is well within construction details of a particular application context and this does not limit the scope of the claimed invention.

Strap/Strip Material not Limitive

The present invention makes use of a variety of "straps" and "strips" in forming the AHS construction. Generally speaking, these straps and strips may be of the same construction, preferred exemplary embodiments utilizing a non-elastic fabric adhesive tape or similar material that may in some contexts be termed "athletic tape" and/or "medical tape." While the specific material comprising the tape may vary, the tape should be non-elastic to ensure proper performance of the claimed invention. While many forms of this material are possible in this context, one preferred tape is DURAPORE™ brand surgical/medical tape manufactured by the 3M Company (Minnesota Mining and Manufacturing Company) (www.3 m.com).

Within the context of the present disclosure, a "strip" is generally defined as an attachment material placed to support horizontal fixation of the AEP, while a "strap" is generally defined as an attachment material placed to support longitudinal and/or vertical fixation of the AEP. Specifically, the long strap collar (LSC) may comprise multiple long straps that are merged (via adhesive) to form a stabilizing collar that extends beyond the AEP around the head of the animal to provide support for the overall AHS and prevent the AHS from excessive movement during the healing of the AEP hematoma. In some cases the "strip" material may be placed in a diagonal position to accomplish both of these objectives.

Applying AEP Covering Tape (ACT) not Limitive

The present invention may be described as incorporating the application of AEP covering tape (ACT) in some preferred embodiments. While not shown in the drawings, the ACT is simply additional strap/strip material layered upon existing strap/strip material present on the AEP and underlying elements. For this reason, one skilled in the art will recognize that there are many ways to accomplish the AEP wrapping using the ACT and as such the precise method by which the ACT wrapping is not limitive of the claimed invention disclosed herein.

Sandwich/Sandwiching Defined

The present invention may in some circumstances be described as "sandwiching" the AEP between layers of strips/straps and/or other materials to contain and/or treat the AEP and associated hematoma. Within this context, the term "sandwich" and its noun/verb variants will include: to make into or as if into a sandwich especially: to insert or enclose between usually two things of another quality or character; and to make a place for (often used with in or between).

Drawings Depict Element Spacing

The present invention makes use of strips/straps and CPP/ASP/RPP/RSP elements in a layered stack configuration. The drawings herein show these elements with spacing between the layers for clarity. As generally implemented in the claimed invention, these spaces are not present and the various layers are in contact with each other to form a unified structure. One skilled in the art will recognize that the drawings depicted herein are for use in assembly and the various layers depicted are to form a single structure when complete.

System Description and Theory of Operation

Overview

The present invention aural hematoma splint (AHS) provides the ability to allow an animal's own rehabilitative properties to regenerate damaged tissues while in a natural position. This is performed by having the AHS suspend the affected ear, after a hypodermic needle aspiration, allowing broken blood vessels to refill into an area under the AHS primary plate and non-elastic fabric taping method, defined by closely matching formation of plates and procedure to closely mimic ear size and shape, preventing uncontrolled blood and fluid to expansion. The remaining volume of area in separated tissues requires fluids re-entering the hematoma to be kept to a thin layer, where upon equalization of fluid pressures causes the fluids to rapidly coagulate into a thin layer of blood clot. This clot then builds and binds to the tissues, acting as a foundry to reproduce the permanent attachment tissues again for holding skin to cartilage. Once re-absorption and removal of the red blood cells occurs, the remaining structures are the recreated elements for tissue(s) reconstruction.

Preparatory Aspiration

The hypodermic needle aspiration is performed according to industry standards in either clinical or field environments, where hematoma fluids are relieved from pool by first disinfecting area with alcohol and then inserting a hypodermic needle through skin and into said pool and allowing fluids to escape through butt end and into napkin or cloth. Veterinary processes may include use of catheter or syringe to assist in relieving fluids. Hematoma fluids generally begin to coagulate after such time hematoma fills completely or upon approximately a week from onset. The hypodermic needle aspiration is performed prior to preparatory taping and application of aural hematoma splint plates.

Preparatory Taping

The aural hematoma splint preparatory taping illustrated in FIG. 1 (0100) shows animal ear pinna (AEP) (0101) with sections of full tape located and pressed against outer (0102) and inner (0103) sides of the AEP, starting before base where pinna meets head, extending outward along ear edge, with minimal portion of tape beyond ear edge, mirrored with tape from other side, pressed against the ear and other tape. This preparatory taping of ear edges provides an enlarged area of adhesive side to ear, with secure bonding of tape to ear and tape to tape. A subsequent long strap collar (0104) begins on underside of ear, extends outward along central vertical axis of the AEP beyond ear tip, folds over itself and ear tip (0104), without folding any portion of ear flesh upon itself, extending down back side of ear, over and passed base of the AEP at head of animal, continuing over head of animal onto neck at location (0104) near back of jaw line, under head and neck leaving ability for animal to function eating and breathing unimpaired, and continuing for two rotations pressing tape to fur and subsequently second rotation tape to tape. The use of this long strap collar is conjoined in purpose with a cross strip (0105) at the base of ear. This initial cross strip (0105) applied horizontal across ear central vertical axis, at base of ear applied to back side of ear folded over past ear edge without folding any portion of ear flesh, and pressed to underside of ear. The specific purpose for the cross strip is to keep long strap collar from lifting away from hair and presenting opportunity for apparatus to slide upward along the vertical axis.

Figure 2:
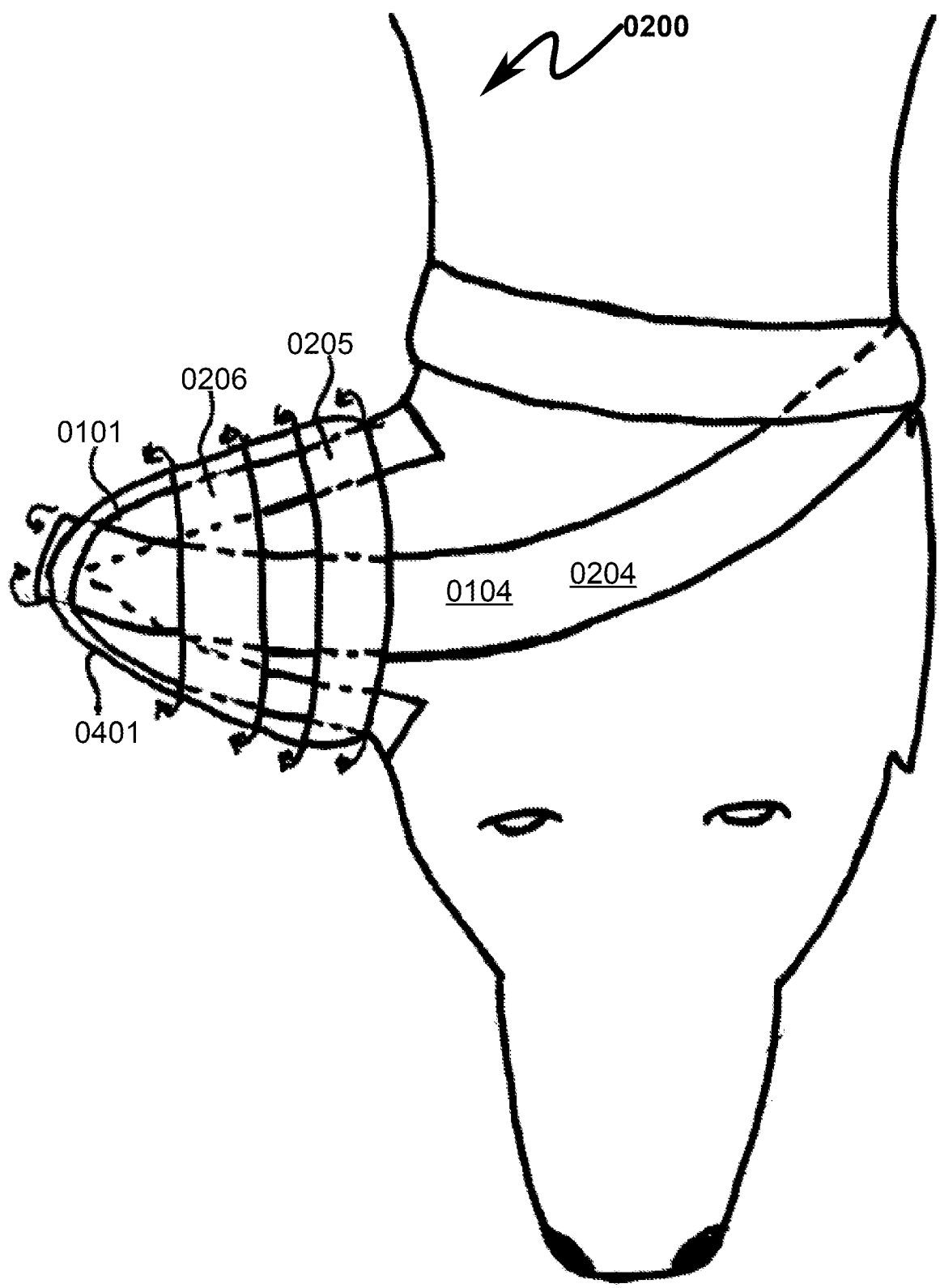
FIG. 2 exhibits location of a primary plate in location, wherein being held by long strap collar and cross strips.

The aural hematoma splint illustrated in FIG. 2 (0200) primary plate, post hypodermic needle aspiration of blood pool and post preparatory taping, shown located in a fixed position generally suspending an auricle pinna, attached by a taping method using a non-elastic fabric medical tape or similar, in taught fashion without impairing freedom of fluid flow to and from ear auricle.

As illustrated in FIG. 2 (0200), the installation of aural hematoma splint primary plate shows location of primary plate (0401) at underside of the AEP (0101), noticing no part of ear flesh is outside bounds of primary plate (0401). An initial cross strip (0205) installed taught around back side of ear, folded over primary plate (0401) edge and firmly pressed against underside primary plate, is used to locate primary plate, then a long strap collar (0204), then a subsequent cross strip (0205) at base of the ear to prevent long strap collar from lifting, and continuing to use taught cross strips (0206) over back of ear, folded over primary plate edge, firmly pressed against underside of primary plate until ear is full covered. Long strap collar (0204) is located over previous long strap collar (0104) from preparatory taping.

Figure 3:
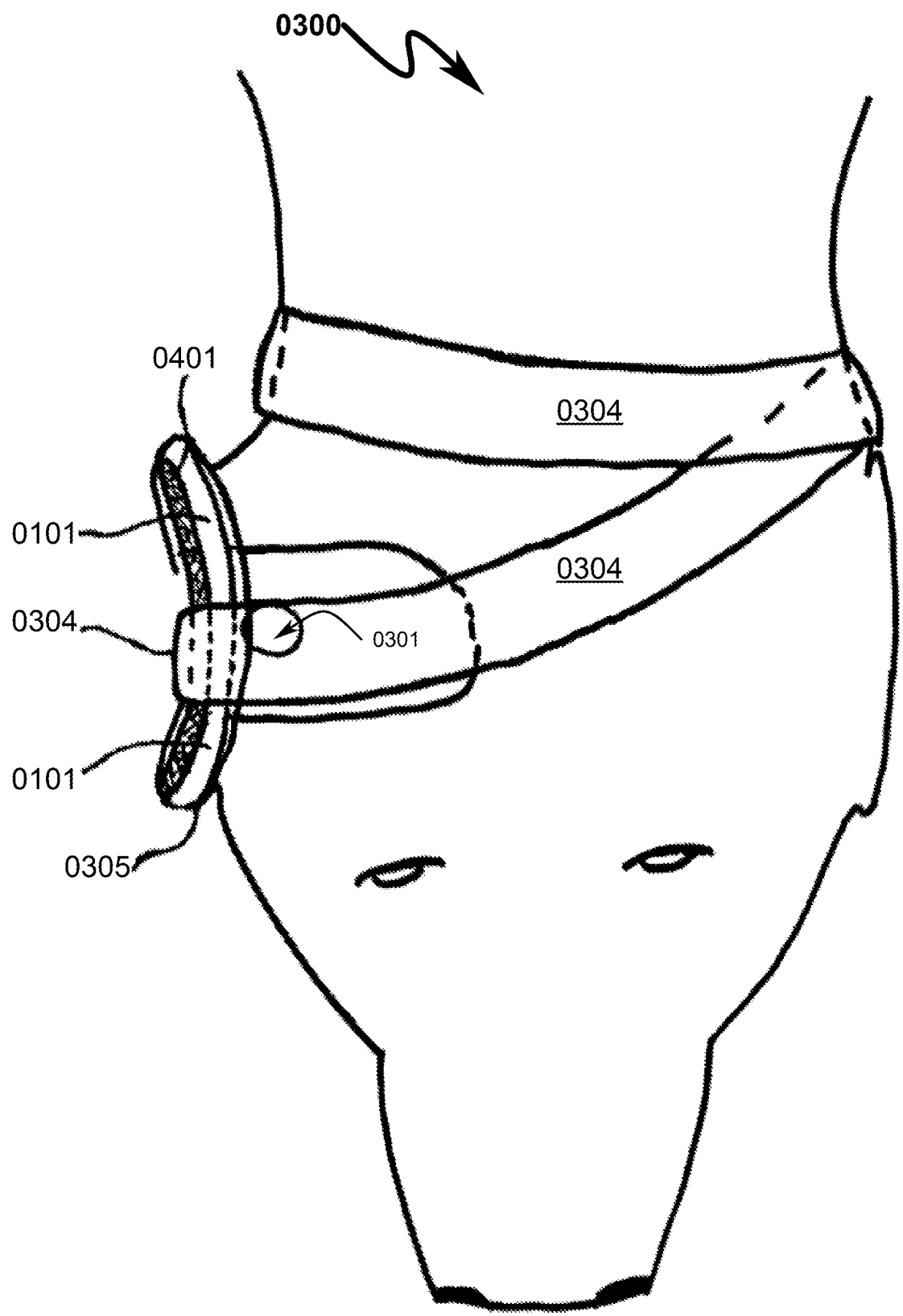
FIG. 3 exhibits location of a secondary plate in location, wherein being held by long strap collar and cross strips.

As illustrated in FIG. 3 (0300), the installation of aural hematoma splint secondary plate stabilizer (0301) shows location of stabilizer behind ear at base of ear at top of head. An initial cross strip (0305) is again used to locate the secondary plate stabilizer (0301), and subsequent long strap collar (0304), and further cross strips (0306) to secure. Layered parts of the AEP in suspension are (0301), (0304), (0305), (0401).

Treatment modality requires 14 days in secured location to allow for blood layer to coagulate, clot to adhere to tissues, and process for re-absorption of the red blood cells to begin. Treatment provides abilities to stop broken blood vessels from freely filling the hematoma, and allows animal's abilities to suffer these arterial and venal breaks, and therefore the allowance for animal to make the regenerative repairs.

Figure 4:
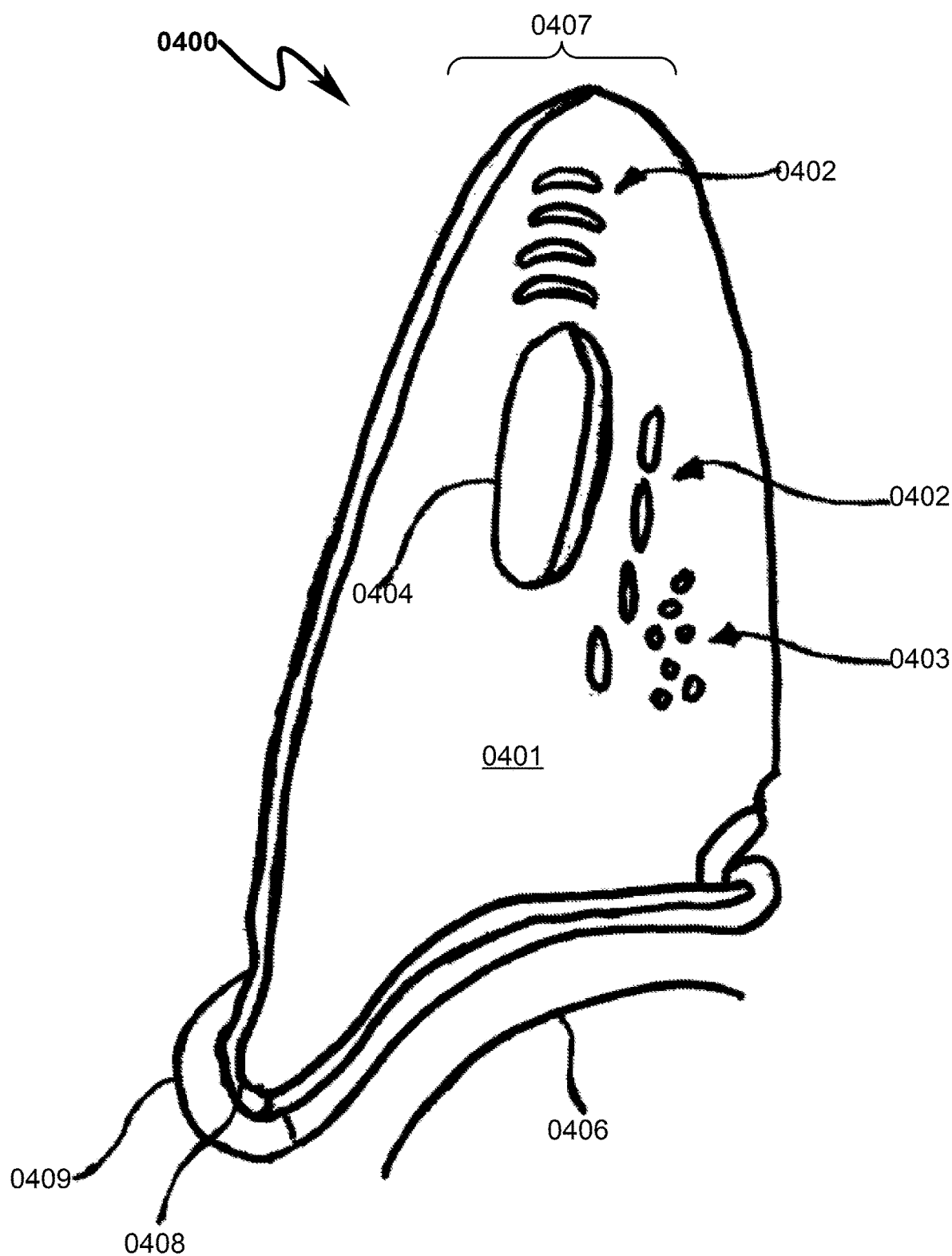
FIG. 4 exhibits an alternate embodiment including variations of features of aural hematoma splint primary plate, with ventilation holes, access window, curvature, foam padding strip (FPS), curved raised portion at base, side of primary plate away from ear tissue.

As illustrated in FIG. 4 (0400), embodiments for the aural hematoma splint include abilities to relieve moisture from building and remaining in the environment under primary plate (0401). Elongated (0402) and circular vents (0403) will have the ability to allow moisture to migrate away from areas of treatment and away to atmosphere. Including an access window (0404) to treat a previous wound or other malady is performed by removing a section of primary plate, without causing detriment to overall structural integrity for said primary plate. By adding foam padding strip (FPS) (0405) at THE base of primary plate, the location where said plate meets the ear at base is relieved as a potential area of irritation and abrasion. The curvature (0406) allows considerable strength to the primary plate, and its conical form with larger radii at base and smaller radii at tip (0407) makes a good reflection of the natural ear embodiment. A raised curvature at base (0408) allowing ease of location at pinna base. Foam padding strip (FPS) (0409) located at base for comfort.

Figure 5:
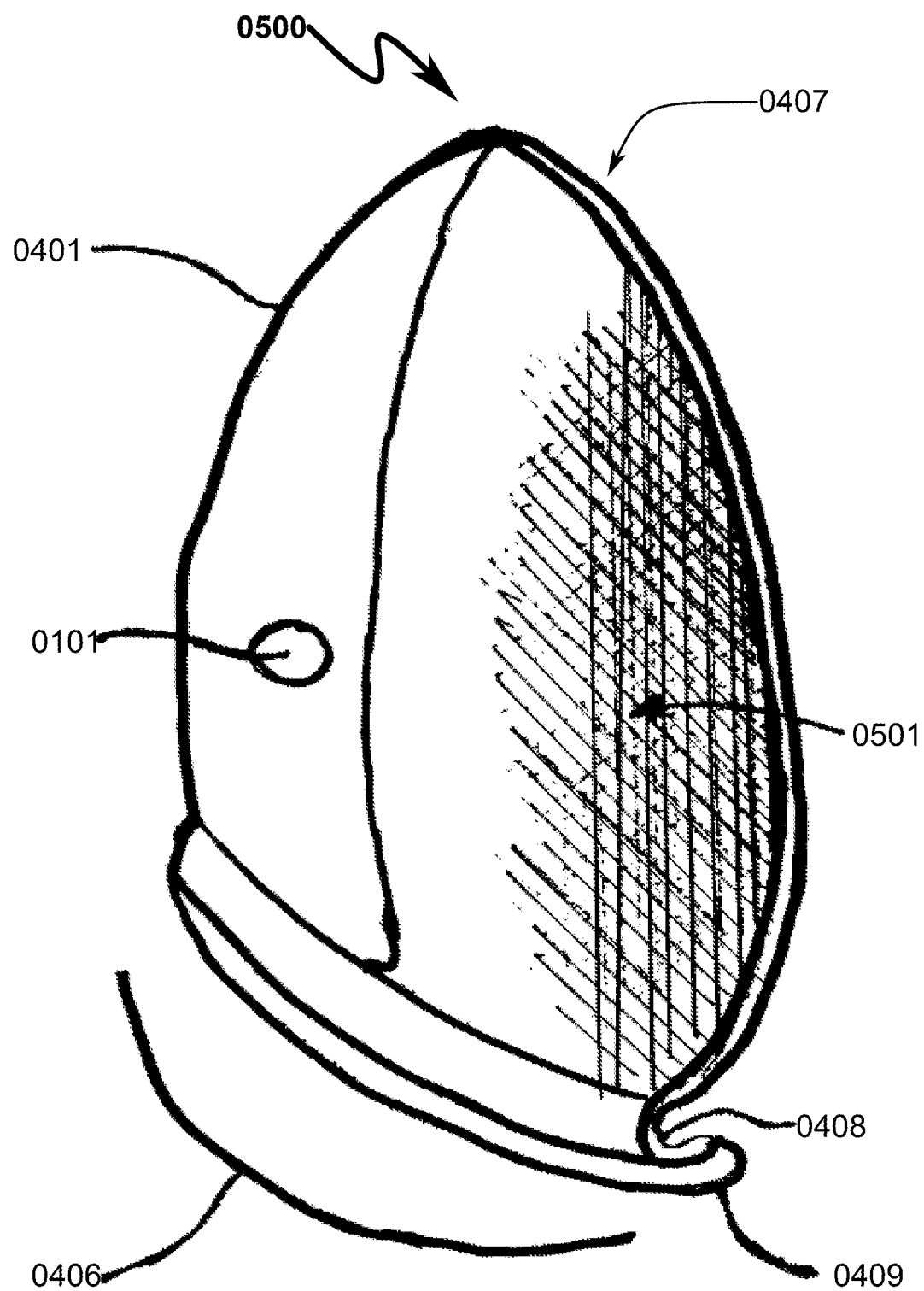
FIG. 5 exhibits an alternate embodiment including variations of features of aural hematoma splint primary plate reverse angle, medical fabric location, curvature, foam padding strip (FPS), curved raised portion at base, side of primary against ear tissue.

As illustrated in FIG. 5 (0500), the radial curvature (0406) is again shown, this time from the side of primary plate (0401) locating against the AEP tissues (0101). Also shown, the medical fabric (0501), located on convex side of primary plate, used to mitigate moisture away from ear tissues. The raised curvature at base (0408) and the foam padding strip (FPS) (0409) is duplicated shown as alternate view.

Figure 6:
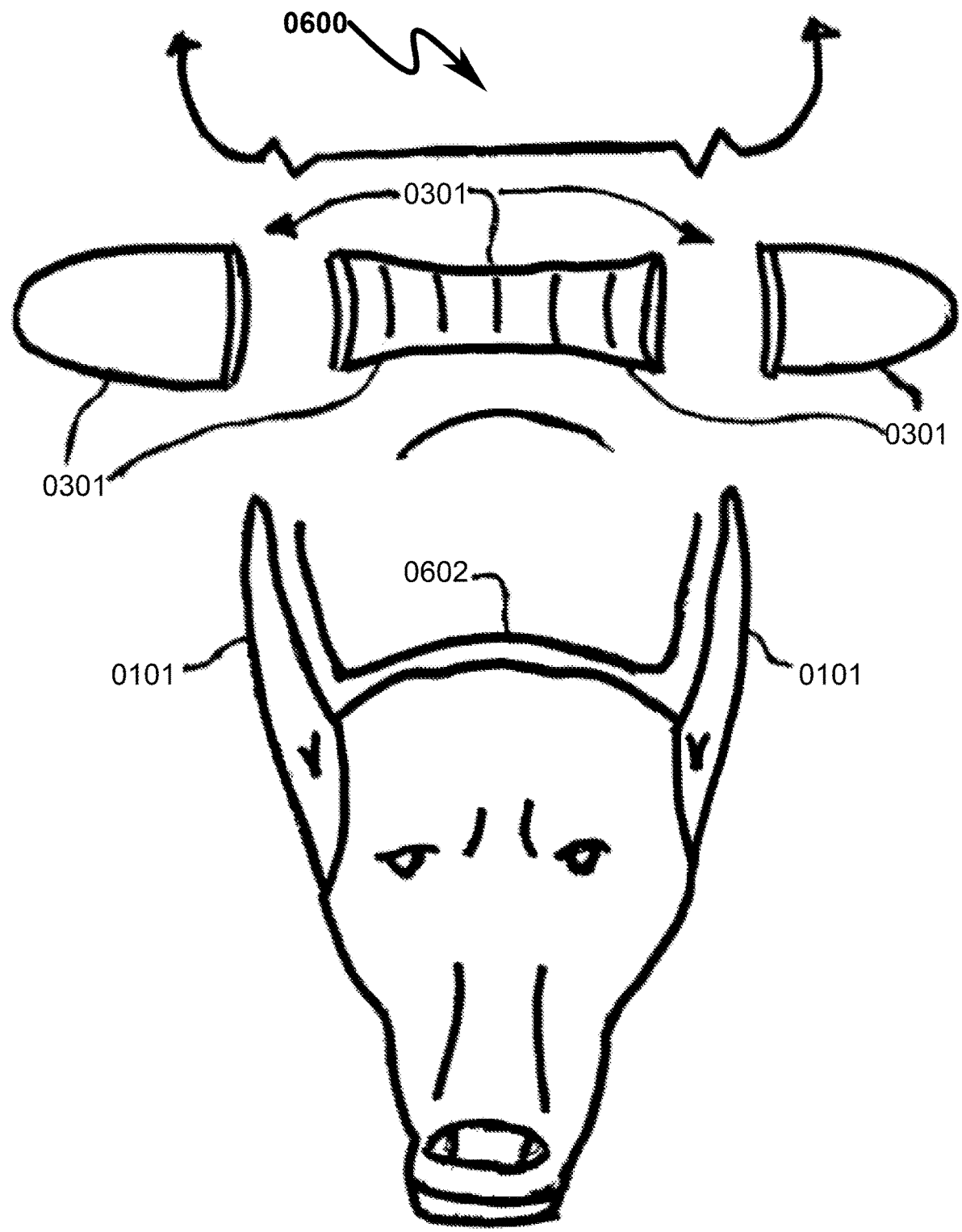
FIG. 6 exhibits integrated stabilizer secondary plate and embodiments.
Figure 7:
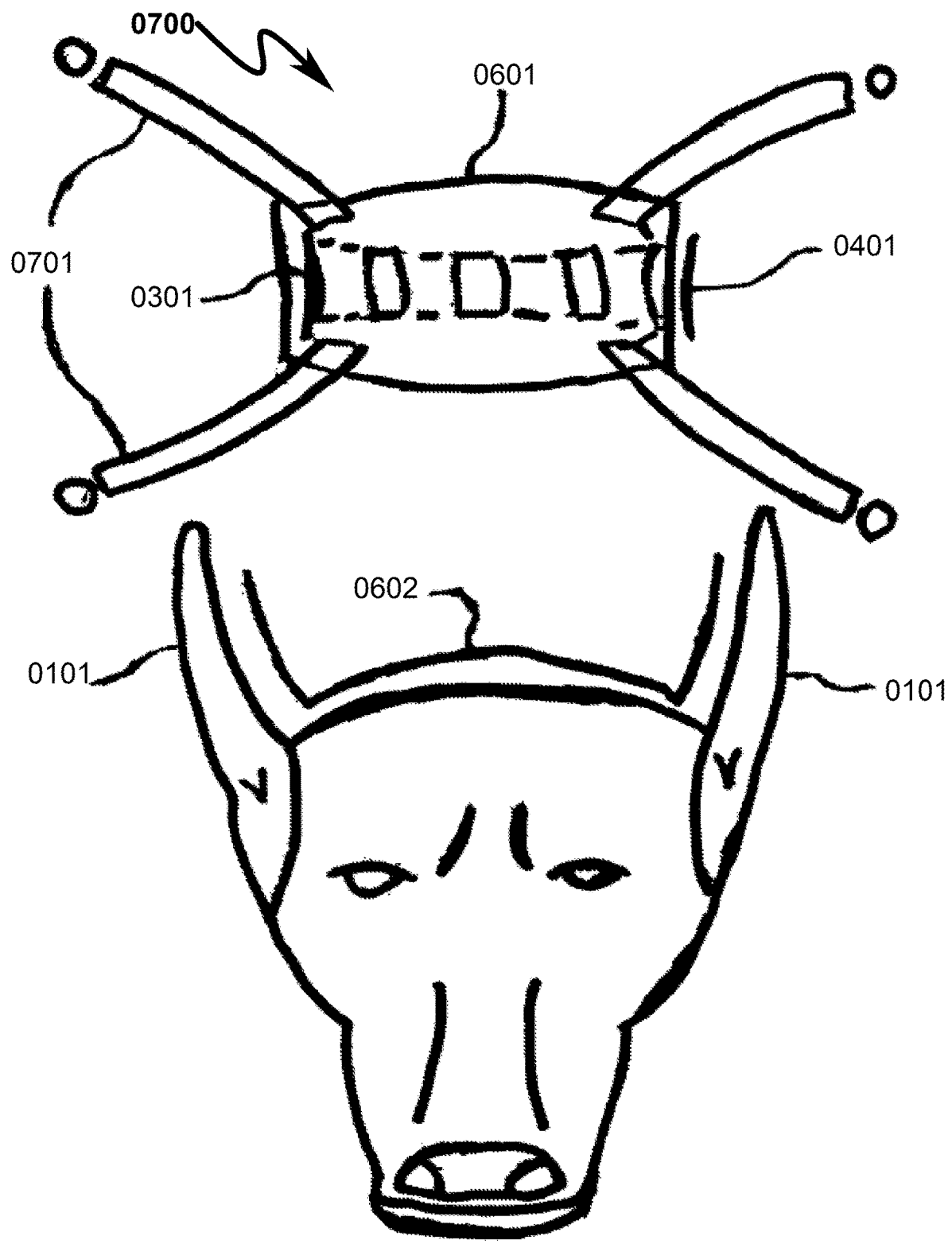
FIG. 7 exhibits an integrated stabilizer harness with adjustable straps for securing the AHS.

As illustrated in FIG. 6 (0600) and FIG. 7 (0700), an integrated secondary plate (0301) (shown separated) can be used to assist in elevating the AEP (0101) into erect position, and alternately used in treating both ears at once. The harness (0601) used to support the integrated secondary plate (0602) can be of materials malleable to animal's own form yet rigid enough to support features for aural hematoma splint modality as a whole. The ability for primary plates (0401) to extend from edge of harness near ear bases allows preparatory taping and primary plate attachment beforehand, and subsequent attachment of secondary plate (0301) to affected ear. Straps (0701) used to secure fit for harness to be adjustable to meet sizing needs of the animal.

Figure 8:
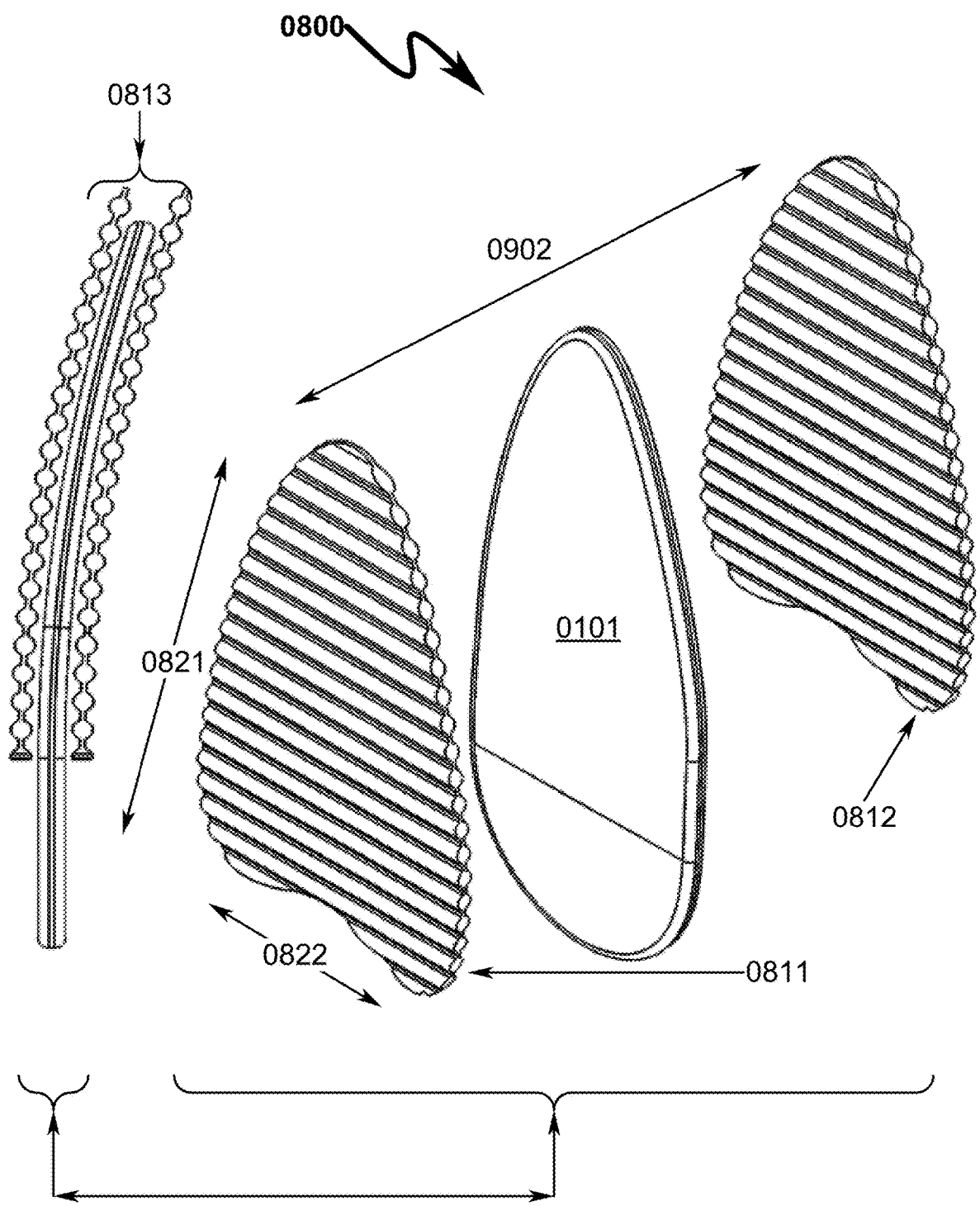
FIG. 8 exhibits an articulated flat primary plates, flat secondary plates used for overly large pendent ears and depicts cross section and expanded views.
Figure 9:
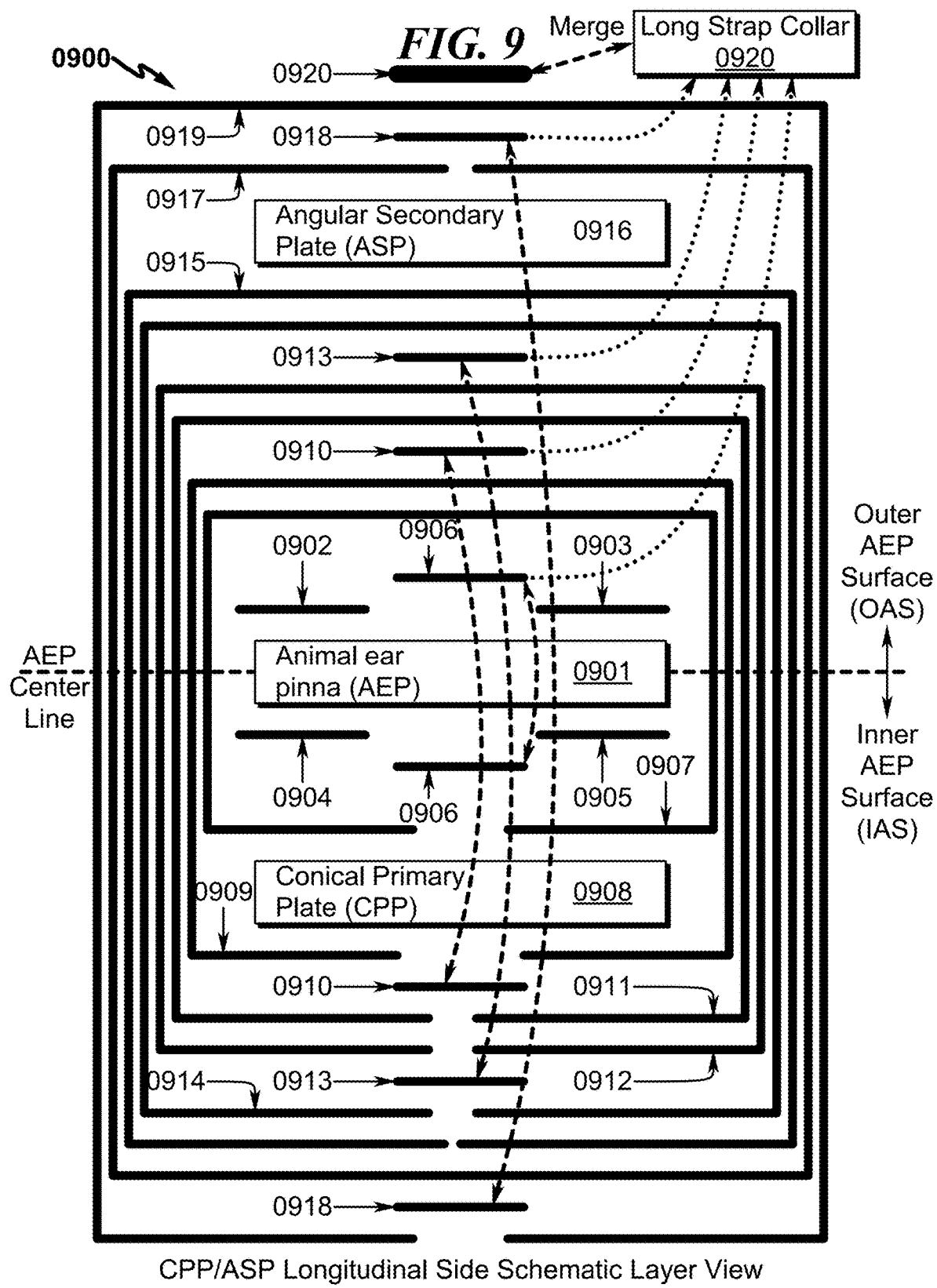
FIG. 9 illustrates an exemplary longitudinal side schematic layer view of a preferred CPP/ASP system embodiment of the present invention.

As illustrated in FIGS. 8 and 9, an aural hematoma splint used to treat an overly large pendent ear, where use of the curved plates would not allow conformity of ear and plates to rest comfortably against side of head of animal.

As illustrated in FIG. 8 (0800), an articulating plate (0811) with ability to flex across one axis, allowing an overly large pendent ear pinna (0101) to have an aural hematoma splint secured in place, and treated in pendent position. Taping procedural same as preparatory and installation of primary plate. Secondary articulating plate (0812) same as primary plate (0811) to allow bending of ear against side of head with taped collar or alternate source of locating to head.

As illustrated in FIG. 8 (0800), the cross section (0813) of primary (0811) and secondary plates (0812) shows segmented rigid plastic tubular bars or similar separated by thin web material, allowing segments to bend against a vertical/longitudinal (0821) axis without flexing against horizontal/transverse (0822) axis. The ability to flex on the vertical/longitudinal axis allows primary and secondary plates to conform to head curvature on side and below head, while staying rigid to control expansion outward from forces due to hematoma refilling.

CPP/ASP Longitudinal Side Schematic Layer View (0900)

A longitudinal side schematic layer view of an AHS CPP/ASP variant preferred exemplary embodiment of the present invention is generally depicted in FIG. 9 (0900). Here it can be seen that the structure of the system may be generally described as having the following elements:
(1) AEP (denoted by having an inner AEP surface (IAS) and an outer AEP surface (OAS)) to which the invention is applied is first identified and isolated (0901);
(2) first outer tape (OT1) (0902);
(3) second outer tape (OT2) (0903);
(4) first inner tape (IT1) (0904);
(5) second inner tape (IT2) (0905);
(6) first long strap (LS1) (0906);
(7) first cross strip (CS1) (0907);
(8) conical primary plate (CPP) (0908);
(9) second cross strip (CS2) (0909);
(10) second long strap (LS2) (0910);
(11) third cross strip (CS3) (0911);
(12) fourth cross strip (CS4) (0912);
(13) third long strap (LS3) (0913);
(14) fifth cross strip (CS5) (0914);
(15) AEP covering tape (ACT) (0915);
(16) angular secondary plate (ASP) (0916);
(17) sixth cross strip (CS6) (0917);
(18) fourth long strap (LS4) (0918);
(19) seventh cross strip (CS7) (0919); and
(20) MERGED LS1/LS2/LS3/LS4 to form a long strap collar (LSC) (0920).

The first outer tape (OT1) (0902), second outer tape (OT2) (0903), first inner tape (IT1) (0904), second inner tape (IT2) (0905), first long strap (LS1) (0906), and first cross strip (CS1) (0907) form an ear pinna foundation (EPF) that sandwiches the AEP to position and stabilize it for further processing.

Figure 17:
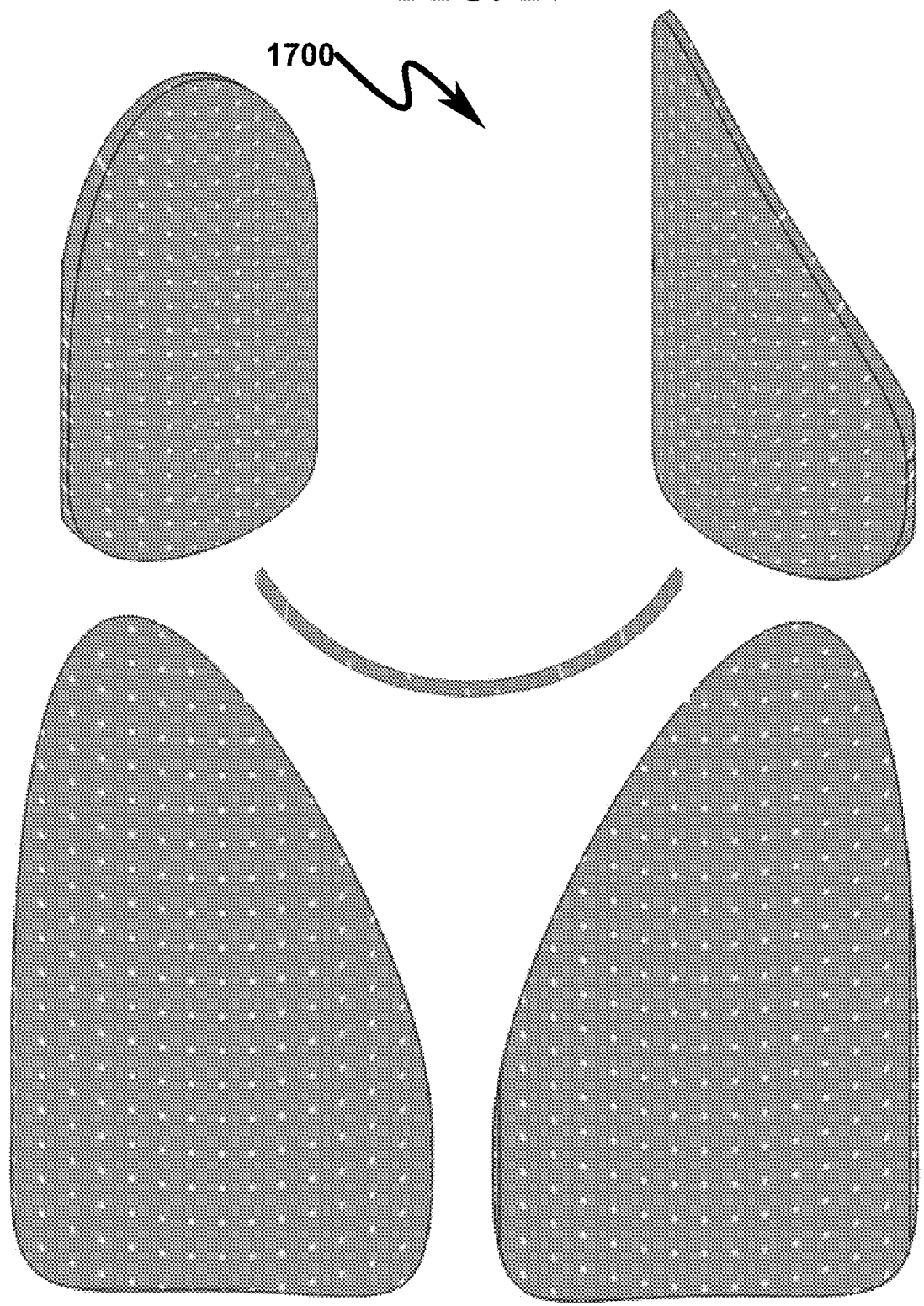
FIG. 17 illustrates an assembly view of a preferred exemplary invention embodiment (page 1/16)
Figure 18:
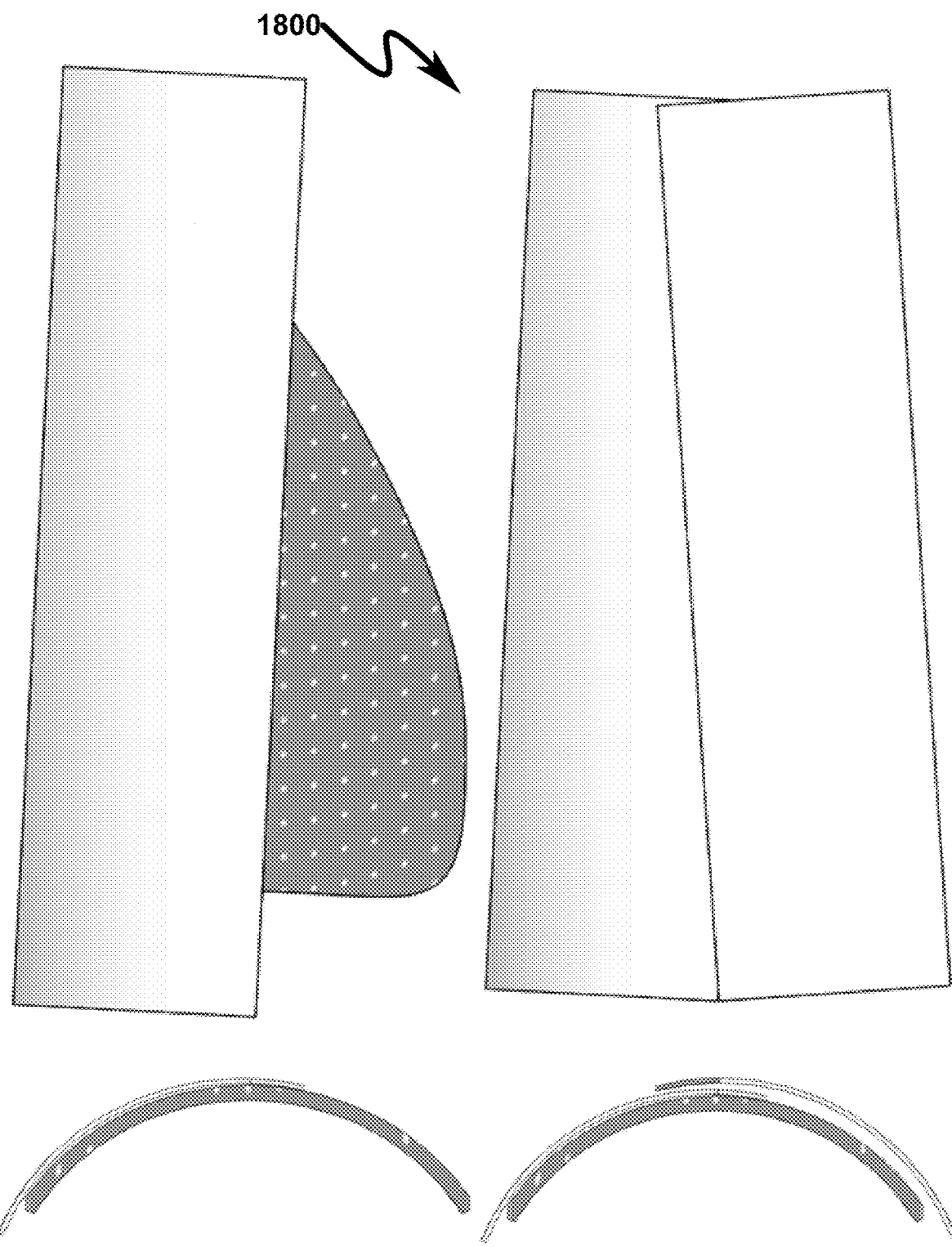
FIG. 18 illustrates an assembly view of a preferred exemplary invention embodiment (page 2/16)
Figure 19:
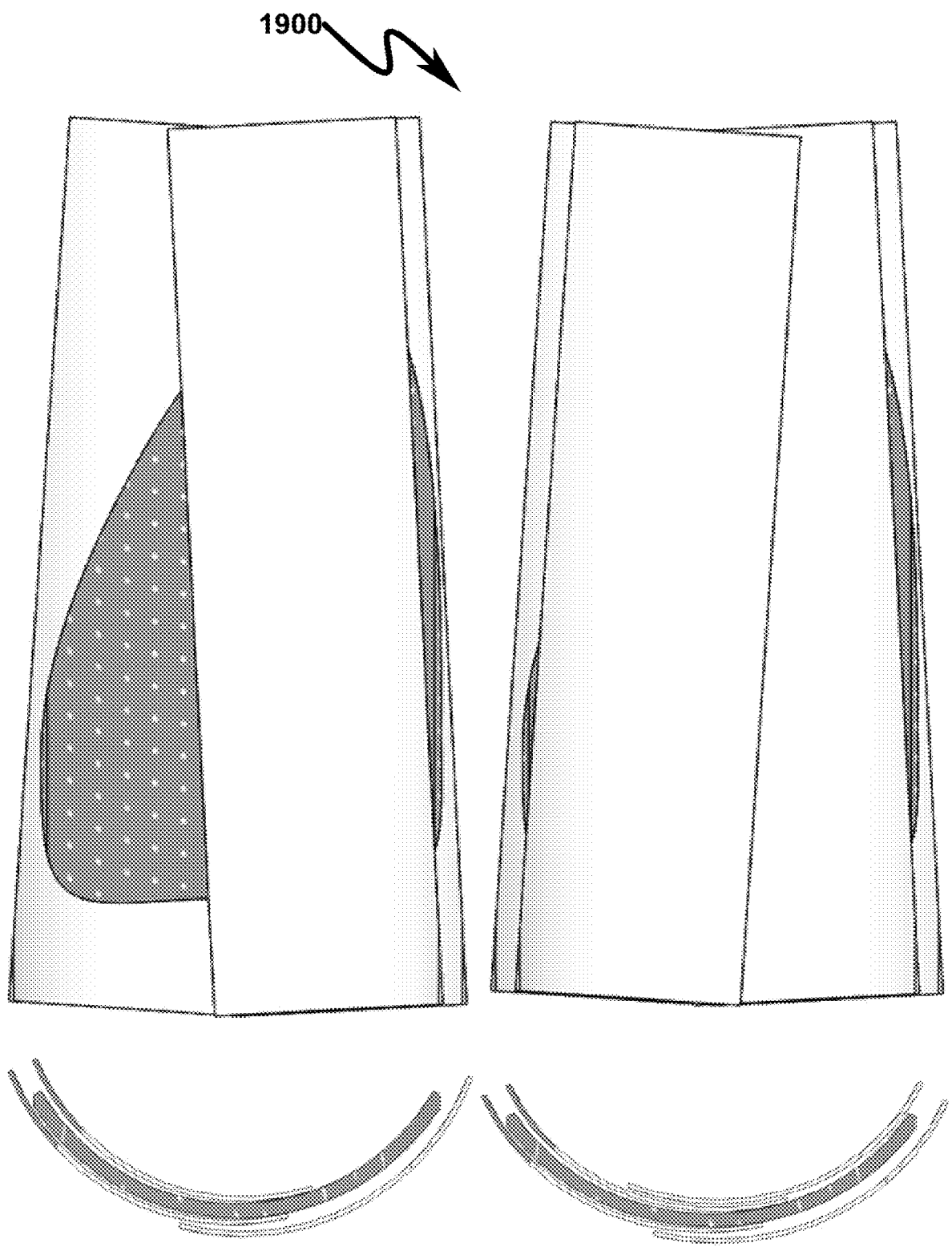
FIG. 19 illustrates an assembly view of a preferred exemplary invention embodiment (page 3/16)
Figure 20:
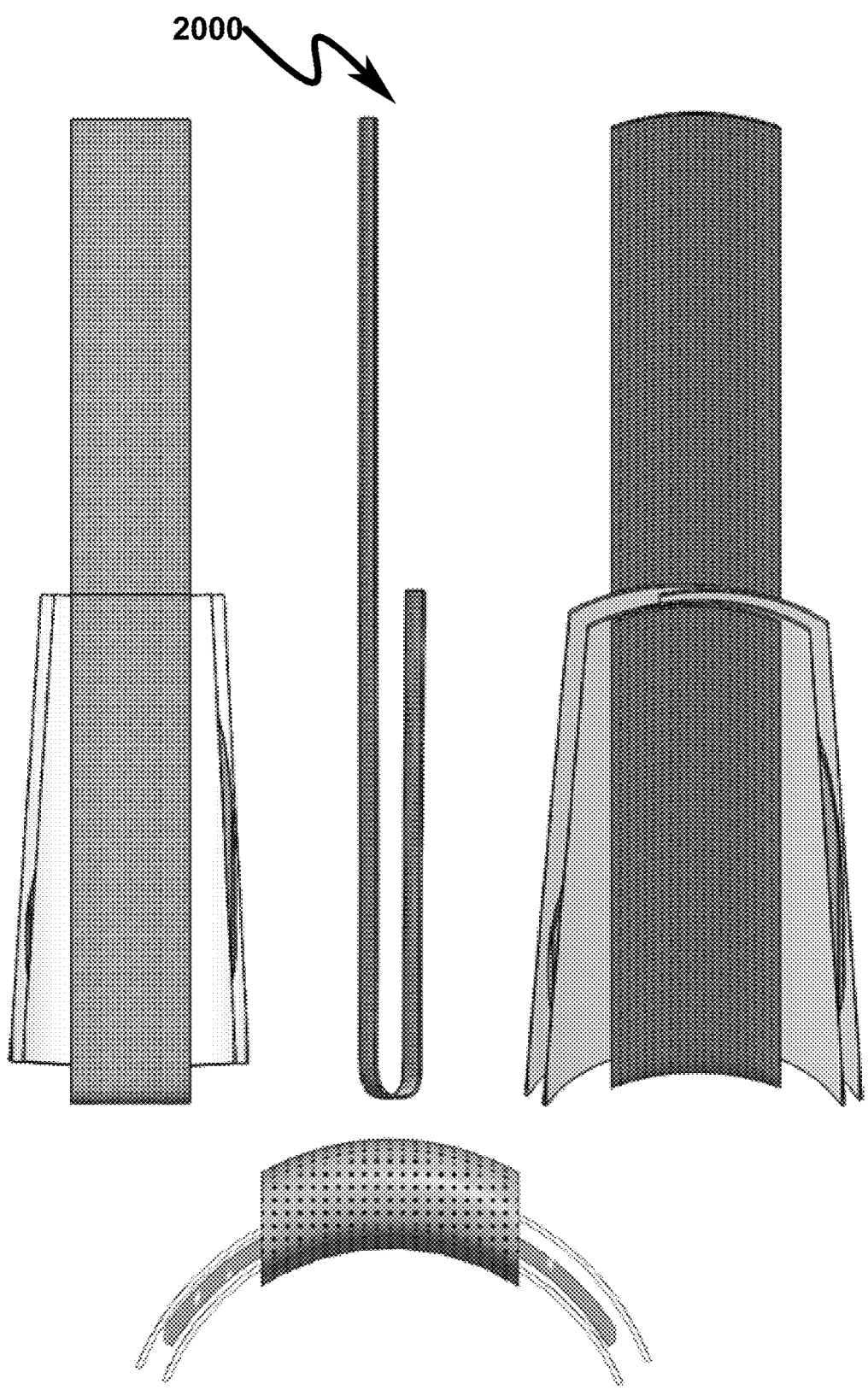
FIG. 20 illustrates an assembly view of a preferred exemplary invention embodiment (page 4/16)
Figure 21:
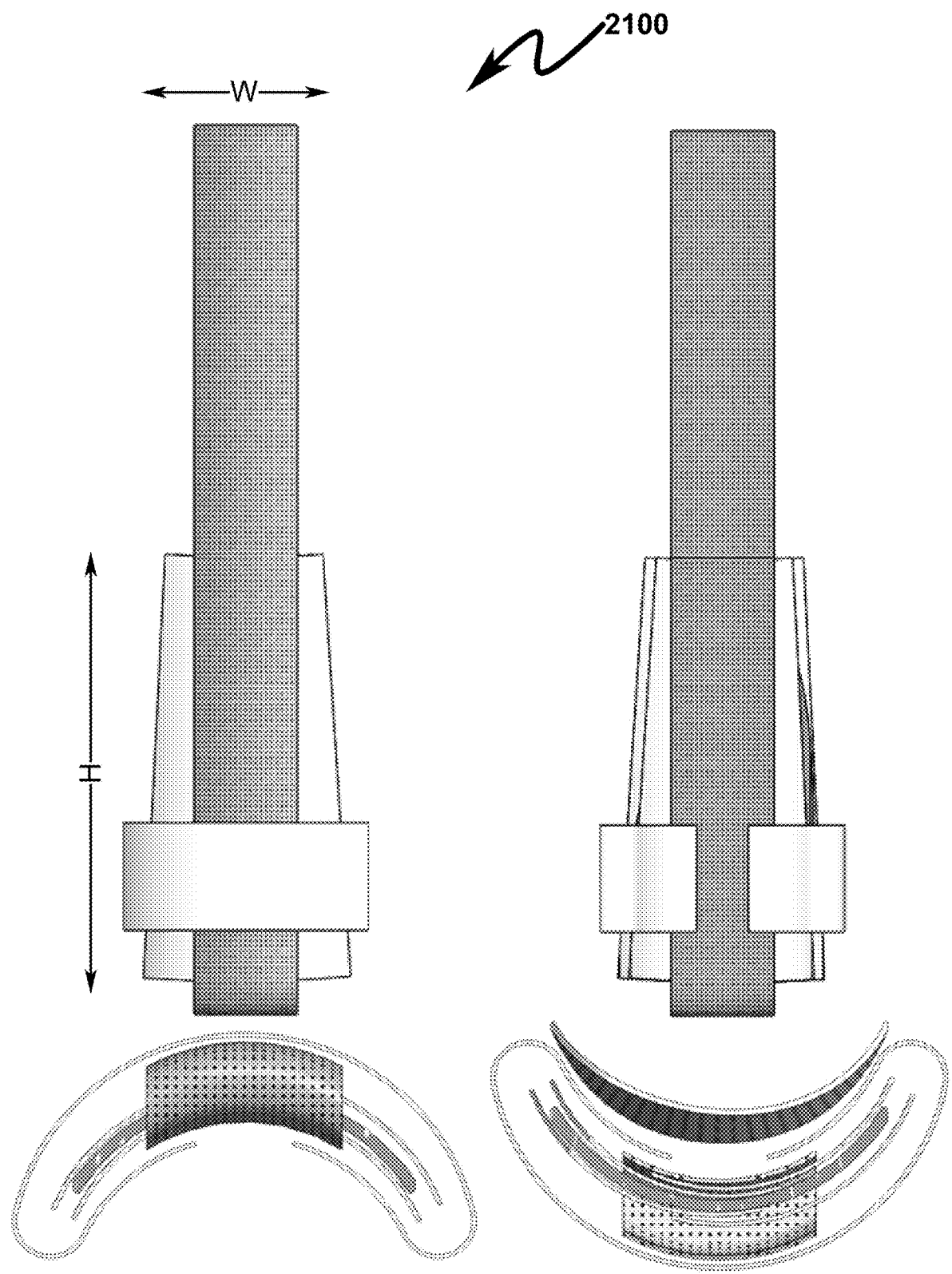
FIG. 21 illustrates an assembly view of a preferred exemplary invention embodiment (page 5/16)
Figure 22:
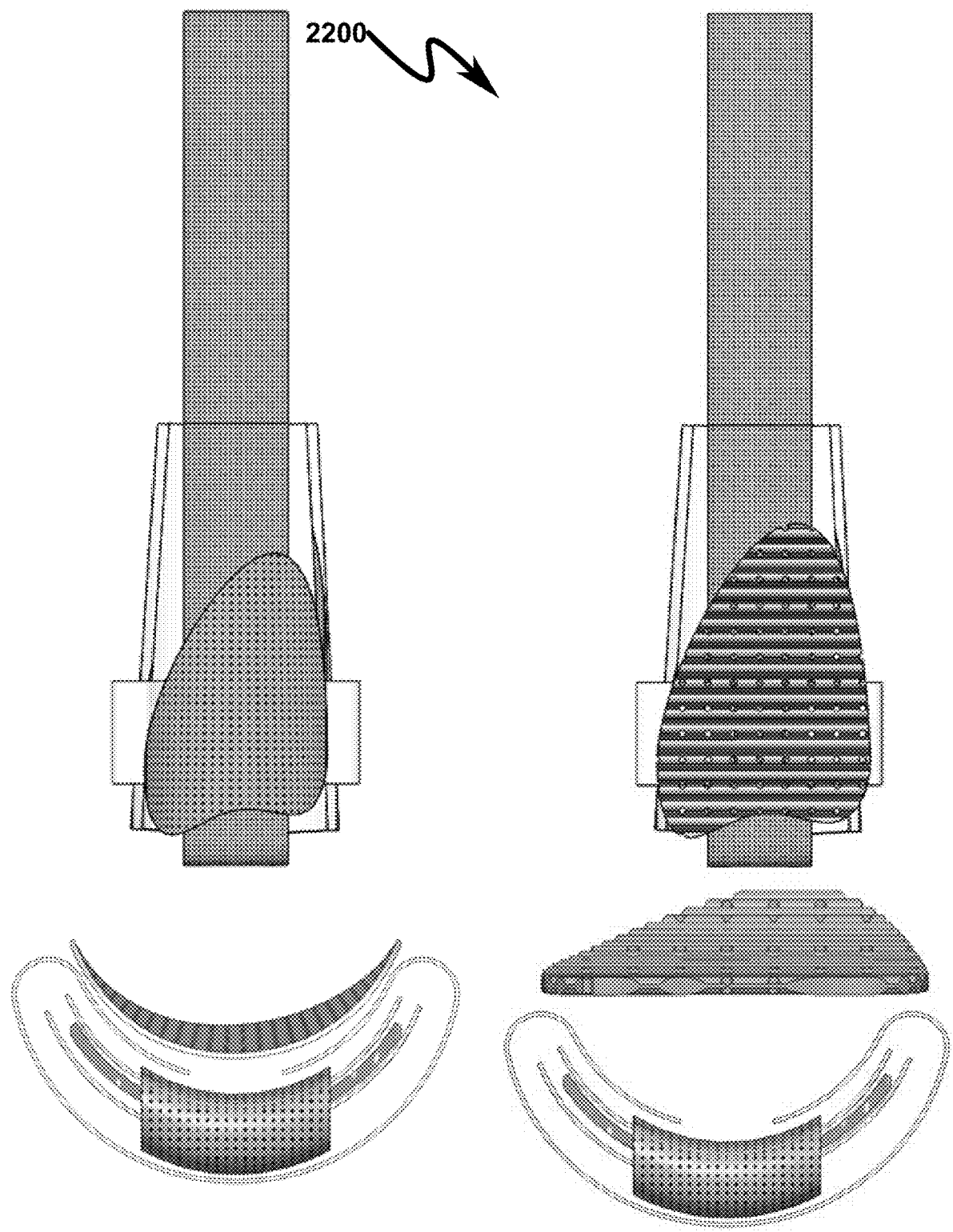
FIG. 22 illustrates an assembly view of a preferred exemplary invention embodiment (page 6/16)
Figure 23:
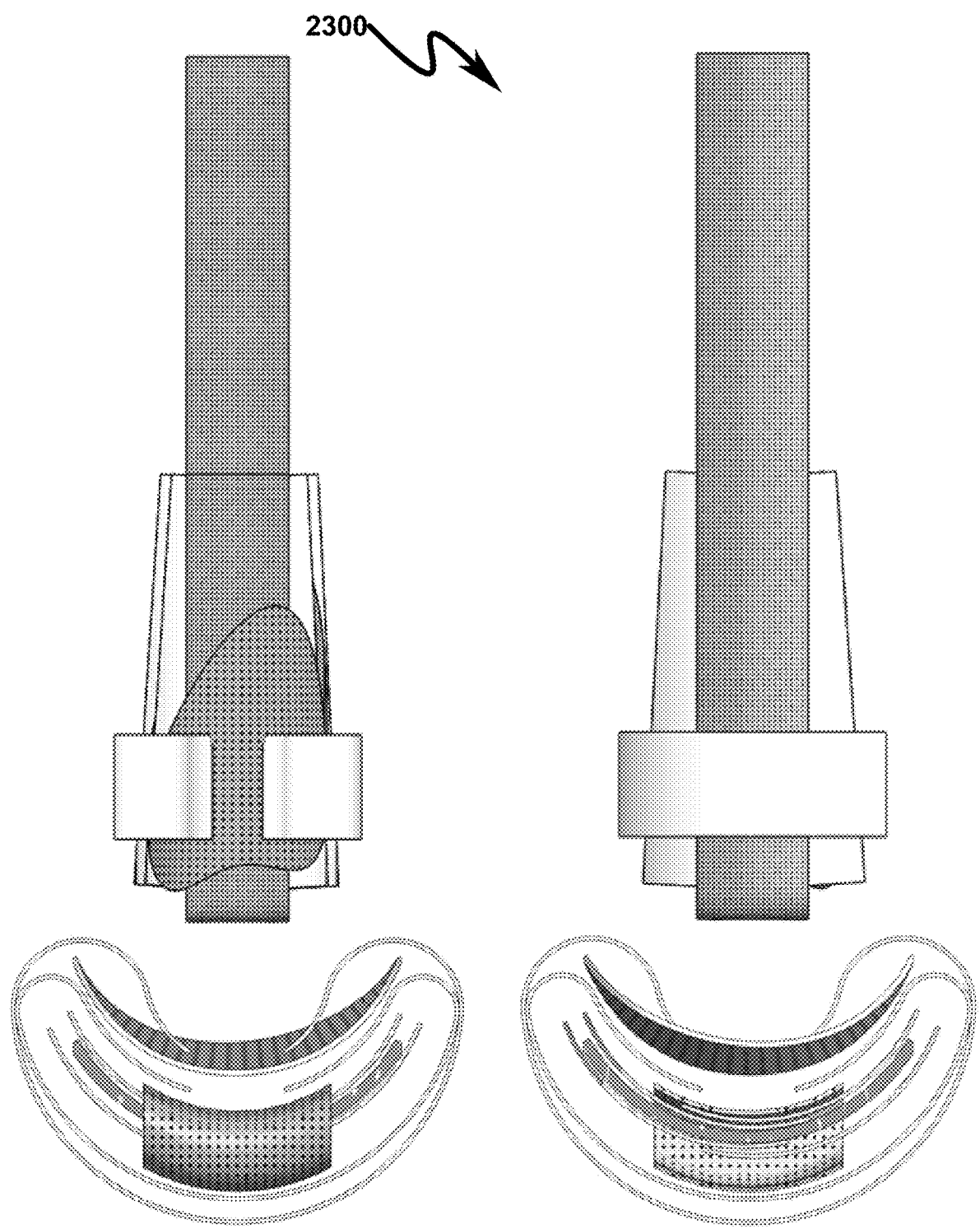
FIG. 23 illustrates an assembly view of a preferred exemplary invention embodiment (page 7/16)
Figure 24:
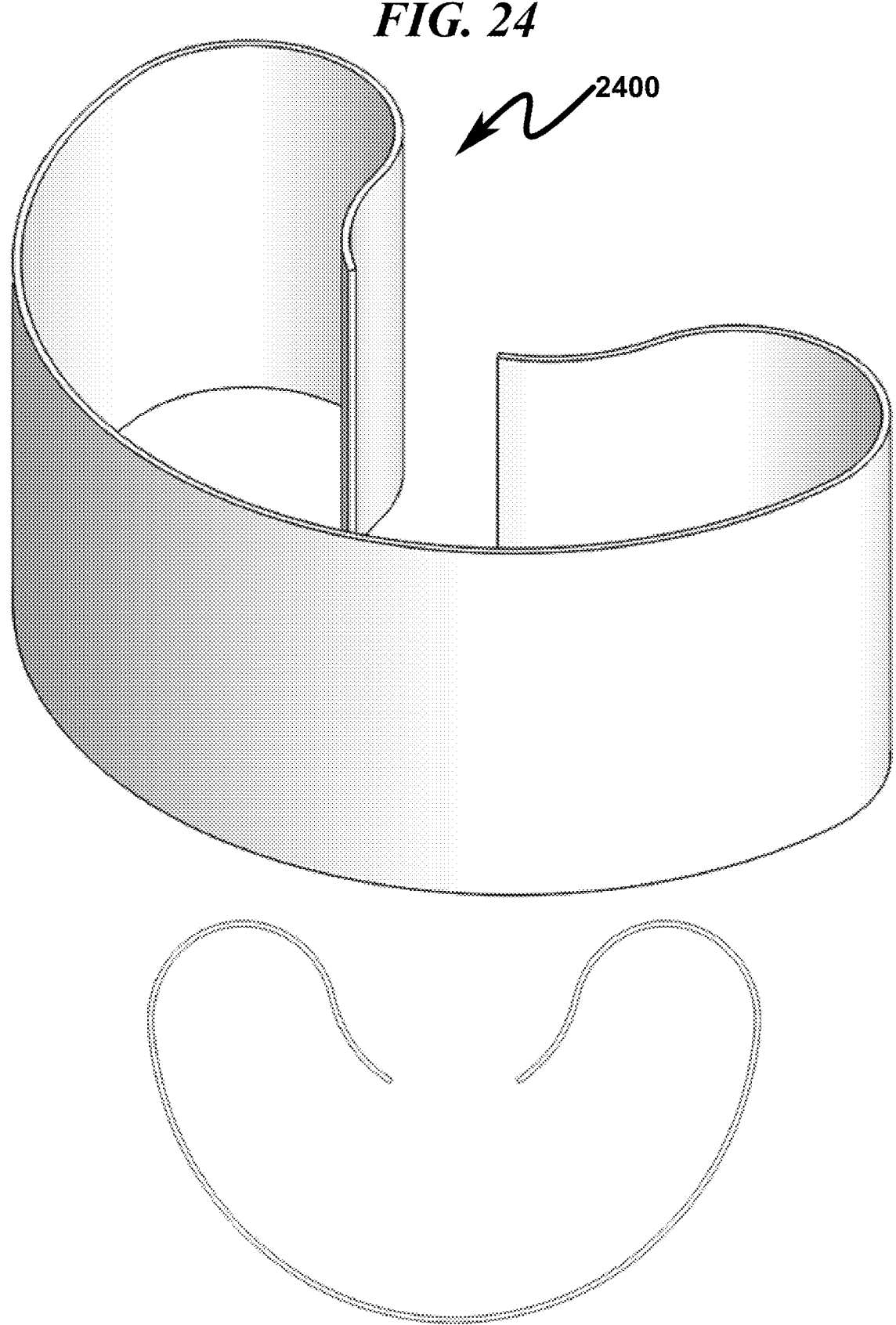
FIG. 24 illustrates an assembly step view of a preferred exemplary invention embodiment (omitting previous layers) (page 8/16)
Figure 25:
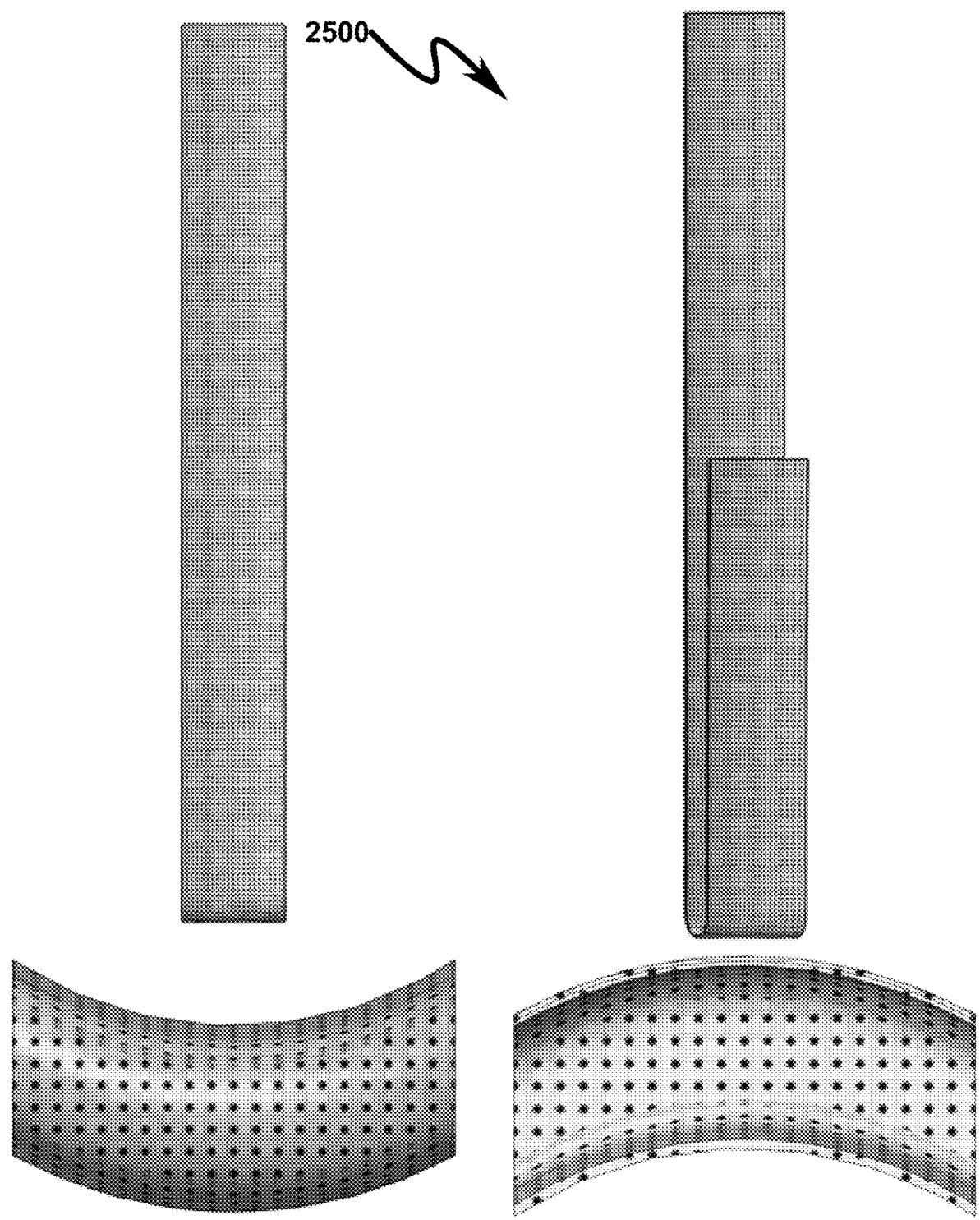
FIG. 25 illustrates an assembly step view of a preferred exemplary invention embodiment (omitting previous layers) (page 9/16)
Figure 26:
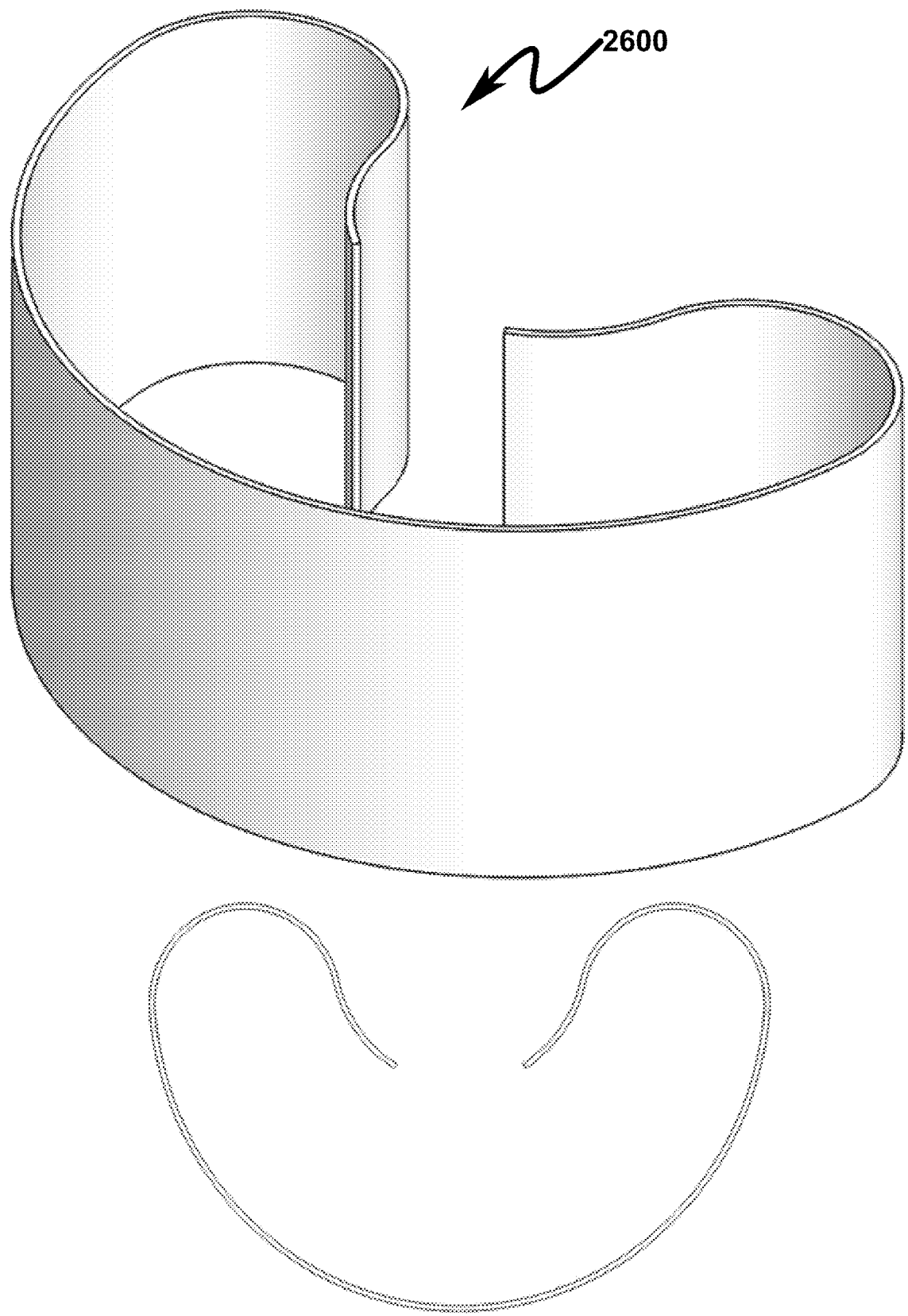
FIG. 26 illustrates an assembly step view of a preferred exemplary invention embodiment (omitting previous layers) (page 10/16)
Figure 27:
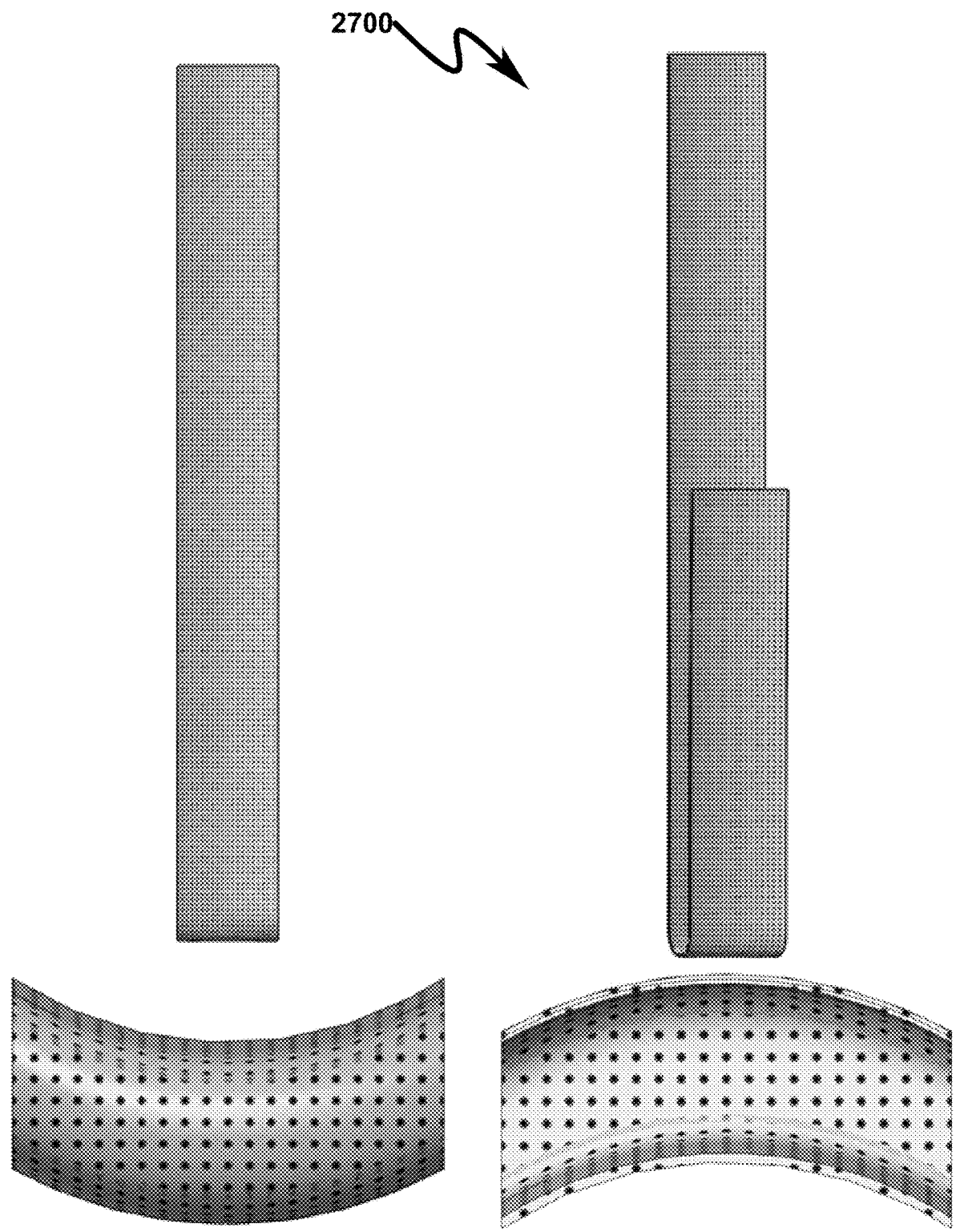
FIG. 27 illustrates an assembly step view of a preferred exemplary invention embodiment (omitting previous layers) (page 11/16)
Figure 28:
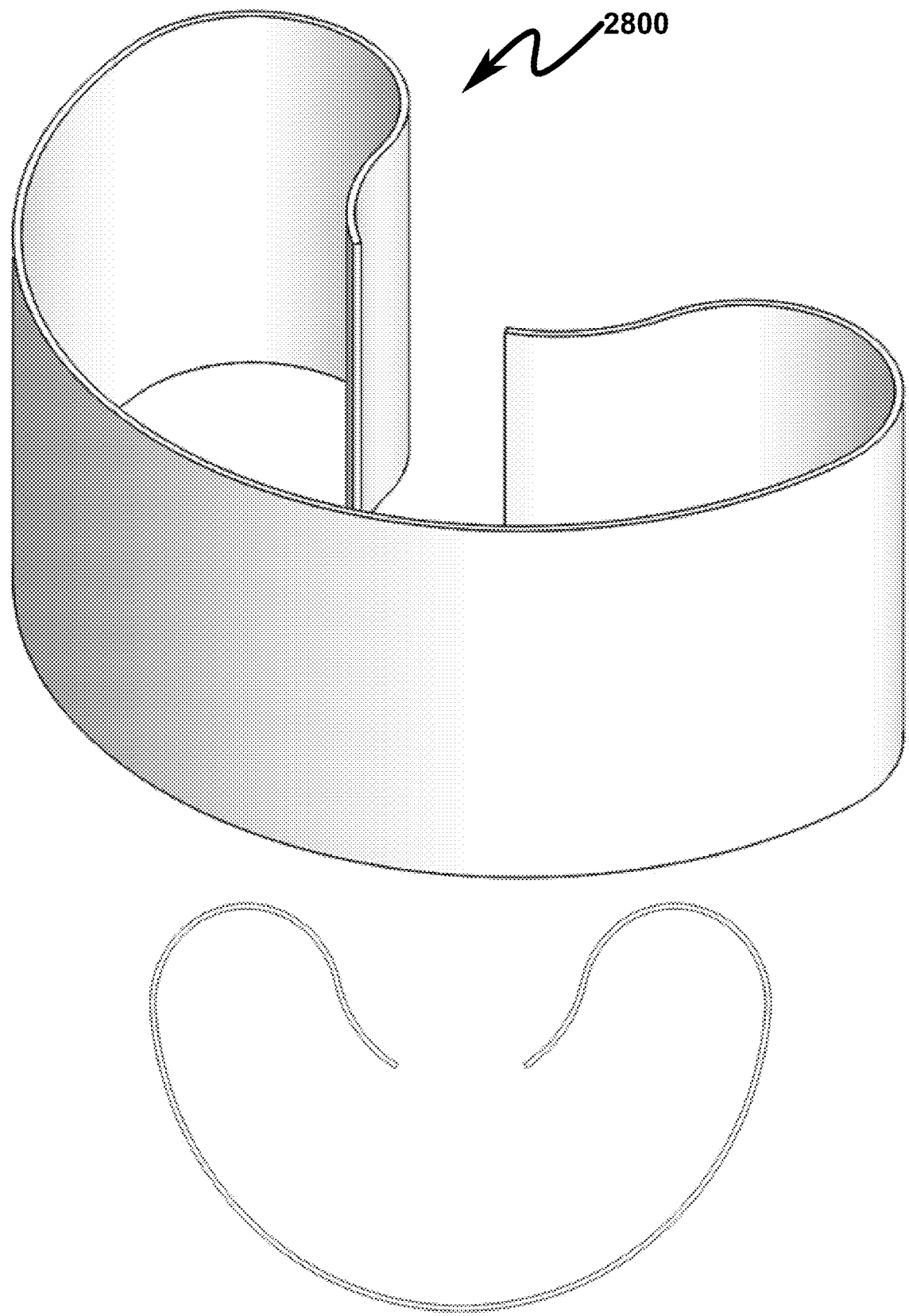
FIG. 28 illustrates an assembly step view of a preferred exemplary invention embodiment (omitting previous layers) (page 12/16)
Figure 29:
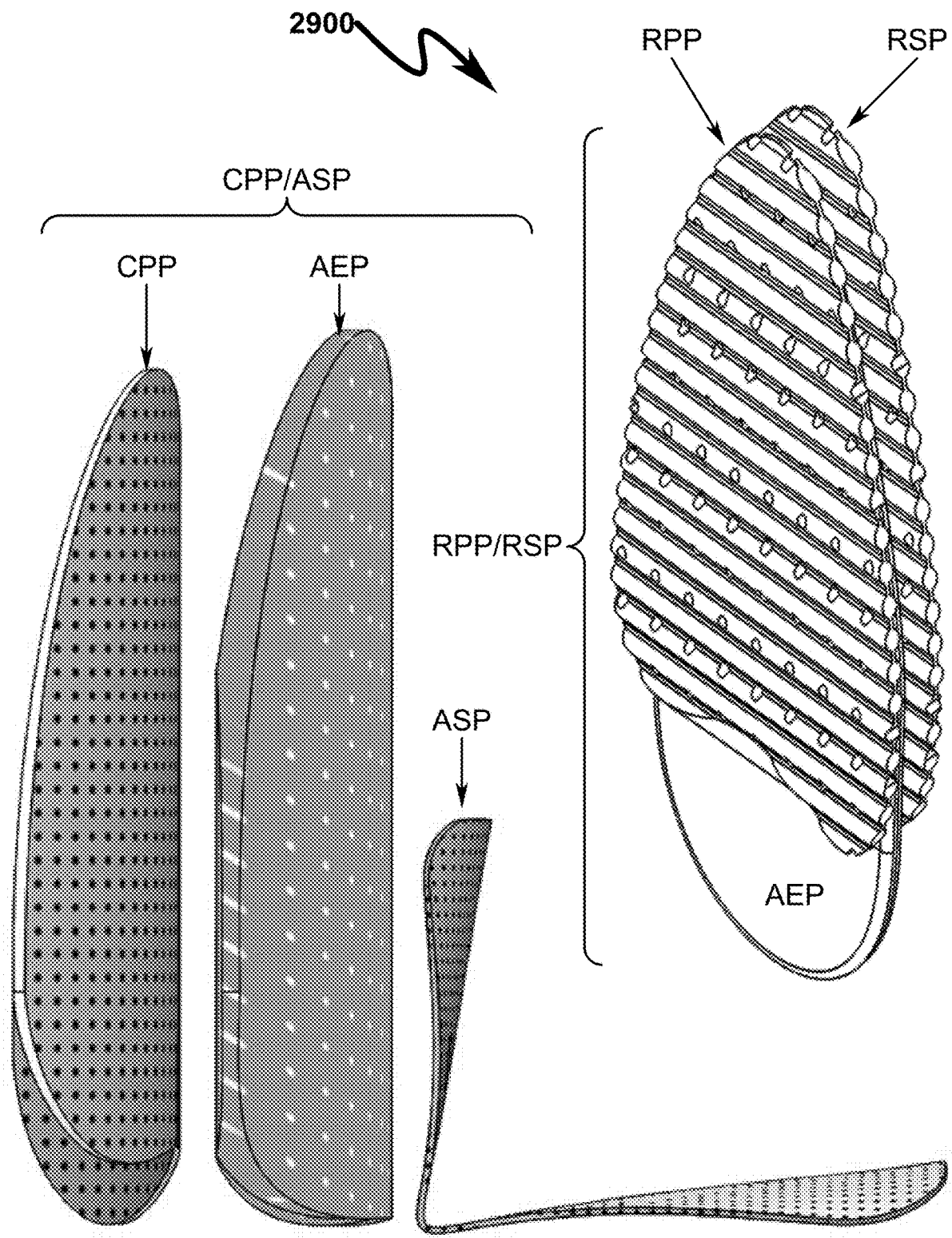
FIG. 29 illustrates an assembly step view of a preferred exemplary invention embodiment (omitting previous layers) (page 13/16)
Figure 30:
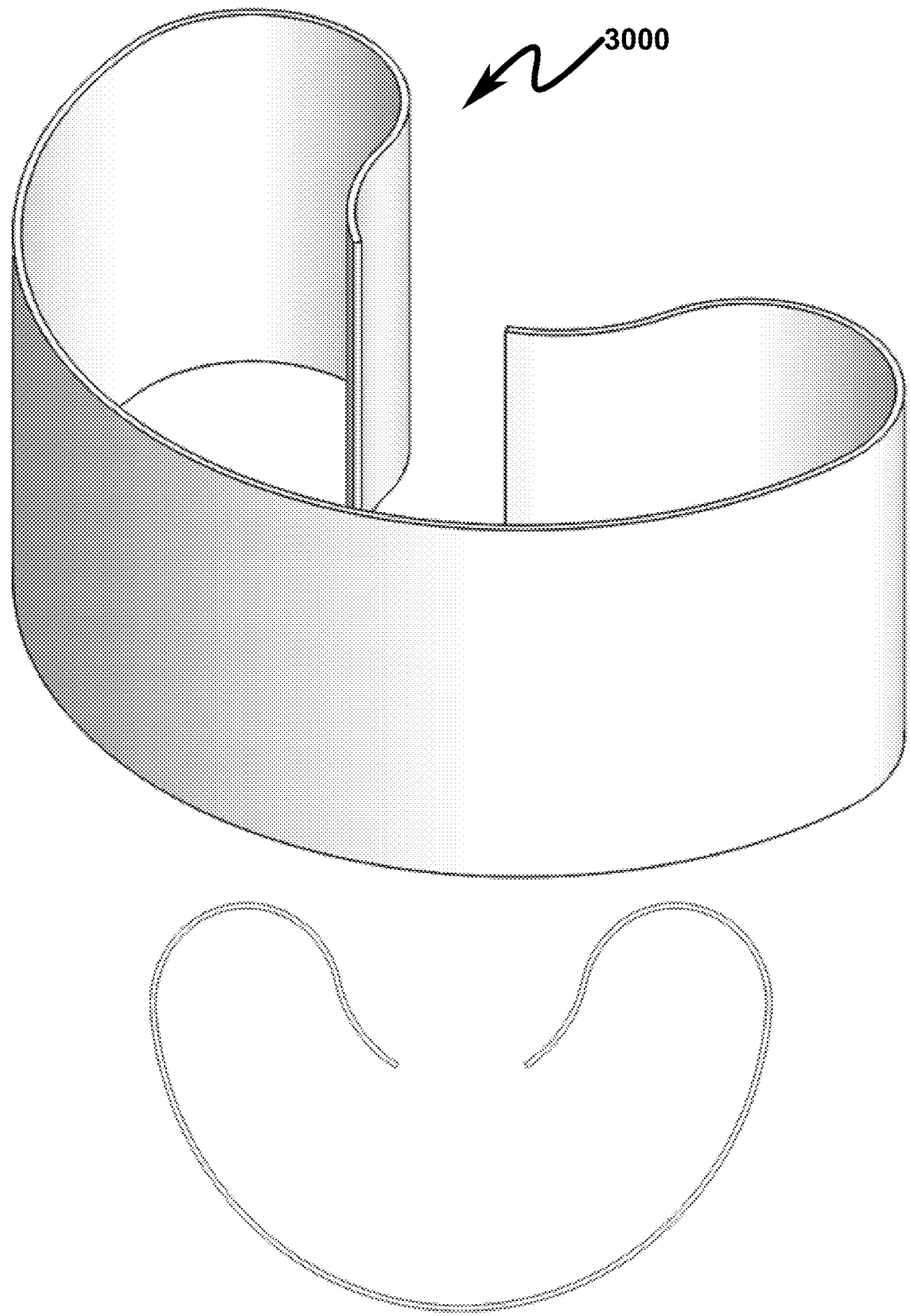
FIG. 30 illustrates an assembly step view of a preferred exemplary invention embodiment (omitting previous layers) (page 14/16)
Figure 31:
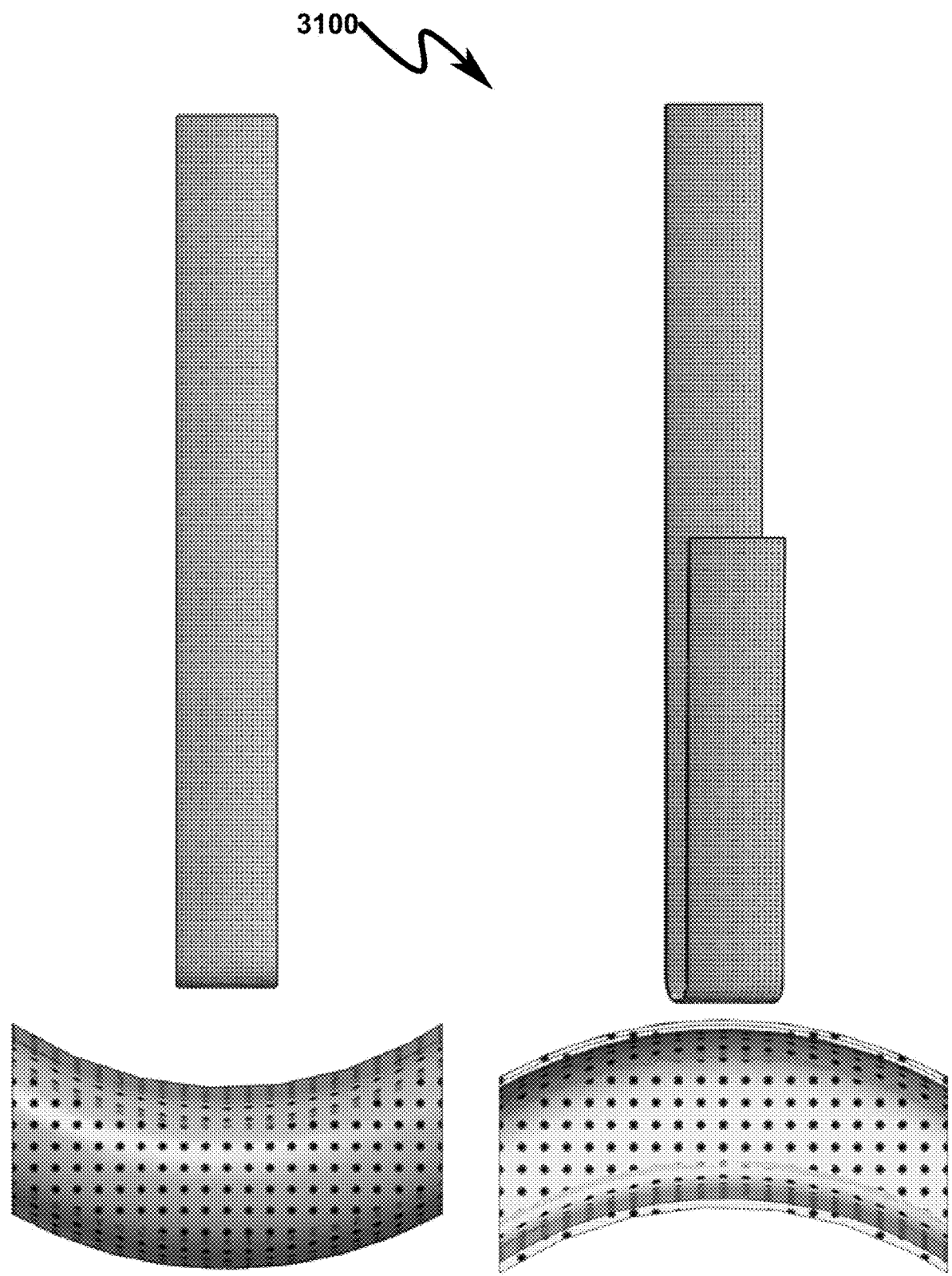
FIG. 31 illustrates an assembly step view of a preferred exemplary invention embodiment (omitting previous layers) (page 15/16)
Figure 32:
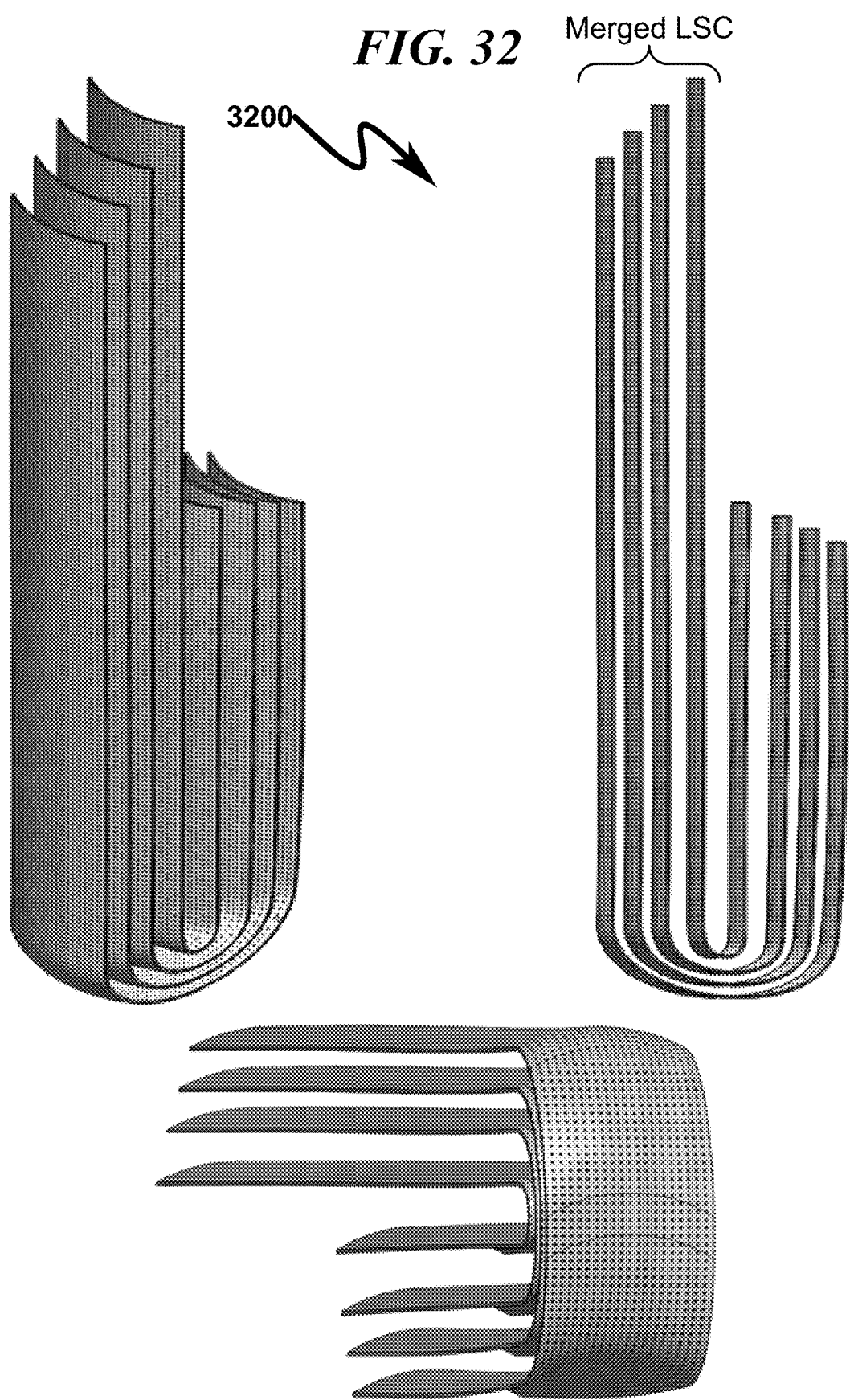
FIG. 32 illustrates an assembly step view of a preferred exemplary invention embodiment (omitting previous layers) (page 16/16)

The methodology of constructing this structure in conjunction with the AEP is described in the method steps generally depicted in FIG. 10 (1000)-FIG. 12 (1200) and the drawings to which they refer and are described below. Assembly details depicting the various components of the CPP/ASP configuration are depicted in FIG. 17 (1700)-FIG. 32 (3200). Note that the layering of elements is specifically depicted in FIG. 17 (1700)-FIG. 23 (2300), whereas the layering of elements on top of existing layers implied by the individual elements depicted in FIG. 25 (2500)-FIG. 32 (3200) for clarity of disclosure. Thus, FIG. 25 (2500)-FIG. 32 (3200) only depict general strips/straps and other features as they are individually applied in sandwich form to the AHS.

CPP/AHS AHS Method Details (1000)-(1200)

Figure 10:
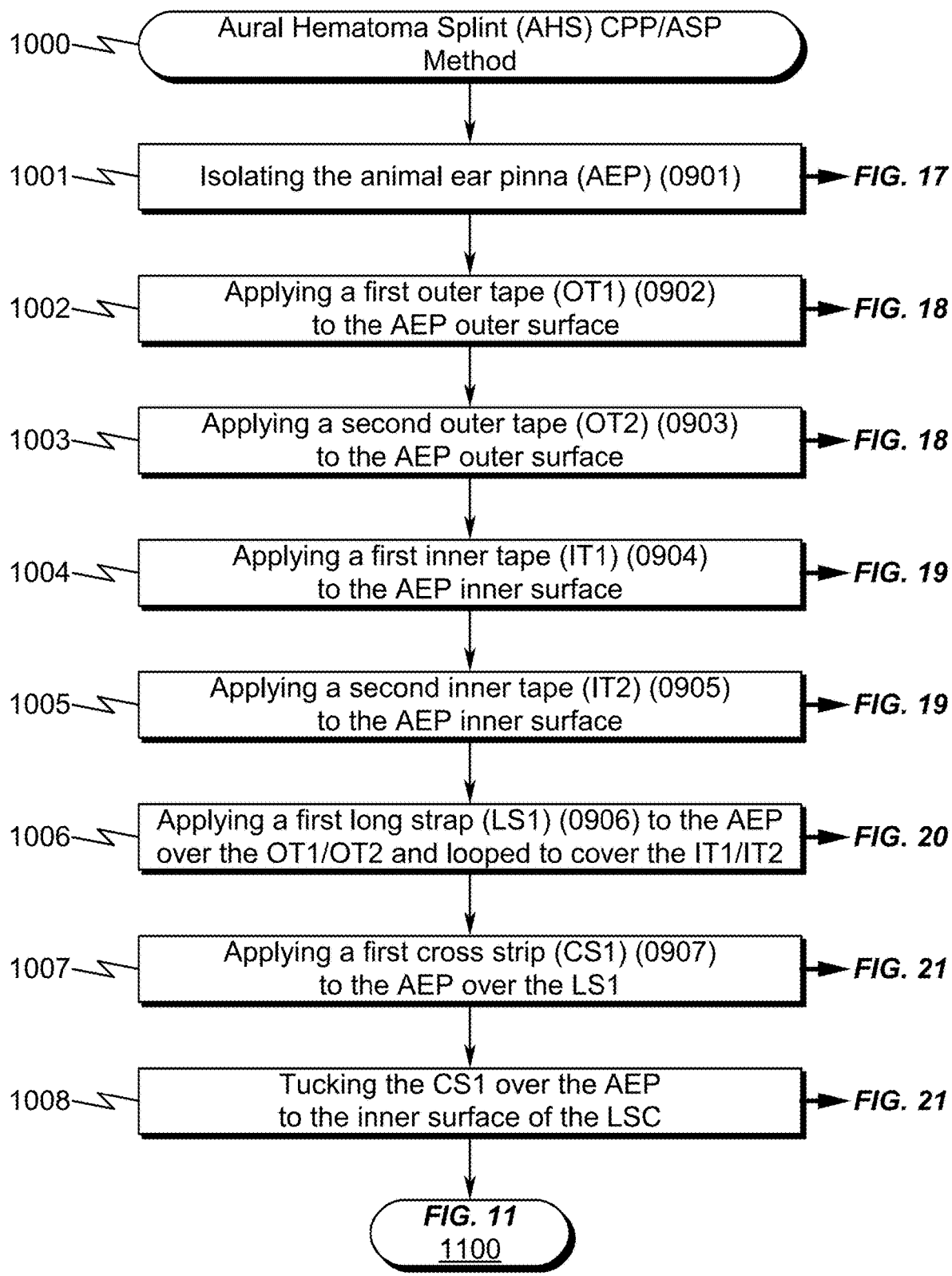
FIG. 10 illustrates an exemplary flowchart depicting a preferred CPP/ASP method embodiment of the present invention (page 1/3)
Figure 11:
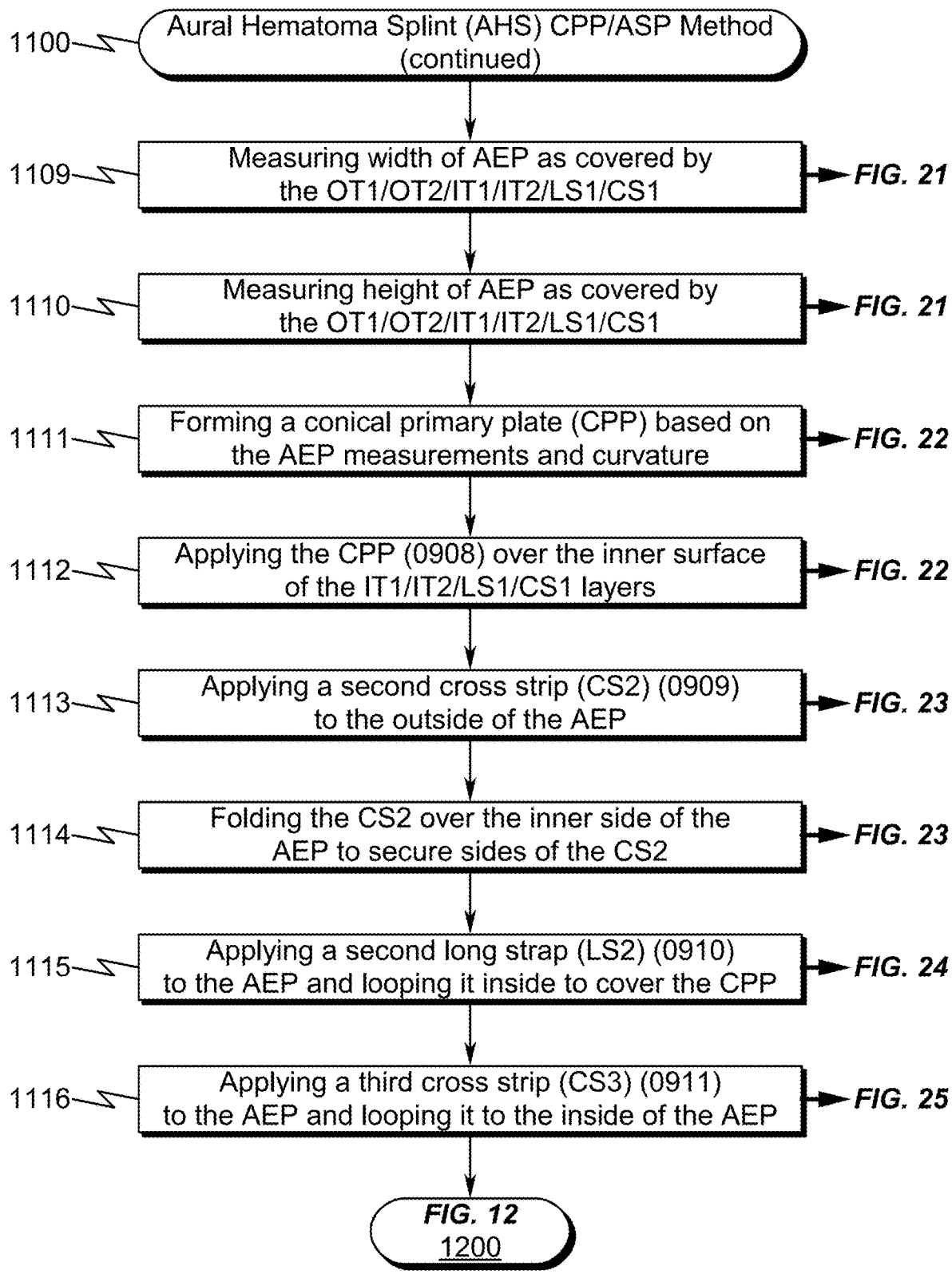
FIG. 11 illustrates an exemplary flowchart depicting a preferred CPP/ASP method embodiment of the present invention (page 2/3)
Figure 12:
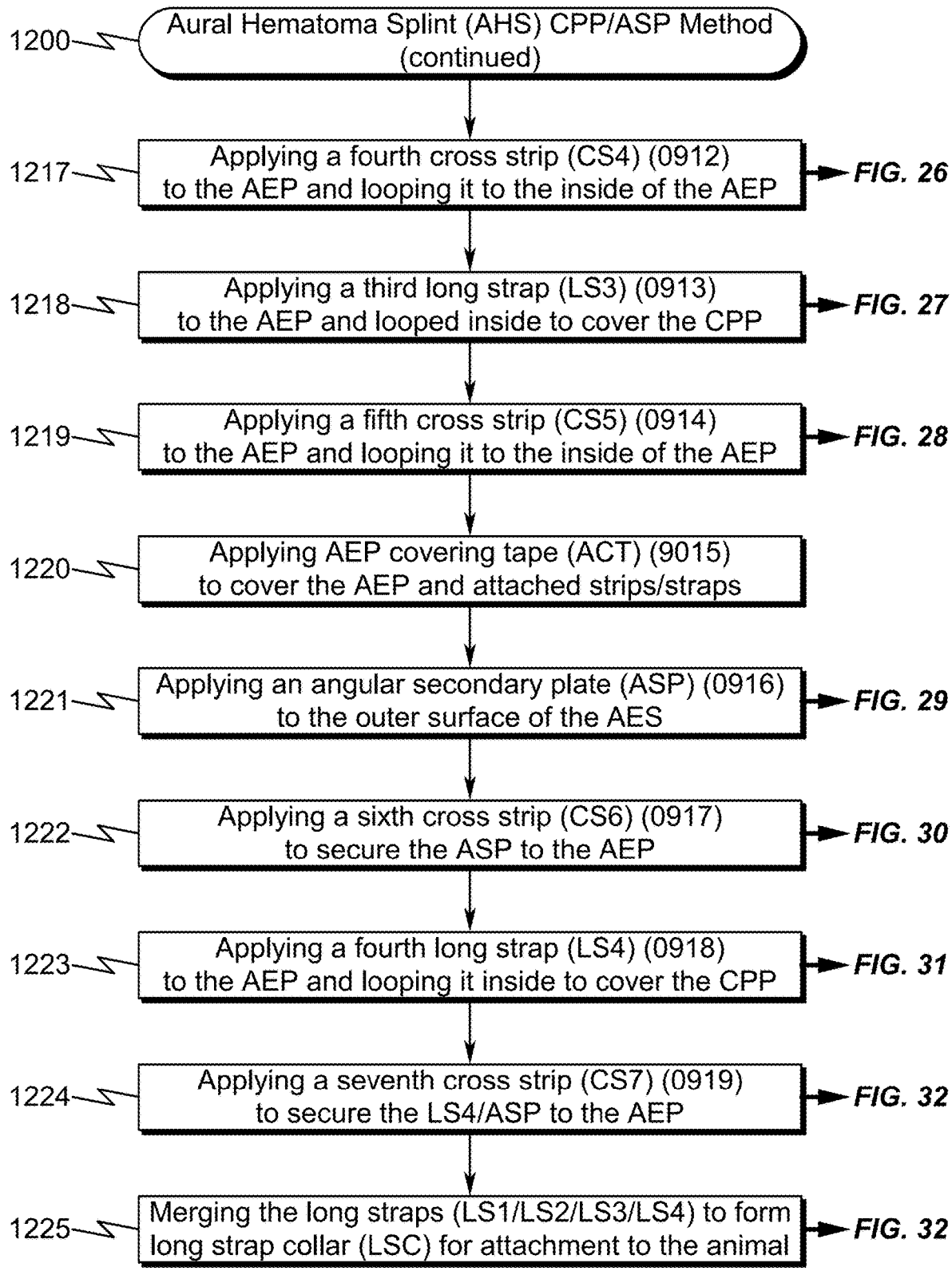
FIG. 12 illustrates an exemplary flowchart depicting a preferred CPP/ASP method embodiment of the present invention (page 3/3)

As generally depicted in the flowcharts of FIG. 10 (1000)-FIG. 12 (1200), the present invention AHS CPP/AHS method variant implements the structure detailed in FIG. 9 (0900) via the following steps:
(1) isolating the AEP (0901) for which the AHS is to be applied (1001);
(2) Applying a first outer tape (OT1) (0902) to the AEP outer surface (1002);
(3) Applying a second outer tape (OT2) (0903) to the AEP outer surface (1003);
(4) Applying a first inner tape (IT1) (0904) to the AEP inner surface (1004);
(5) Applying a second inner tape (IT2) (0905) to the AEP inner surface (1005);
(6) Applying a first long strap (LS1) (0906) to the AEP over the OT1/OT2 and looped to cover said IT1/IT2 (1006);
(7) Applying a first cross strip (CS1) (0907) to the AEP over the LS1 (1007);
(8) Tucking the CS1 over the AEP to the inner surface of the LSC (1008);
(9) Measuring width of AEP as covered by the OT1/OT2/IT1/IT2/LS1/CS1 (1109);
(10) Measuring height of AEP as covered by the OT1/OT2/IT1/IT2/LS1/CS1 (1110);
(11) Forming a conical primary plate (CPP) based on the AEP measurements and curvature (1111);
(12) Applying the CPP (0908) over the inner surface of the IT1/IT2/LS1/CS1 layers (1112);
(13) Applying a second cross strip (CS2) (0909) to the outside of the AEP (1113);
(14) Folding the CS2 over the inner side of the AEP to secure sides of the CS2 (1114);
(15) Applying a second long strap (LS2) (0910) to the AEP and looping it inside to cover the CPP (1115);
(16) Applying a third cross strip (CS3) (0911) to the AEP and looping it inside of the AEP (1116);
(17) Applying a fourth cross strip (CS4) (0912) to the AEP and looping it inside of the AEP (1217);
(18) Applying a third long strap (LS3) (0913) to the AEP and looped inside to cover the CPP (1218);
(19) Applying a fifth cross strip (CS5) (0914) to the AEP and looping it inside of the AEP (1219);
(20) Applying AEP covering tape (ACT) (0915) to cover the AEP and attached strips/straps (1220);
(21) Applying an angular secondary plate (ASP) (0916) to the outer surface of the AES (1221);
(22) Applying a sixth cross strip (CS6) (0917) to secure the ASP to the AEP (1222);
(23) Applying a fourth long strap (LS4) (0918) to the AEP and looping it inside to cover the CPP (1223);
(24) Applying a seventh cross strip (CS7) (0919) to secure the LS4/ASP to the AEP (1224); and
(25) Merging the long straps (LS1/LS2/LS3/LS4) (0920) to form a long strap collar (LSC) (1225).

This general method depicted herein may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

RPP/RSP Longitudinal Side Schematic Layer View (1300)

Figure 13:
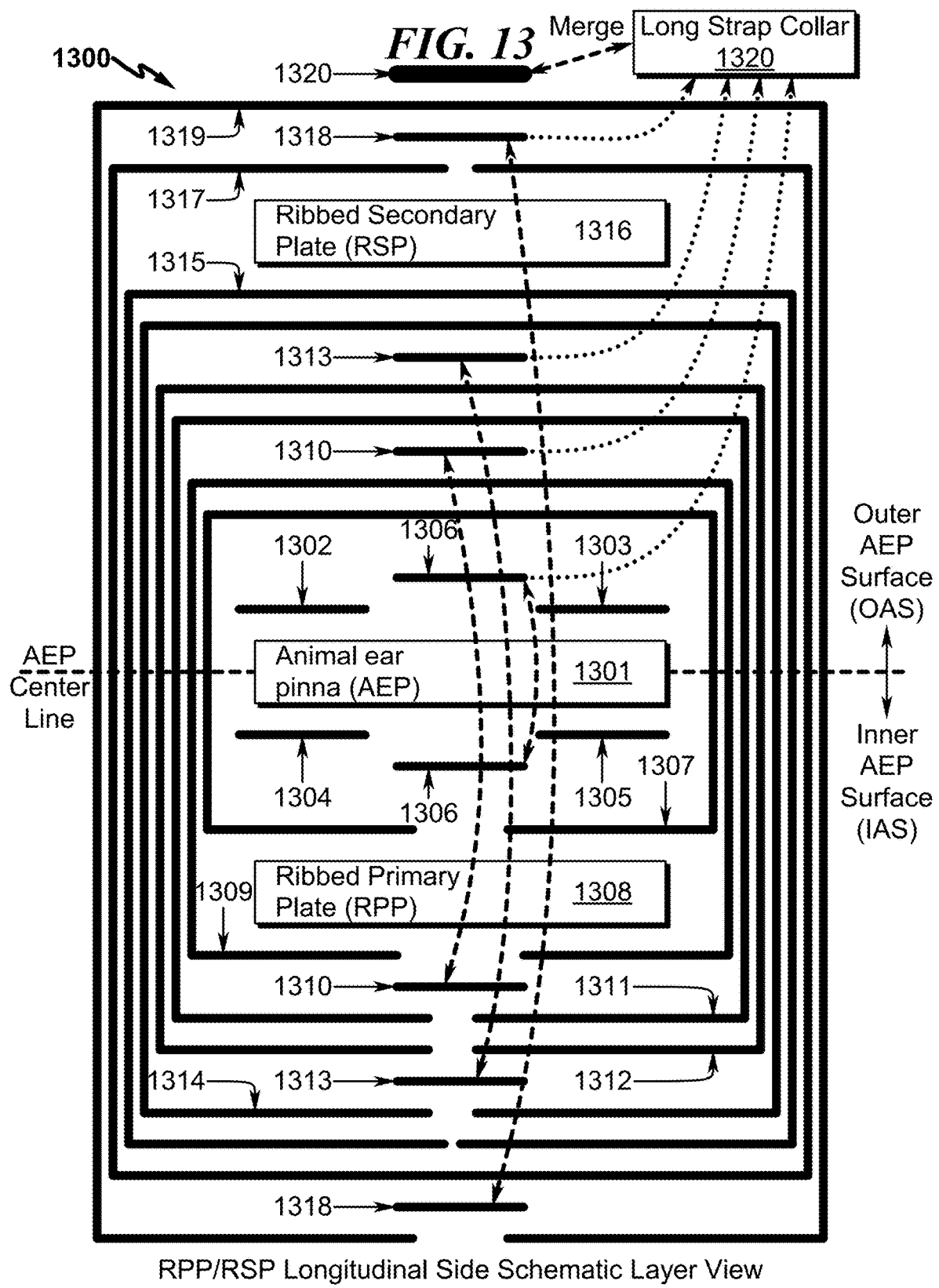
FIG. 13 illustrates an exemplary longitudinal side schematic layer view of a preferred RPP/RSP system embodiment of the present invention.

A longitudinal side schematic layer view of an AHS RPP/RSP variant preferred exemplary embodiment of the present invention is generally depicted in FIG. 13 (1300). Here it can be seen that the structure of the system may be generally described as having the following elements:

(1) AEP (denoted by having an inner AEP surface (IAS) and an outer AEP surface (OAS)) to which the invention is applied is first identified and isolated (1301);
(2) first outer tape (OT1) (1302);
(3) second outer tape (OT2) (1303);
(4) first inner tape (IT1) (1304);
(5) second inner tape (IT2) (1305);
(6) first long strap (LS1) (1306);
(7) first cross strip (CS1) (1307);
(8) ribbed primary plate (RPP) (1308);
(9) second cross strip (CS2) (1309);
(10) second long strap (LS2) (1310);
(11) third cross strip (CS3) (1311);
(12) fourth cross strip (CS4) (1312);
(13) third long strap (LS3) (1313);
(14) fifth cross strip (CS5) (1314);
(15) AEP covering tape (ACT) (1315);
(16) ribbed secondary plate (RSP) (1316);
(17) sixth cross strip (CS6) (1317);
(18) fourth long strap (LS4) (1318);
(19) seventh cross strip (CS7) (1319); and
(20) MERGED LS1/LS2/LS3/LS4 to form a long strap collar (LSC) (1320).

The first outer tape (OT1) (1302), second outer tape (OT2) (1303), first inner tape (IT1) (1304), second inner tape (IT2) (1305), first long strap (LS1) (1306), and first cross strip (CS1) (1307) form an ear pinna foundation (EPF) that sandwiches the AEP to position and stabilize it for further processing.

The methodology of constructing this structure in conjunction with the AEP is described in the method steps generally depicted in FIG. 14 (1400)-FIG. 16 (1600) and the drawings to which they refer and are described below. Assembly details depicting the various components of the RPP/RSP configuration are depicted in FIG. 17 (1700)-FIG. 32 (3200). Note that the layering of elements is specifically depicted in FIG. 17 (1700)-FIG. 23 (2300), whereas the layering of elements on top of existing layers implied by the individual elements depicted in FIG. 25 (2500)-FIG. 32 (3200) for clarity of disclosure. Thus, FIG. 25 (2500)-FIG. 32 (3200) only depict general strips/straps and other features as they are individually applied in sandwich form to the AHS.

RPP/AHS AHS Method Details (1400)-(1600)

Figure 14:
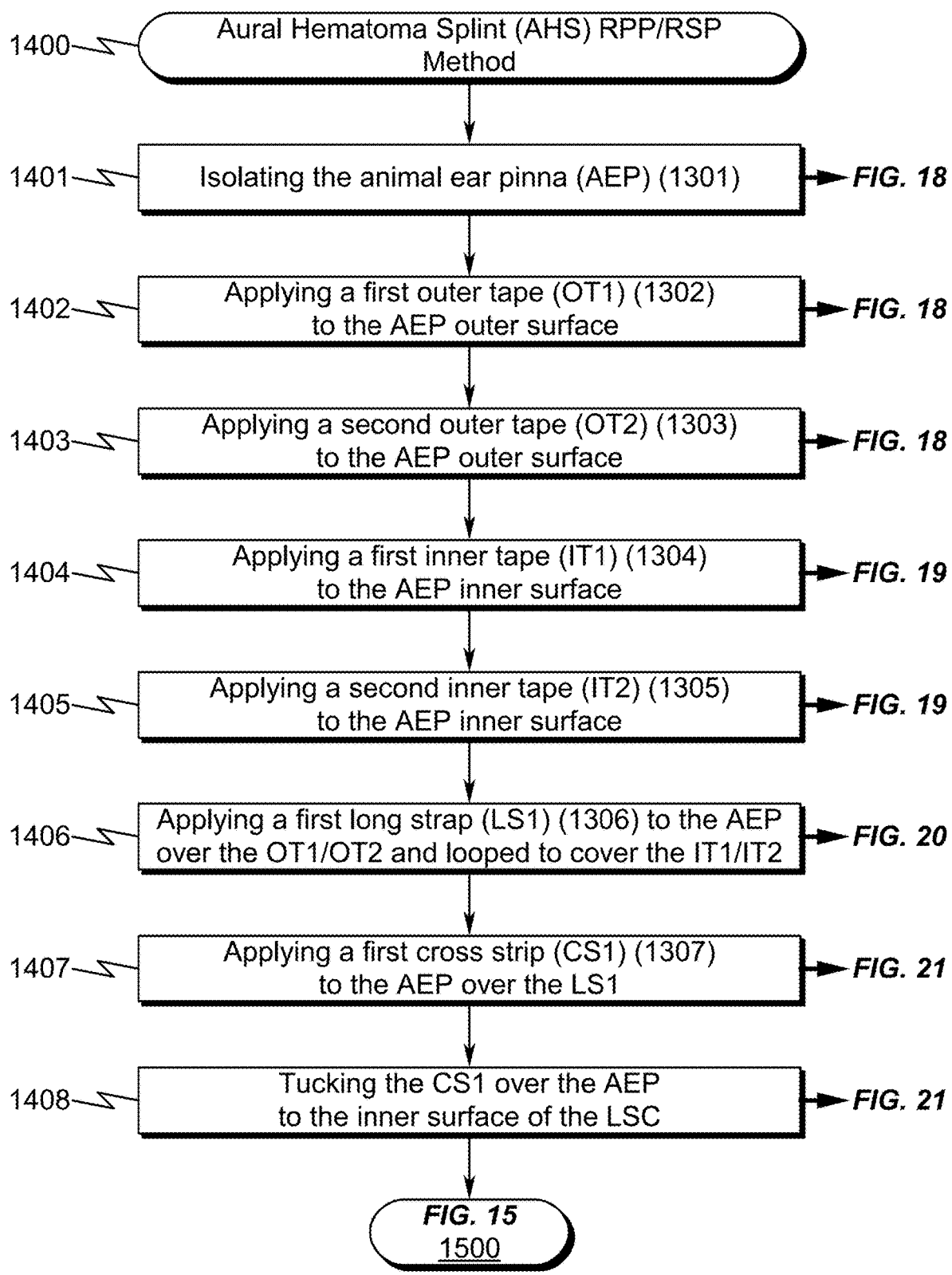
FIG. 14 illustrates an exemplary flowchart depicting a preferred RPP/RSP method embodiment of the present invention (page 1/3)
Figure 15:
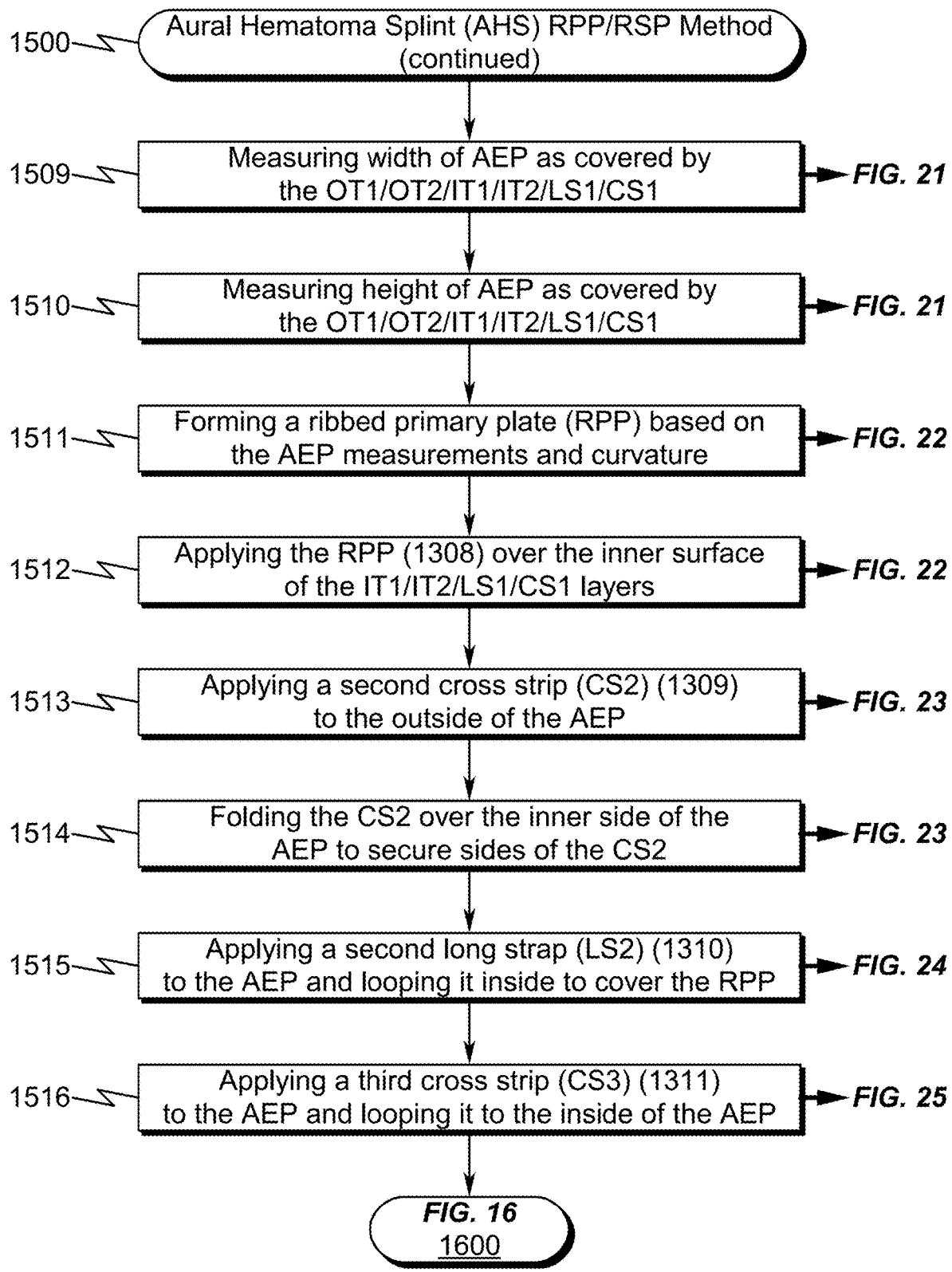
FIG. 15 illustrates an exemplary flowchart depicting a preferred RPP/RSP method embodiment of the present invention (page 2/3)
Figure 16:
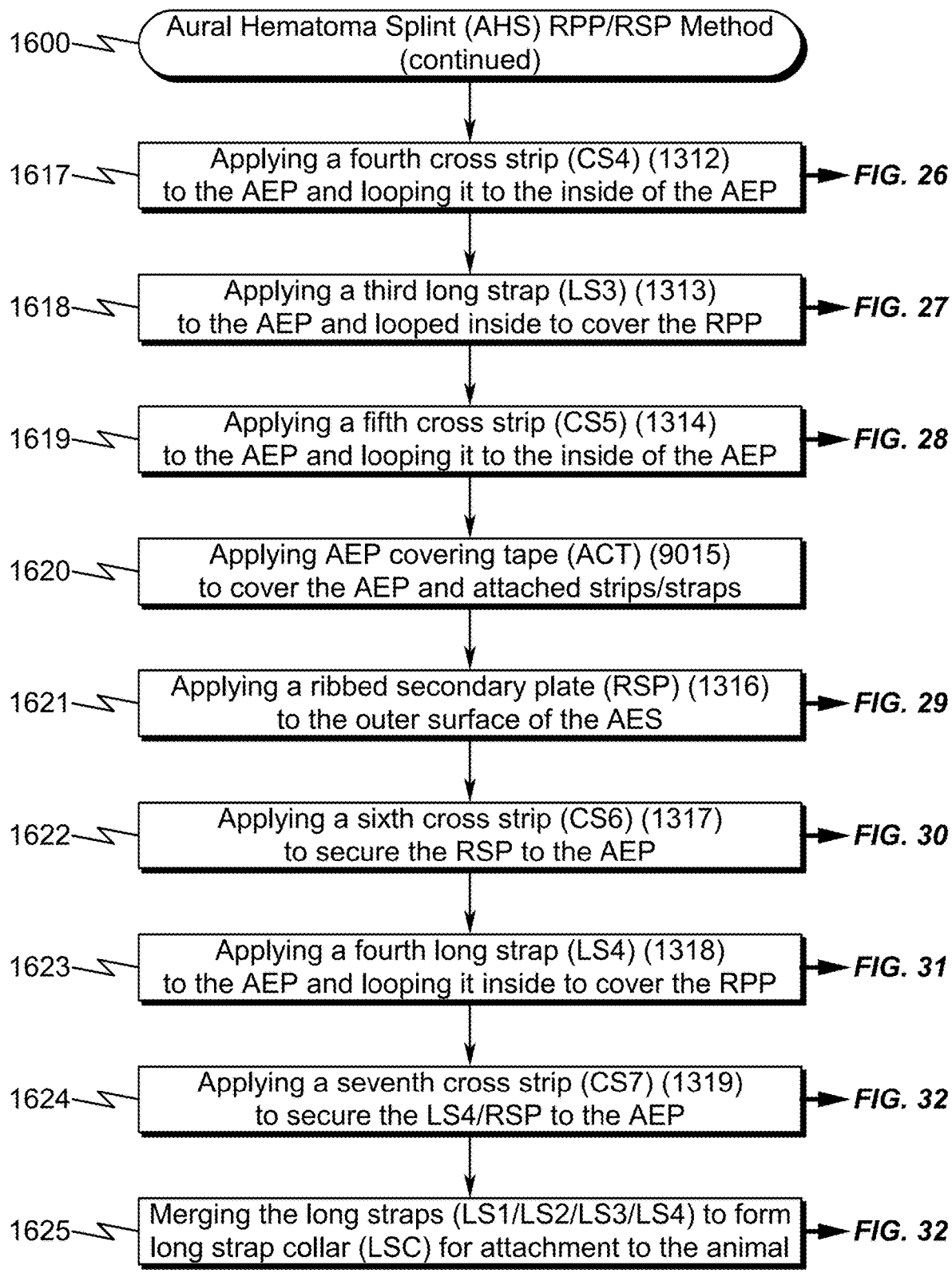
FIG. 16 illustrates an exemplary flowchart depicting a preferred CPP/ASP method embodiment of the present invention (page 3/3)

As generally depicted in the flowcharts of FIG. 14 (1400)-FIG. 16 (1600), the present invention AHS RPP/AHS method variant implements the structure detailed in FIG. 13 (1300) via the following steps:

(1) isolating the AEP (1301) for which the AHS is to be applied (1401);
(2) applying a first outer tape (OT1) (1302) to the AEP outer surface (1402);
(3) applying a second outer tape (OT2) (1303) to the AEP outer surface (1403);
(4) applying a first inner tape (IT1) (1304) to the AEP inner surface (1404);
(5) applying a second inner tape (IT2) (1305) to the AEP inner surface (1405);
(6) applying a first long strap (LS1) (1306) to the AEP over the OT1/OT2 and looped to cover said IT1/IT2 (1406);
(7) applying a first cross strip (CS1) (1307) to the AEP over the LS1 (1407);
(8) tucking the CS1 over the AEP to the inner surface of the LSC (1408);
(9) measuring width of AEP as covered by the OT1/OT2/IT1/IT2/LS1/CS1 (1509);
(10) measuring height of AEP as covered by the OT1/OT2/IT1/IT2/LS1/CS1 (1510);
(11) forming a ribbed primary plate (RPP) based on the AEP measurements and curvature (1511);
(12) applying the RPP (1308) over the inner surface of the IT1/IT2/LS1/CS1 layers (1512);
(13) applying a second cross strip (CS2) (1309) to the outside of the AEP (1513);
(14) folding the CS2 over the inner side of the AEP to secure sides of the CS2 (1514);
(15) applying a second long strap (LS2) (1310) to the AEP and looping it inside to cover the RPP (1515);
(16) applying a third cross strip (CS3) (1311) to the AEP and looping it inside of the AEP (1516);
(17) applying a fourth cross strip (CS4) (1312) to the AEP and looping it inside of the AEP (1617);
(18) applying a third long strap (LS3) (1313) to the AEP and looped inside to cover the RPP (1618);
(19) applying a fifth cross strip (CS5) (1314) to the AEP and looping it inside of the AEP (1619);
(20) applying AEP covering tape (ACT) (1315) to cover the AEP and attached strips/straps (1620);
(21) applying a ribbed secondary plate (RSP) (1316) to the outer surface of the AES (1621);
(22) applying a sixth cross strip (CS6) (1317) to secure the RSP to the AEP (1622);
(23) applying a fourth long strap (LS4) (1318) to the AEP and looping it inside to cover the RPP (1623);
(24) applying a seventh cross strip (CS7) (1319) to secure the LS4/RSP to the AEP (1624); and
(25) merging the long straps (LS1/LS2/LS3/LS4) (1320) to form a long strap collar (LSC) (1625).

This general method depicted herein may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

Conical Primary Plate (CPP) Detail (3300)-(6400)

Figure 33:
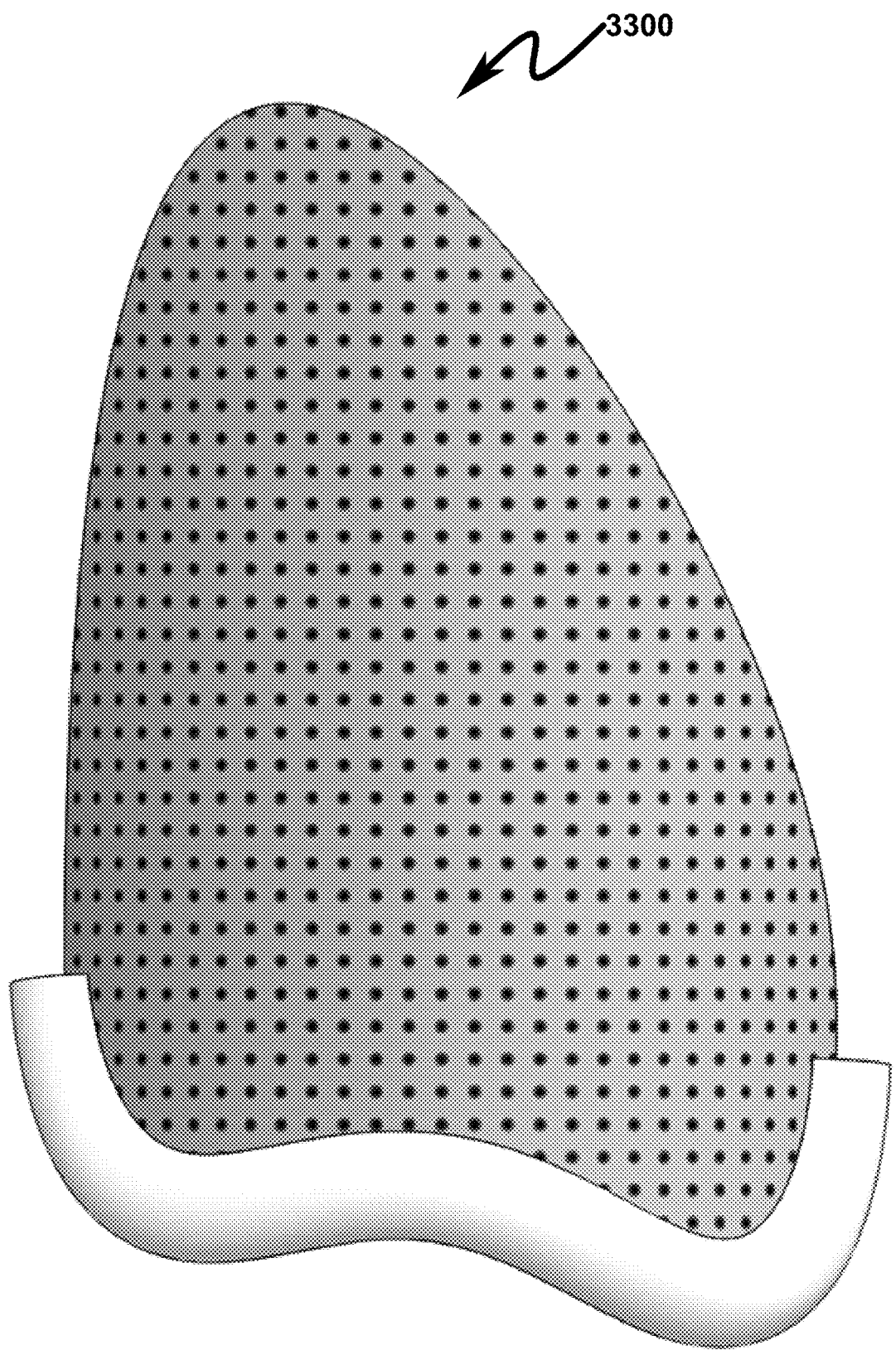
FIG. 33 illustrates a front view of a preferred exemplary embodiment of a conical primary plate (CPP) incorporating uniform curvatures useful in some preferred invention embodiments.
Figure 34:
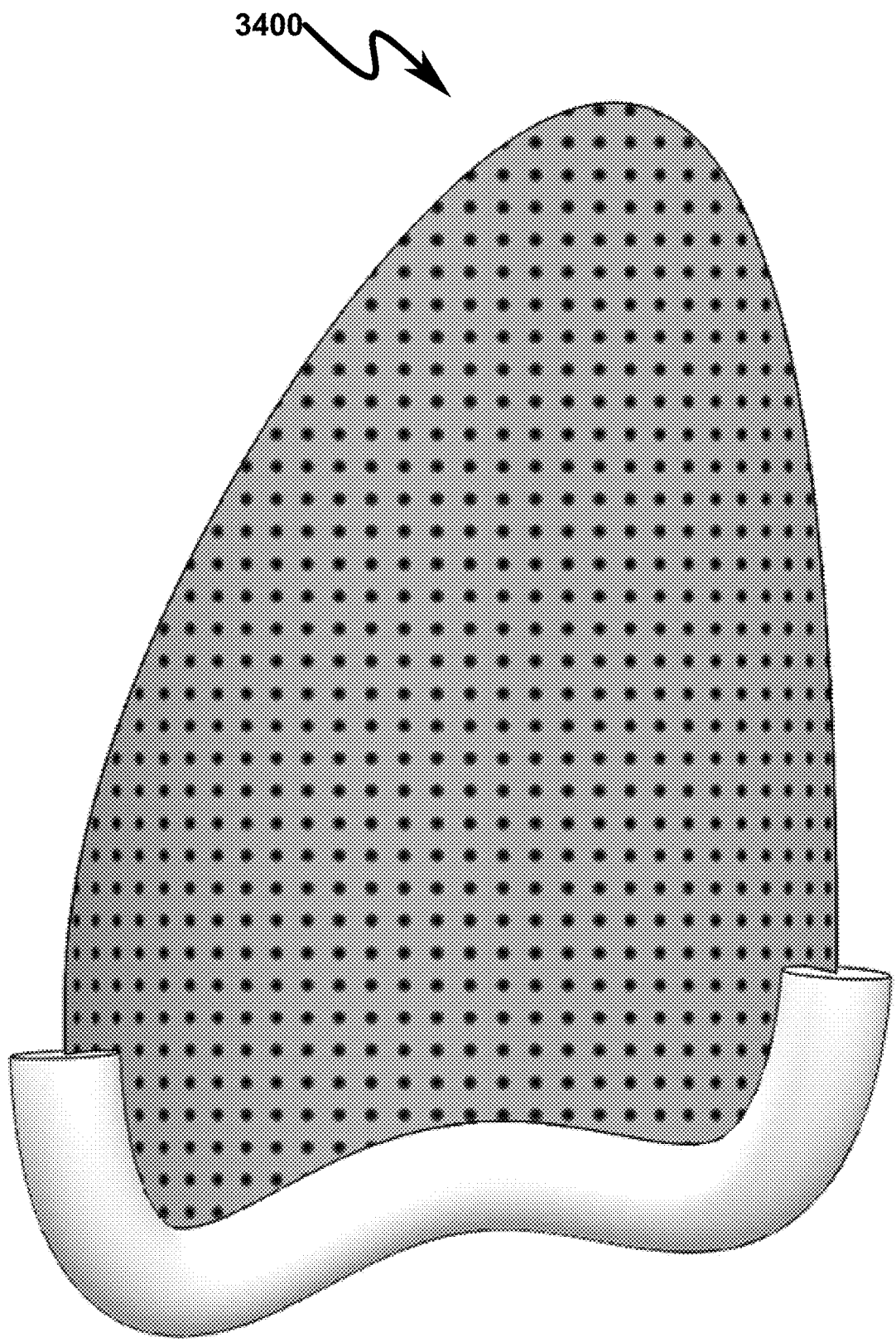
FIG. 34 illustrates a rear view of a preferred exemplary embodiment of a conical primary plate (CPP) incorporating uniform curvatures useful in some preferred invention embodiments.
Figure 35:
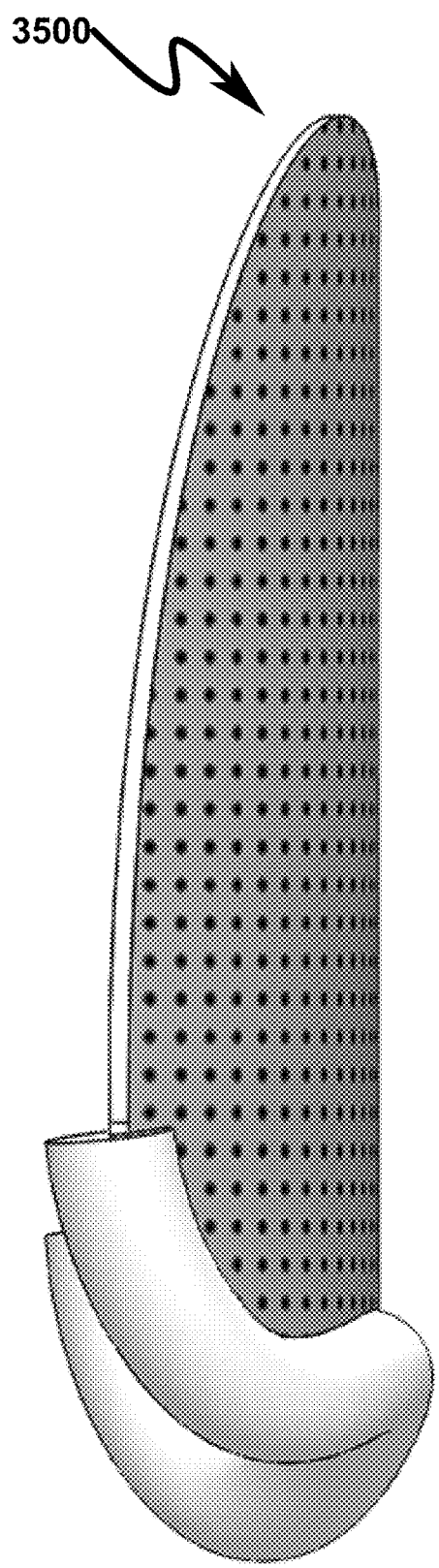
FIG. 35 illustrates a left side view of a preferred exemplary embodiment of a conical primary plate (CPP) incorporating uniform curvatures useful in some preferred invention embodiments.
Figure 36:
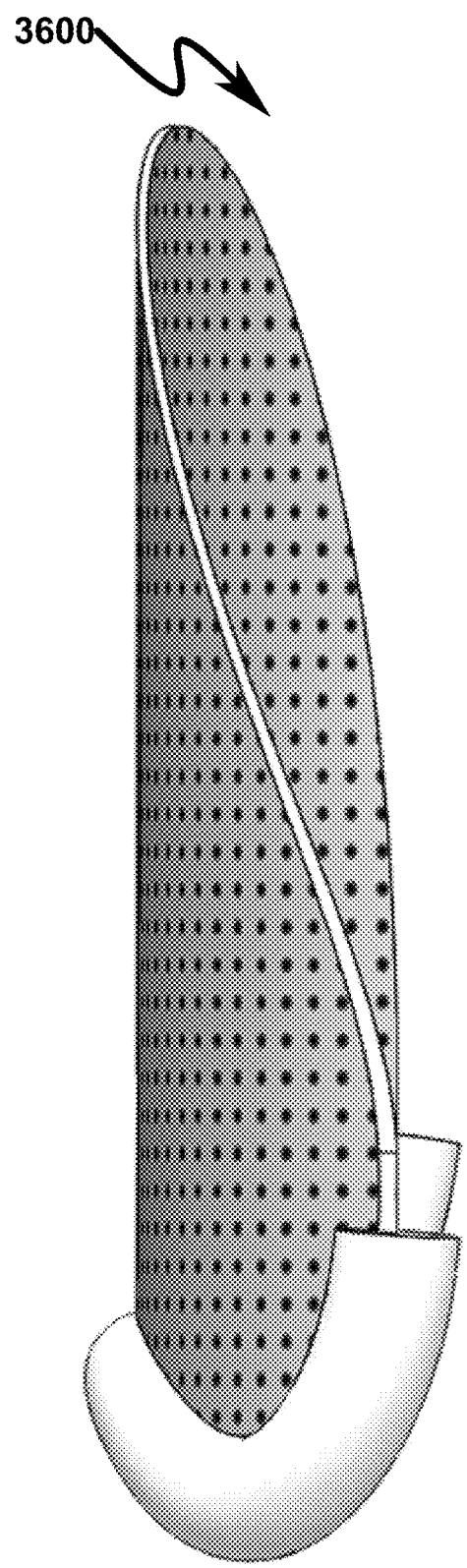
FIG. 36 illustrates a right side view of a preferred exemplary embodiment of a conical primary plate (CPP) incorporating uniform curvatures useful in some preferred invention embodiments.
Figure 48:
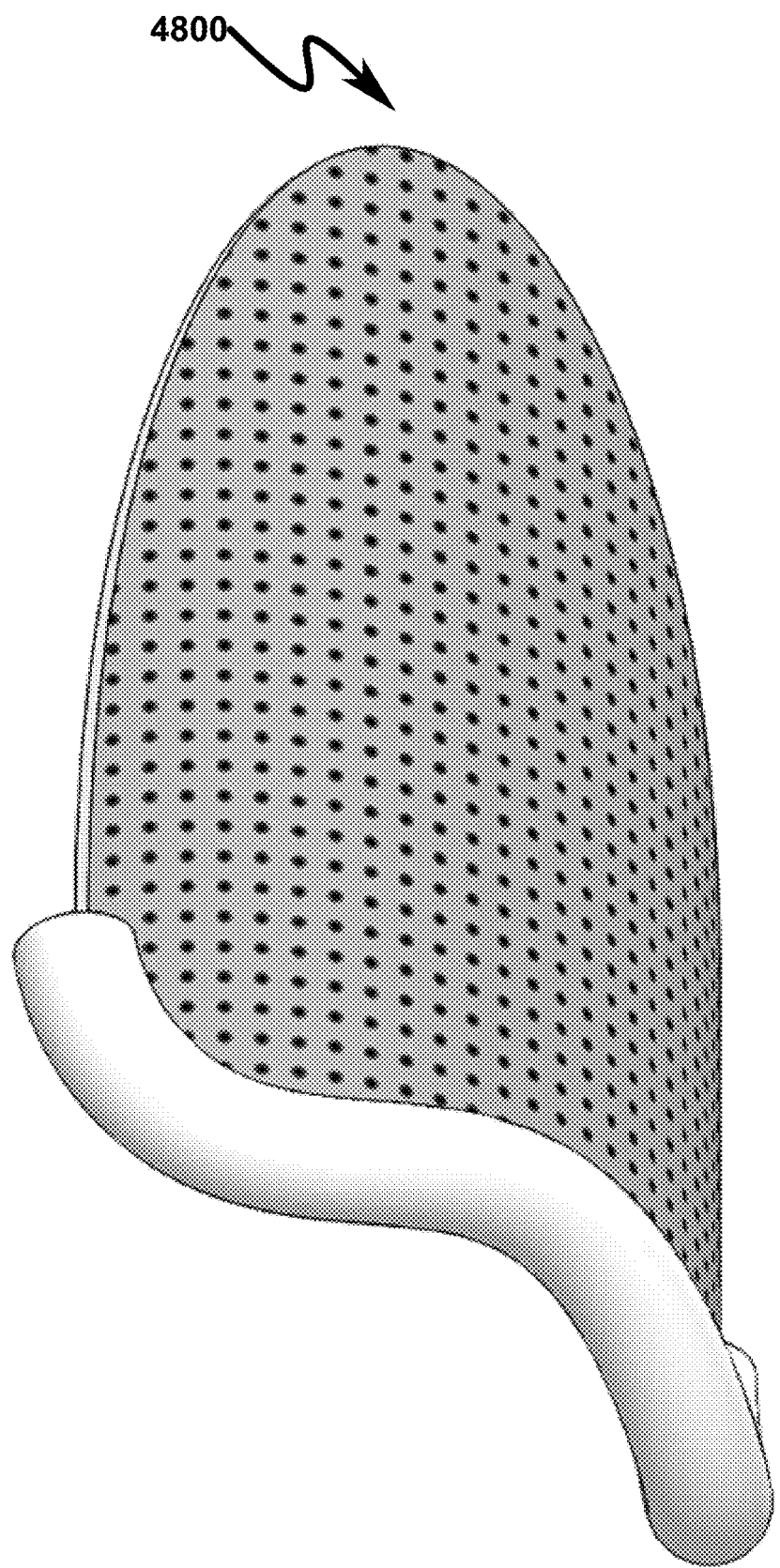
FIG. 48 illustrates a front bottom left perspective view of a preferred exemplary embodiment of a conical primary plate (CPP) incorporating uniform curvatures useful in some preferred invention embodiments.
Figure 49:
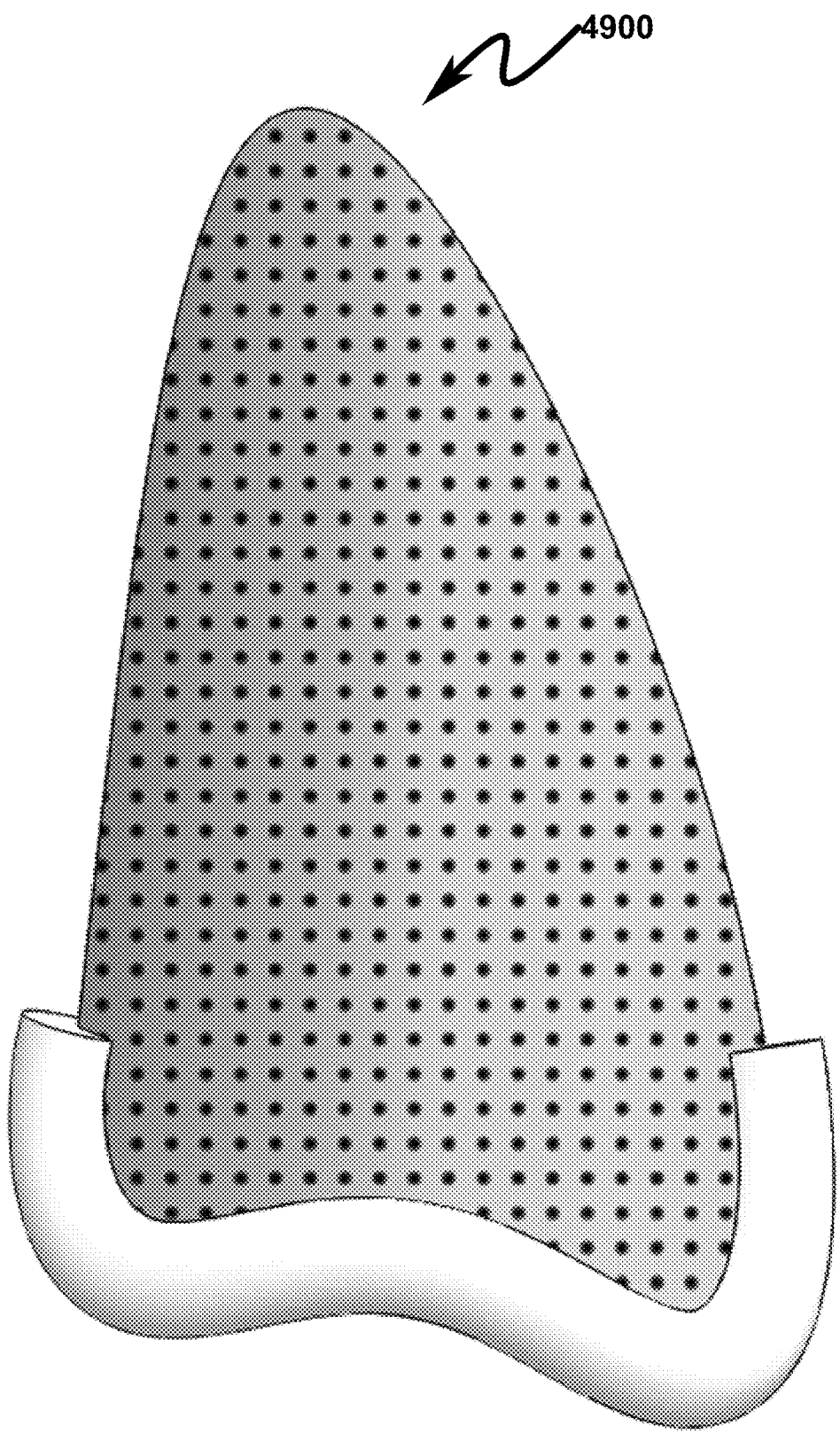
FIG. 49 illustrates a front view of a preferred exemplary embodiment of a conical primary plate (CPP) incorporating varying curvatures useful in some preferred invention embodiments.
Figure 50:
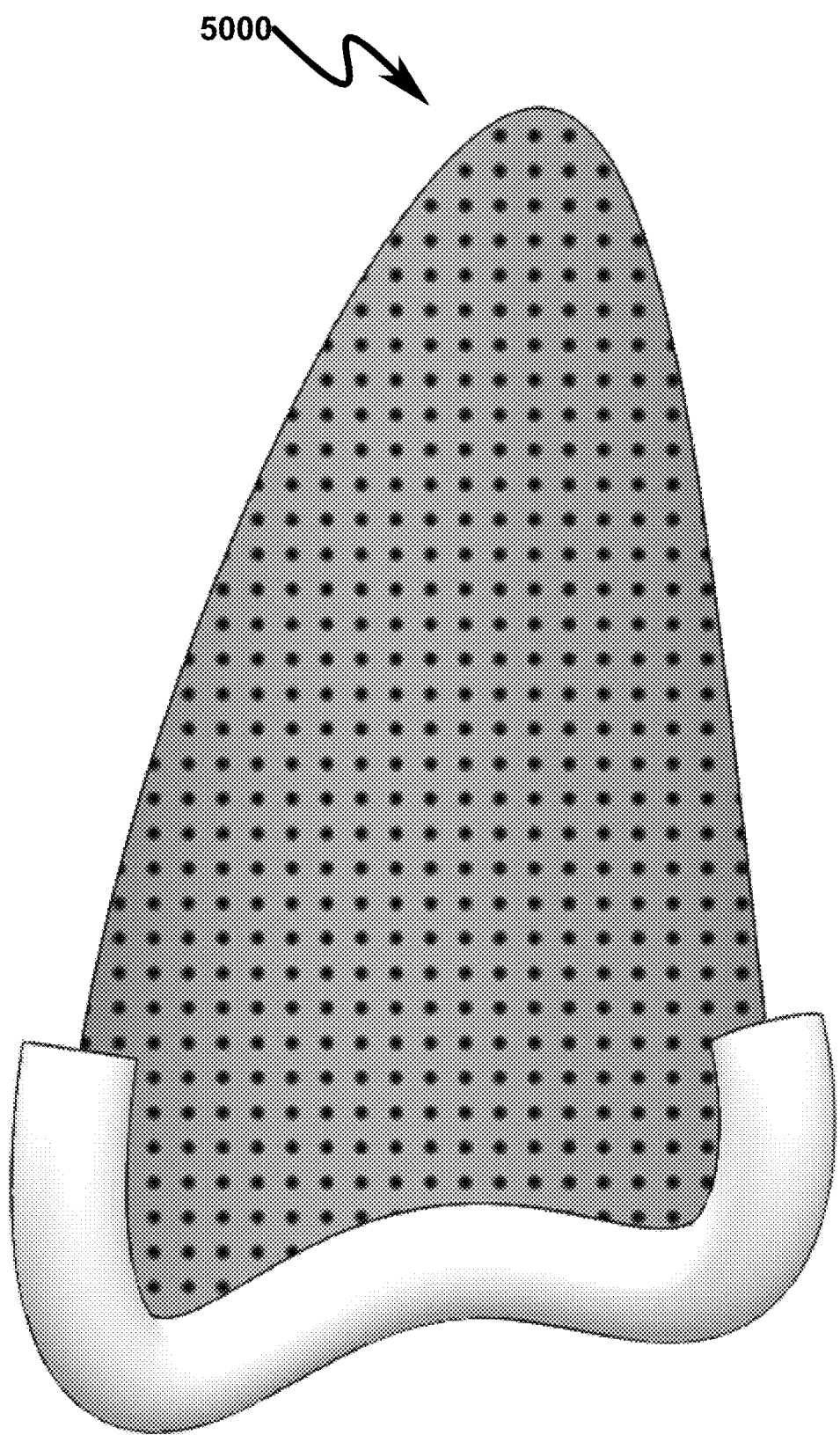
FIG. 50 illustrates a rear view of a preferred exemplary embodiment of a conical primary plate (CPP) incorporating varying curvatures useful in some preferred invention embodiments.
Figure 51:
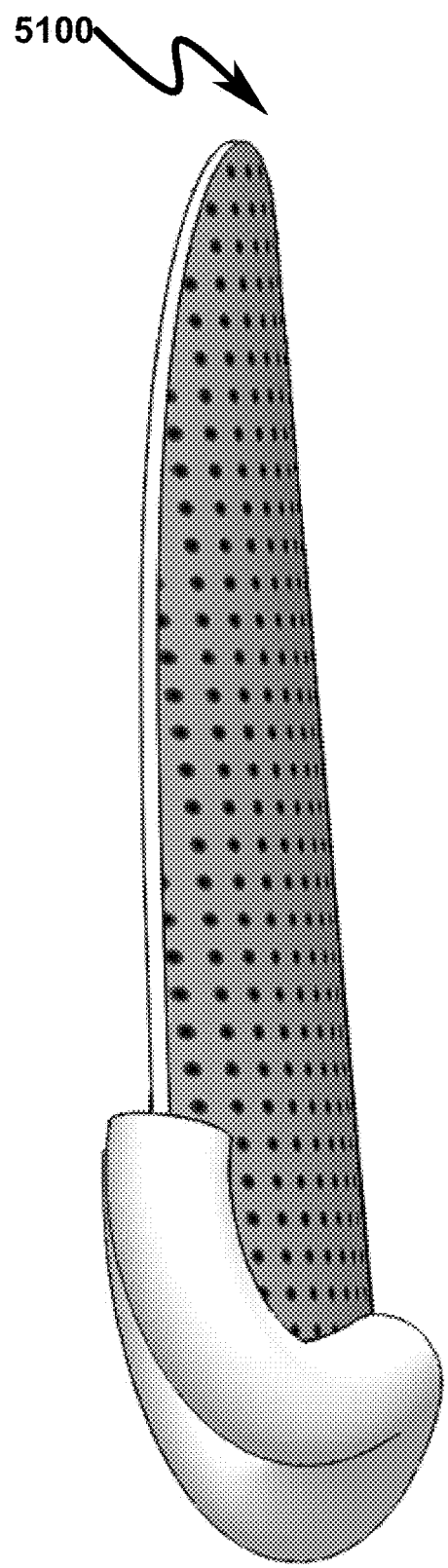
FIG. 51 illustrates a left side view of a preferred exemplary embodiment of a conical primary plate (CPP) incorporating varying curvatures useful in some preferred invention embodiments.
Figure 52:
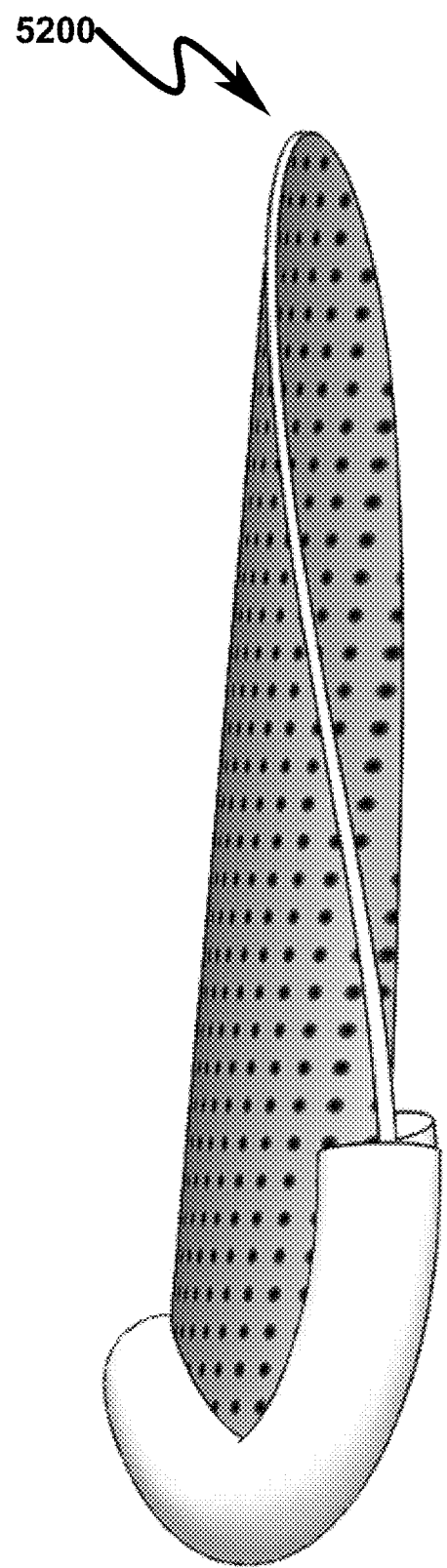
FIG. 52 illustrates a right side view of a preferred exemplary embodiment of a conical primary plate (CPP) incorporating varying curvatures useful in some preferred invention embodiments.
Figure 64:
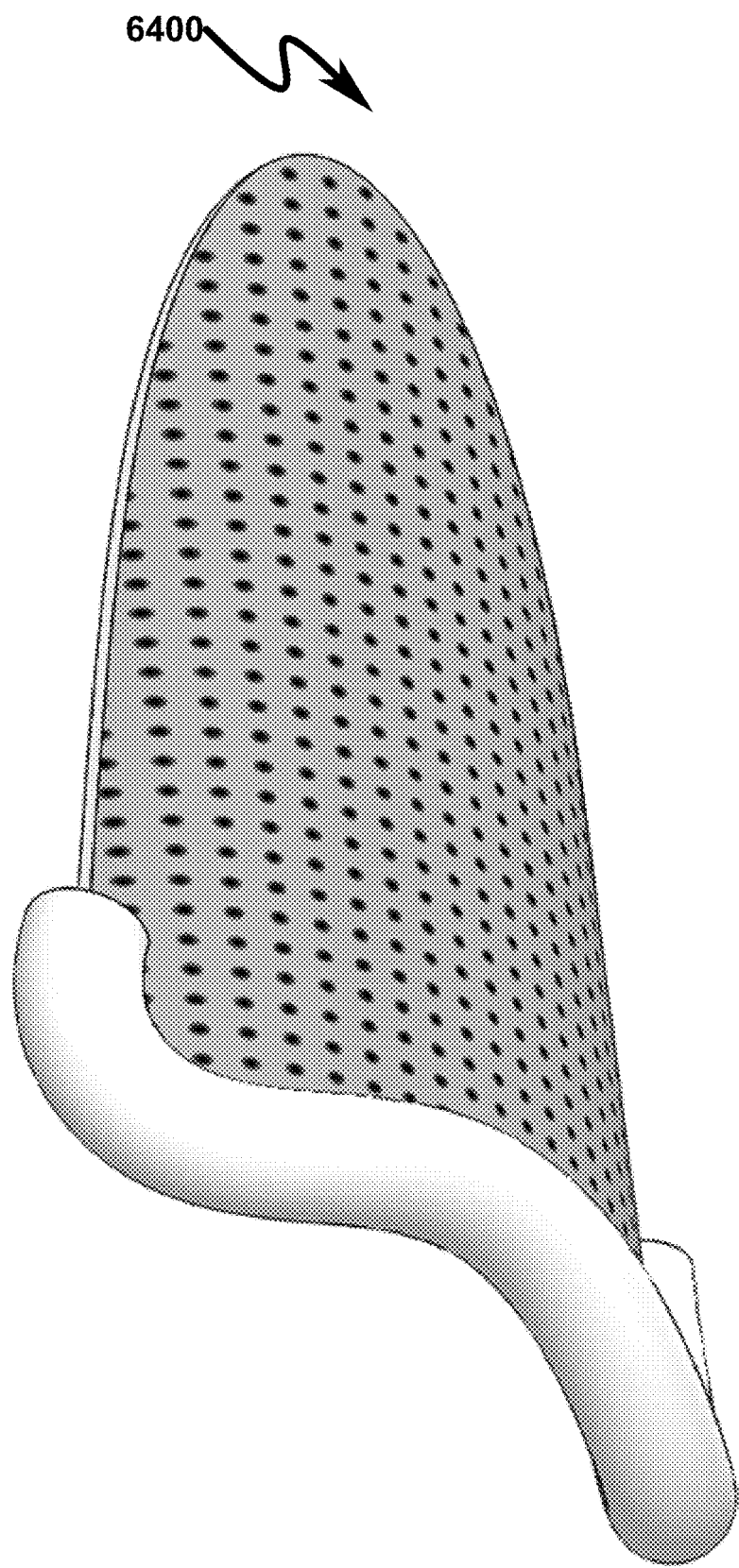
FIG. 64 illustrates a front bottom left perspective view of a preferred exemplary embodiment of a conical primary plate (CPP) incorporating varying curvatures useful in some preferred invention embodiments.

FIG. 33 (3300)-FIG. 48 (4800) and FIG. 49 (4900)-FIG. 64 (6400) depict various views of two preferred embodiments of the conical primary plate (CPP). FIG. 33 (3300)-FIG. 48 (4800) depict an embodiment of the CPP in which the curvature of the CPP is uniform over its entire length. FIG. 49 (4900)-FIG. 64 (6400) depict an embodiment of the CPP in which the curvature of the CPP varies over its length and in which the CPP is formed as a lofted curve having non-uniform curvature that may more closely conform to the animal ear pinna (AEP).

Figure 37:
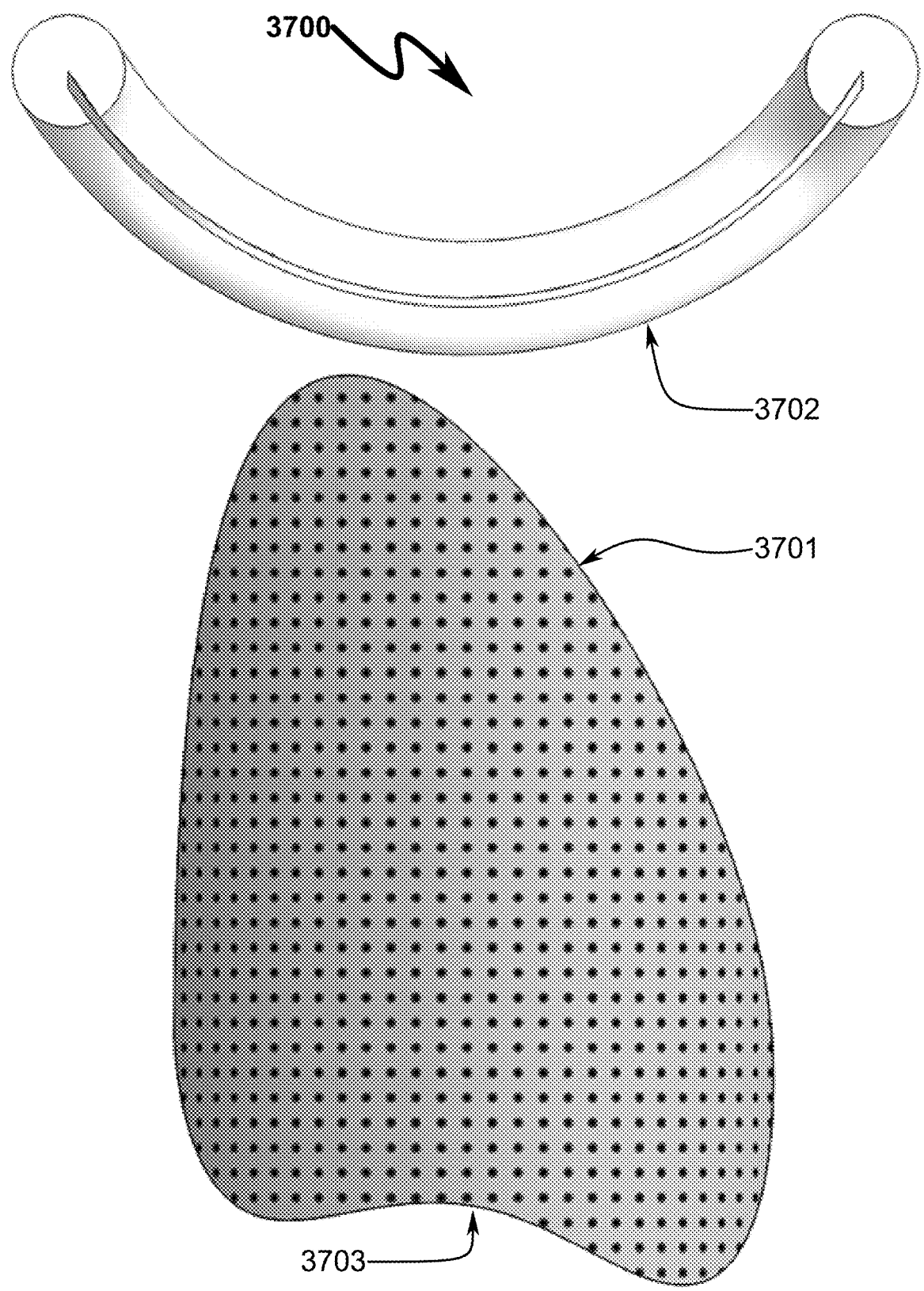
FIG. 37 illustrates a top view of a preferred exemplary embodiment of a conical primary plate (CPP) incorporating uniform curvatures useful in some preferred invention embodiments and depicts a foam padding strip (FPS) and CPP lower perimeter comprising a curved raised portion (CRP) in isolation.
Figure 38:
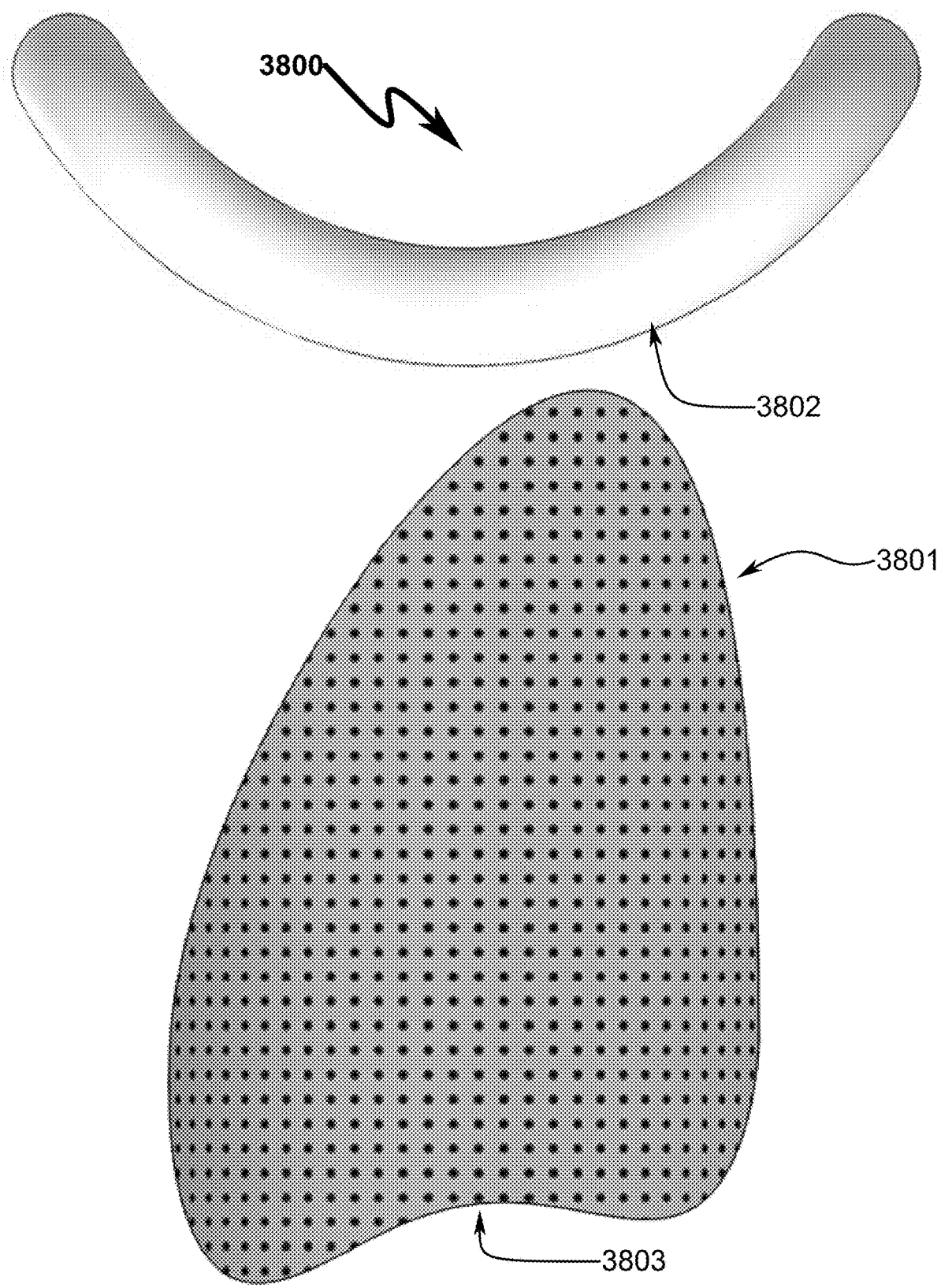
FIG. 38 illustrates a bottom view of a preferred exemplary embodiment of a conical primary plate (CPP) incorporating uniform curvatures useful in some preferred invention embodiments and depicts a foam padding strip (FPS) and CPP lower perimeter comprising a curved raised portion (CRP) in isolation.
Figure 39:
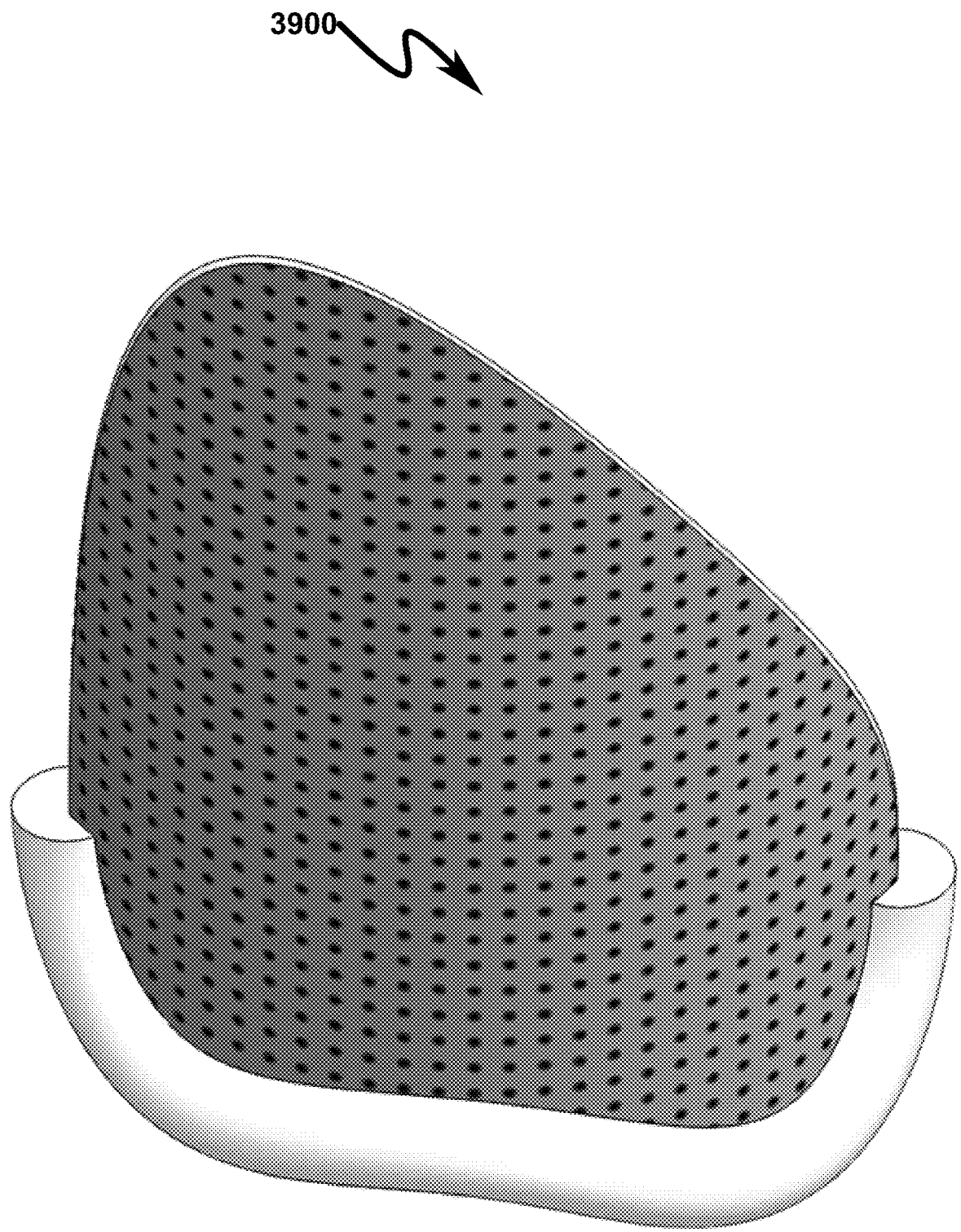
FIG. 39 illustrates a top front diagonal view of a preferred exemplary embodiment of a conical primary plate (CPP) incorporating uniform curvatures useful in some preferred invention embodiments.
Figure 40:
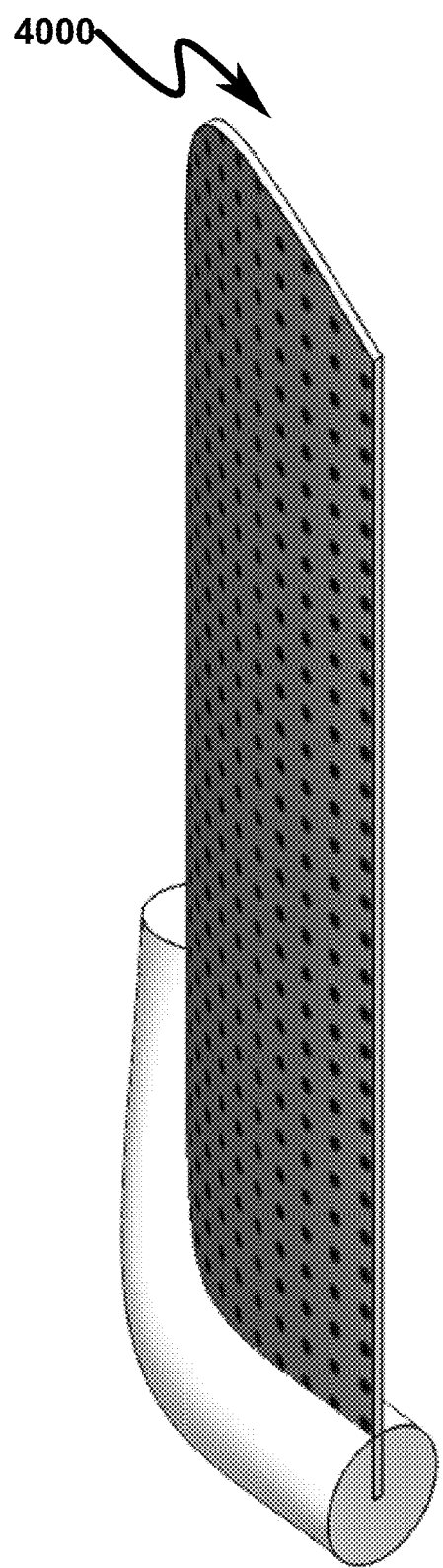
FIG. 40 illustrates a front top right perspective section view of a preferred exemplary embodiment of a conical primary plate (CPP) incorporating uniform curvatures useful in some preferred invention embodiments.
Figure 41:
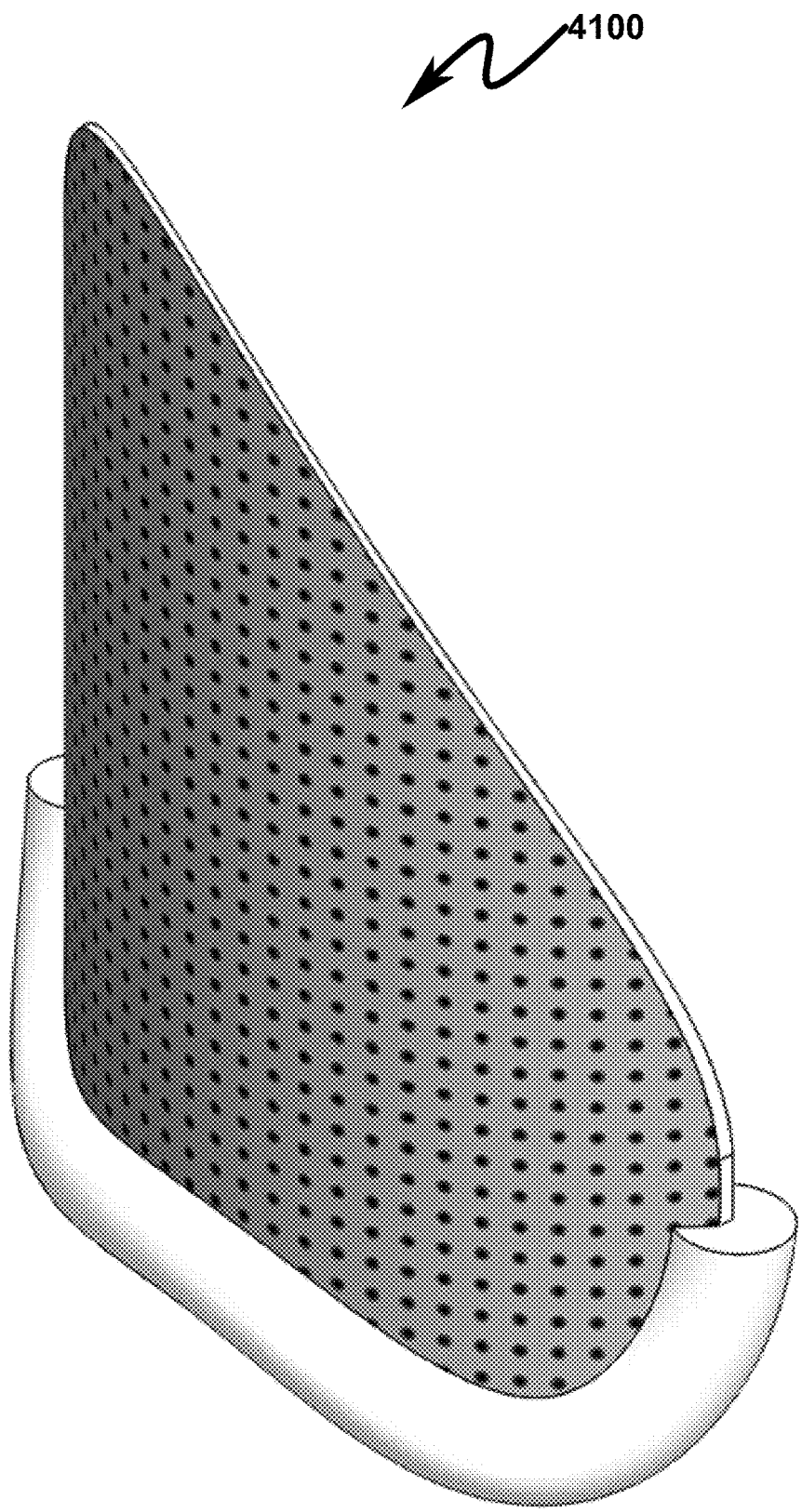
FIG. 41 illustrates a front top right perspective view of a preferred exemplary embodiment of a conical primary plate (CPP) incorporating uniform curvatures useful in some preferred invention embodiments.
Figure 42:
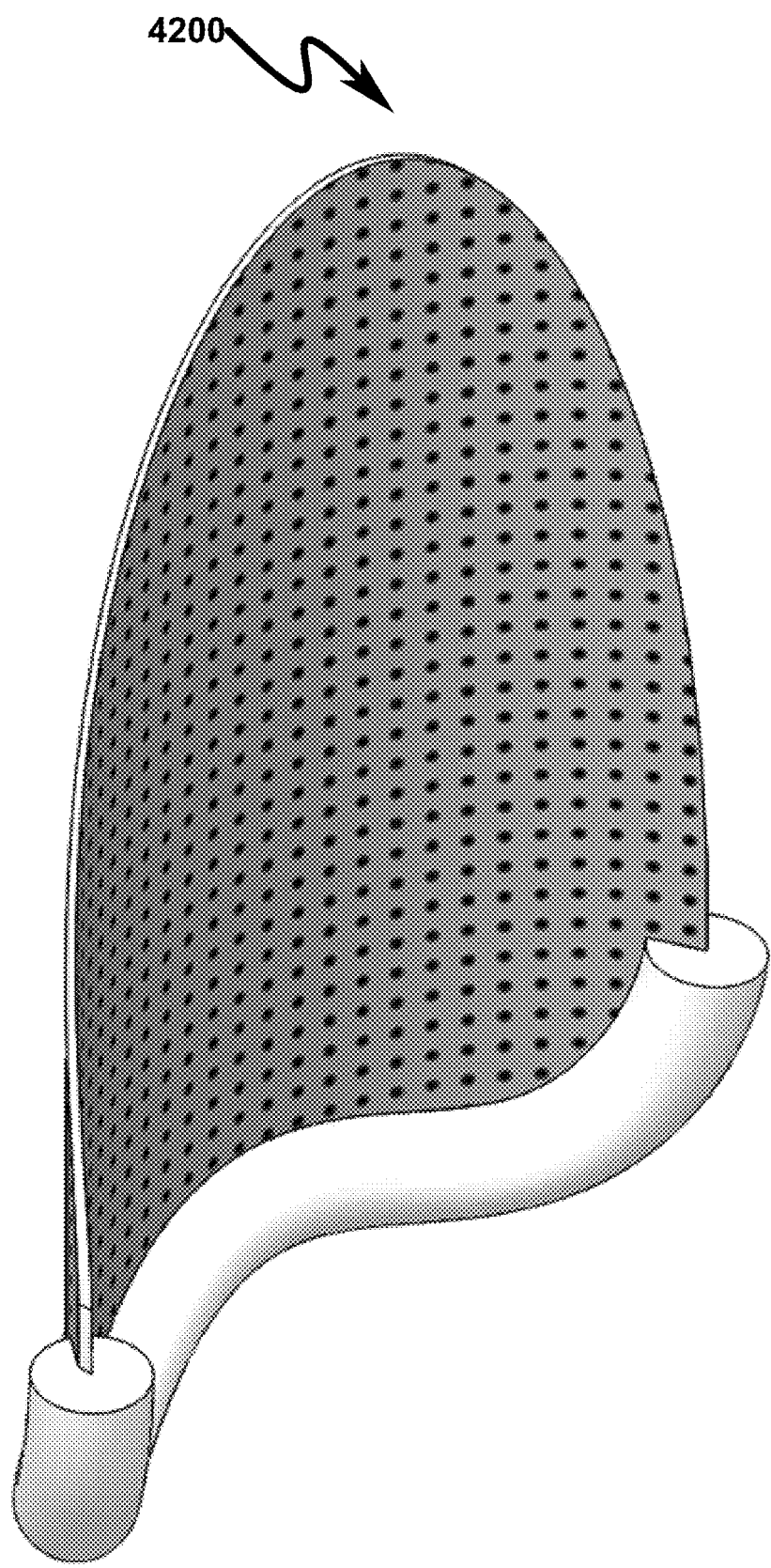
FIG. 42 illustrates a rear top right perspective view of a preferred exemplary embodiment of a conical primary plate (CPP) incorporating uniform curvatures useful in some preferred invention embodiments.
Figure 43:
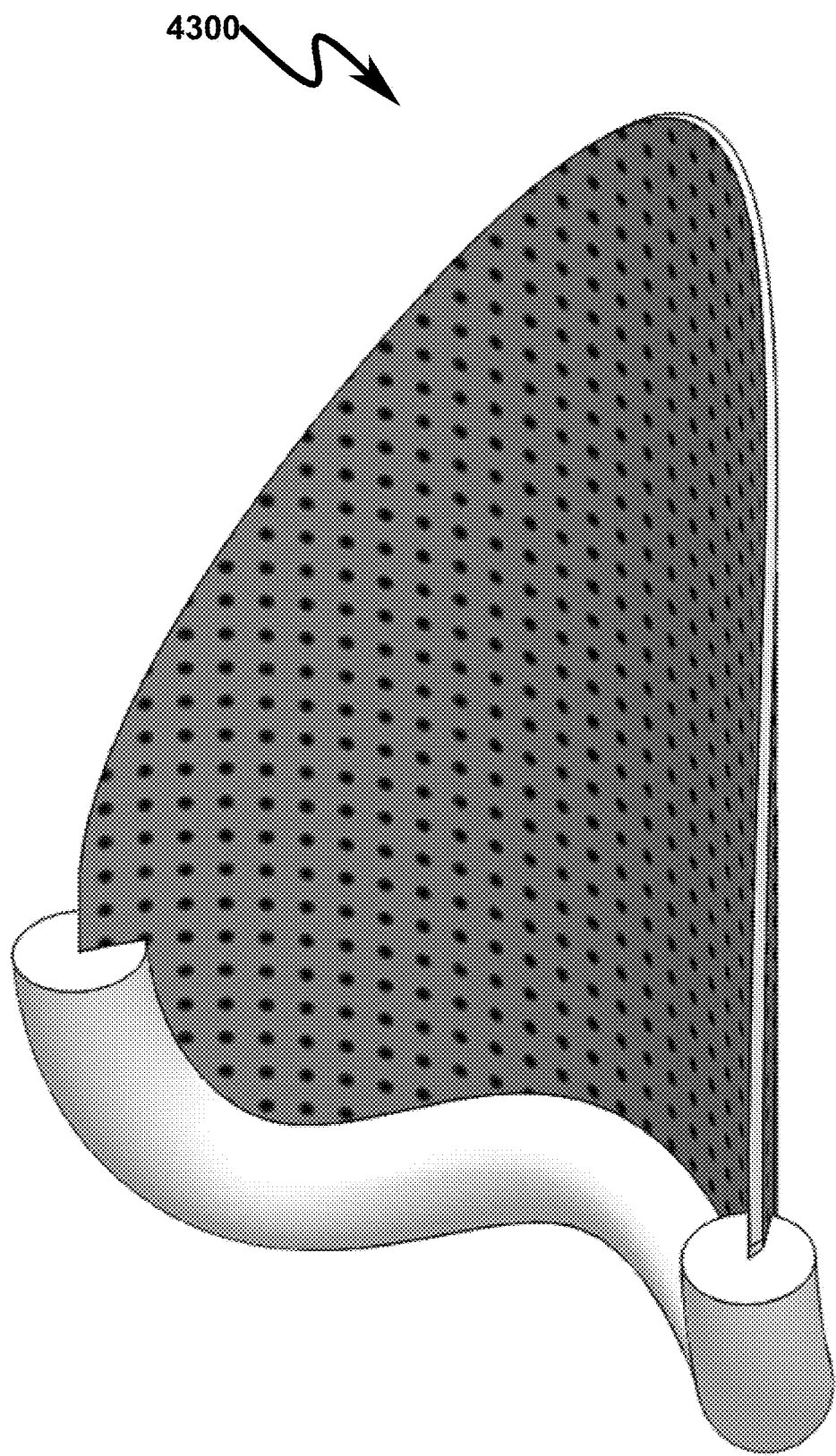
FIG. 43 illustrates a rear top left perspective view of a preferred exemplary embodiment of a conical primary plate (CPP) incorporating uniform curvatures useful in some preferred invention embodiments.
Figure 44:
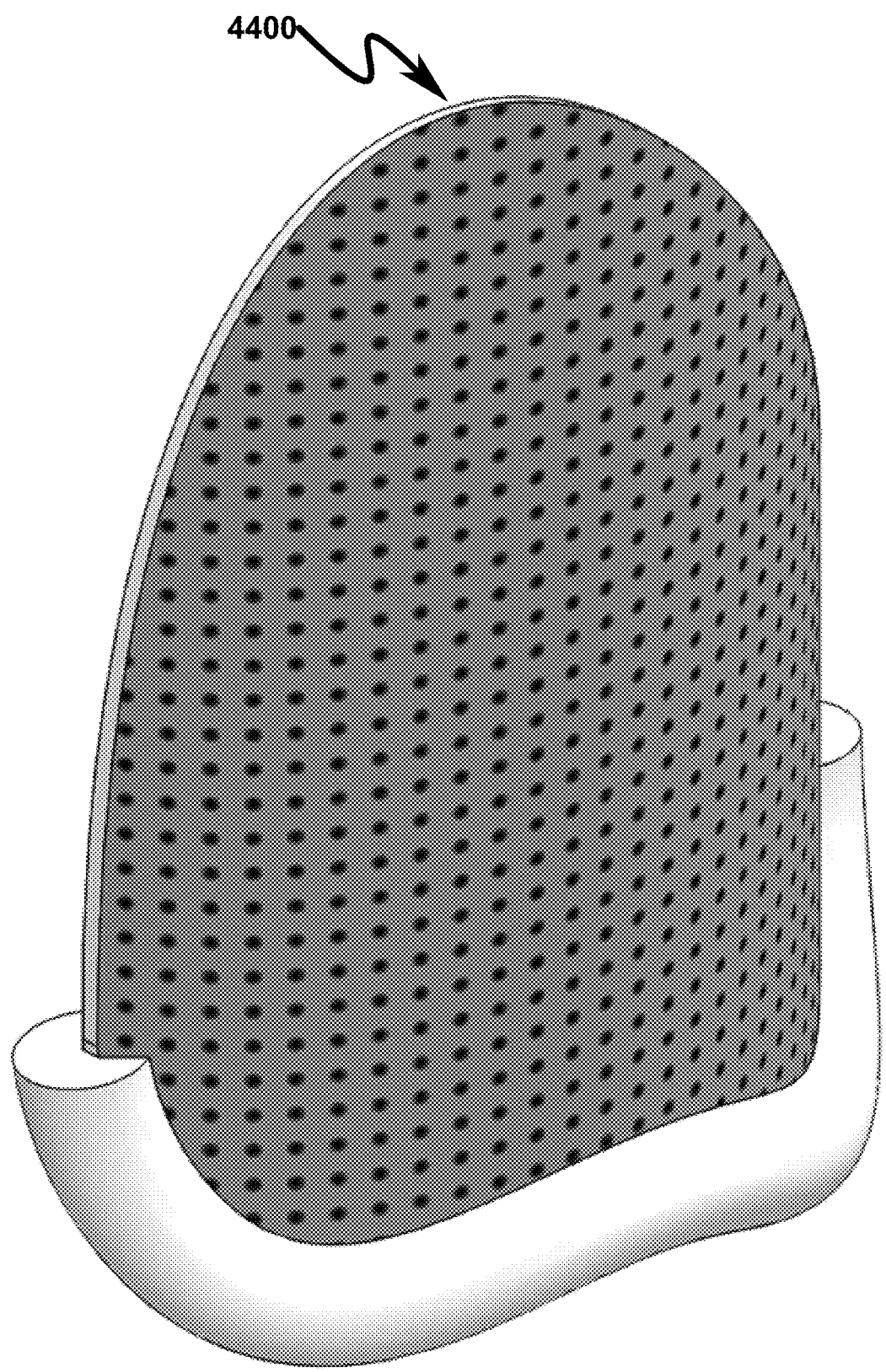
FIG. 44 illustrates a front top left perspective view of a preferred exemplary embodiment of a conical primary plate (CPP) incorporating uniform curvatures useful in some preferred invention embodiments.
Figure 45:
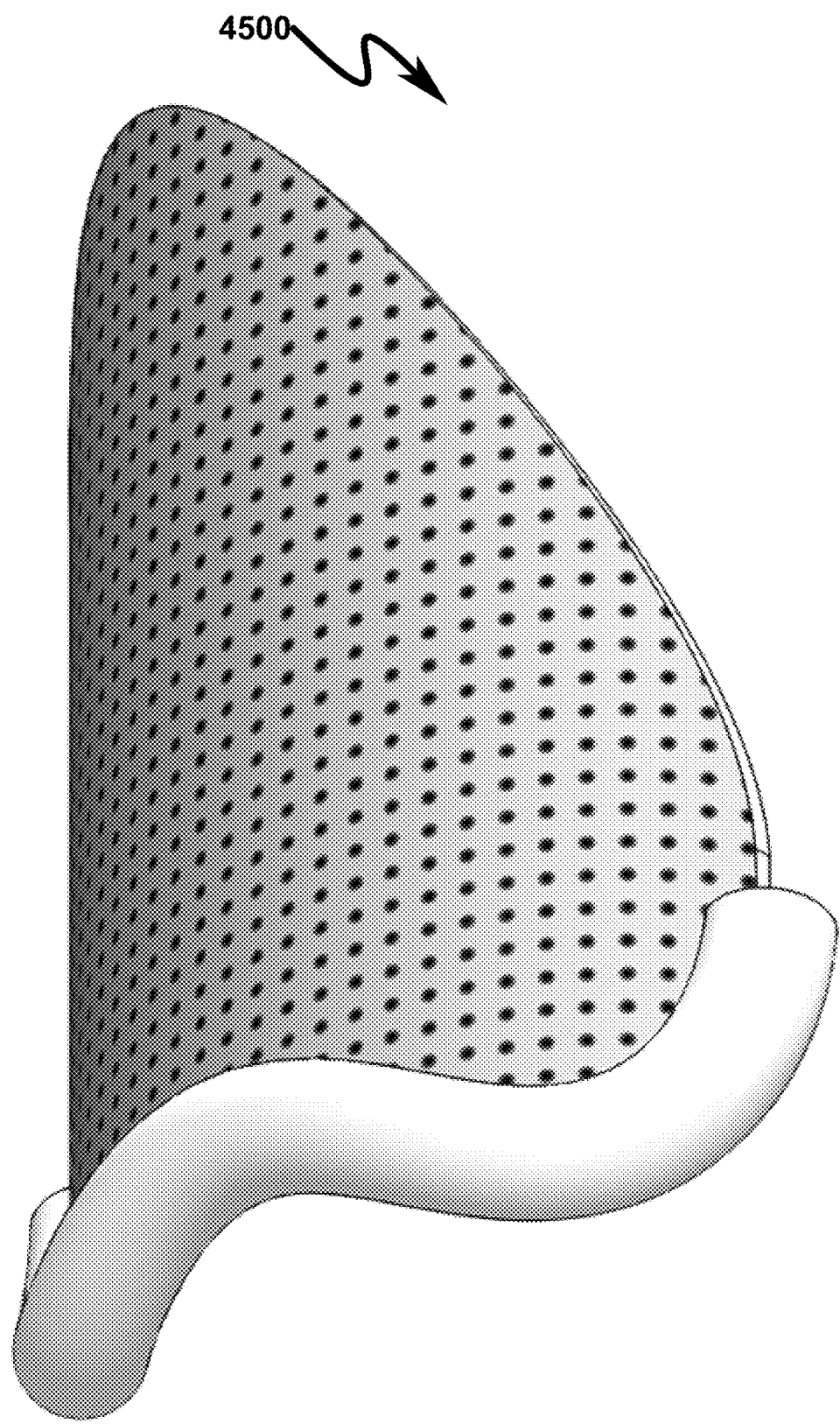
FIG. 45 illustrates a front bottom right perspective view of a preferred exemplary embodiment of a conical primary plate (CPP) incorporating uniform curvatures useful in some preferred invention embodiments.
Figure 46:
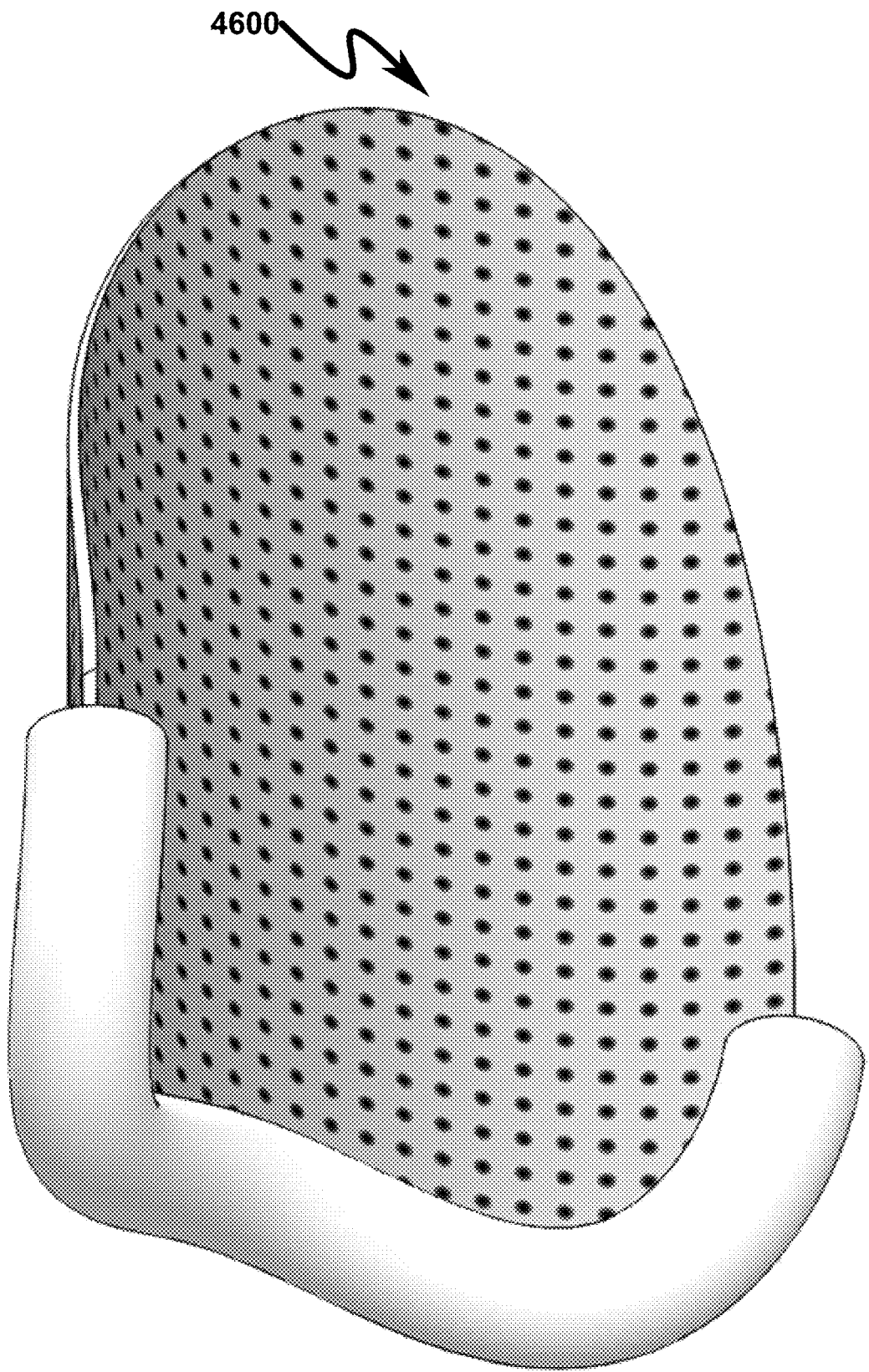
FIG. 46 illustrates a rear bottom right perspective view of a preferred exemplary embodiment of a conical primary plate (CPP) incorporating uniform curvatures useful in some preferred invention embodiments.
Figure 47:
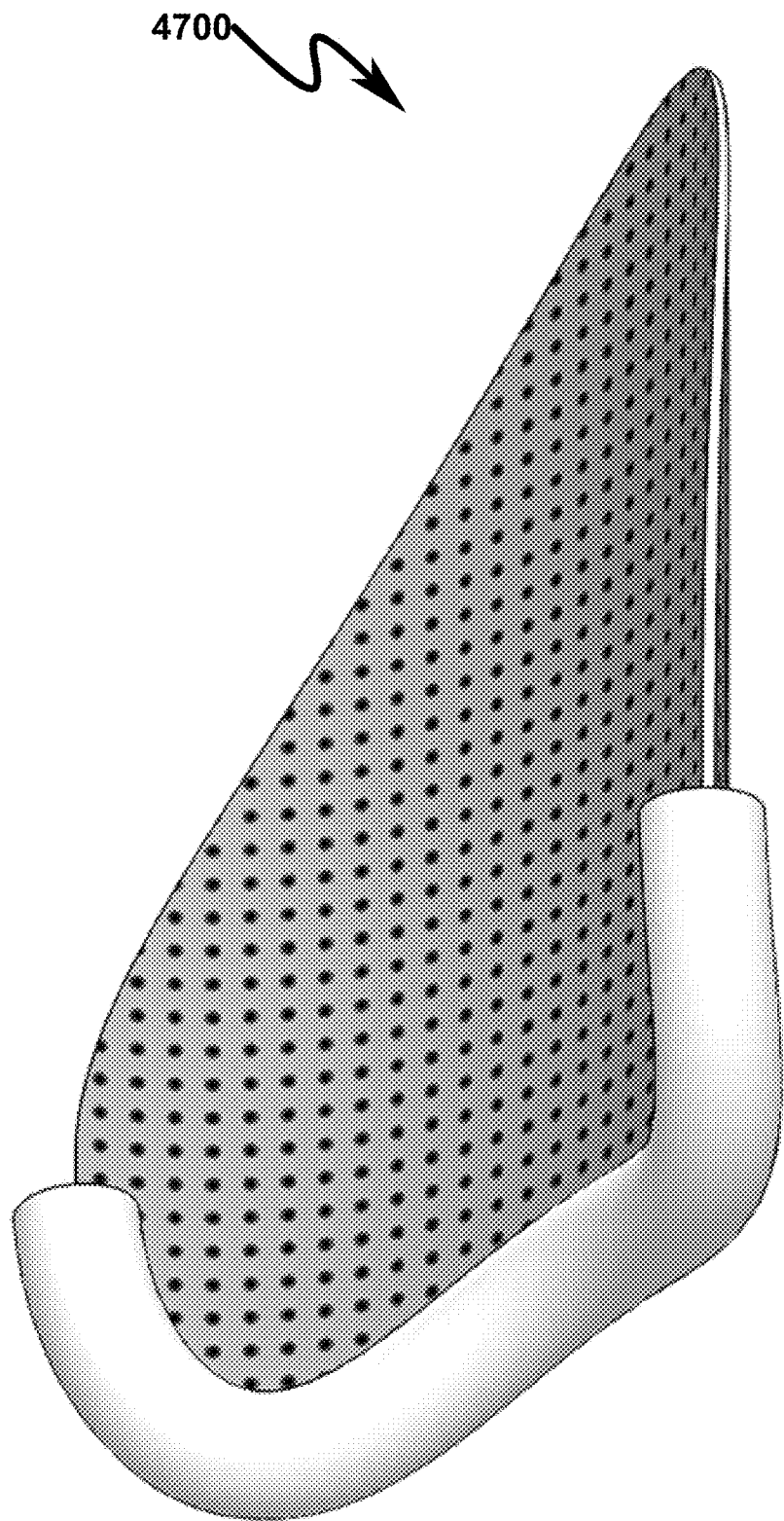
FIG. 47 illustrates a rear bottom left perspective view of a preferred exemplary embodiment of a conical primary plate (CPP) incorporating uniform curvatures useful in some preferred invention embodiments.
Figure 53:
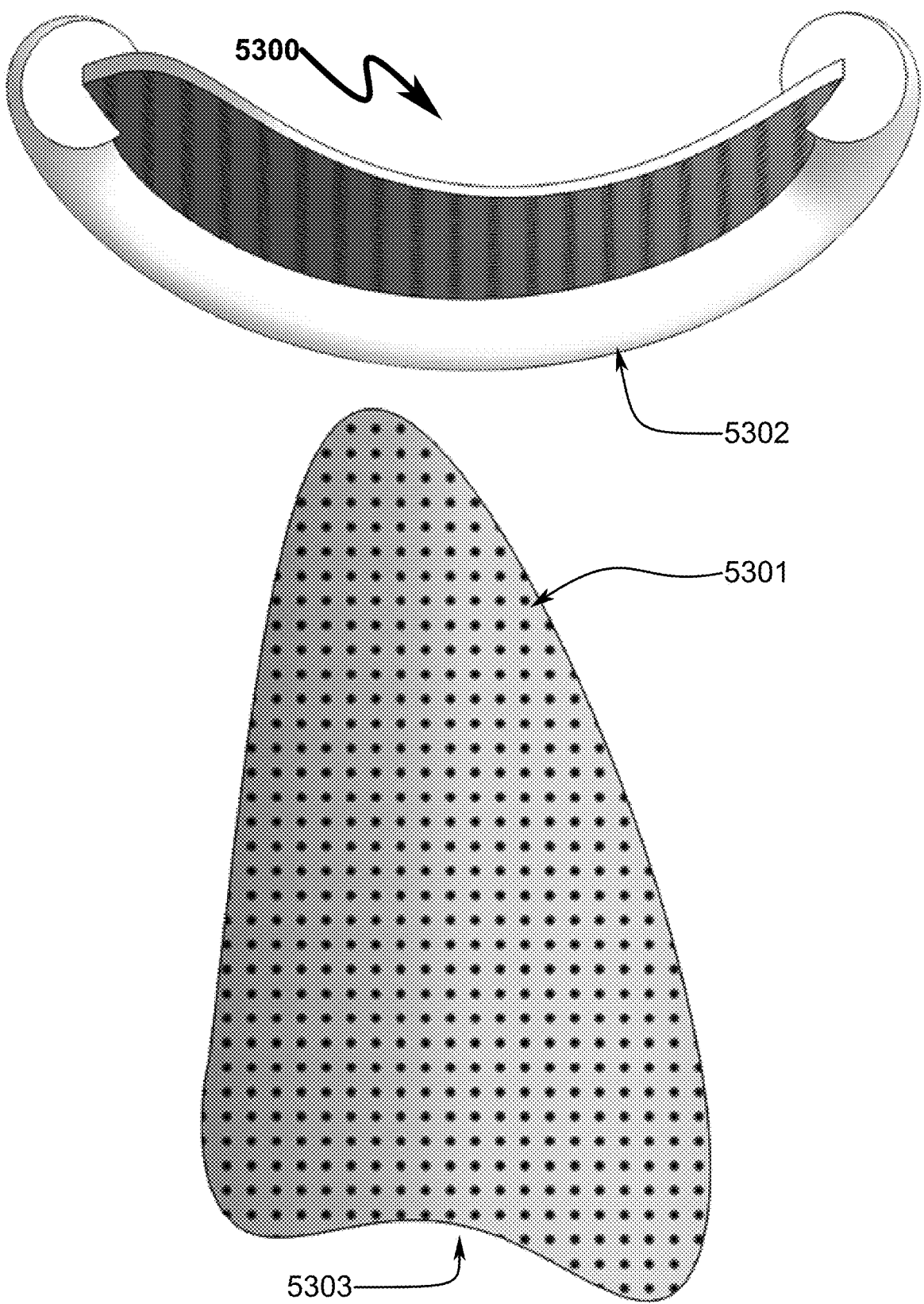
FIG. 53 illustrates a top view of a preferred exemplary embodiment of a conical primary plate (CPP) incorporating varying curvatures useful in some preferred invention embodiments and depicts a foam padding strip (FPS) and CPP lower perimeter comprising a curved raised portion (CRP) in isolation.
Figure 54:
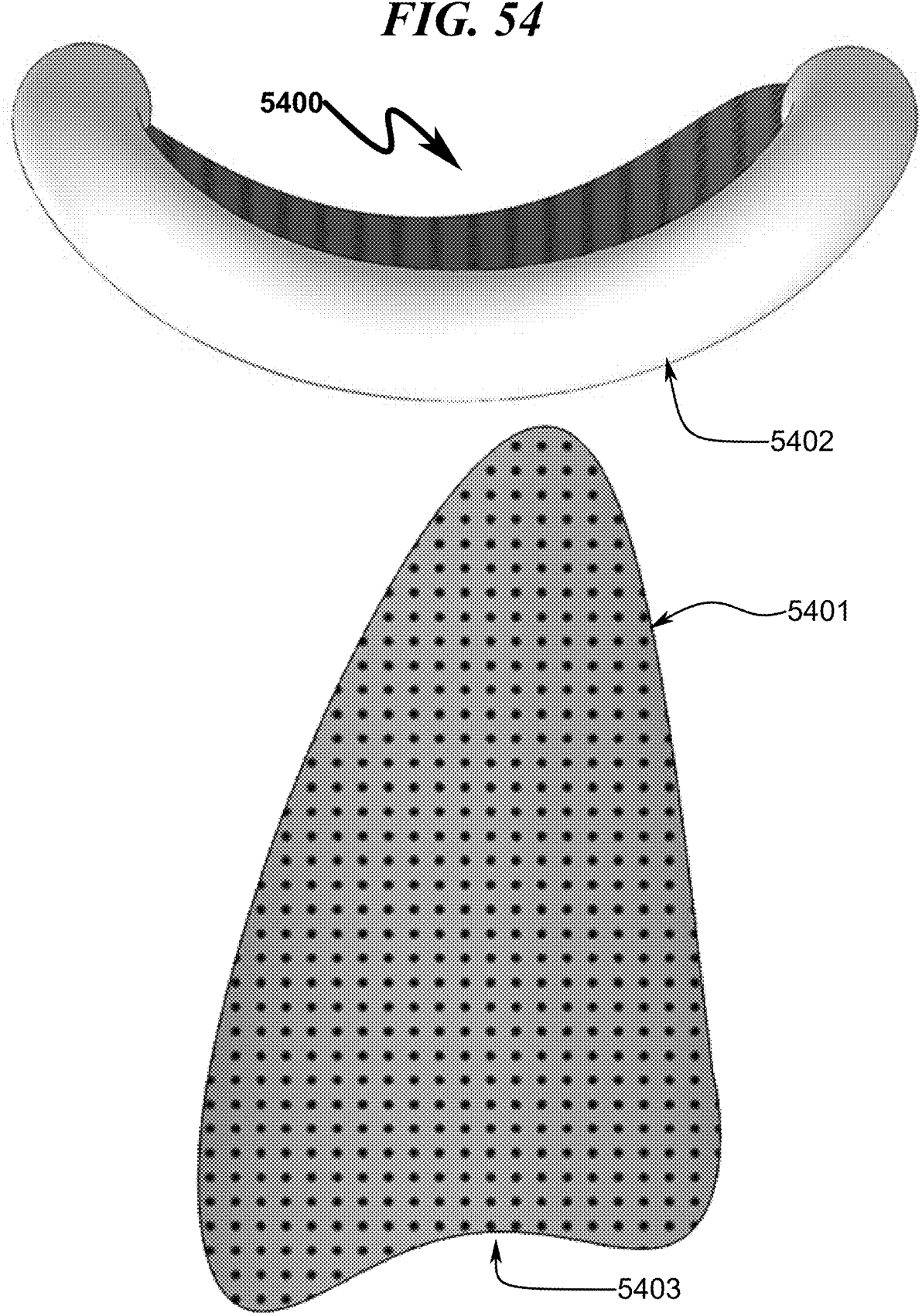
FIG. 54 illustrates a bottom view of a preferred exemplary embodiment of a conical primary plate (CPP) incorporating varying curvatures useful in some preferred invention embodiments and depicts a foam padding strip (FPS) and CPP lower perimeter comprising a curved raised portion (CRP) in isolation.
Figure 55:
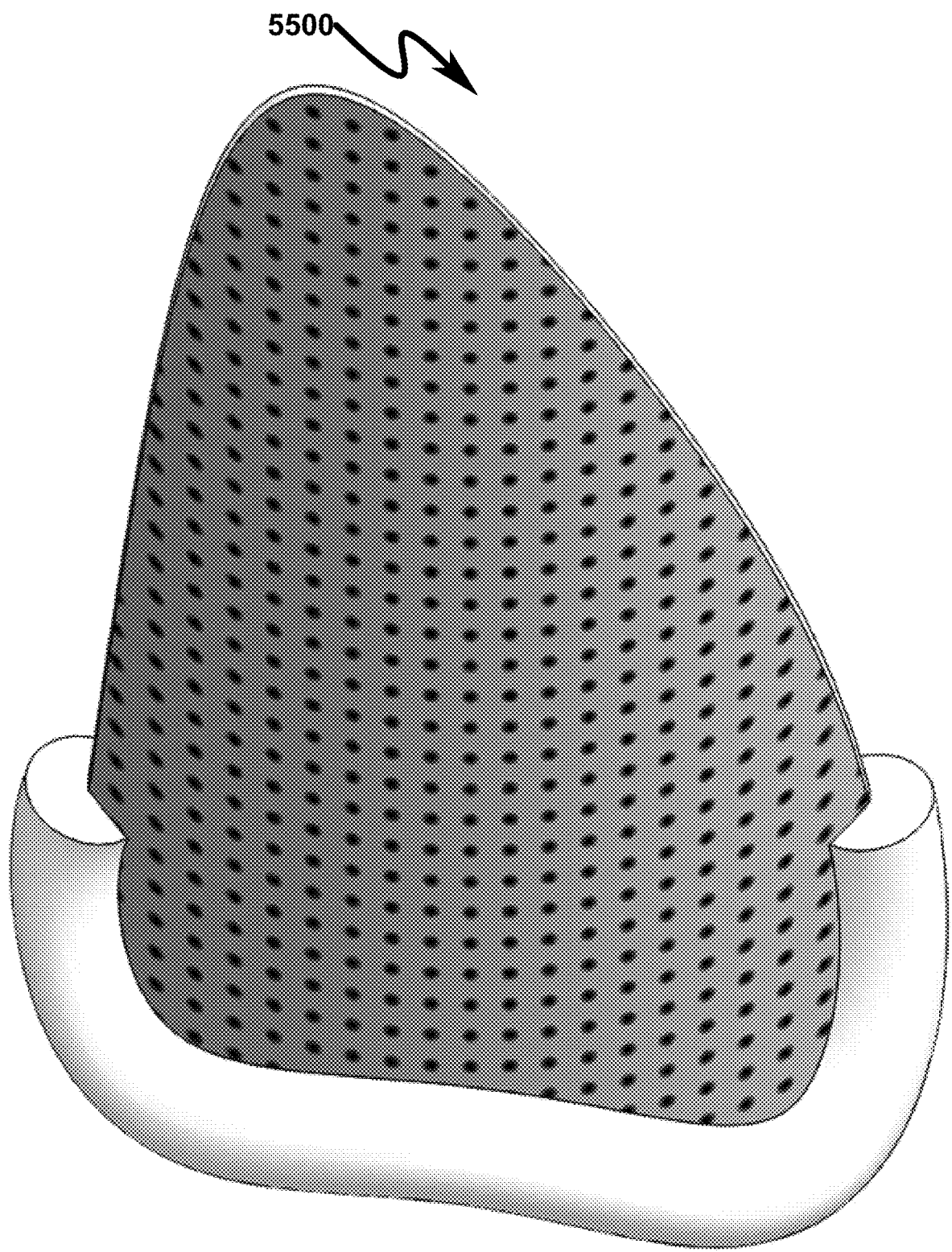
FIG. 55 illustrates a top front diagonal view of a preferred exemplary embodiment of a conical primary plate (CPP) incorporating varying curvatures useful in some preferred invention embodiments.
Figure 56:
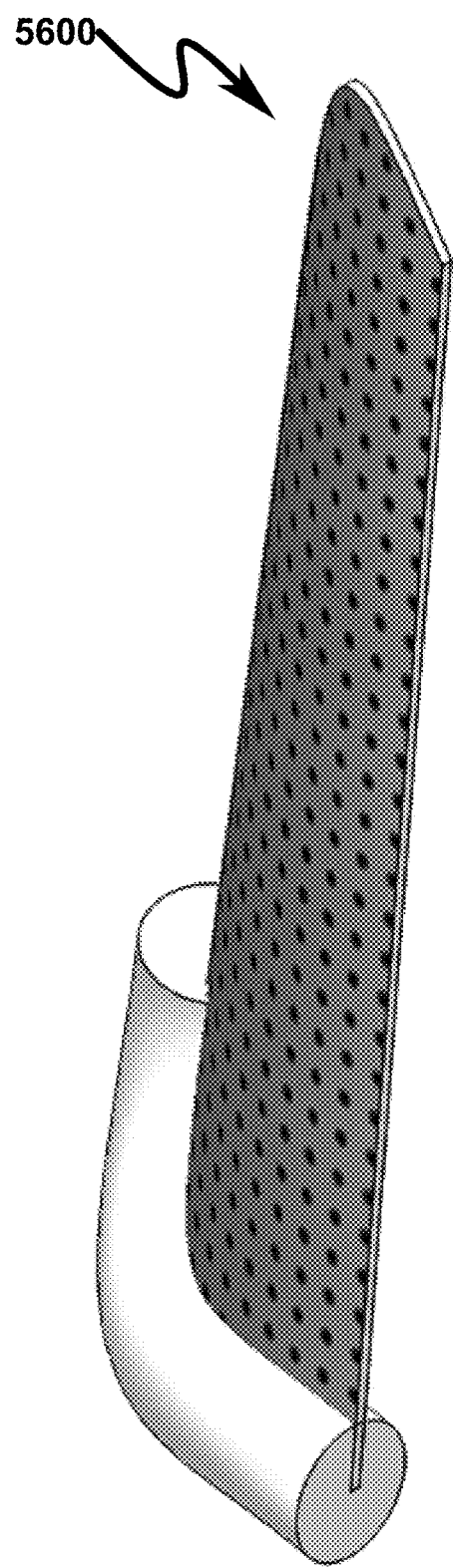
FIG. 56 illustrates a front top right perspective section view of a preferred exemplary embodiment of a conical primary plate (CPP) incorporating varying curvatures useful in some preferred invention embodiments.
Figure 57:
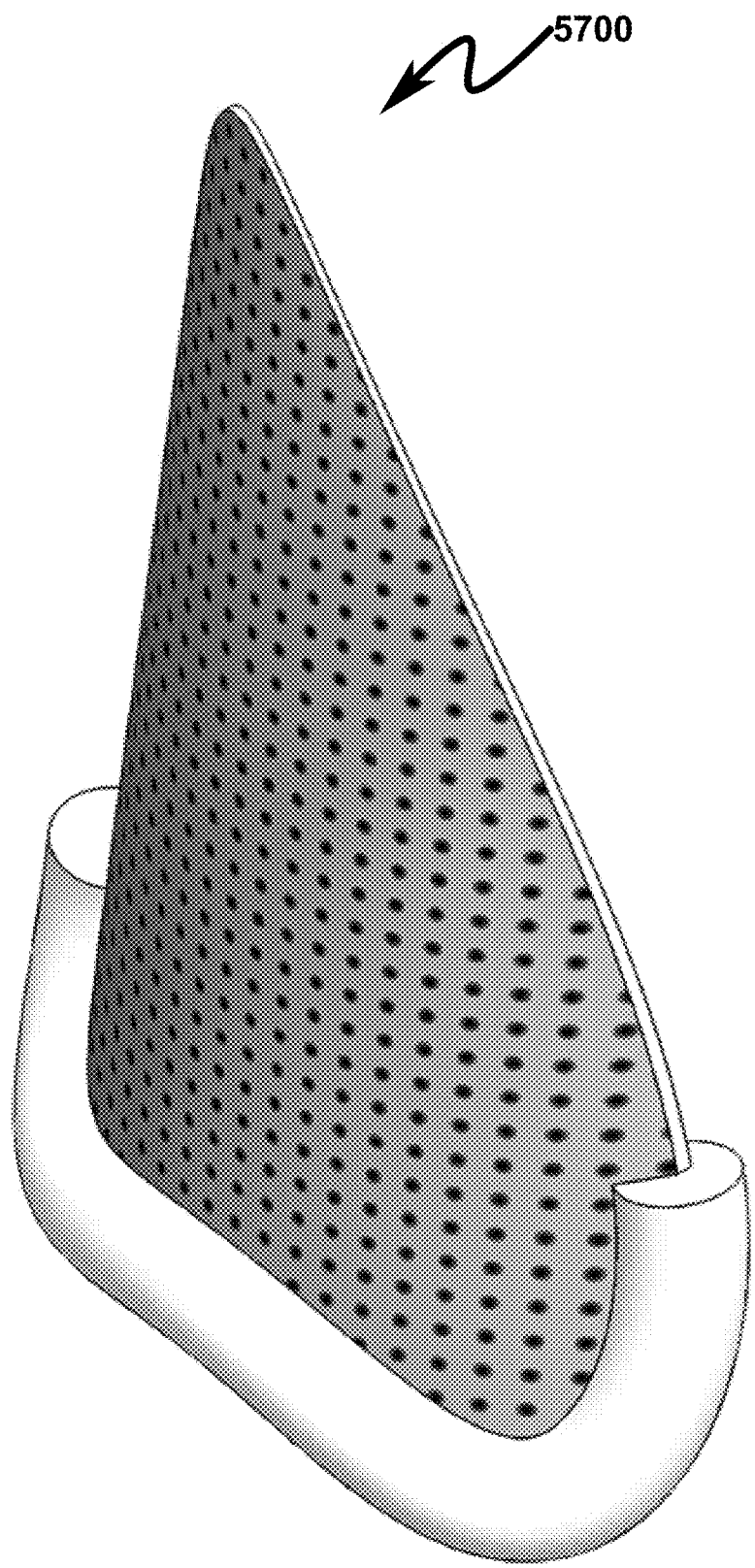
FIG. 57 illustrates a front top right perspective view of a preferred exemplary embodiment of a conical primary plate (CPP) incorporating varying curvatures useful in some preferred invention embodiments.
Figure 58:
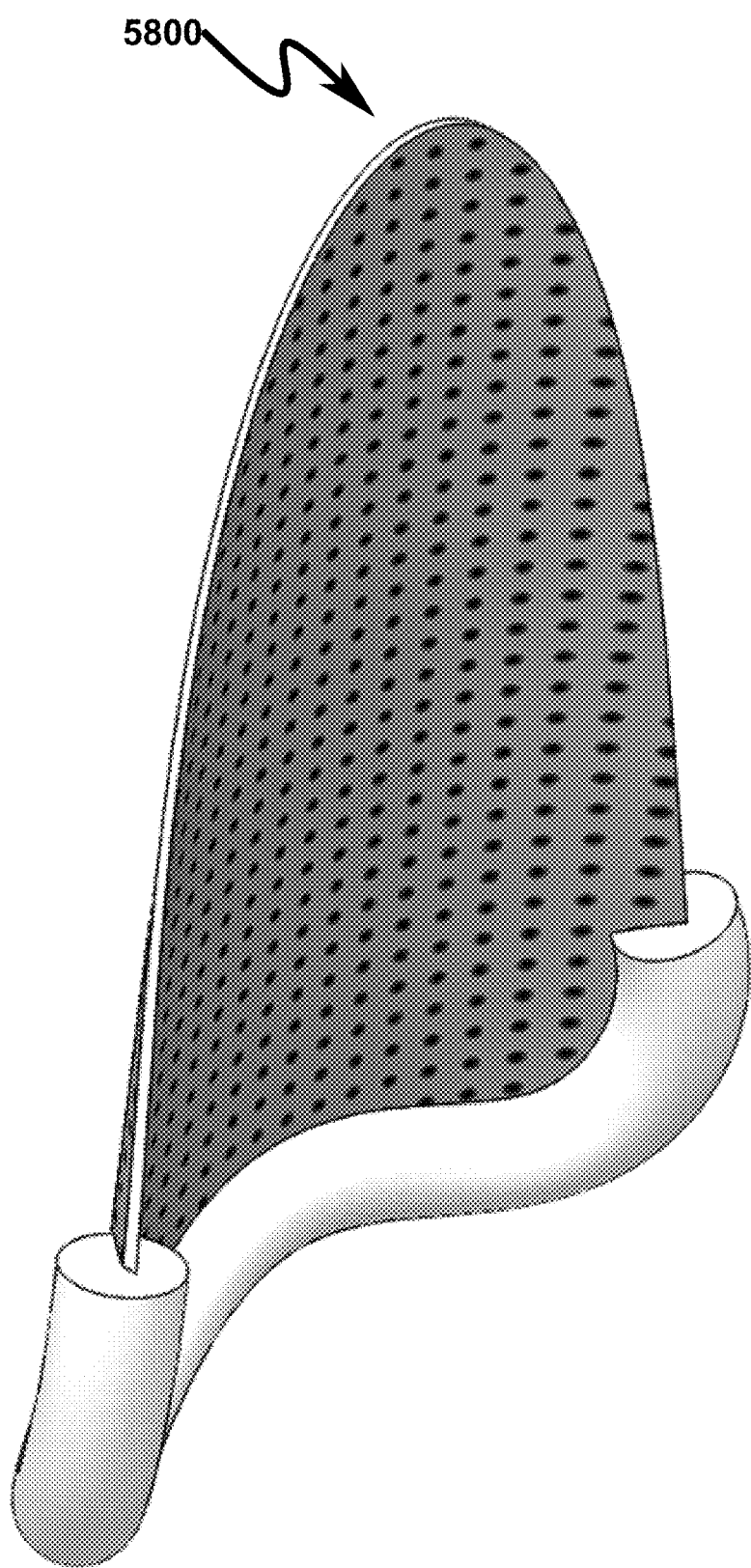
FIG. 58 illustrates a rear top right perspective view of a preferred exemplary embodiment of a conical primary plate (CPP) incorporating varying curvatures useful in some preferred invention embodiments.
Figure 59:
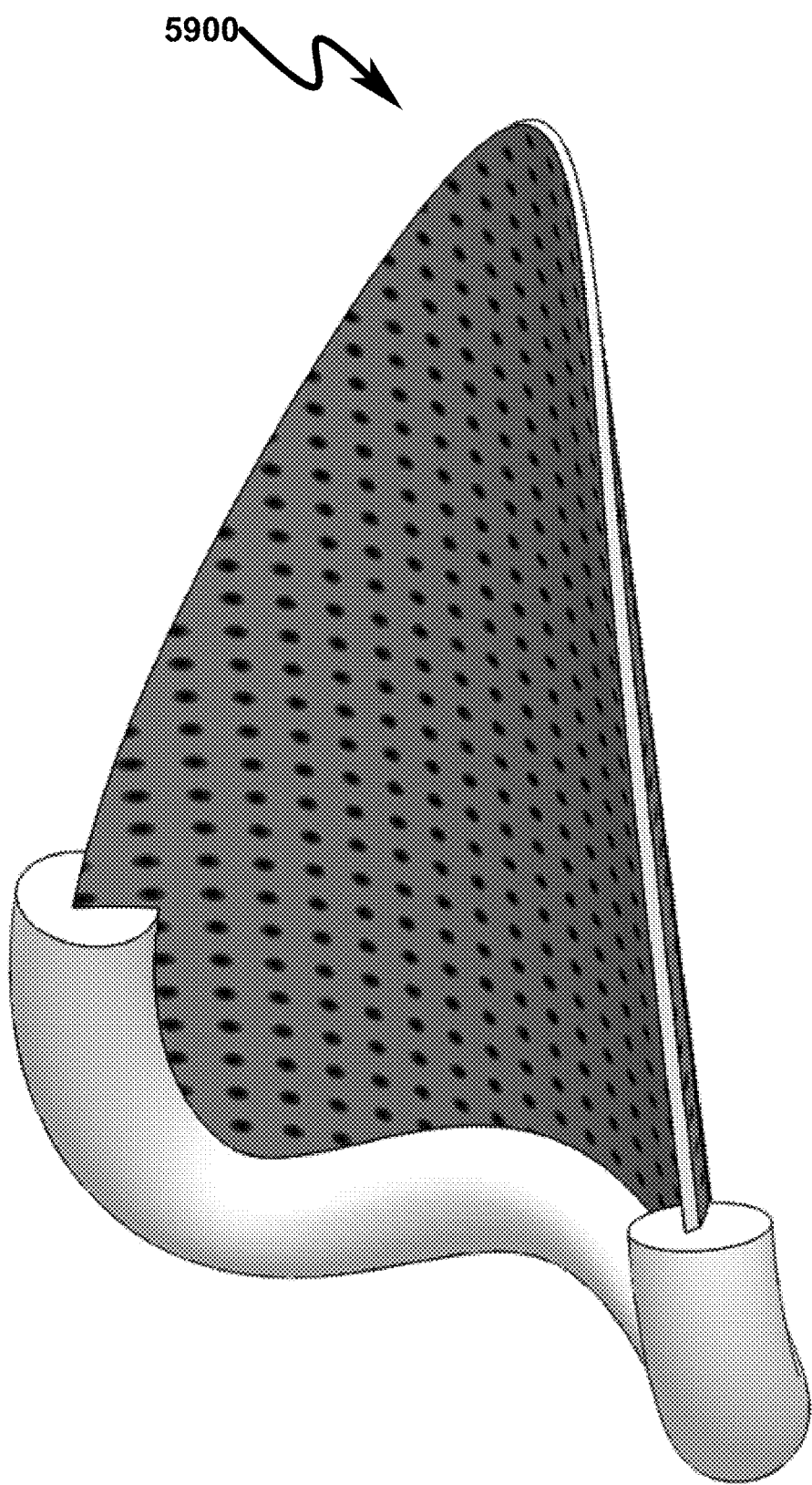
FIG. 59 illustrates a rear top left perspective view of a preferred exemplary embodiment of a conical primary plate (CPP) incorporating varying curvatures useful in some preferred invention embodiments.
Figure 60:
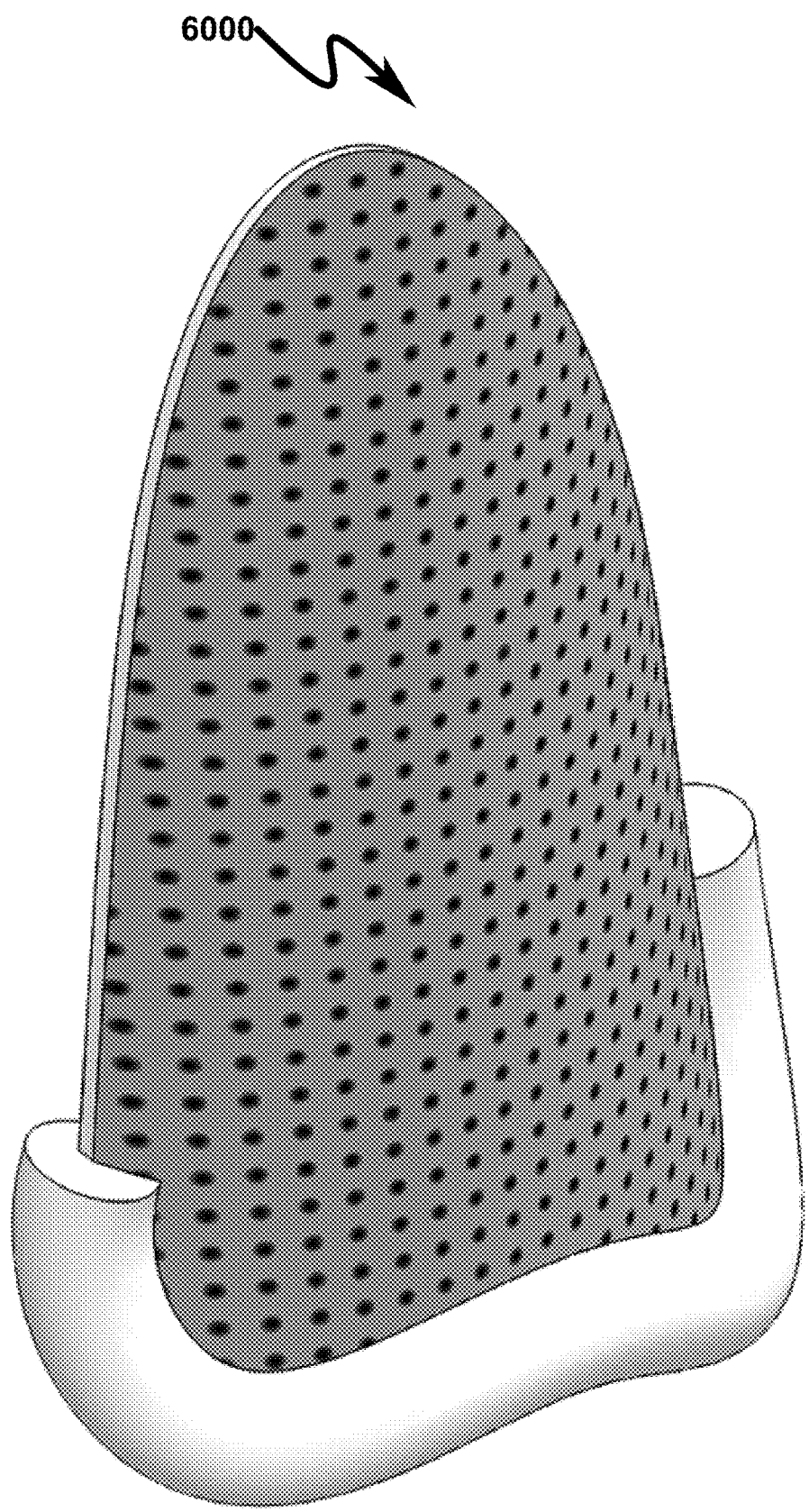
FIG. 60 illustrates a front top left perspective view of a preferred exemplary embodiment of a conical primary plate (CPP) incorporating varying curvatures useful in some preferred invention embodiments.
Figure 61:
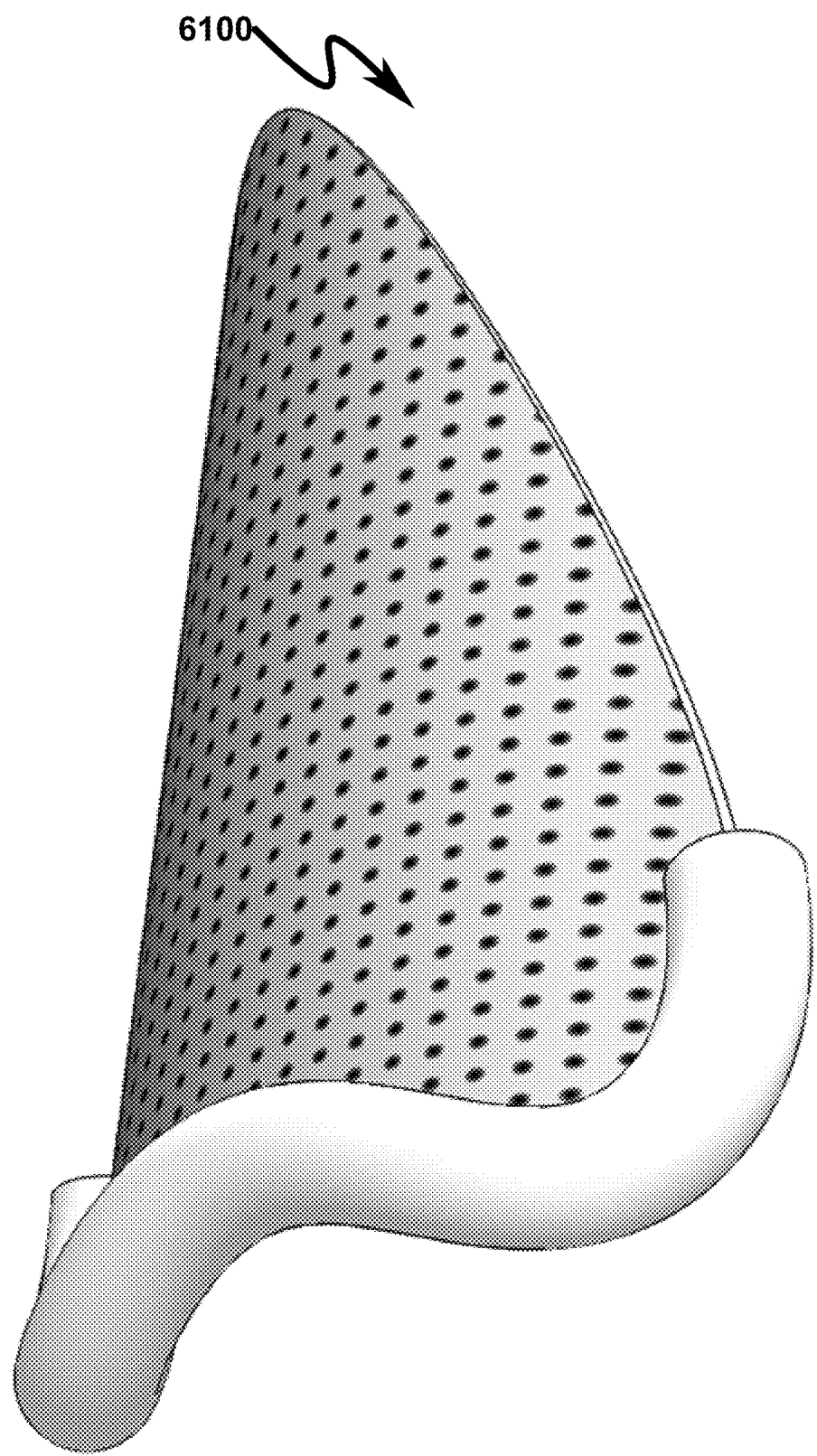
FIG. 61 illustrates a front bottom right perspective view of a preferred exemplary embodiment of a conical primary plate (CPP) incorporating varying curvatures useful in some preferred invention embodiments.
Figure 62:
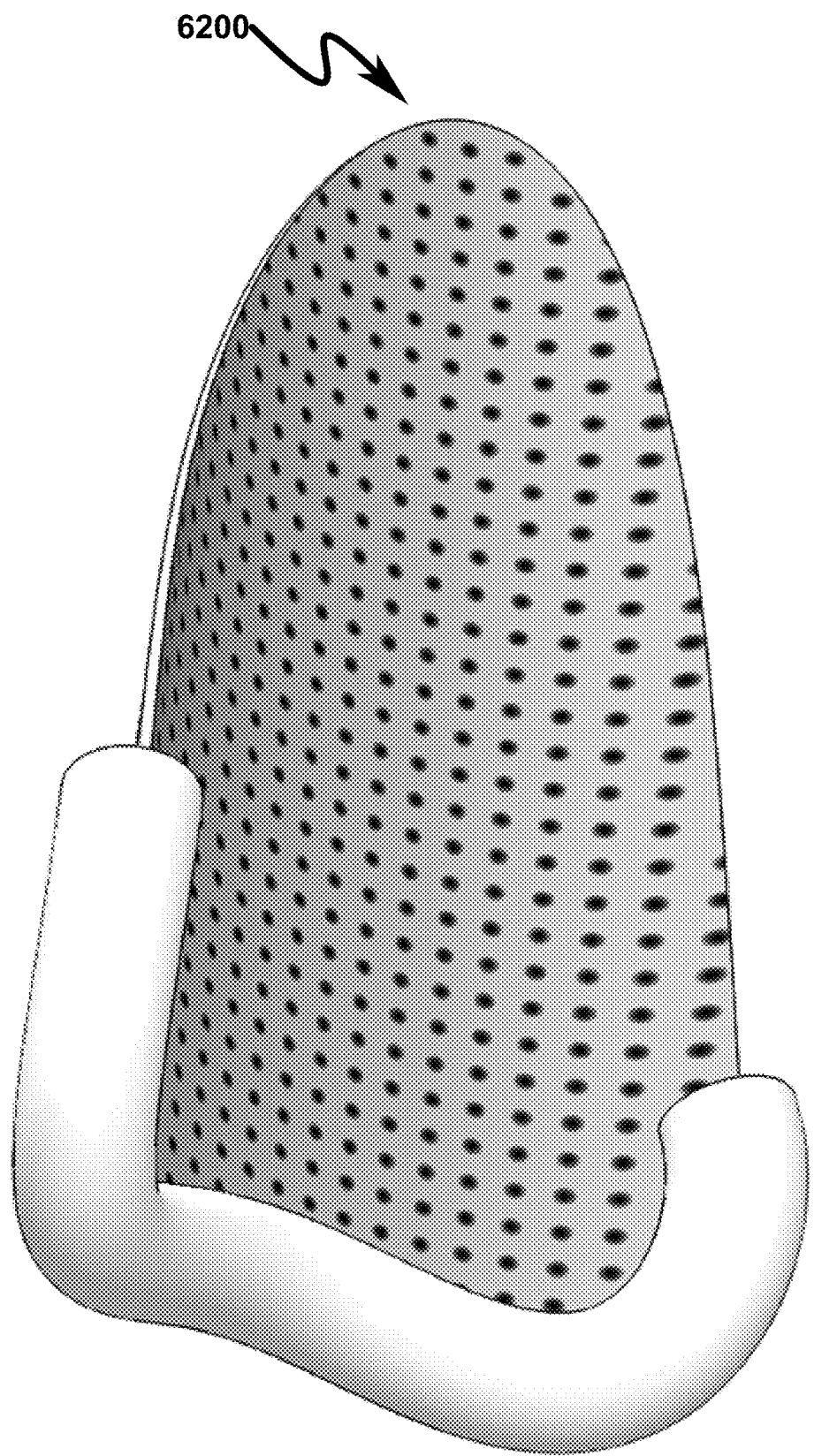
FIG. 62 illustrates a rear bottom right perspective view of a preferred exemplary embodiment of a conical primary plate (CPP) incorporating varying curvatures useful in some preferred invention embodiments.
Figure 63:
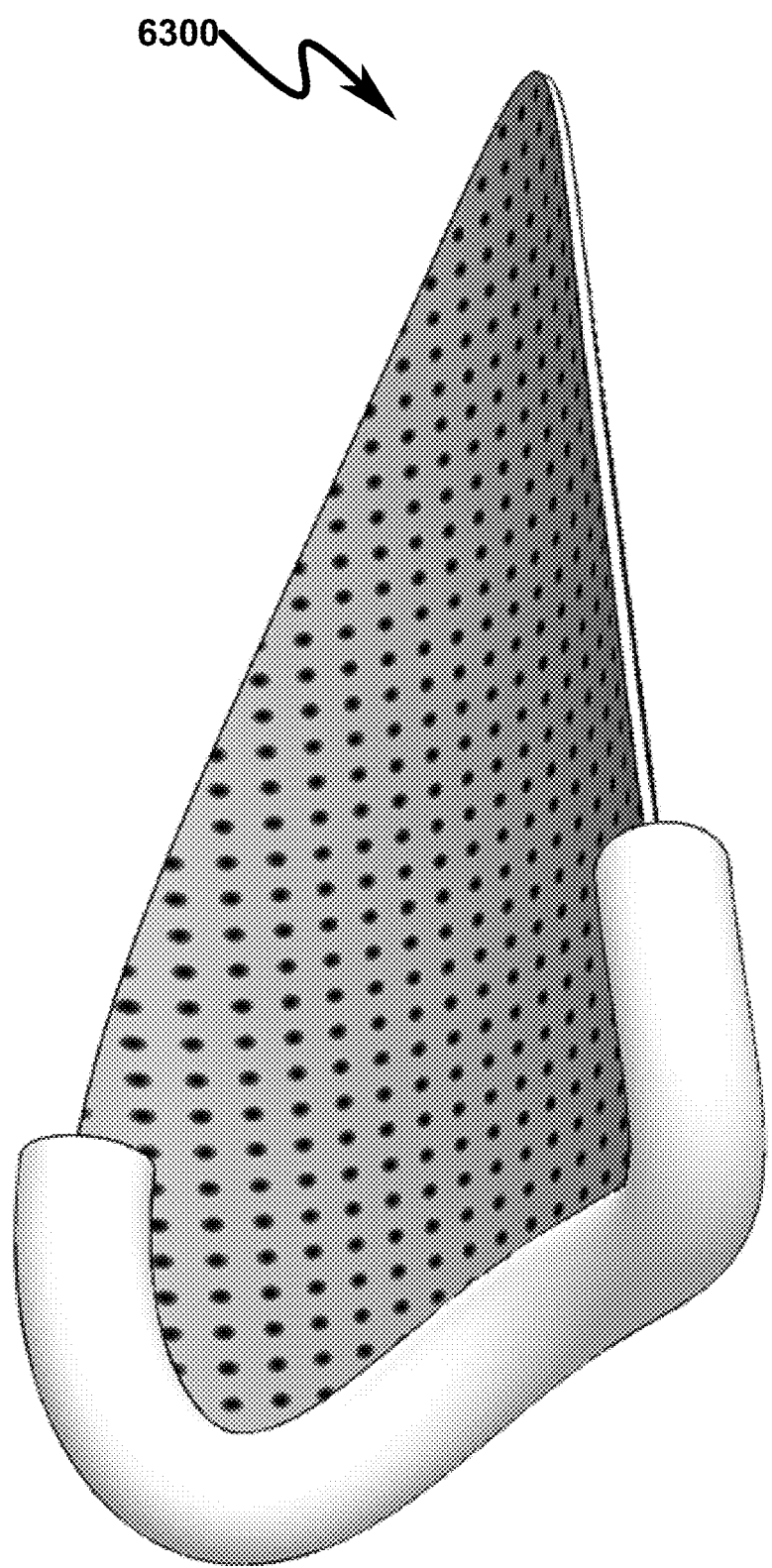
FIG. 63 illustrates a rear bottom left perspective view of a preferred exemplary embodiment of a conical primary plate (CPP) incorporating varying curvatures useful in some preferred invention embodiments.

As generally depicted in FIG. 37 (3700)-FIG. 38 (3800) and FIG. 53 (5300)-FIG. 54 (5400), the CPP body (3701, 3801, 5301, 5401) may incorporate an optional foam padding strip (FPS) (3702, 3802, 5302, 5402) on its lower perimeter edge that forms a curved raised portion (CRP) (3703, 3803, 5303, 5403) used to conform the CPP to the surface of the patient.

Angular Secondary Plate (ASP) Detail (6500)-(9600)

Figure 65:
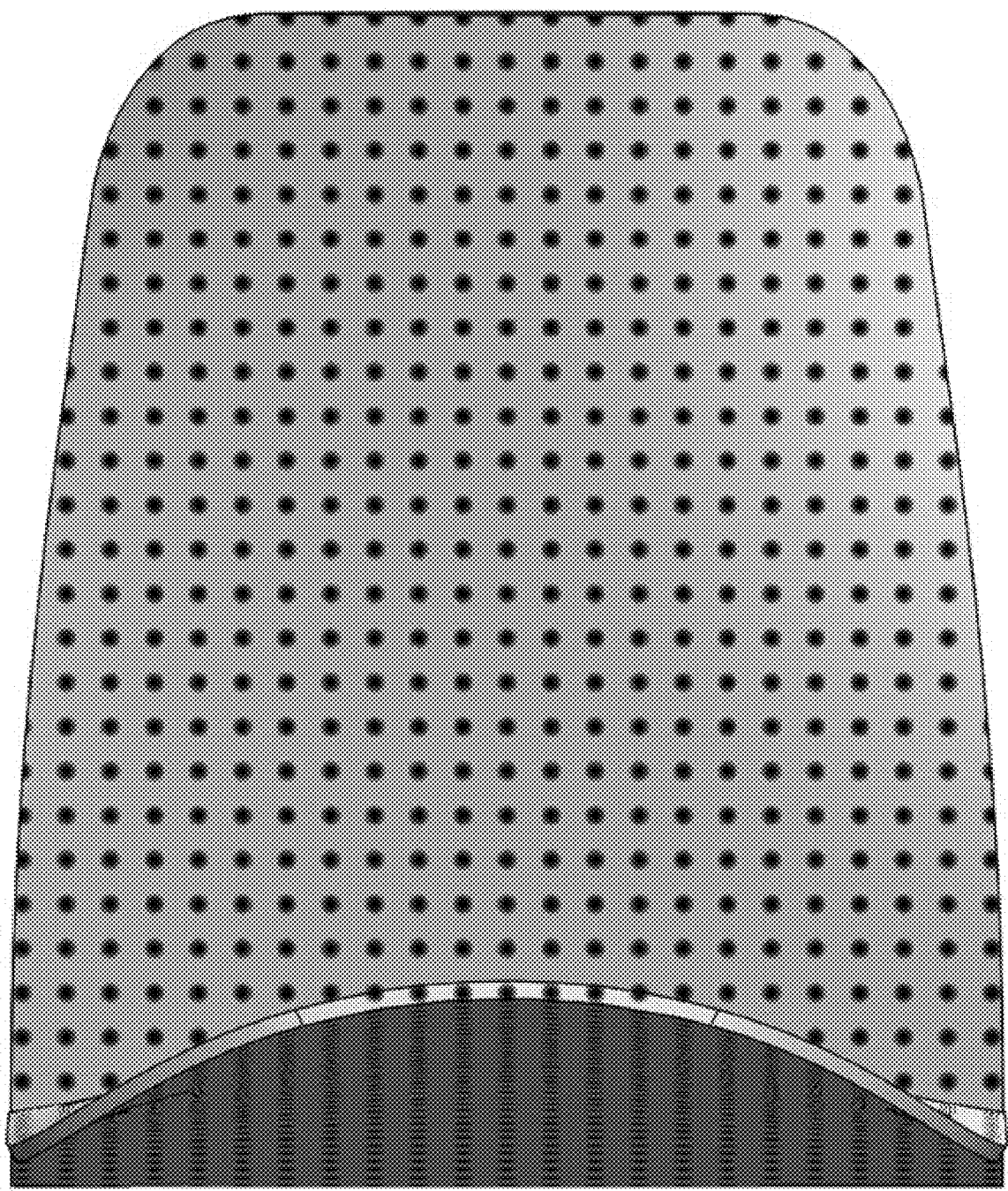
FIG. 65 illustrates a front view of a preferred exemplary embodiment of an angular secondary plate (ASP) (incorporating a curved angular base plate (ABP) and a curved angular vertical plate (AVP)) useful in some preferred invention embodiments.
Figure 66:
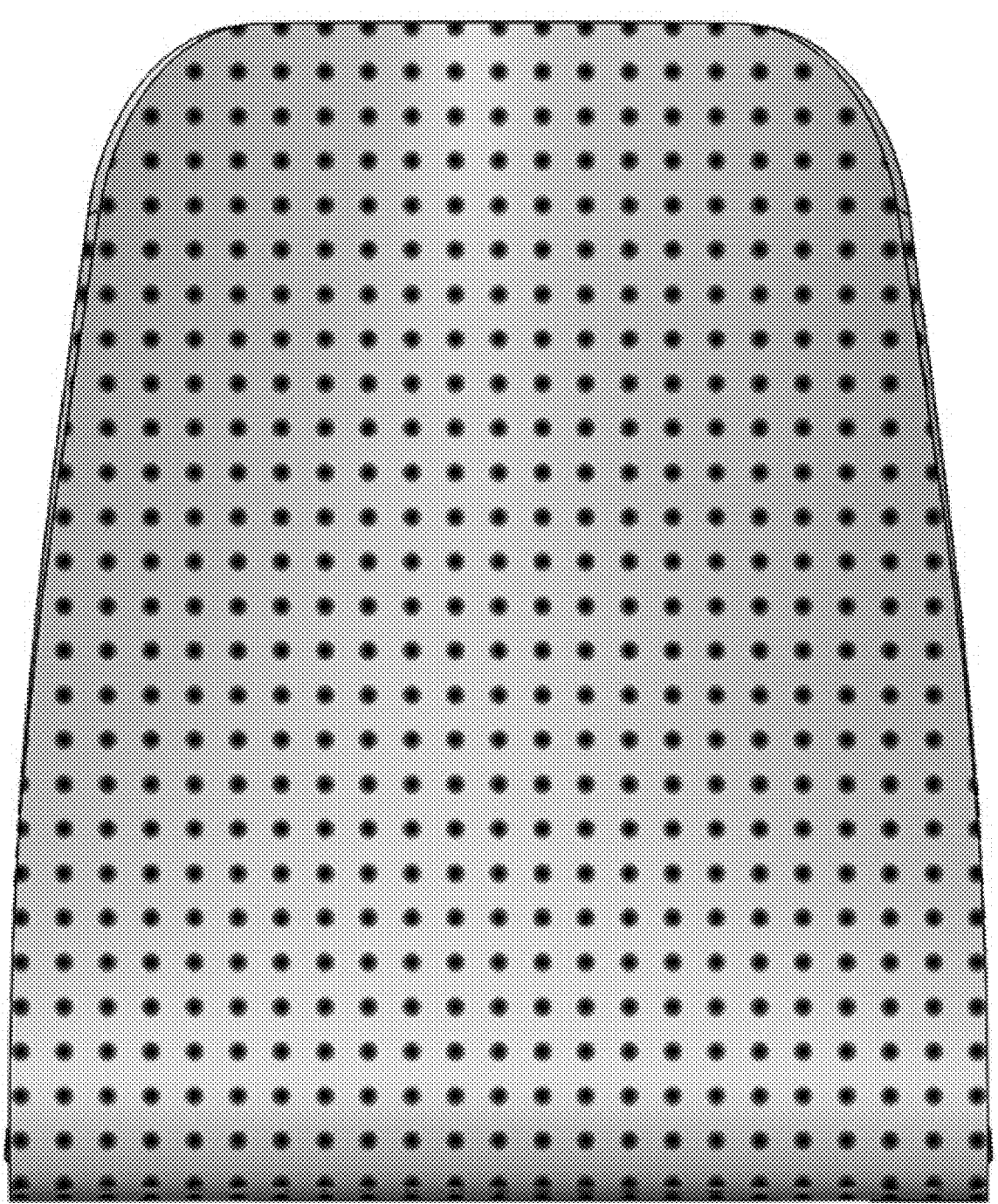
FIG. 66 illustrates a rear view of a preferred exemplary embodiment of an angular secondary plate (ASP) (incorporating a curved angular base plate (ABP) and a curved angular vertical plate (AVP)) useful in some preferred invention embodiments.
Figure 67:
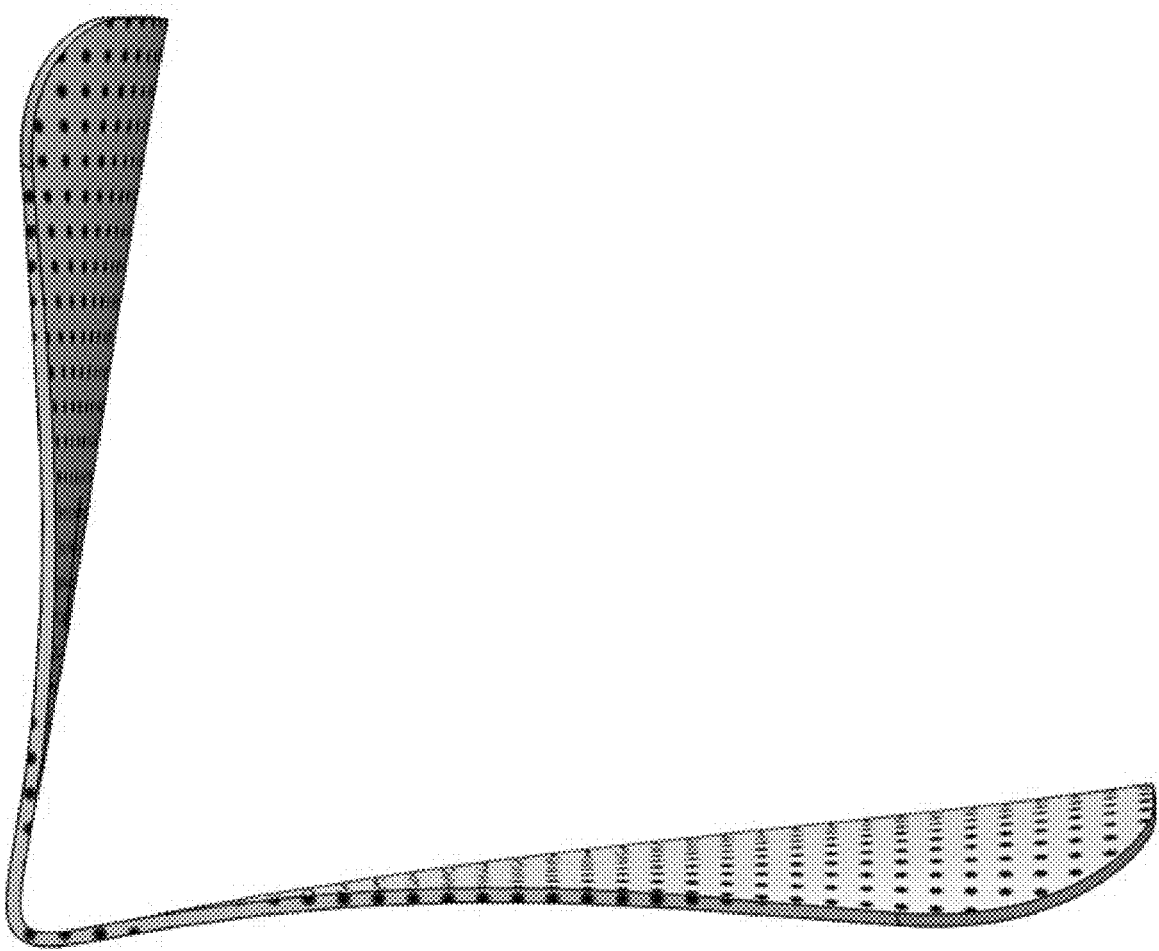
FIG. 67 illustrates a left side view of a preferred exemplary embodiment of an angular secondary plate (ASP) (incorporating a curved angular base plate (ABP) and a curved angular vertical plate (AVP)) useful in some preferred invention embodiments.
Figure 68:
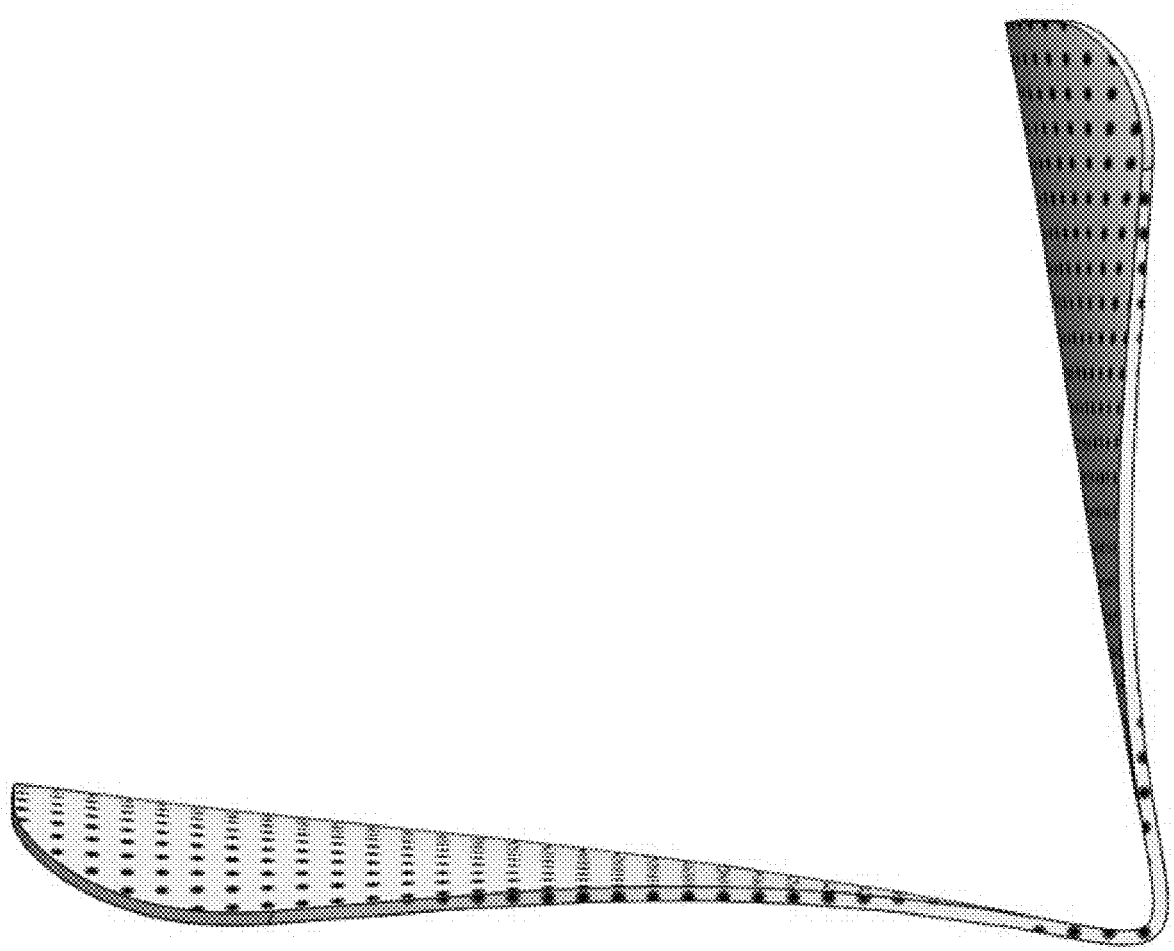
FIG. 68 illustrates a right side view of a preferred exemplary embodiment of an angular secondary plate (ASP) (incorporating a curved angular base plate (ABP) and a curved angular vertical plate (AVP)) useful in some preferred invention embodiments.
Figure 69:
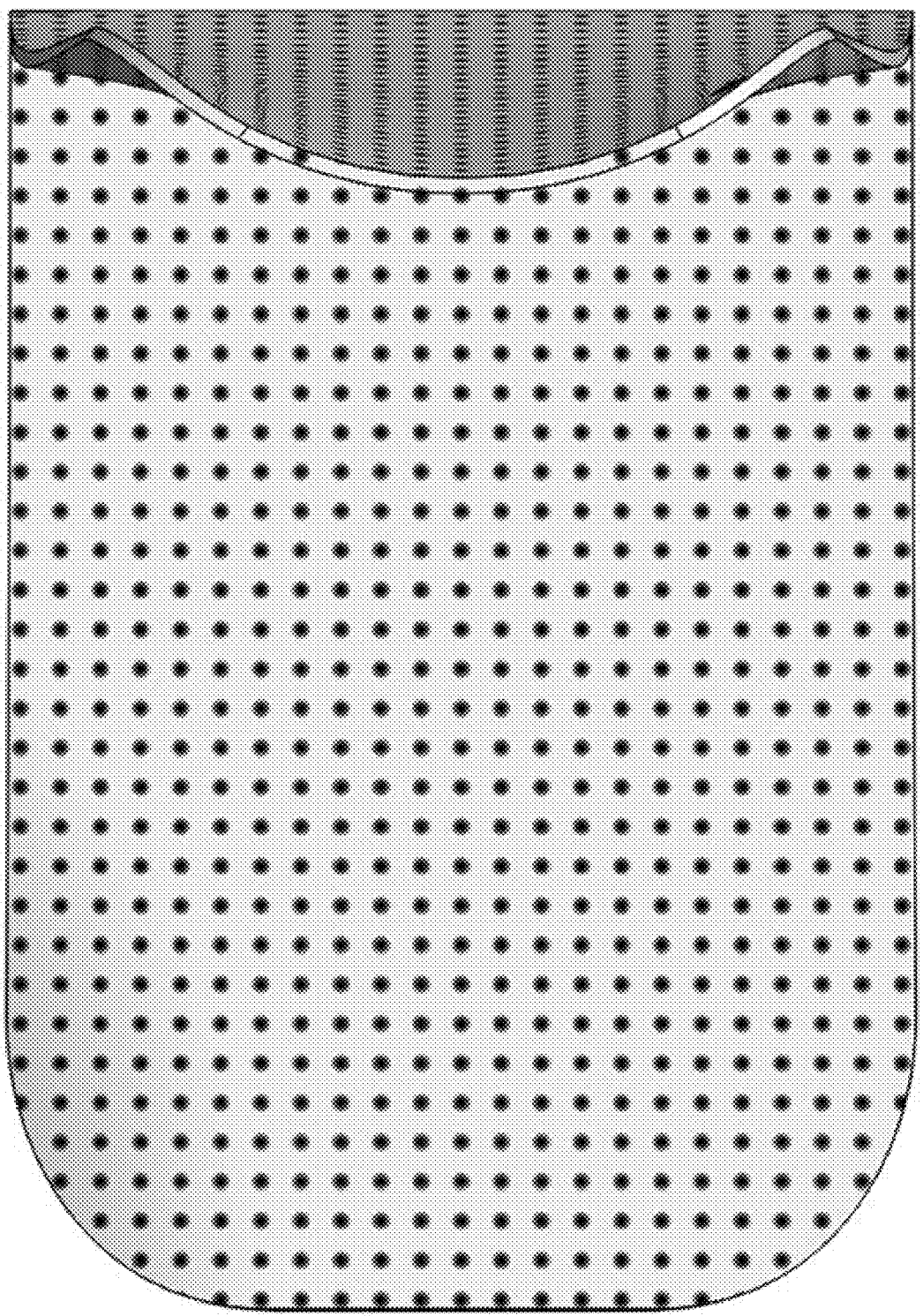
FIG. 69 illustrates a top view of a preferred exemplary embodiment of an angular secondary plate (ASP) (incorporating a curved angular base plate (ABP) and a curved angular vertical plate (AVP)) useful in some preferred invention embodiments.
Figure 70:
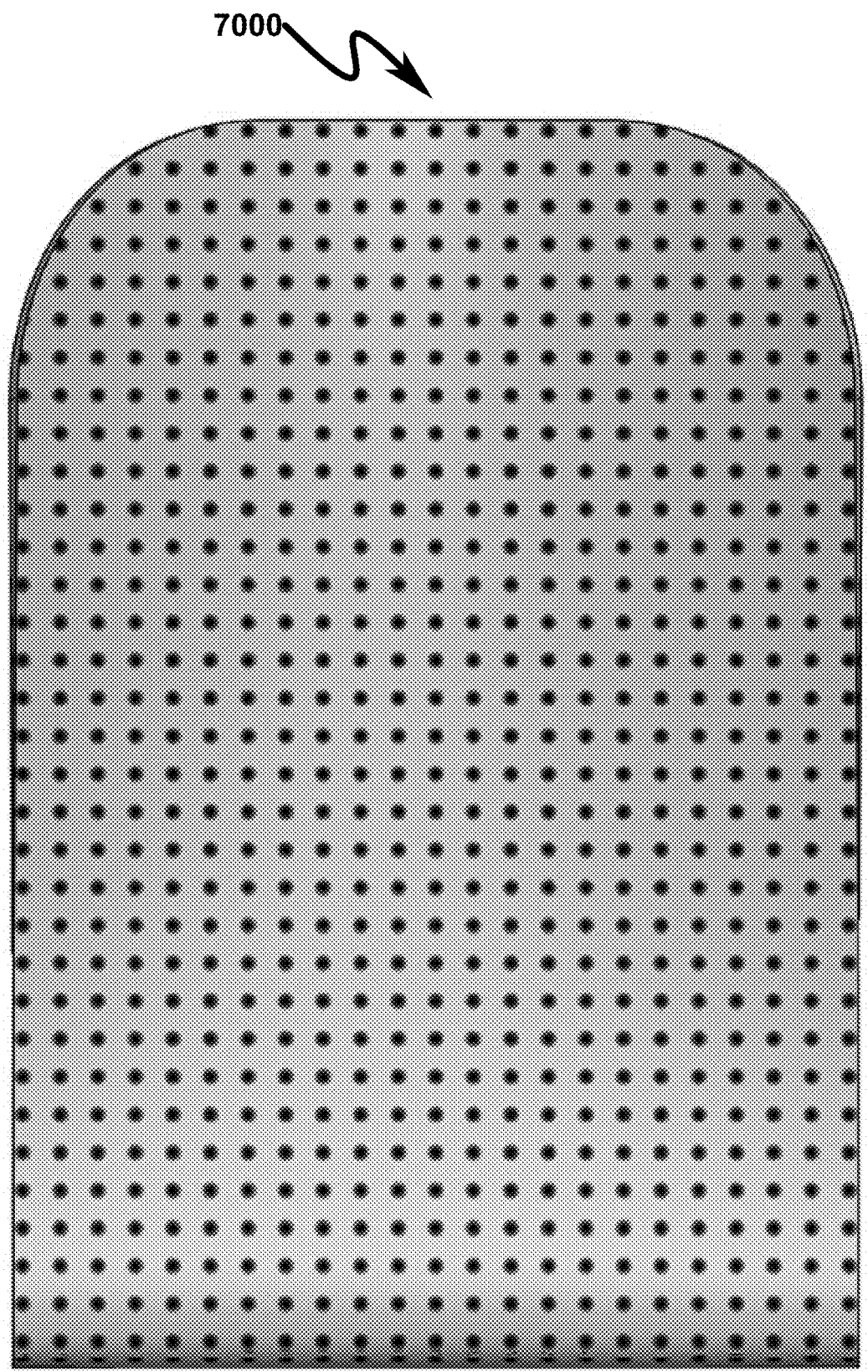
FIG. 70 illustrates a bottom view of a preferred exemplary embodiment of an angular secondary plate (ASP) (incorporating a curved angular base plate (ABP) and a curved angular vertical plate (AVP)) useful in some preferred invention embodiments.
Figure 71:
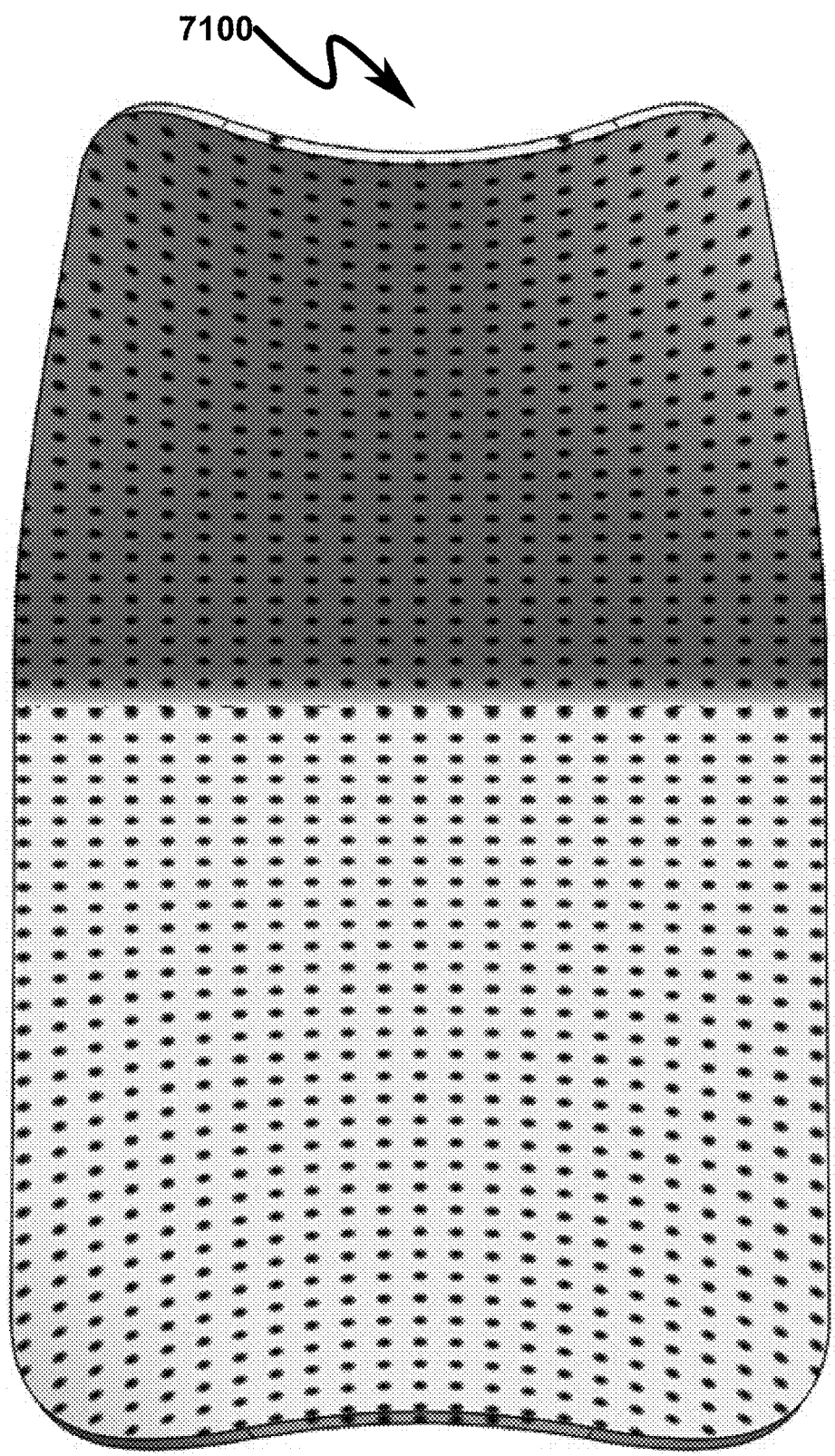
FIG. 71 illustrates a top front diagonal view of a preferred exemplary embodiment of an angular secondary plate (ASP) (incorporating a curved angular base plate (ABP) and a curved angular vertical plate (AVP)) useful in some preferred invention embodiments.
Figure 72:
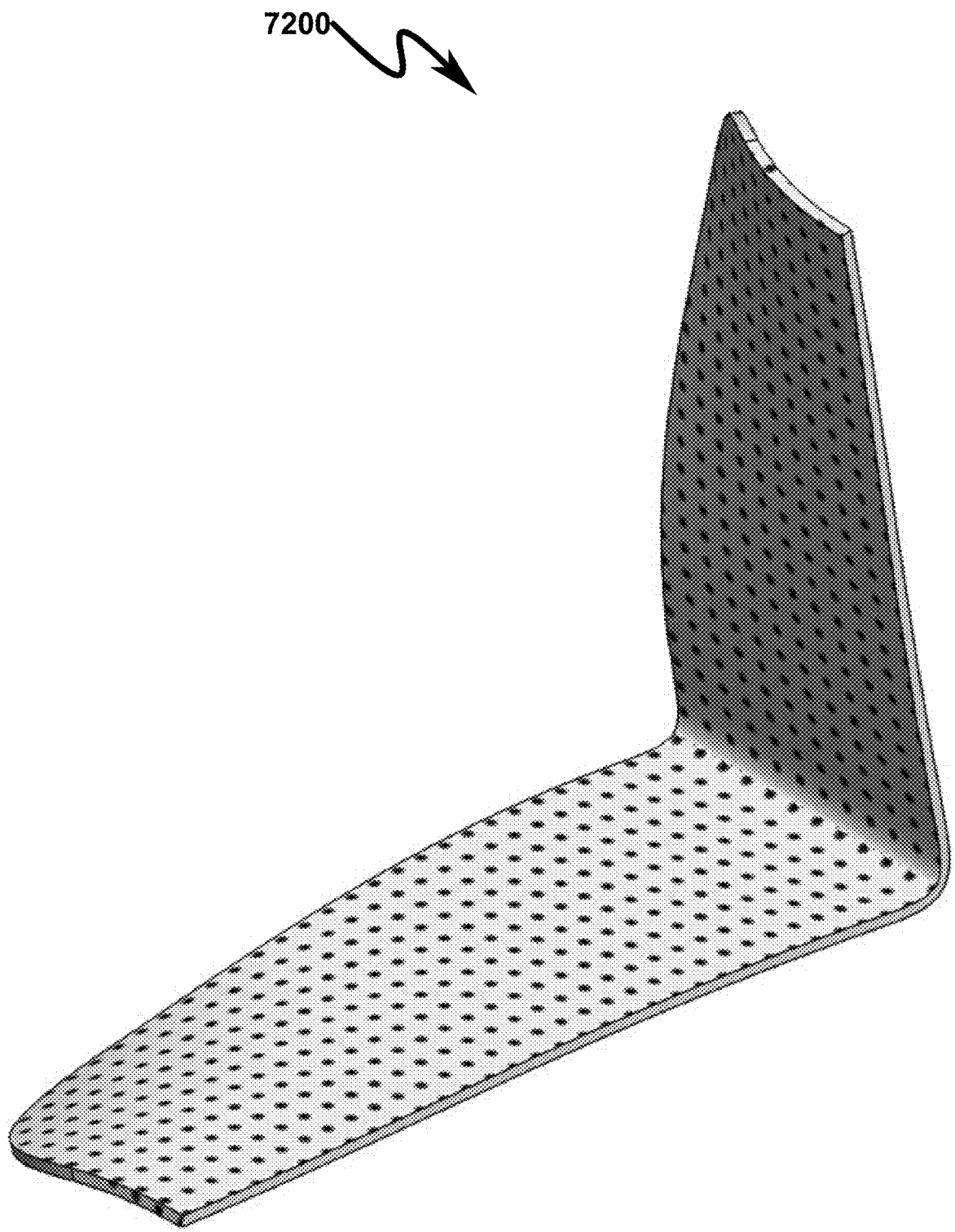
FIG. 72 illustrates a front top right perspective section view of a preferred exemplary embodiment of an angular secondary plate (ASP) (incorporating a curved angular base plate (ABP) and a curved angular vertical plate (AVP)) useful in some preferred invention embodiments.
Figure 73:
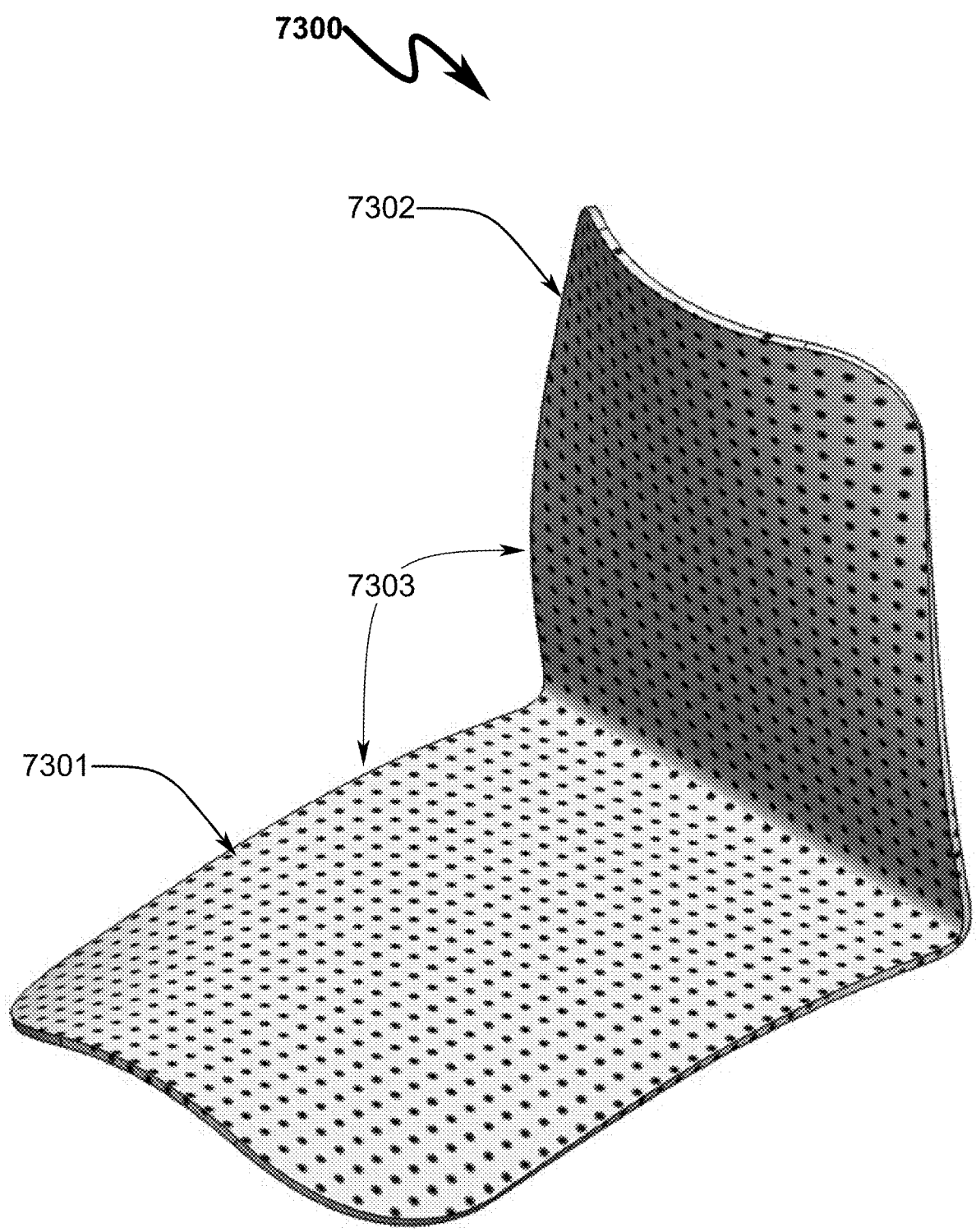
FIG. 73 illustrates a front top right perspective view of a preferred exemplary embodiment of an angular secondary plate (ASP) (incorporating a curved angular base plate (ABP) and a curved angular vertical plate (AVP)) useful in some preferred invention embodiments.
Figure 74:
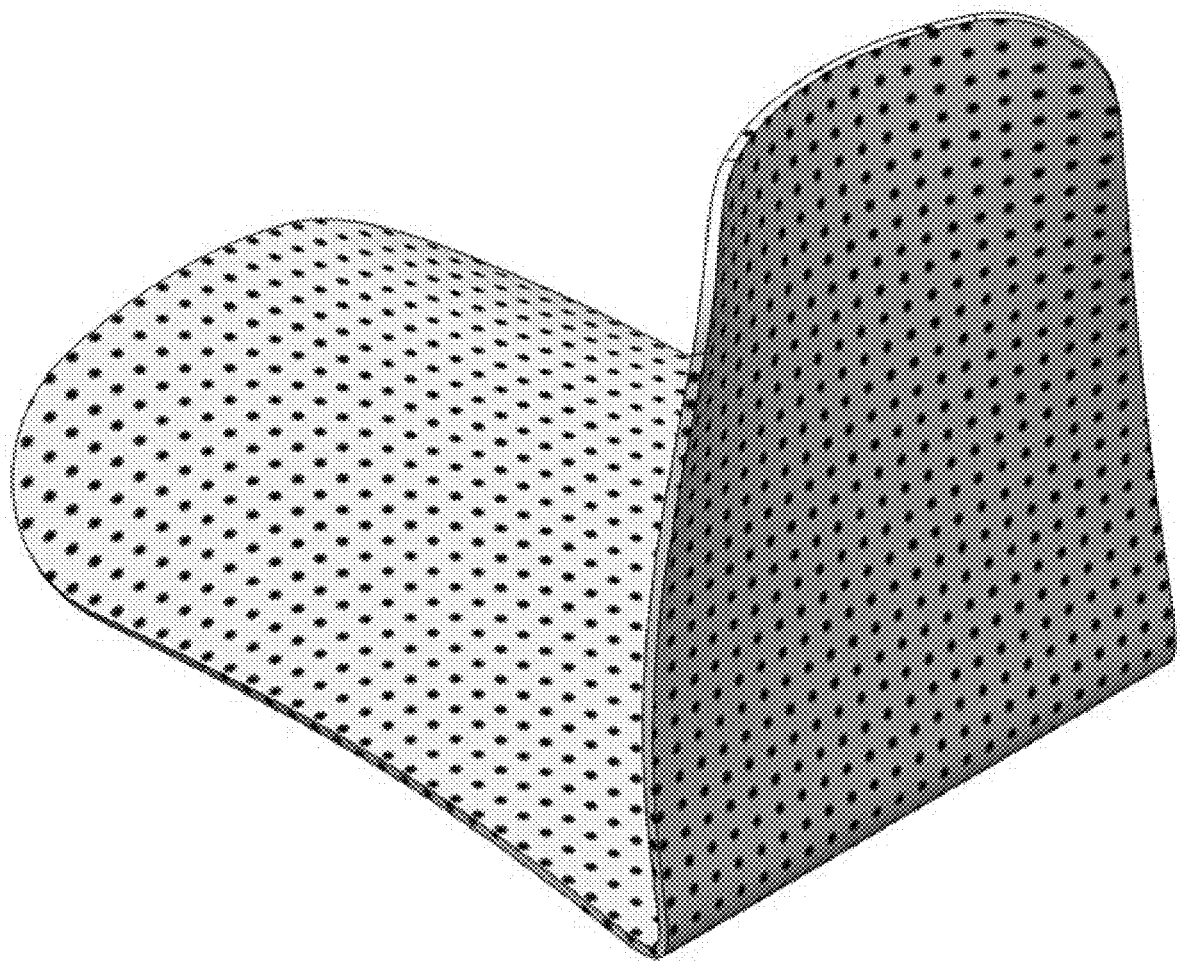
FIG. 74 illustrates a rear top right perspective view of a preferred exemplary embodiment of an angular secondary plate (ASP) (incorporating a curved angular base plate (ABP) and a curved angular vertical plate (AVP)) useful in some preferred invention embodiments.
Figure 75:
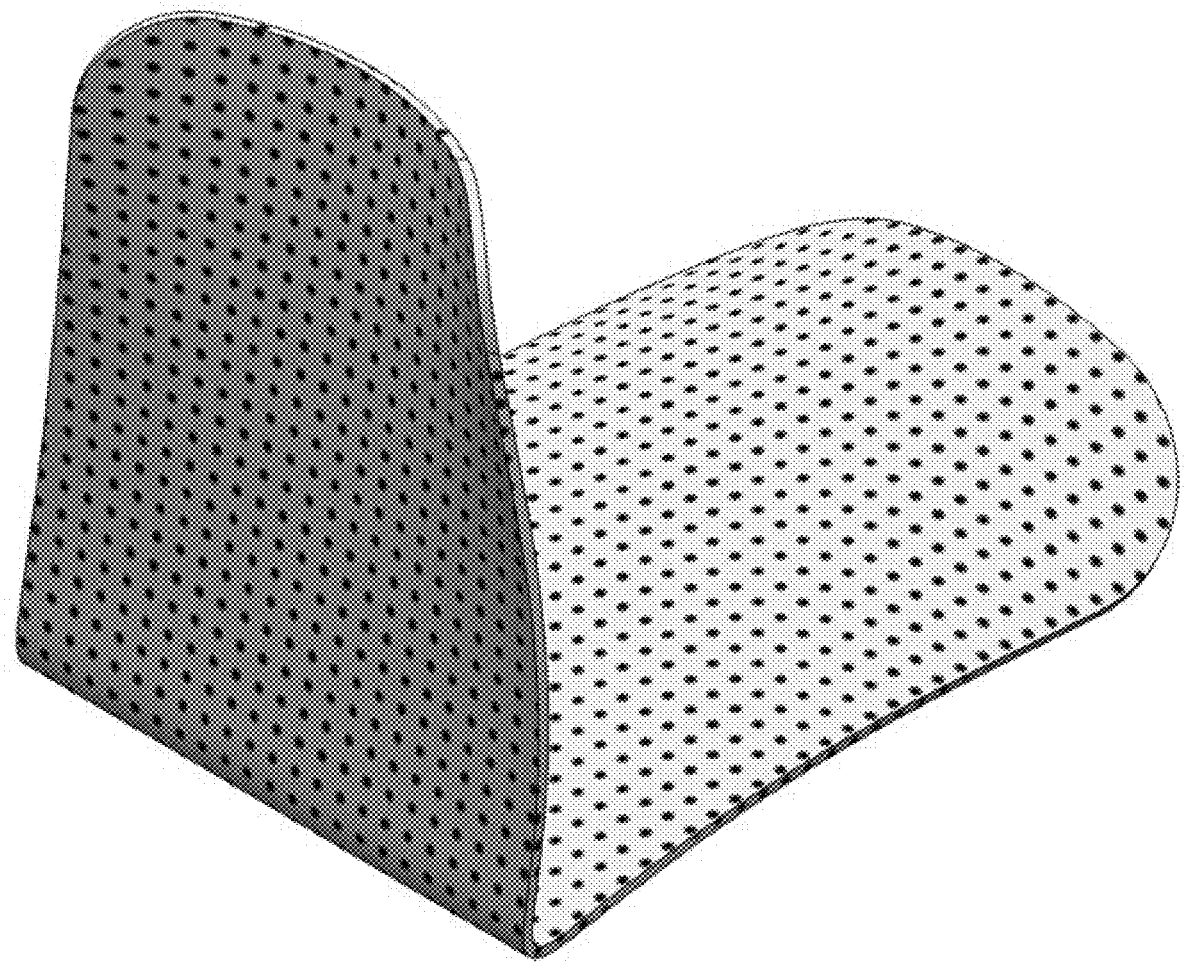
FIG. 75 illustrates a rear top left perspective view of a preferred exemplary embodiment of an angular secondary plate (ASP) (incorporating a curved angular base plate (ABP) and a curved angular vertical plate (AVP)) useful in some preferred invention embodiments.
Figure 76:
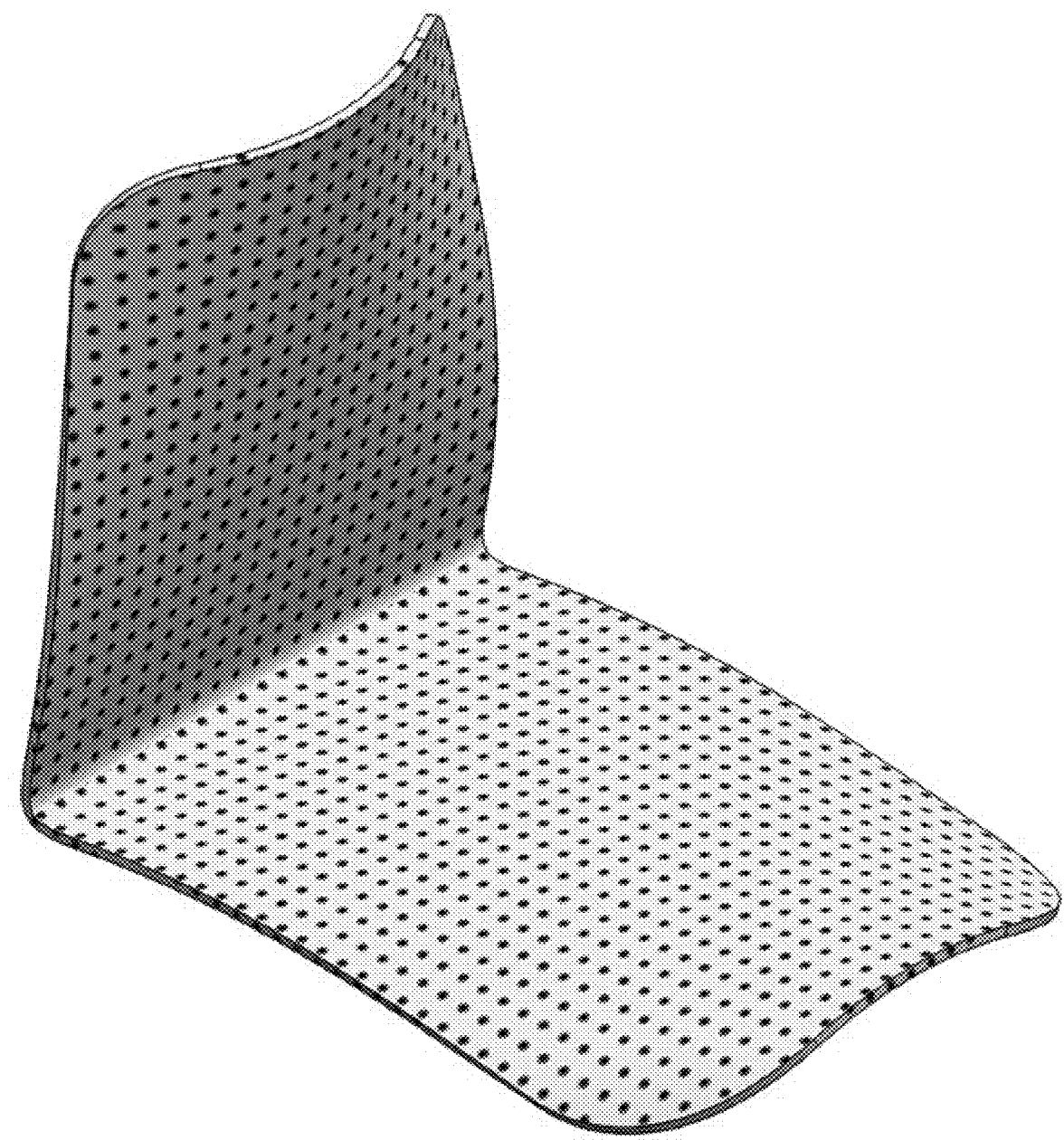
FIG. 76 illustrates a front top left perspective view of a preferred exemplary embodiment of an angular secondary plate (ASP) (incorporating a curved angular base plate (ABP) and a curved angular vertical plate (AVP)) useful in some preferred invention embodiments.
Figure 77:
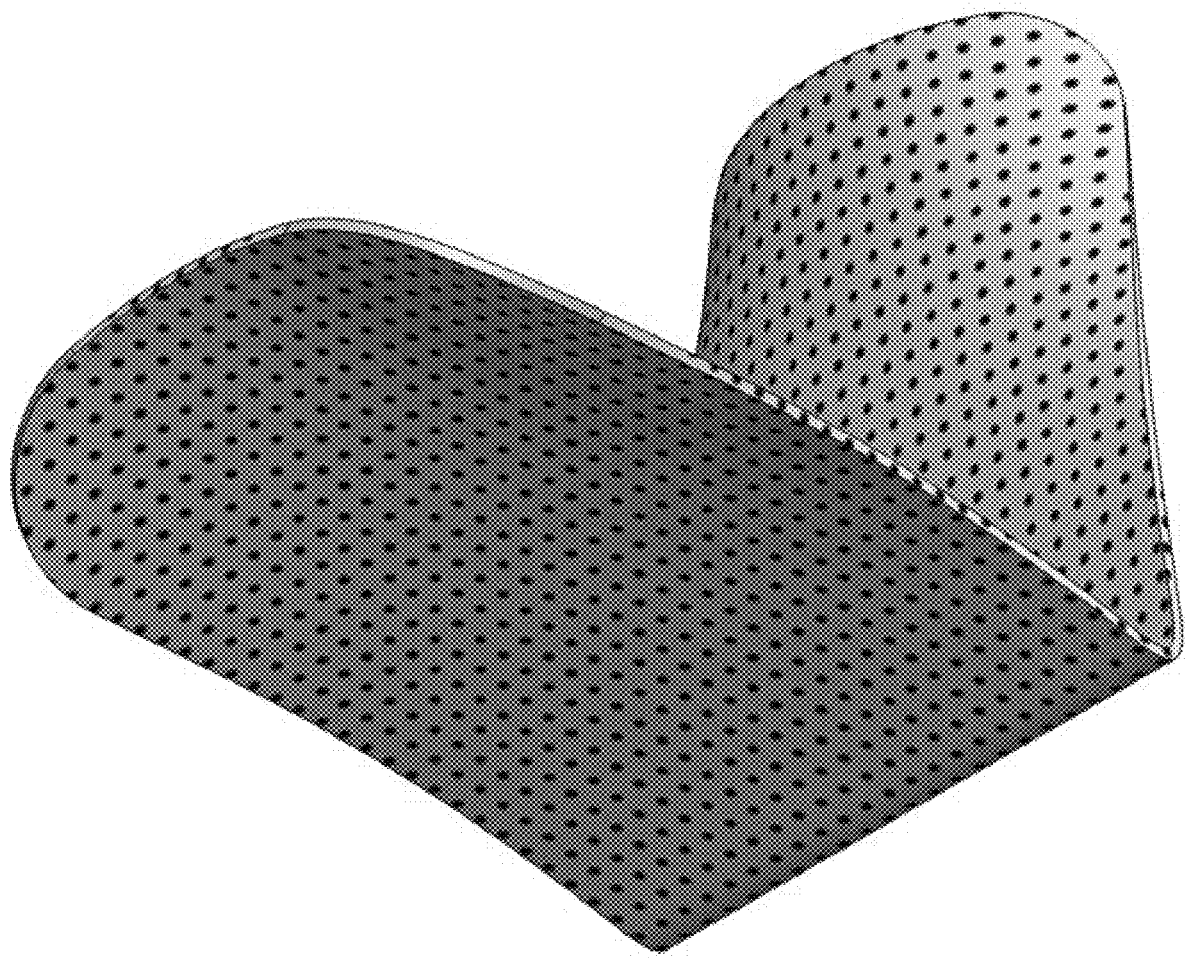
FIG. 77 illustrates a front bottom right perspective view of a preferred exemplary embodiment of an angular secondary plate (ASP) (incorporating a curved angular base plate (ABP) and a curved angular vertical plate (AVP)) useful in some preferred invention embodiments.
Figure 78:
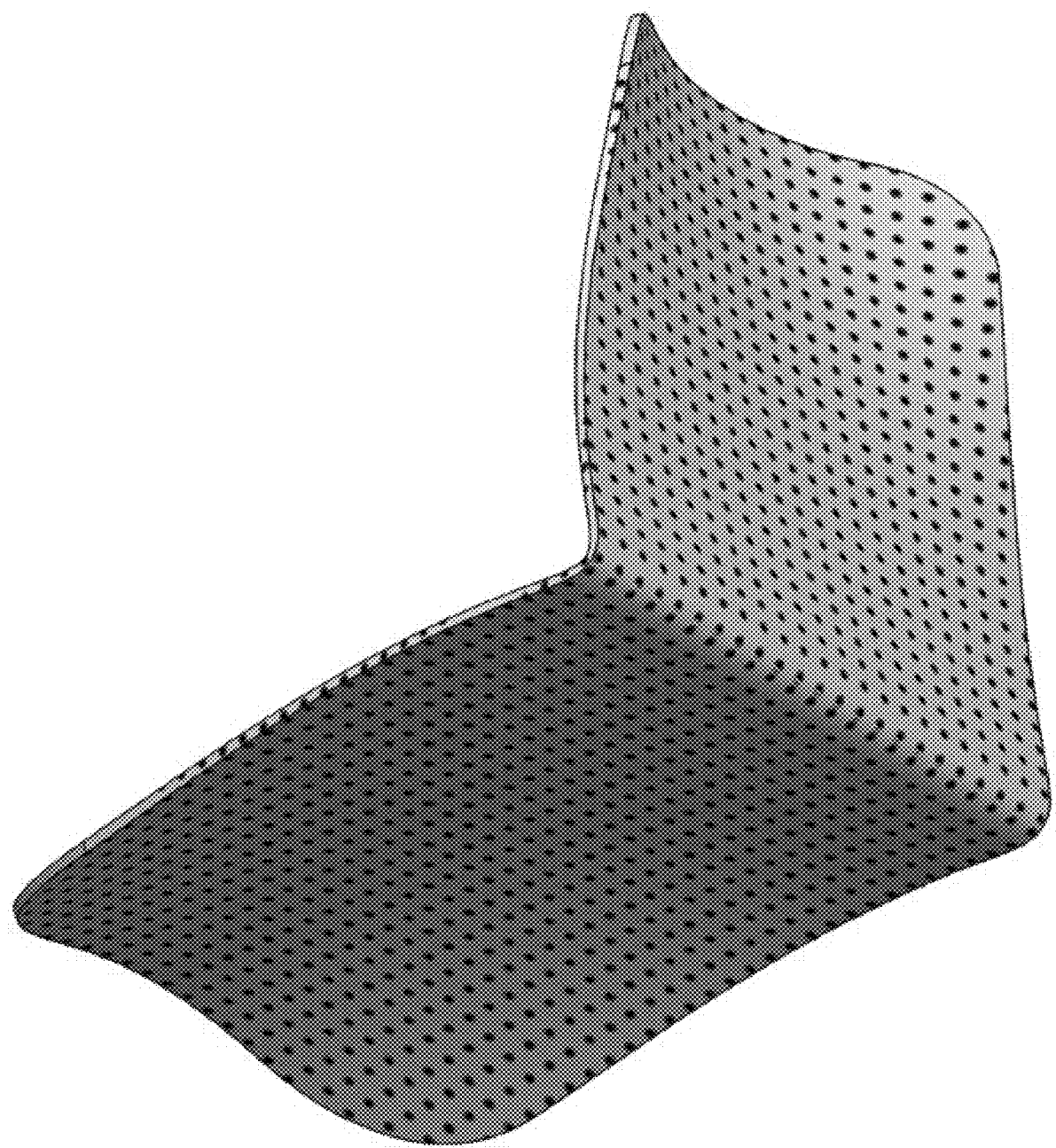
FIG. 78 illustrates a rear bottom right perspective view of a preferred exemplary embodiment of an angular secondary plate (ASP) (incorporating a curved angular base plate (ABP) and a curved angular vertical plate (AVP)) useful in some preferred invention embodiments.
Figure 79:
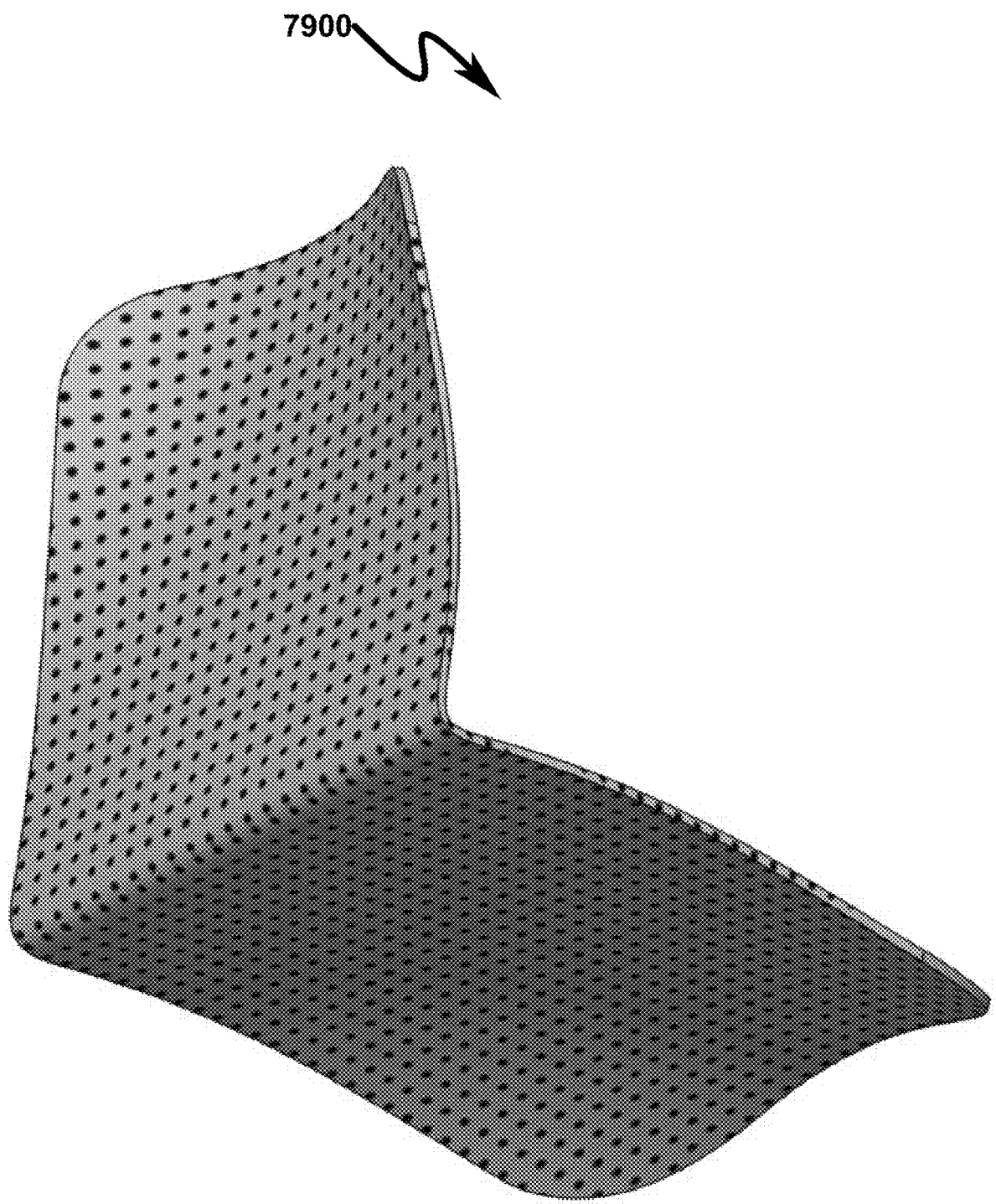
FIG. 79 illustrates a rear bottom left perspective view of a preferred exemplary embodiment of an angular secondary plate (ASP) (incorporating a curved angular base plate (ABP) and a curved angular vertical plate (AVP)) useful in some preferred invention embodiments.
Figure 80:
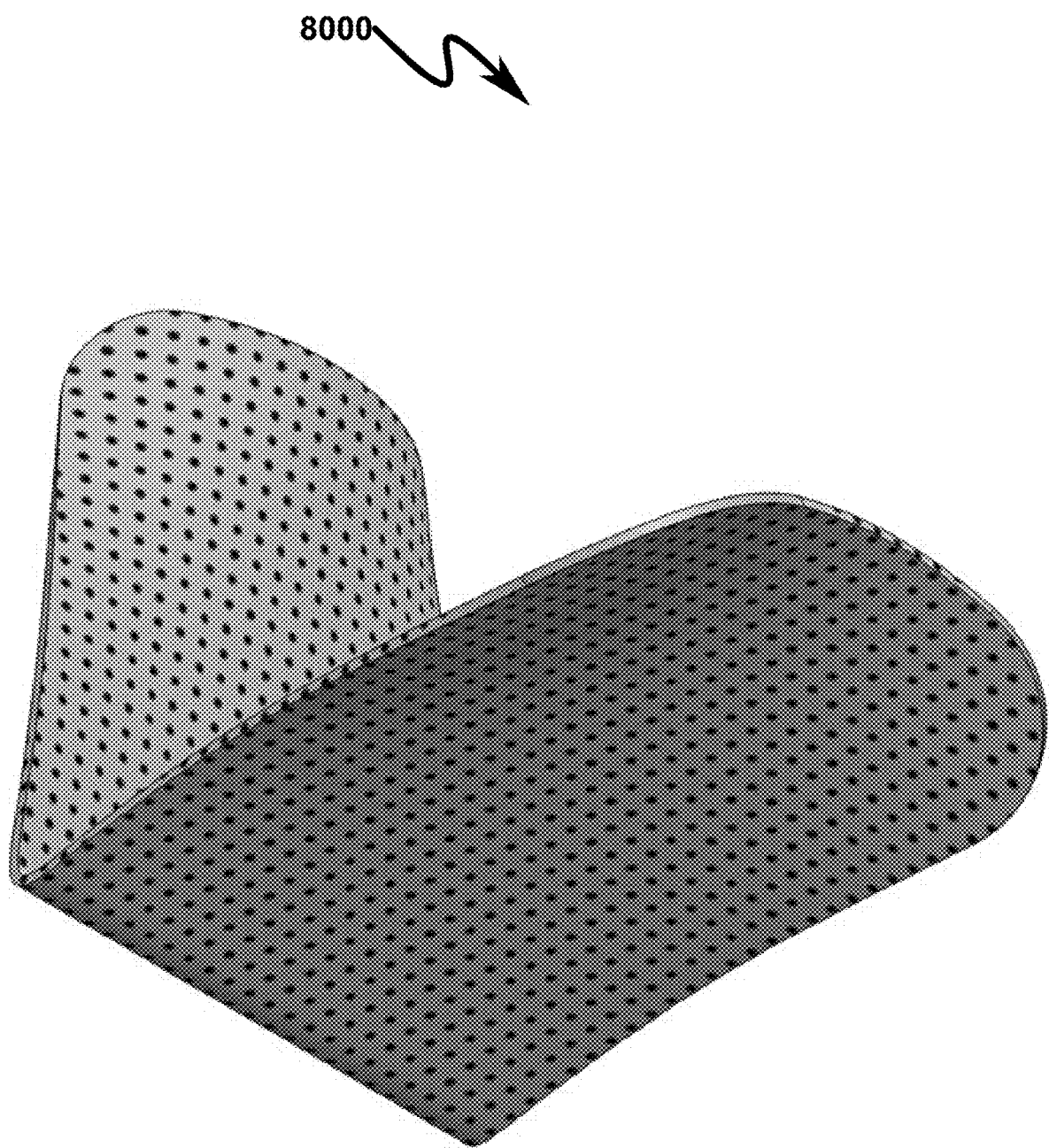
FIG. 80 illustrates a front bottom left perspective view of a preferred exemplary embodiment of an angular secondary plate (ASP) (incorporating a curved angular base plate (ABP) and a curved angular vertical plate (AVP)) useful in some preferred invention embodiments.
Figure 81:
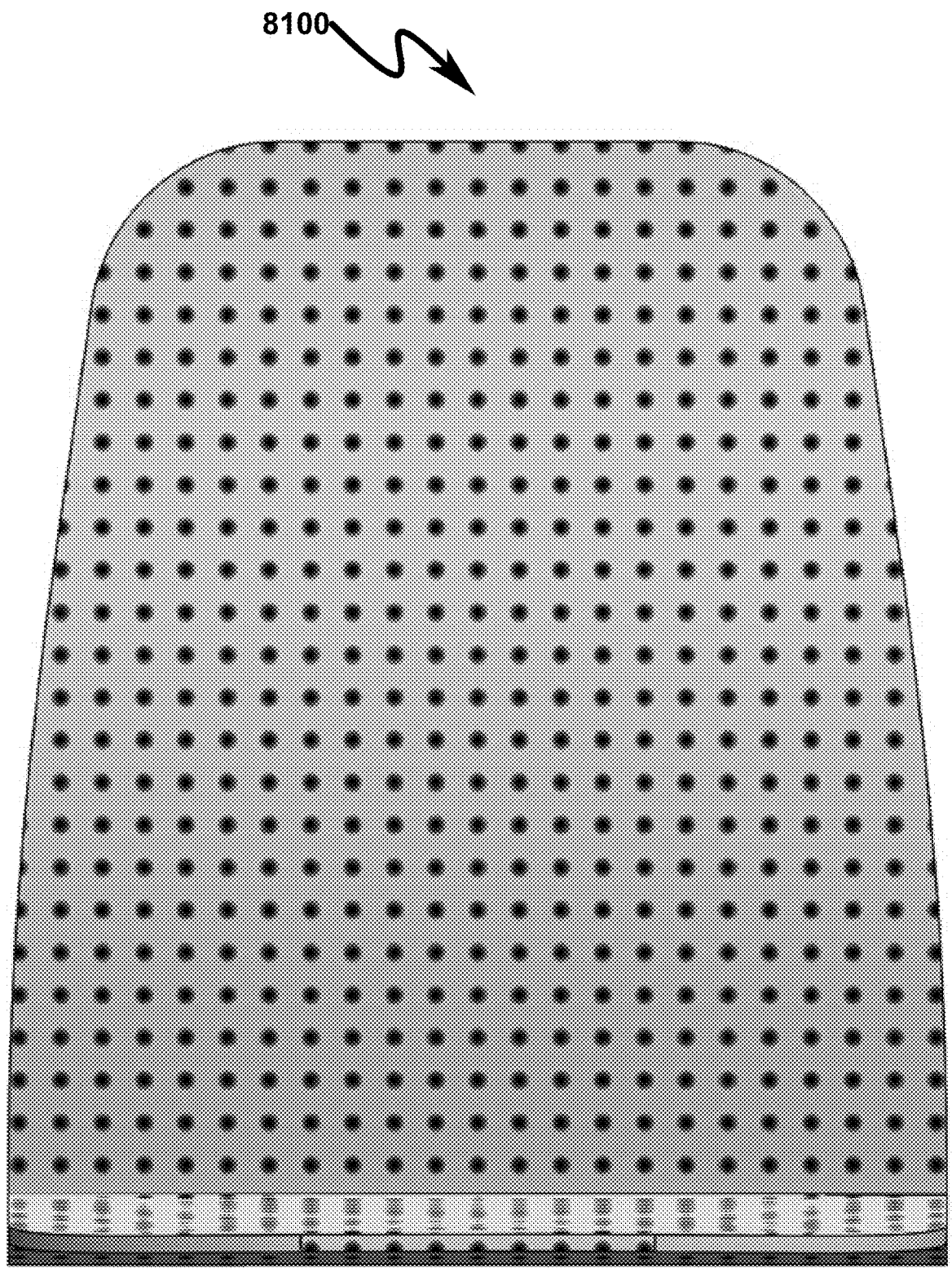
FIG. 81 illustrates a front view of a preferred exemplary embodiment of an angular secondary plate (ASP) (incorporating a flat angular base plate (ABP) and a curved angular vertical plate (AVP)) useful in some preferred invention embodiments.
Figure 82:
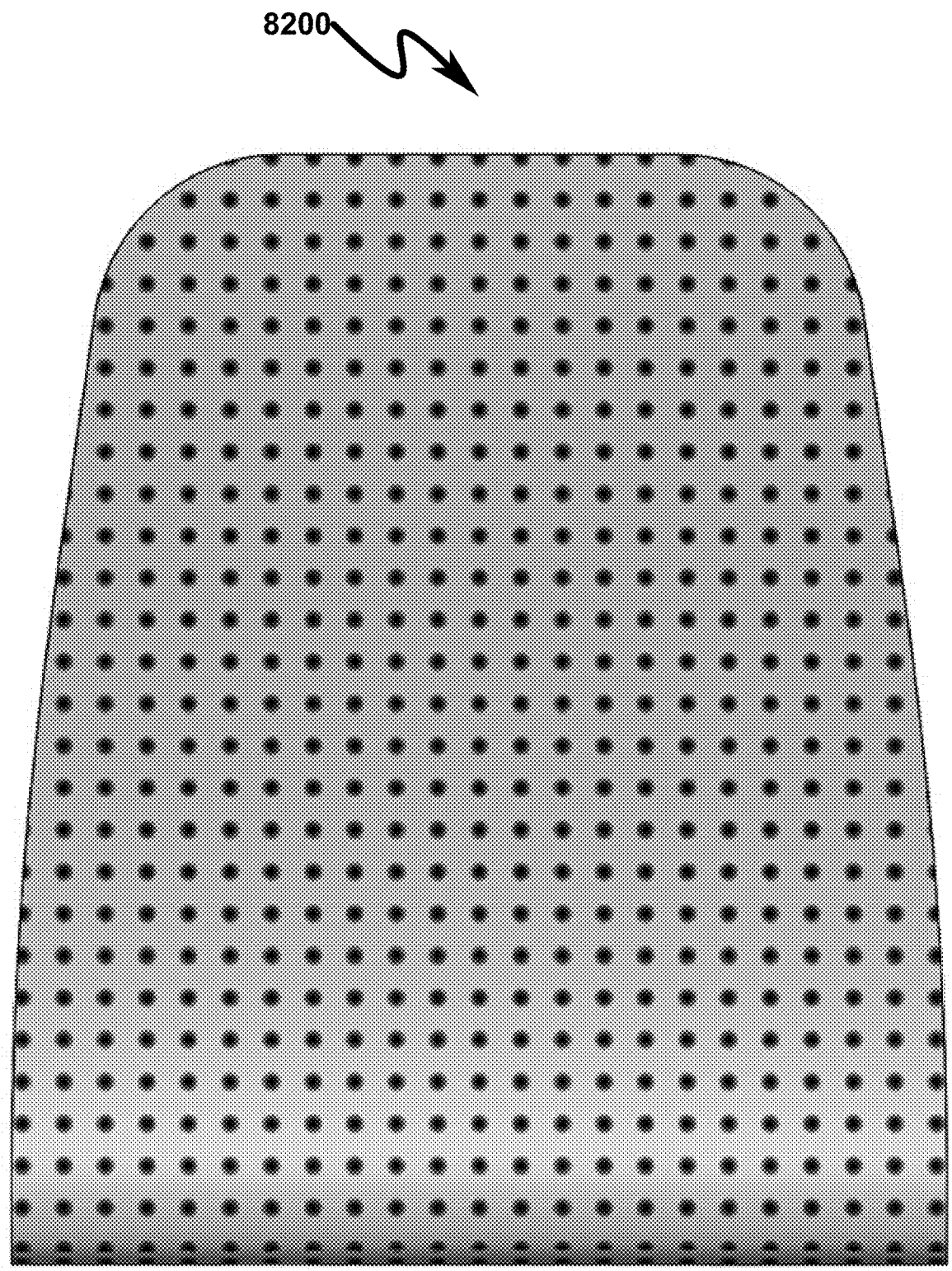
FIG. 82 illustrates a rear view of a preferred exemplary embodiment of an angular secondary plate (ASP) (incorporating a flat angular base plate (ABP) and a curved angular vertical plate (AVP)) useful in some preferred invention embodiments.
Figure 83:
FIG. 83 illustrates a left side view of a preferred exemplary embodiment of an angular secondary plate (ASP) (incorporating a flat angular base plate (ABP) and a curved angular vertical plate (AVP)) useful in some preferred invention embodiments.
Figure 84:
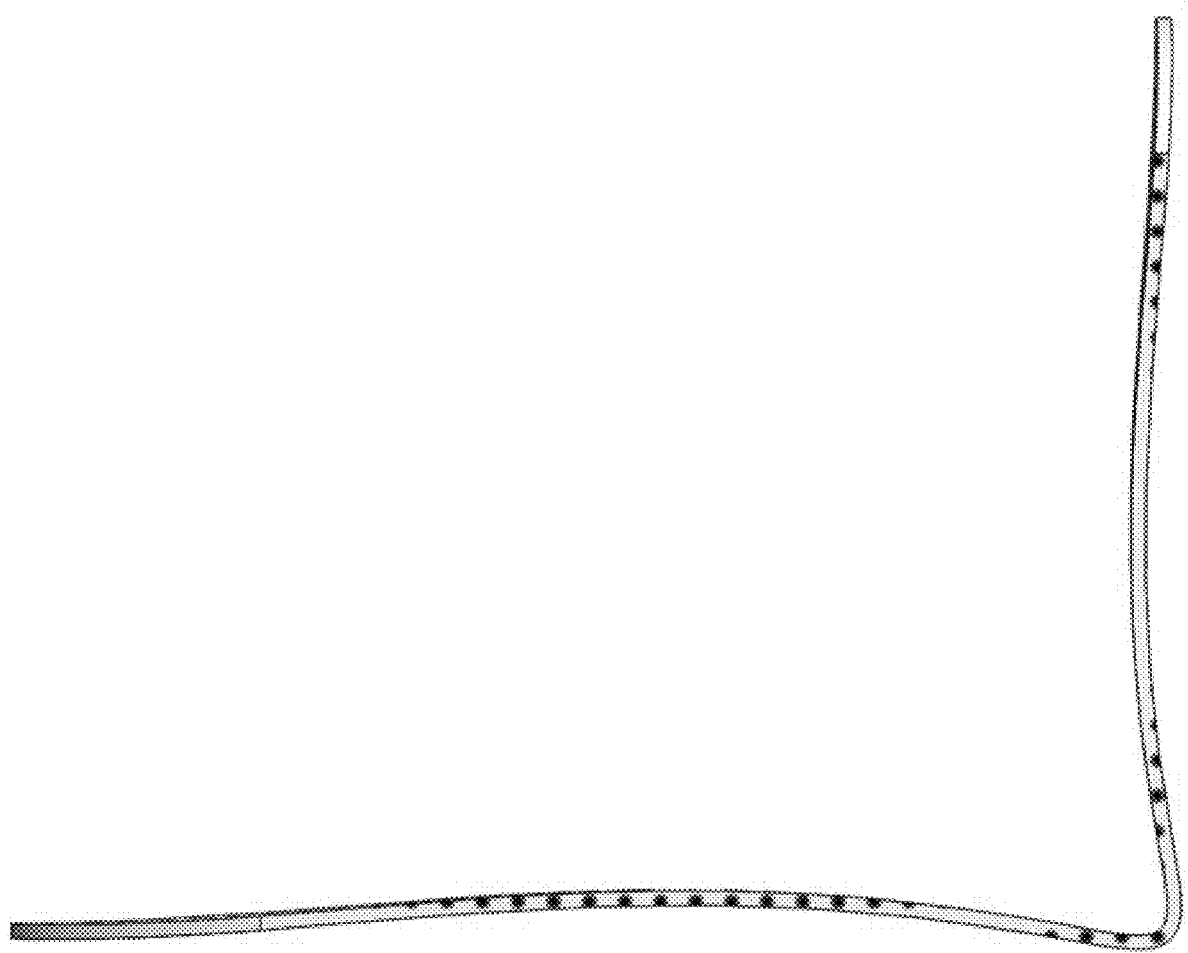
FIG. 84 illustrates a right side view of a preferred exemplary embodiment of an angular secondary plate (ASP) (incorporating a flat angular base plate (ABP) and a curved angular vertical plate (AVP)) useful in some preferred invention embodiments.
Figure 85:
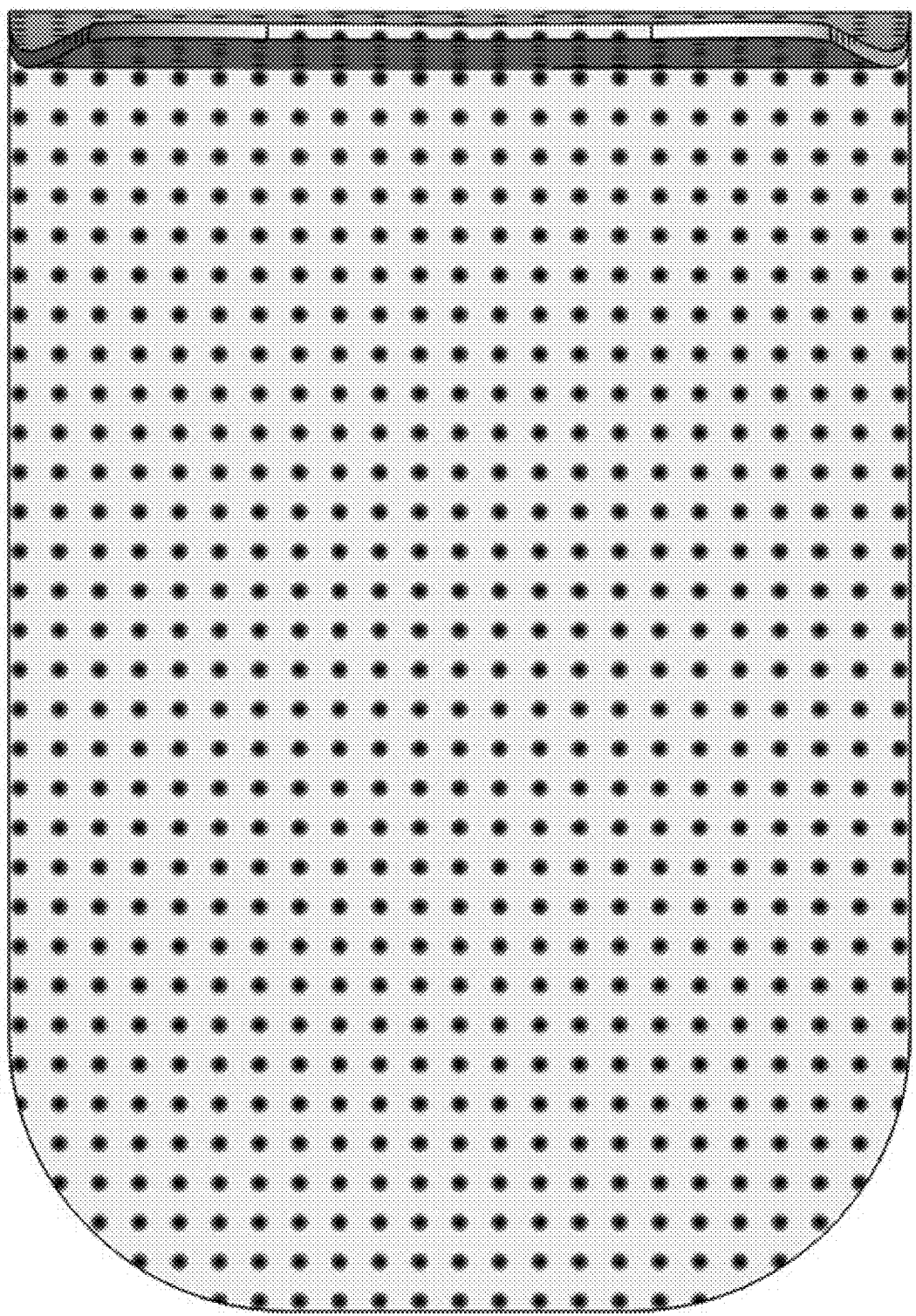
FIG. 85 illustrates a top view of a preferred exemplary embodiment of an angular secondary plate (ASP) (incorporating a flat angular base plate (ABP) and a curved angular vertical plate (AVP)) useful in some preferred invention embodiments.
Figure 86:
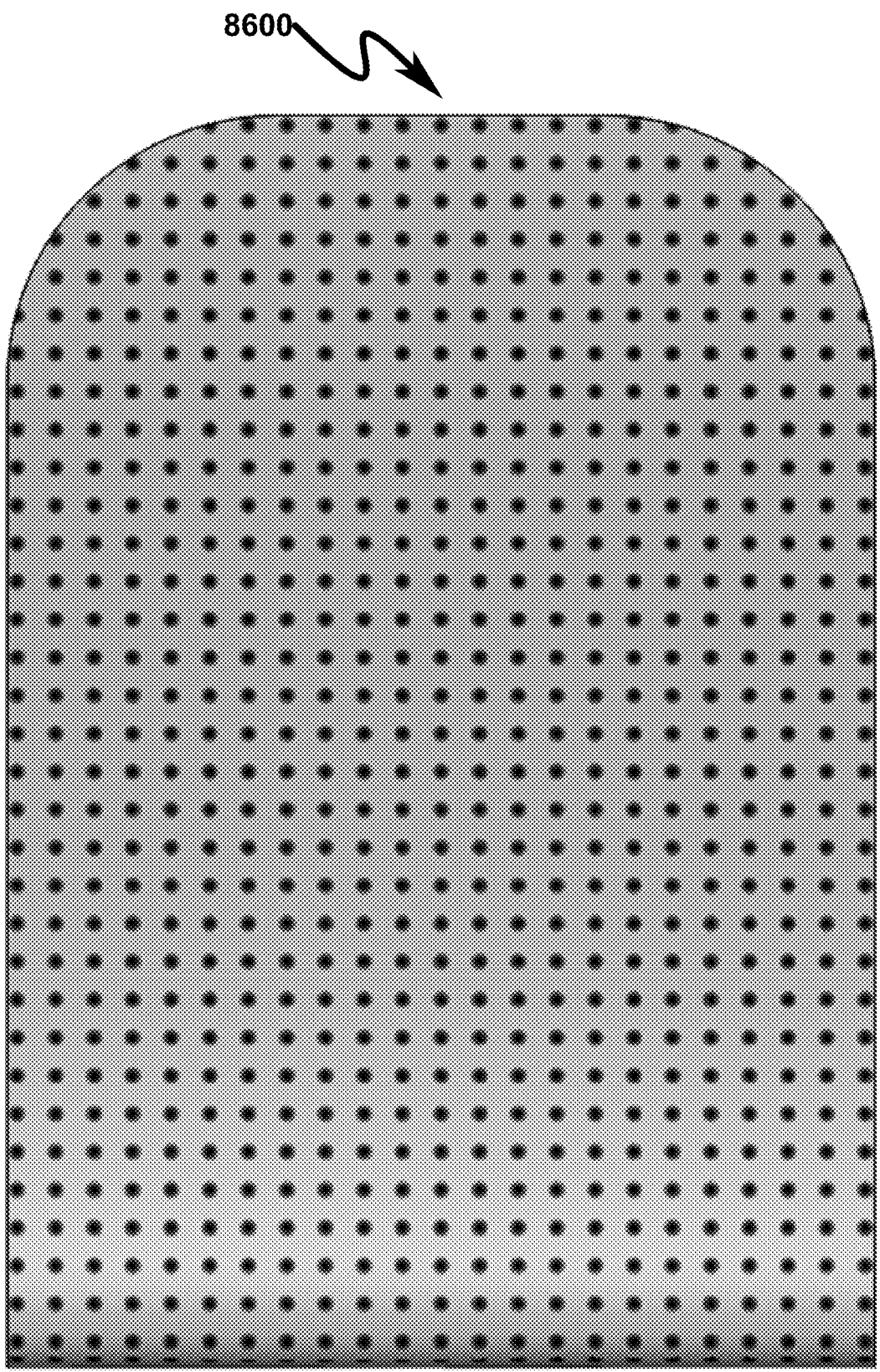
FIG. 86 illustrates a bottom view of a preferred exemplary embodiment of an angular secondary plate (ASP) (incorporating a flat angular base plate (ABP) and a curved angular vertical plate (AVP)) useful in some preferred invention embodiments.
Figure 87:
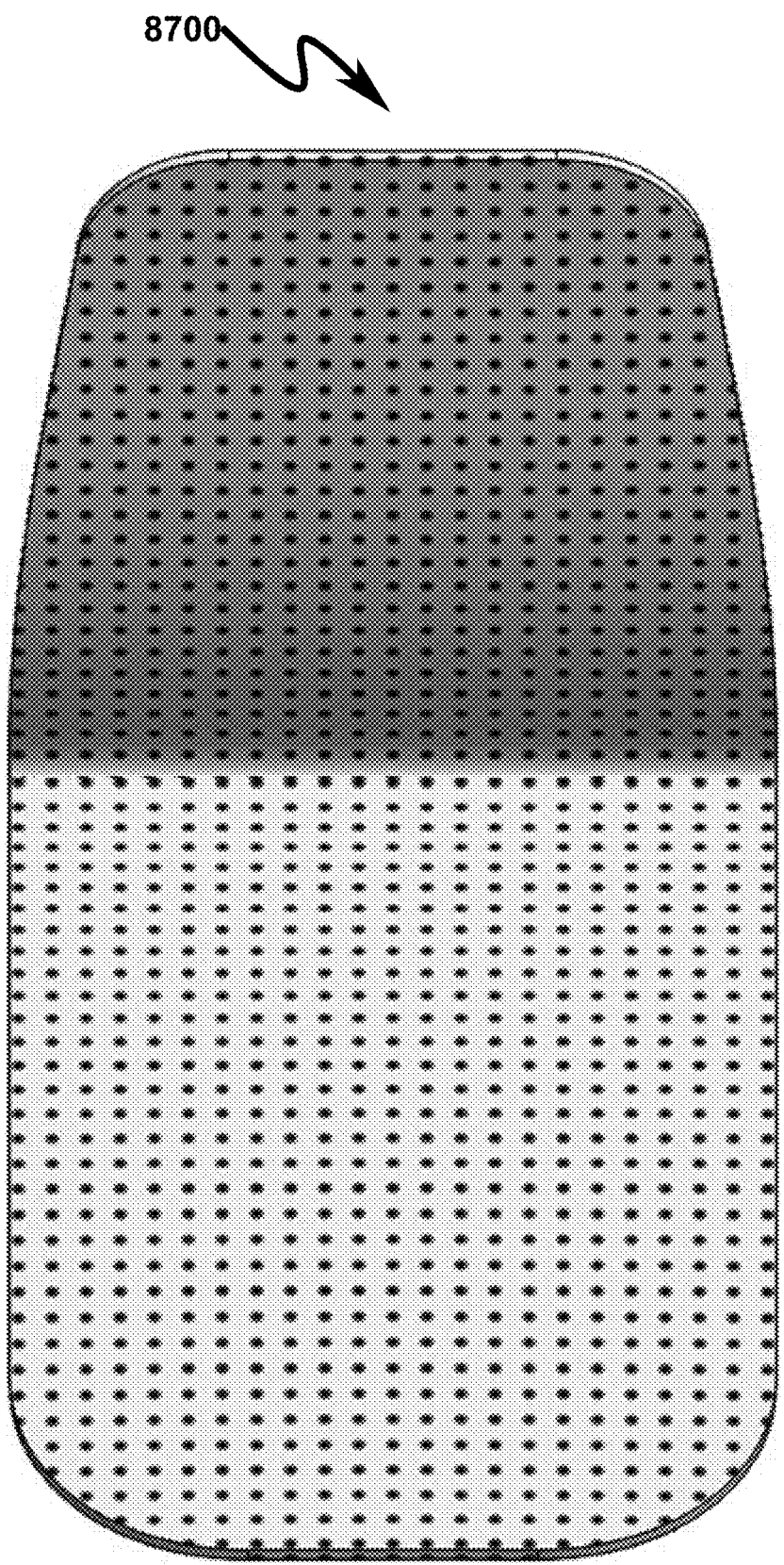
FIG. 87 illustrates a top front diagonal view of a preferred exemplary embodiment of an angular secondary plate (ASP) (incorporating a flat angular base plate (ABP) and a curved angular vertical plate (AVP)) useful in some preferred invention embodiments.
Figure 88:
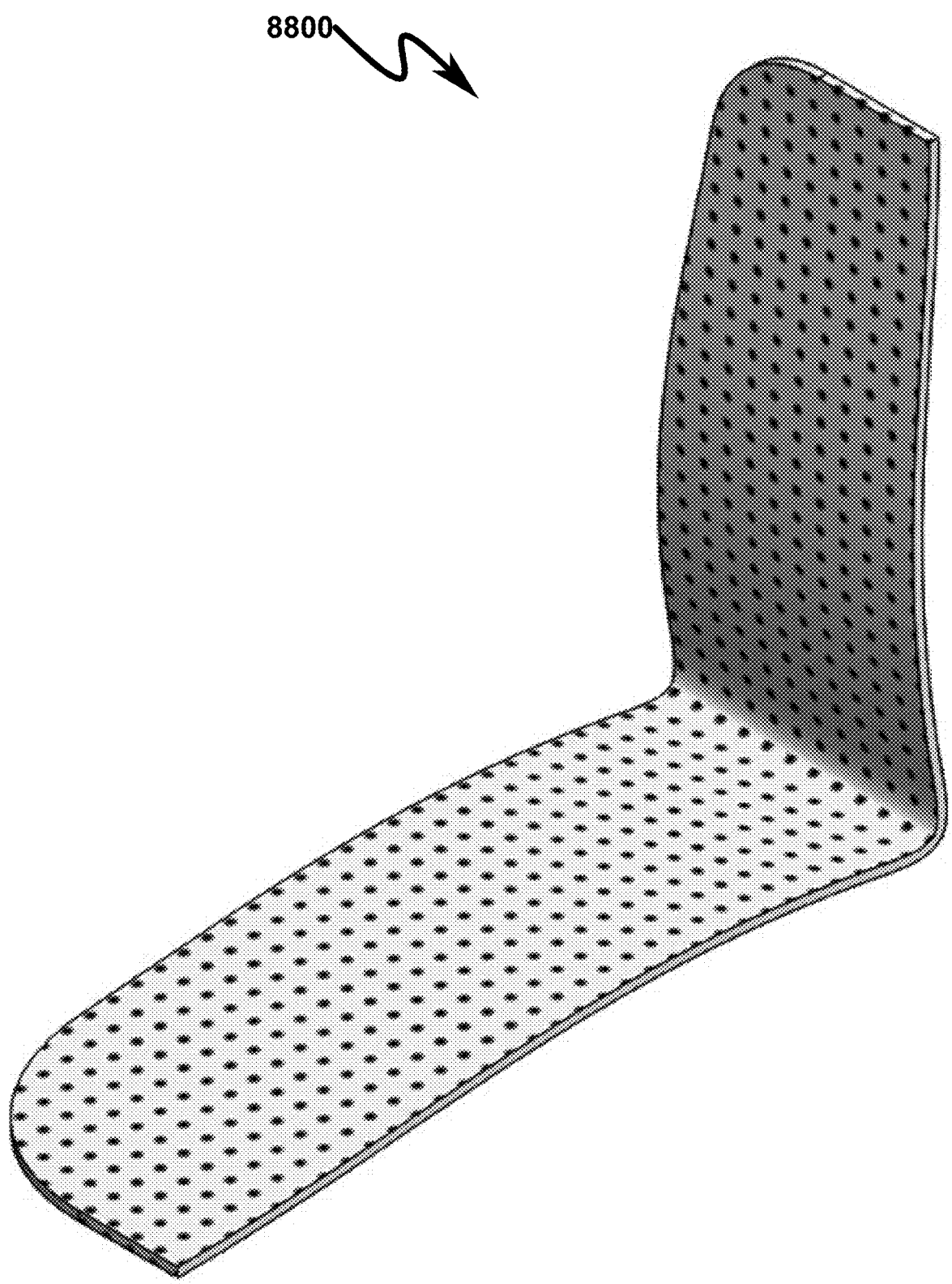
FIG. 88 illustrates a front top right perspective section view of a preferred exemplary embodiment of an angular secondary plate (ASP) (incorporating a flat angular base plate (ABP) and a curved angular vertical plate (AVP)) useful in some preferred invention embodiments.
Figure 89:
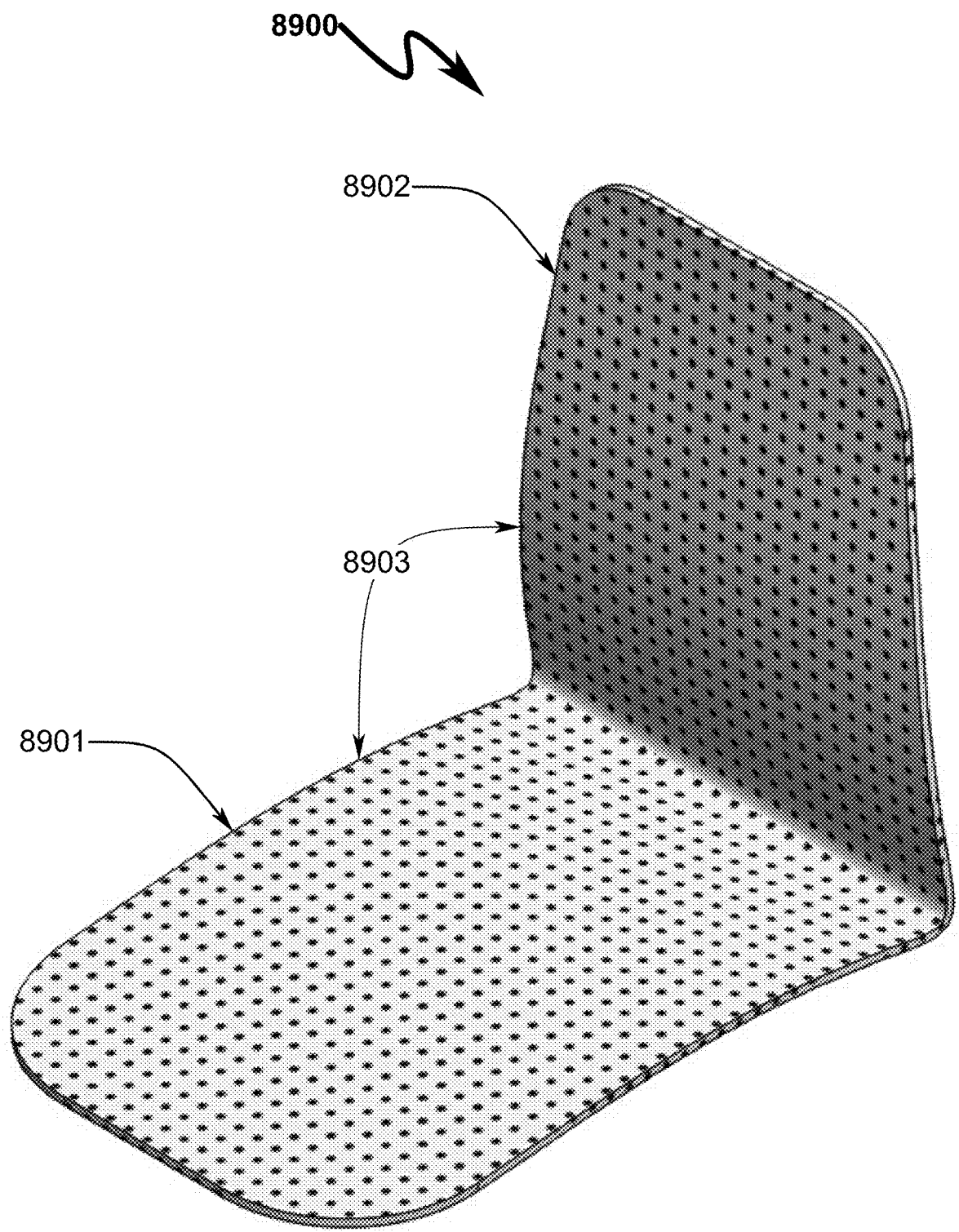
FIG. 89 illustrates a front top right perspective view of a preferred exemplary embodiment of an angular secondary plate (ASP) (incorporating a flat angular base plate (ABP) and a curved angular vertical plate (AVP)) useful in some preferred invention embodiments.
Figure 90:
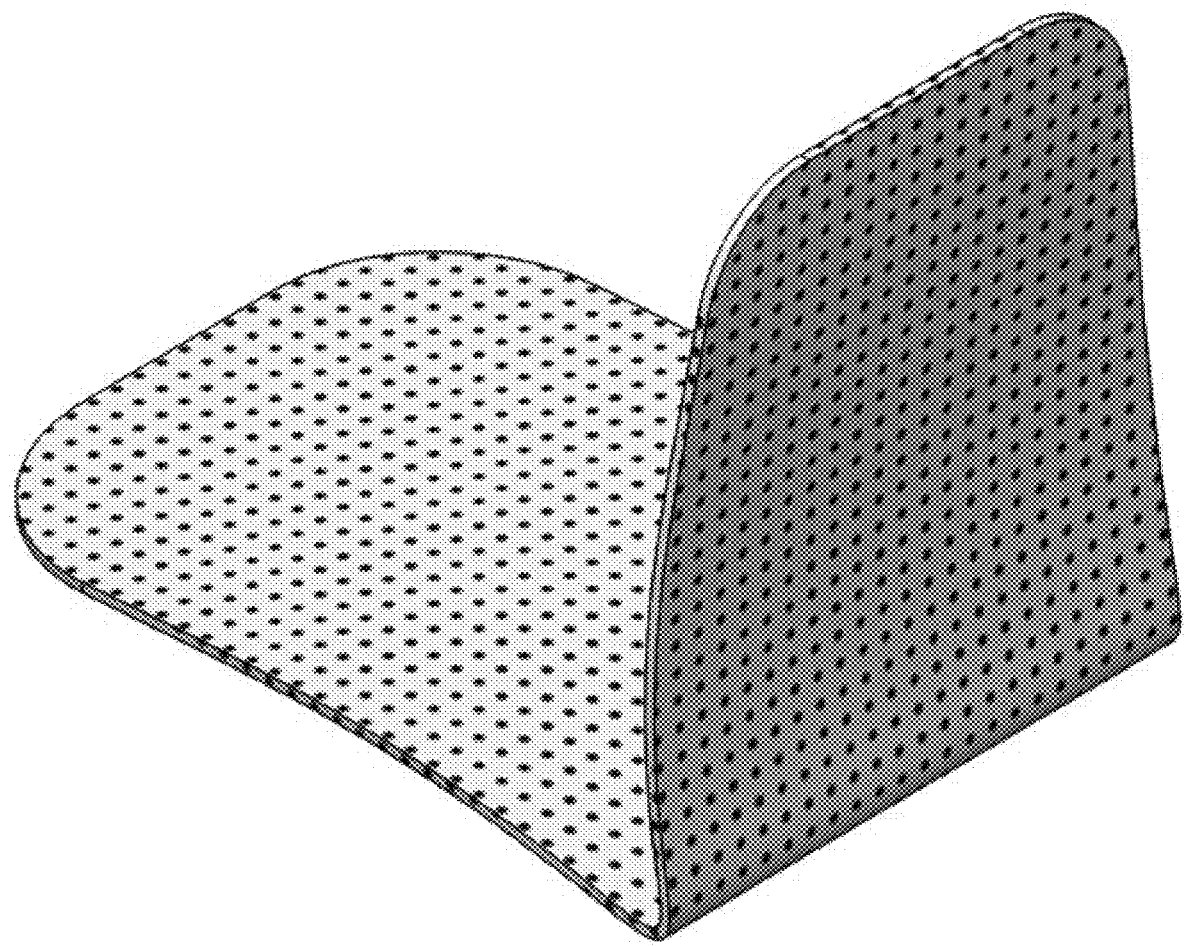
FIG. 90 illustrates a rear top right perspective view of a preferred exemplary embodiment of an angular secondary plate (ASP) (incorporating a flat angular base plate (ABP) and a curved angular vertical plate (AVP)) useful in some preferred invention embodiments.
Figure 91:
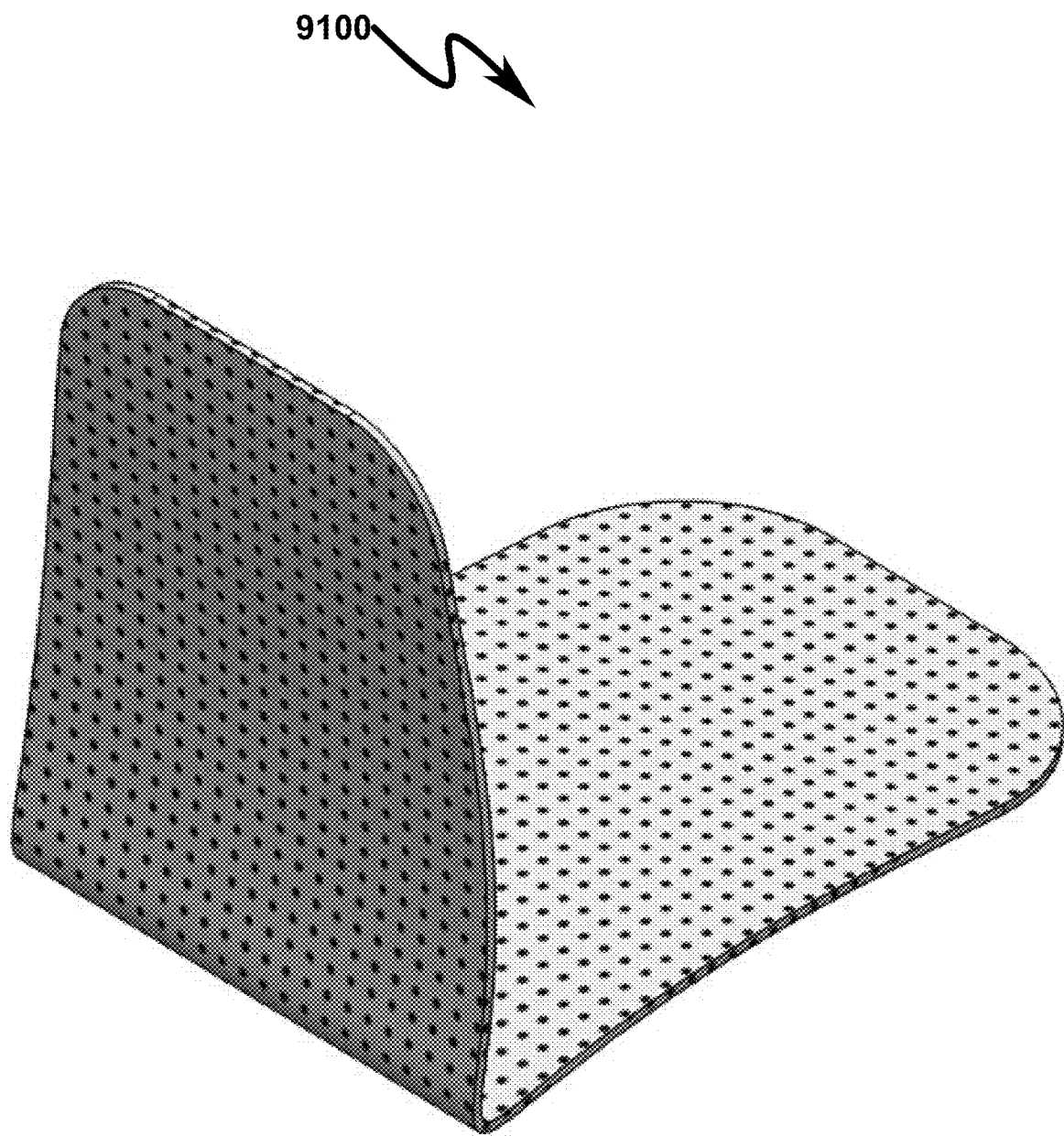
FIG. 91 illustrates a rear top left perspective view of a preferred exemplary embodiment of an angular secondary plate (ASP) (incorporating a flat angular base plate (ABP) and a curved angular vertical plate (AVP)) useful in some preferred invention embodiments.
Figure 92:
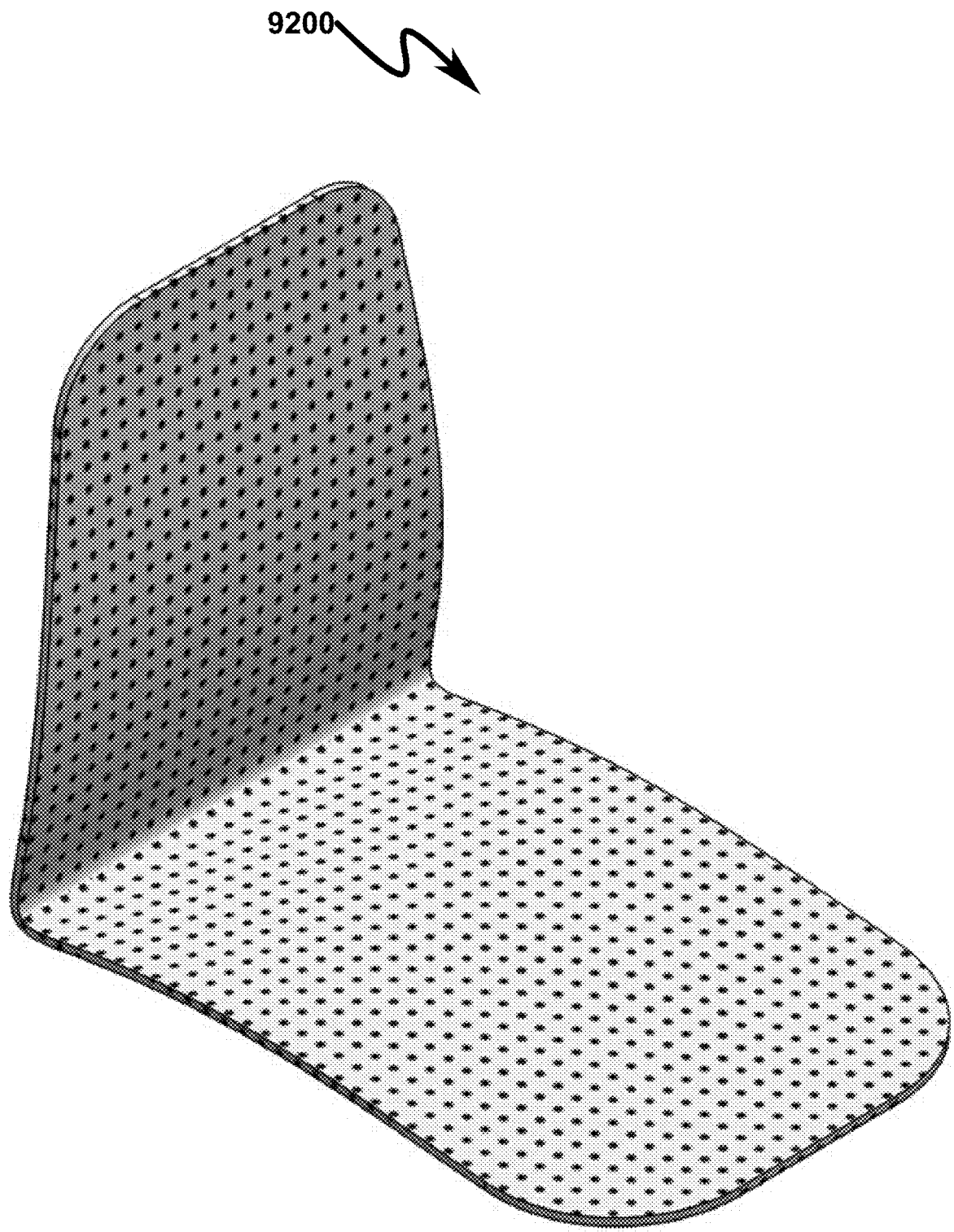
FIG. 92 illustrates a front top left perspective view of a preferred exemplary embodiment of an angular secondary plate (ASP) (incorporating a flat angular base plate (ABP) and a curved angular vertical plate (AVP)) useful in some preferred invention embodiments.
Figure 93:
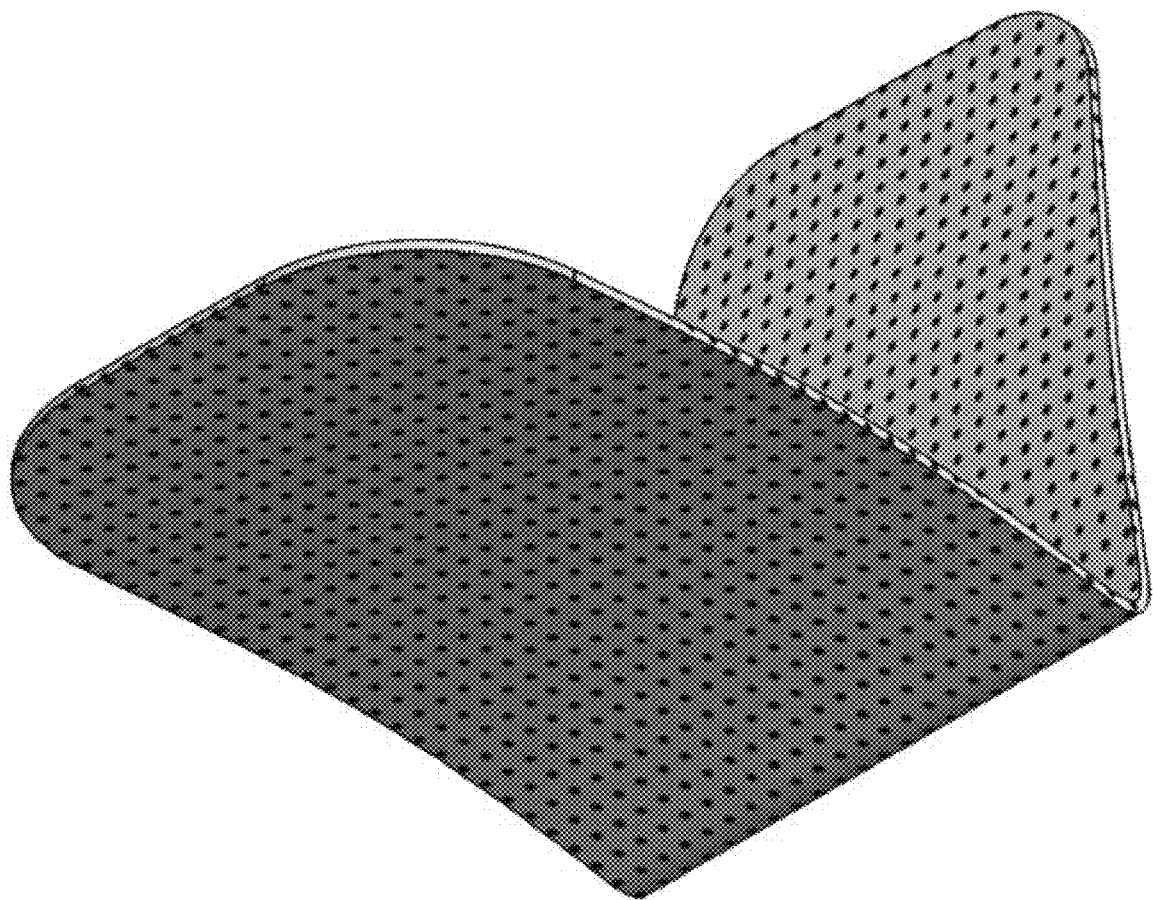
FIG. 93 illustrates a front bottom right perspective view of a preferred exemplary embodiment of an angular secondary plate (ASP) (incorporating a flat angular base plate (ABP) and a curved angular vertical plate (AVP)) useful in some preferred invention embodiments.
Figure 94:
FIG. 94 illustrates a rear bottom right perspective view of a preferred exemplary embodiment of an angular secondary plate (ASP) (incorporating a flat angular base plate (ABP) and a curved angular vertical plate (AVP)) useful in some preferred invention embodiments.
Figure 95:
FIG. 95 illustrates a rear bottom left perspective view of a preferred exemplary embodiment of an angular secondary plate (ASP) (incorporating a flat angular base plate (ABP) and a curved angular vertical plate (AVP)) useful in some preferred invention embodiments.
Figure 96:
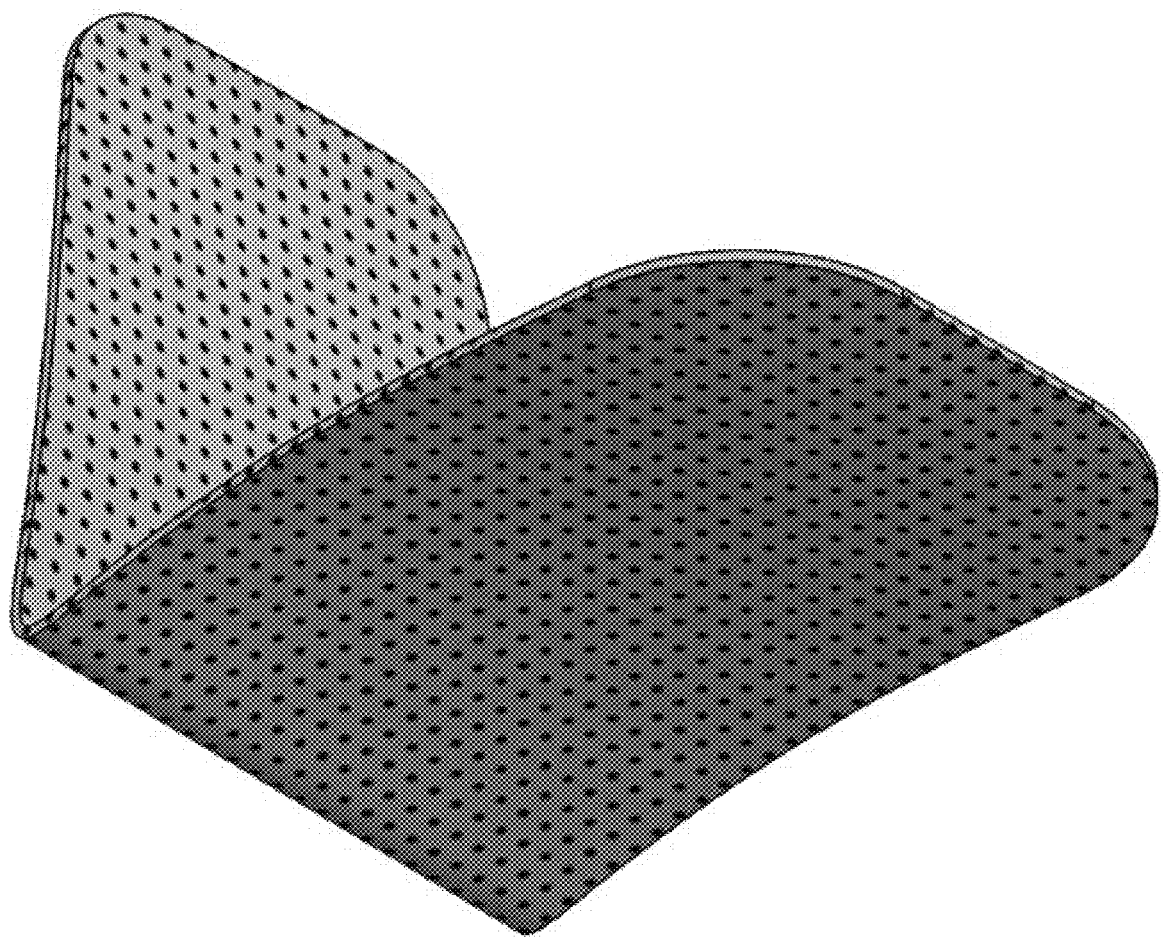
FIG. 96 illustrates a front bottom left perspective view of a preferred exemplary embodiment of an angular secondary plate (ASP) (incorporating a flat angular base plate (ABP) and a curved angular vertical plate (AVP)) useful in some preferred invention embodiments.

FIG. 65 (6500)-FIG. 80 (8000) and FIG. 81 (8100)-FIG. 96 (9600) depict various views of two preferred embodiments of the angular secondary plate (ASP). The ASP shown in these diagrams depicts an embodiment in which the ASP comprises an angular base plate (ABP) (7301, 8901) and an angular vertical plate (AVP) (7302, 8902) with the angle (7303, 8903) between the ABP and AVP being in the range of 60 degrees to 120 degrees with a 90-degree variant shown in these drawings. The ABP and AVP shown in FIG. 65 (6500)-FIG. 80 (8000) are depicted as curved but in some embodiments as generally depicted in FIG. 81 (8100)-FIG. 96 (9600) may be flat or substantially flat as illustrated by the drawings. The AVP is typically curved and may conform in some preferred embodiments to the uniform or non-uniform curvature of the CPP.

RPP/RSP Ribbed Plate Sandwich (RPS) Detail (9700)-(11200)

Figure 97:
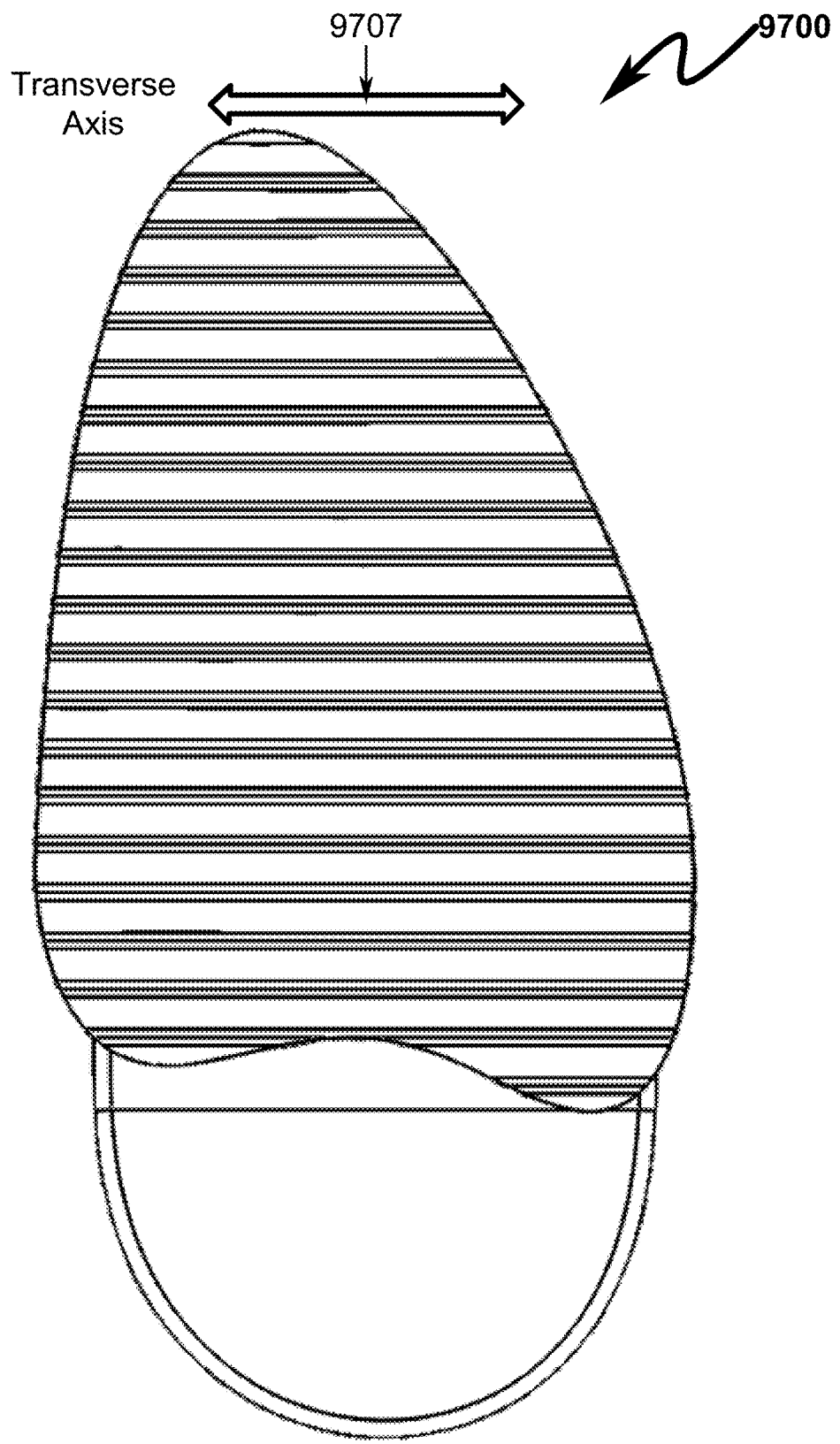
FIG. 97 illustrates a front view of a preferred exemplary embodiment of a ribbed primary plate (RPP) and ribbed secondary plate (RSP) useful in some preferred invention embodiments that are configured to retain a portion of an AEP.
Figure 98:
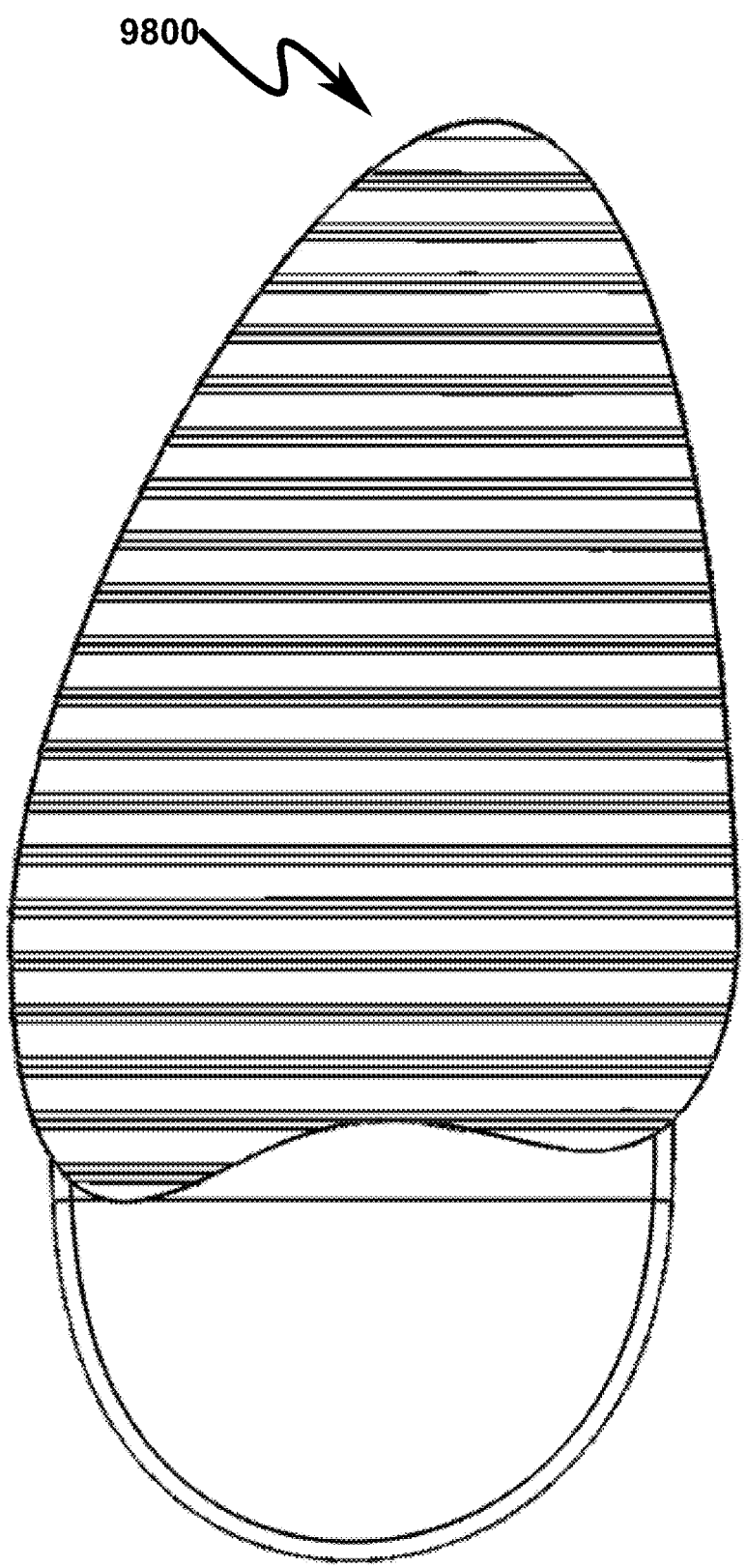
FIG. 98 illustrates a rear view of a preferred exemplary embodiment of a ribbed primary plate (RPP) and ribbed secondary plate (RSP) useful in some preferred invention embodiments that are configured to retain a portion of an AEP.
Figure 99:
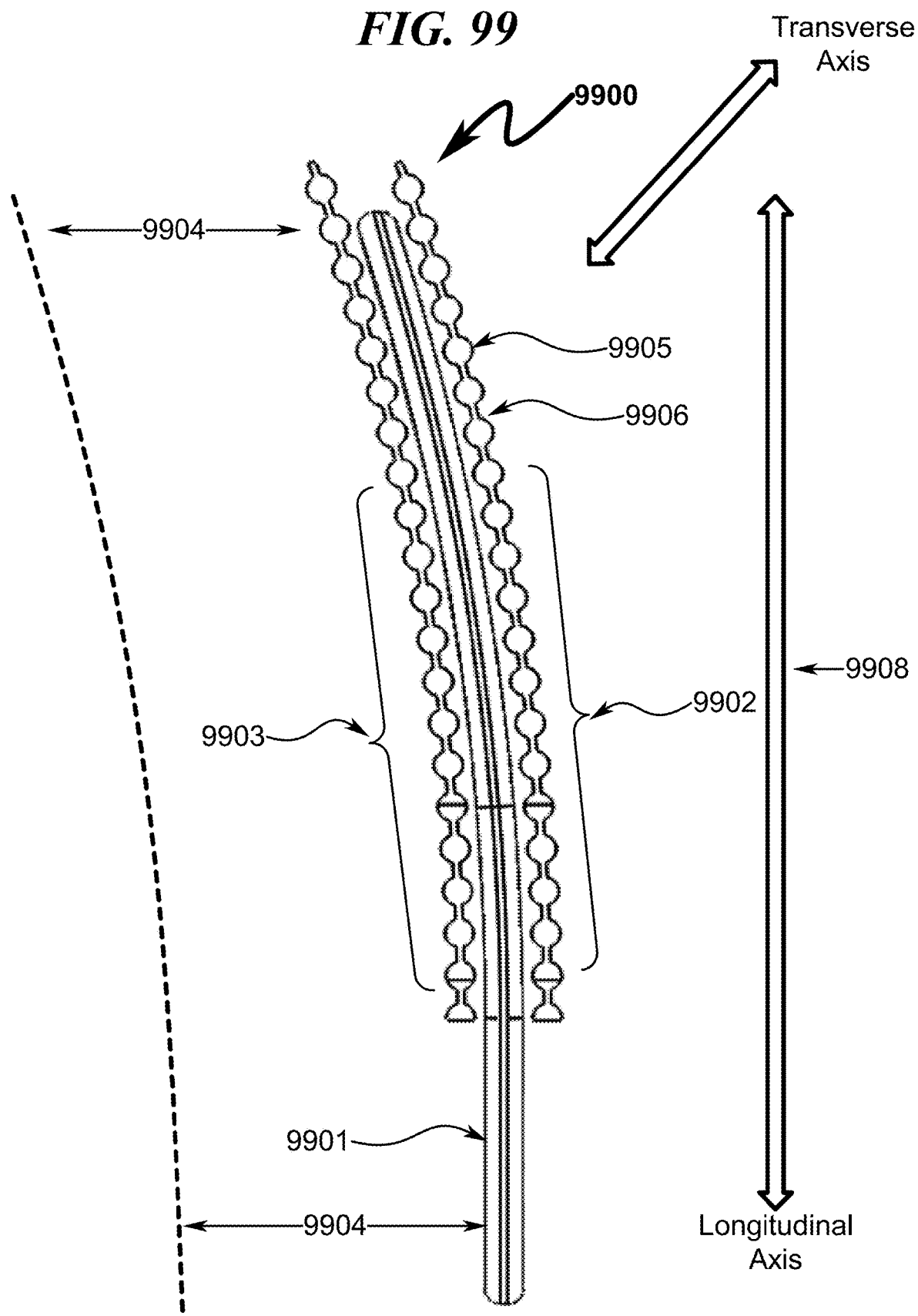
FIG. 99 illustrates a left side view of a preferred exemplary embodiment of a ribbed primary plate (RPP) and ribbed secondary plate (RSP) useful in some preferred invention embodiments that are configured to retain a portion of an AEP.
Figure 100:
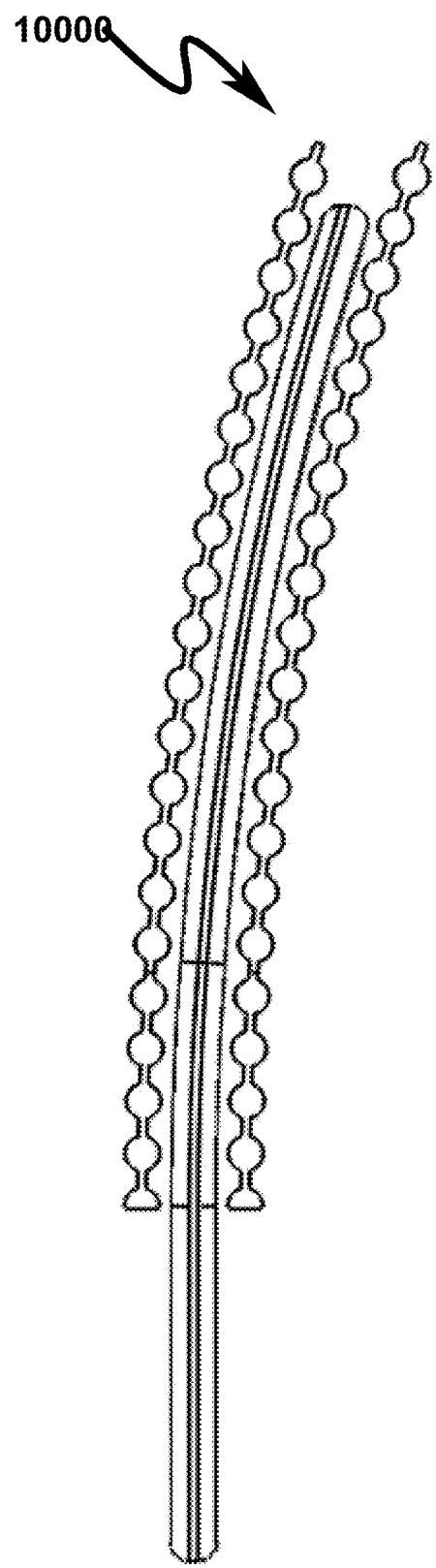
FIG. 100 illustrates a right side view of a preferred exemplary embodiment of a ribbed primary plate (RPP) and ribbed secondary plate (RSP) useful in some preferred invention embodiments that are configured to retain a portion of an AEP.
Figure 101:
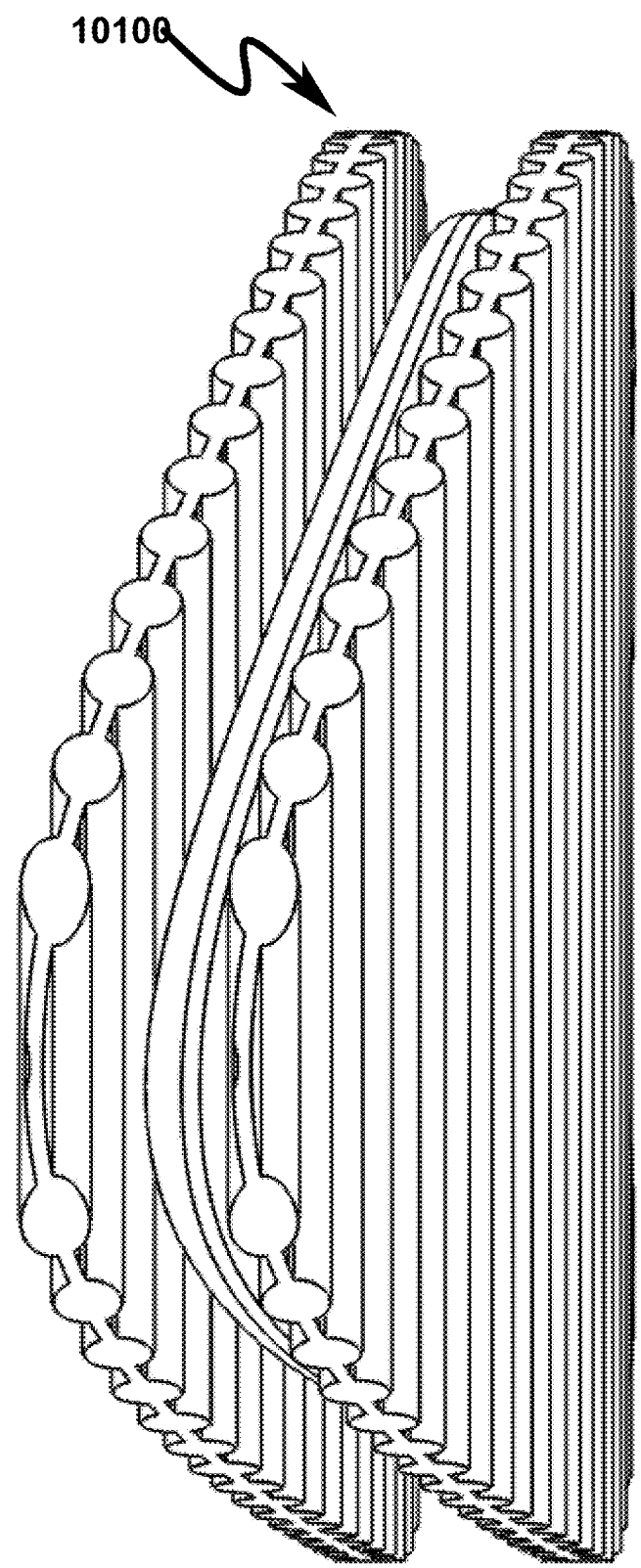
FIG. 101 illustrates a top view of a preferred exemplary embodiment of a ribbed primary plate (RPP) and ribbed secondary plate (RSP) useful in some preferred invention embodiments that are configured to retain a portion of an AEP.
Figure 102:
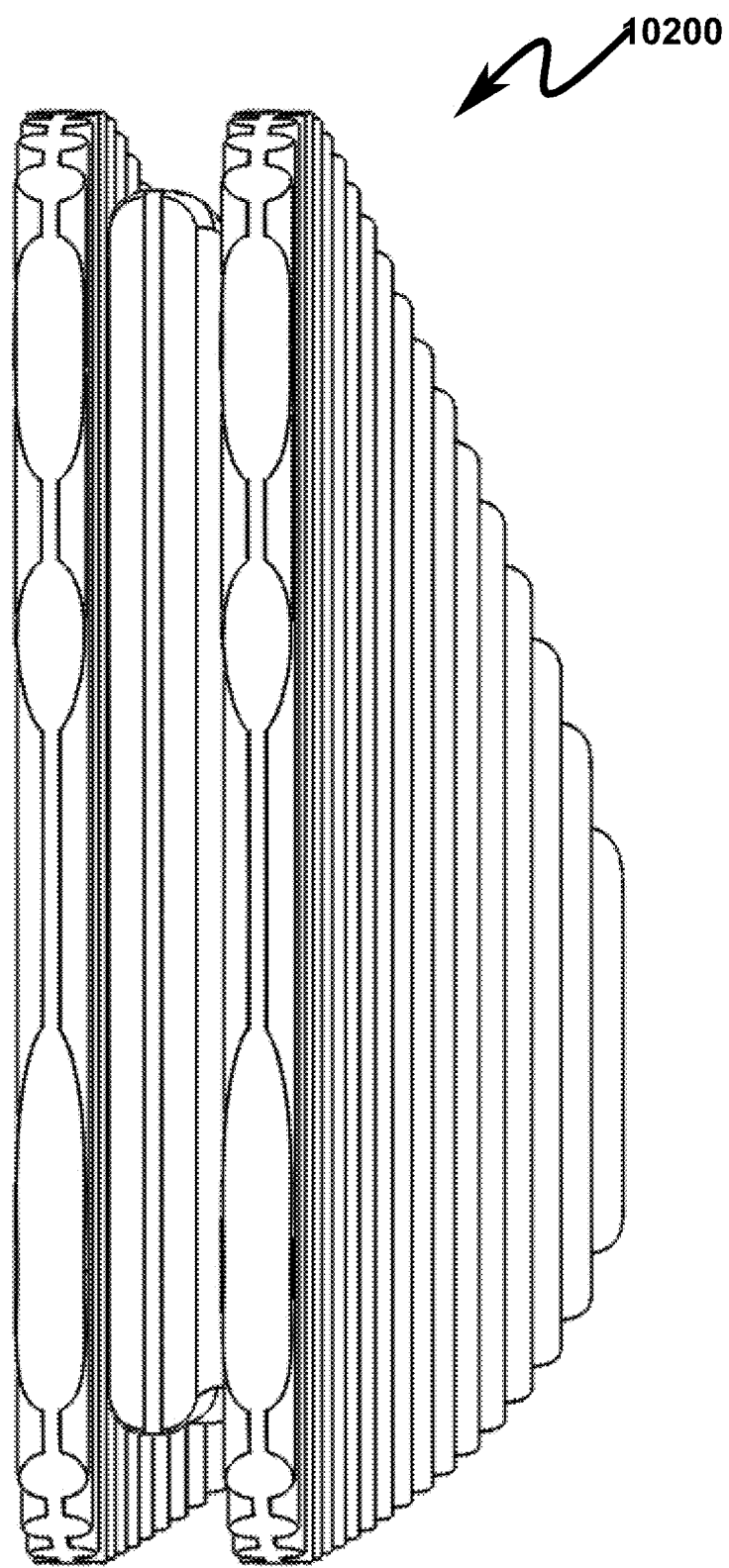
FIG. 102 illustrates a bottom view of a preferred exemplary embodiment of a ribbed primary plate (RPP) and ribbed secondary plate (RSP) useful in some preferred invention embodiments that are configured to retain a portion of an AEP.
Figure 103:
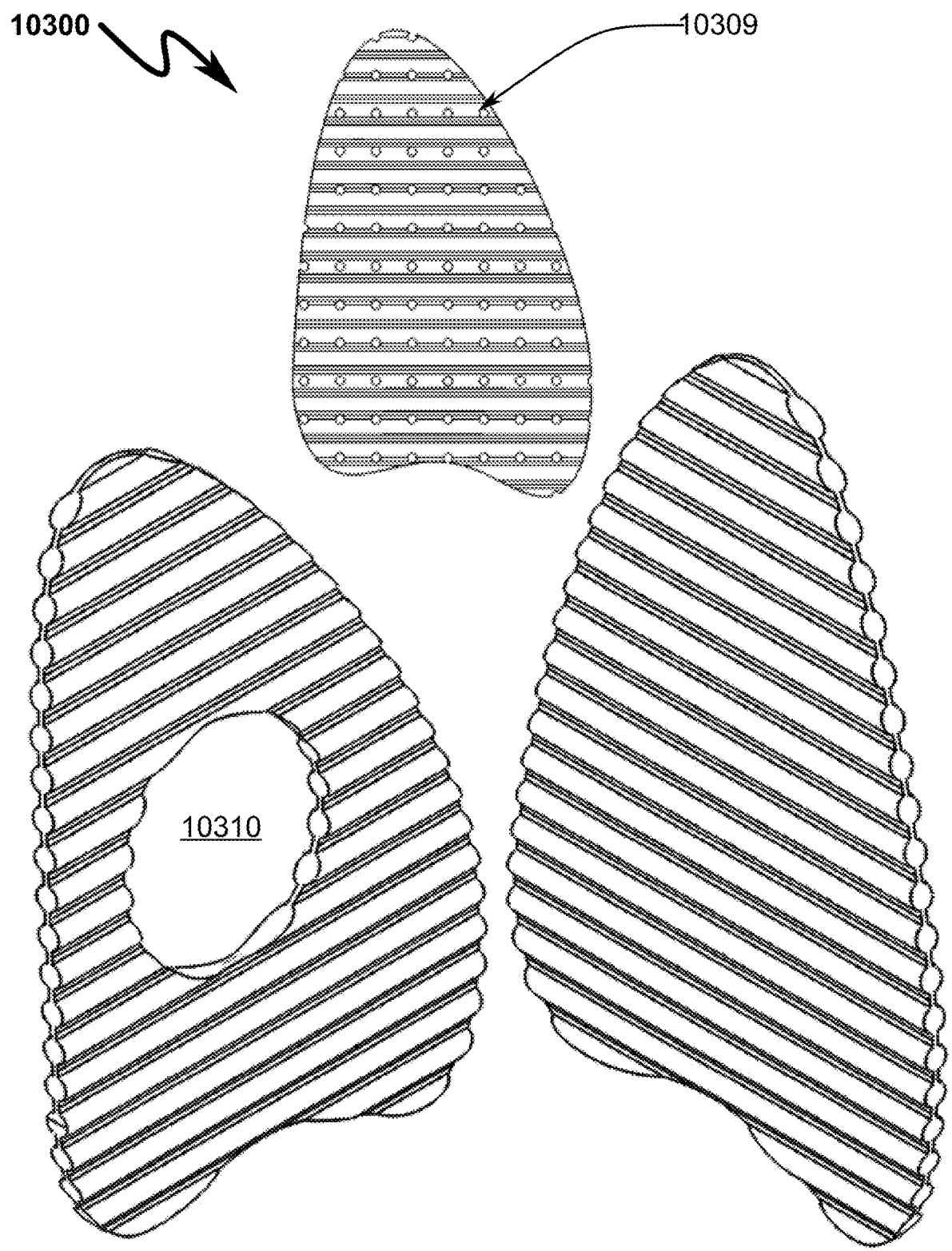
FIG. 103 illustrates front side, front top left, and front top right perspective views of some preferred exemplary embodiments of a ribbed primary plate (RPP)/ribbed secondary plate (RSP) useful in some preferred invention embodiments and illustrates the use of an access port for hematoma inspection.
Figure 104:
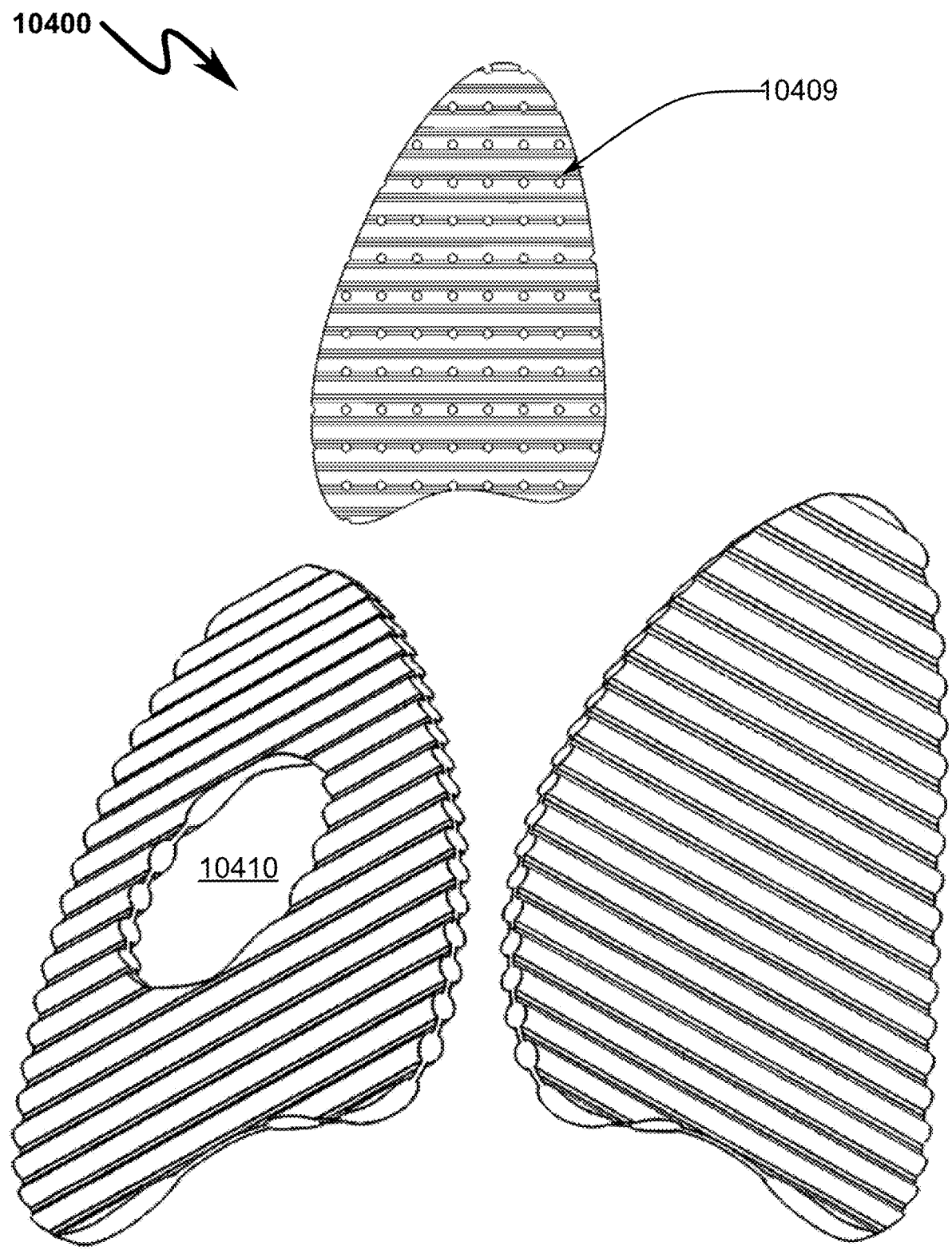
FIG. 104 illustrates rear side, rear bottom right, and rear bottom left perspective views of some preferred exemplary embodiments of a ribbed primary plate (RPP)/ribbed secondary plate (RSP) useful in some preferred invention embodiments and illustrates the use of an access port for hematoma inspection.
Figure 105:
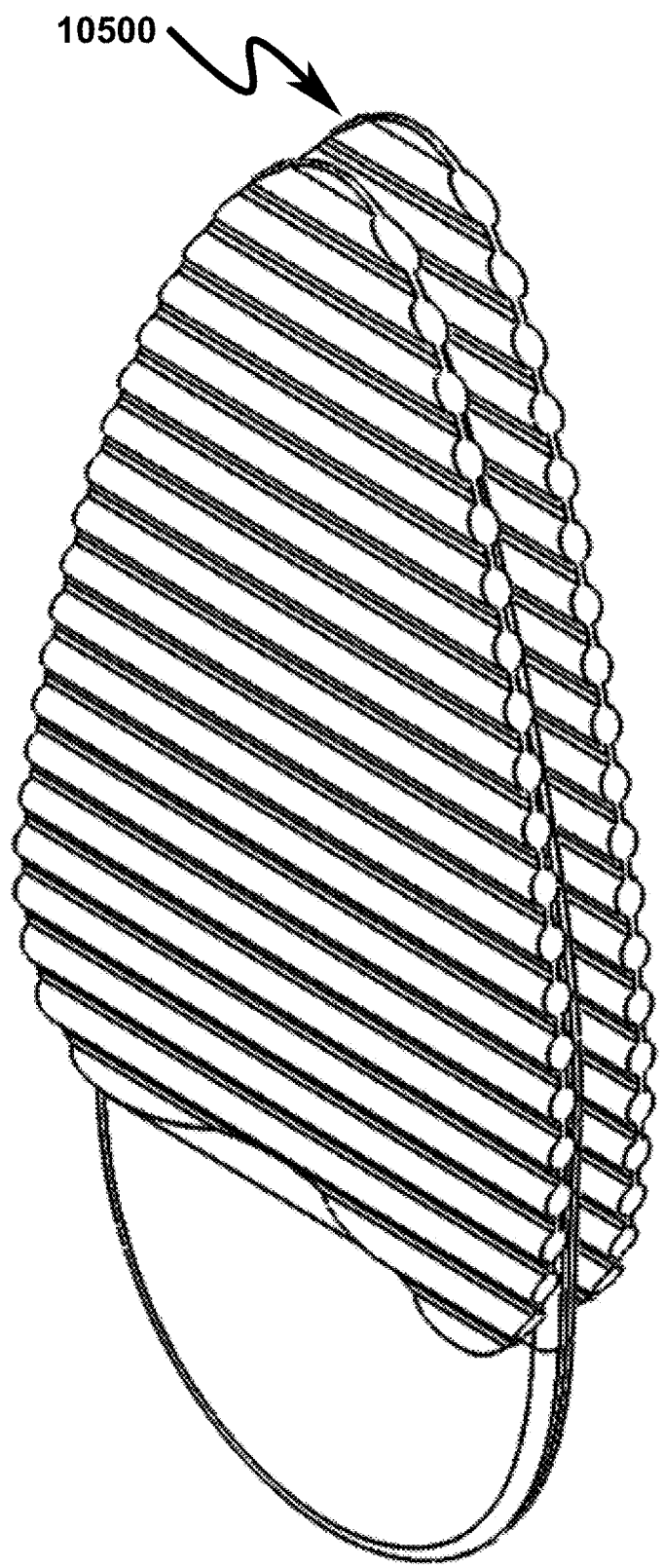
FIG. 105 illustrates a front top right perspective view of a ribbed primary plate (RPP) and ribbed secondary plate (RSP) useful in some preferred invention embodiments that are configured to retain a portion of an AEP.
Figure 106:
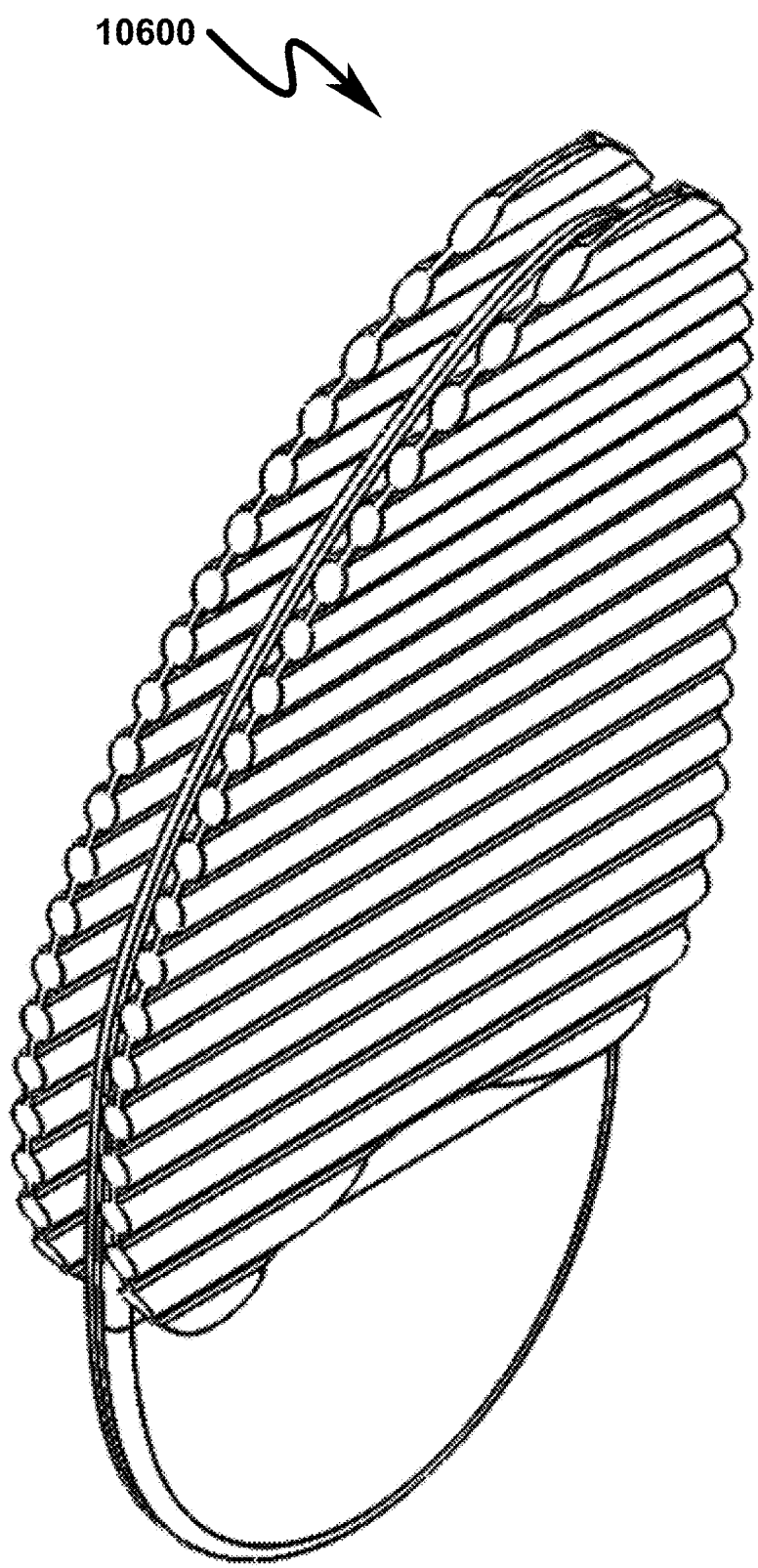
FIG. 106 illustrates a rear top right perspective view of a preferred exemplary embodiment of a ribbed primary plate (RPP) and ribbed secondary plate (RSP) useful in some preferred invention embodiments that are configured to retain a portion of an AEP.
Figure 107:
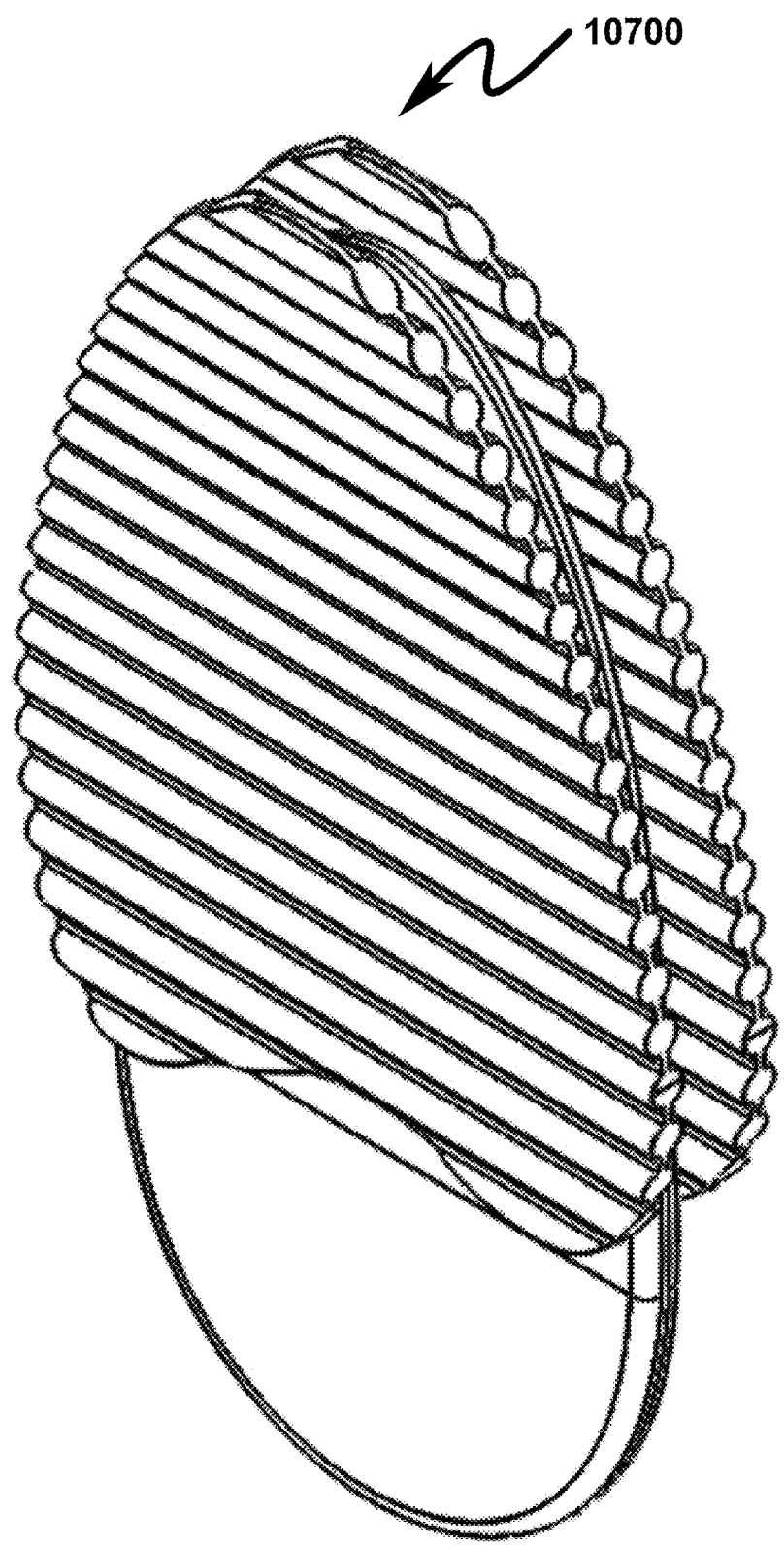
FIG. 107 illustrates a rear top left perspective view of a preferred exemplary embodiment of a ribbed primary plate (RPP) and ribbed secondary plate (RSP) useful in some preferred invention embodiments that are configured to retain a portion of an AEP.
Figure 108:
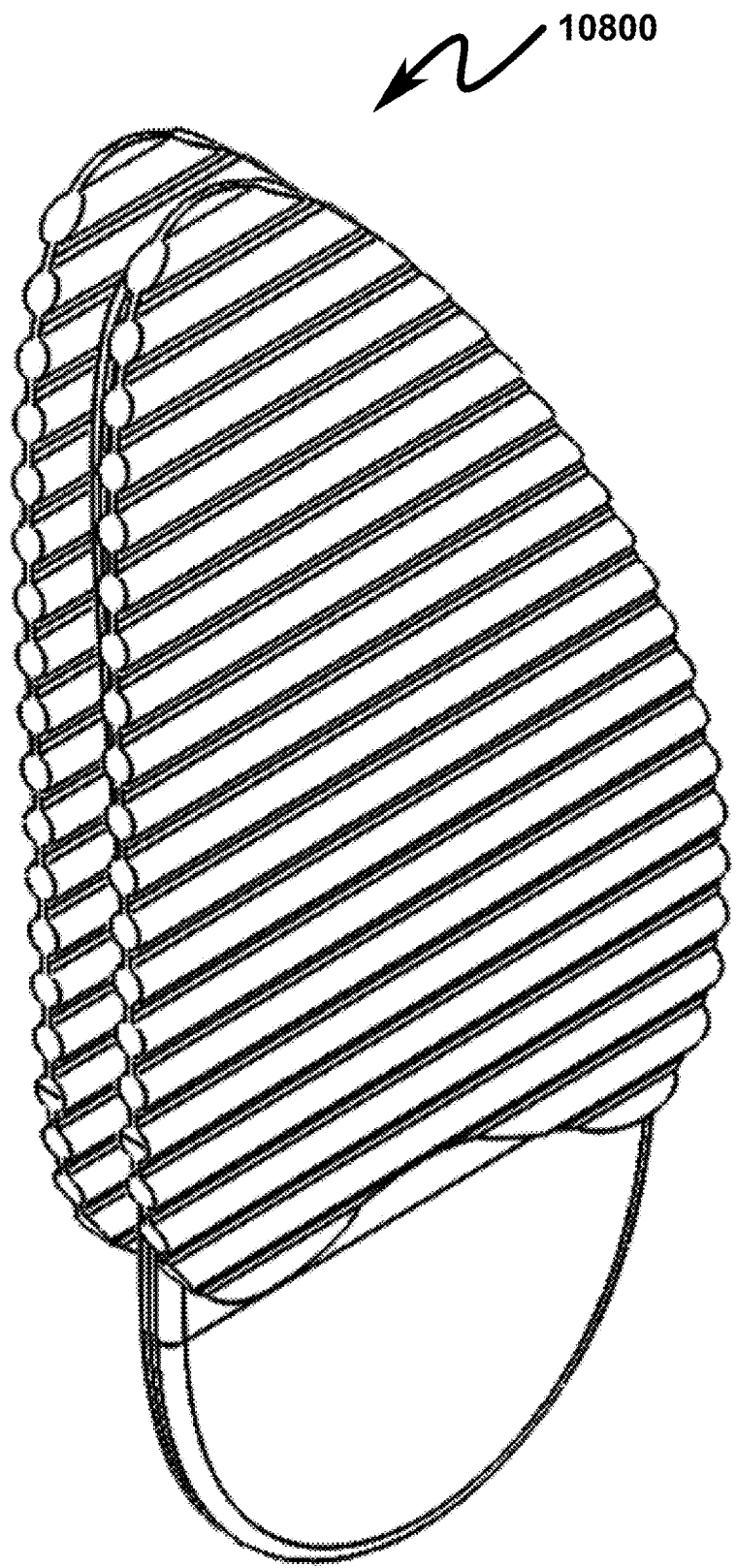
FIG. 108 illustrates a front top left perspective view of a preferred exemplary embodiment of a ribbed primary plate (RPP) and ribbed secondary plate (RSP) useful in some preferred invention embodiments that are configured to retain a portion of an AEP.
Figure 109:
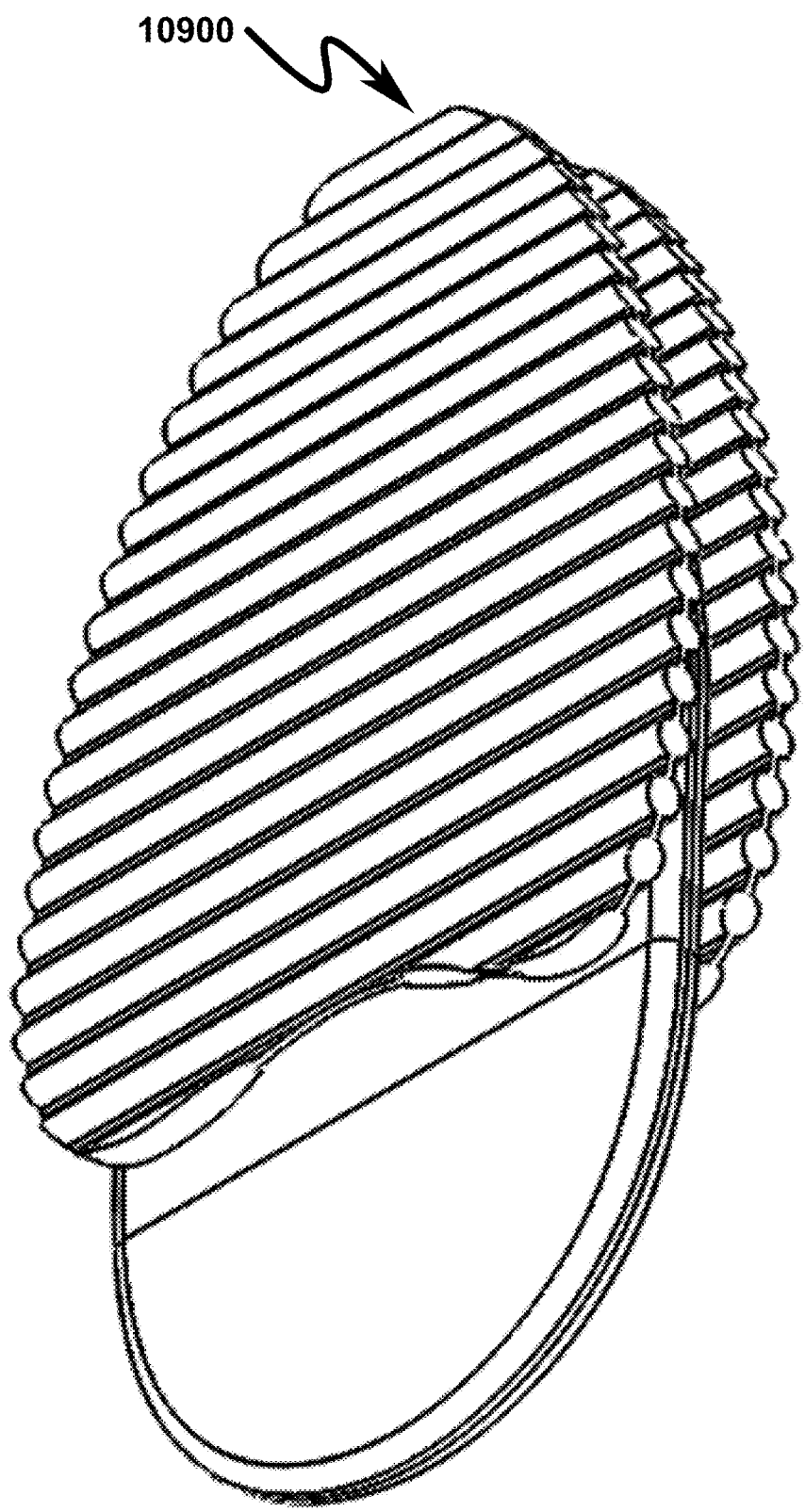
FIG. 109 illustrates a front bottom right perspective view of a preferred exemplary embodiment of a ribbed primary plate (RPP) and ribbed secondary plate (RSP) useful in some preferred invention embodiments that are configured to retain a portion of an AEP.
Figure 110:
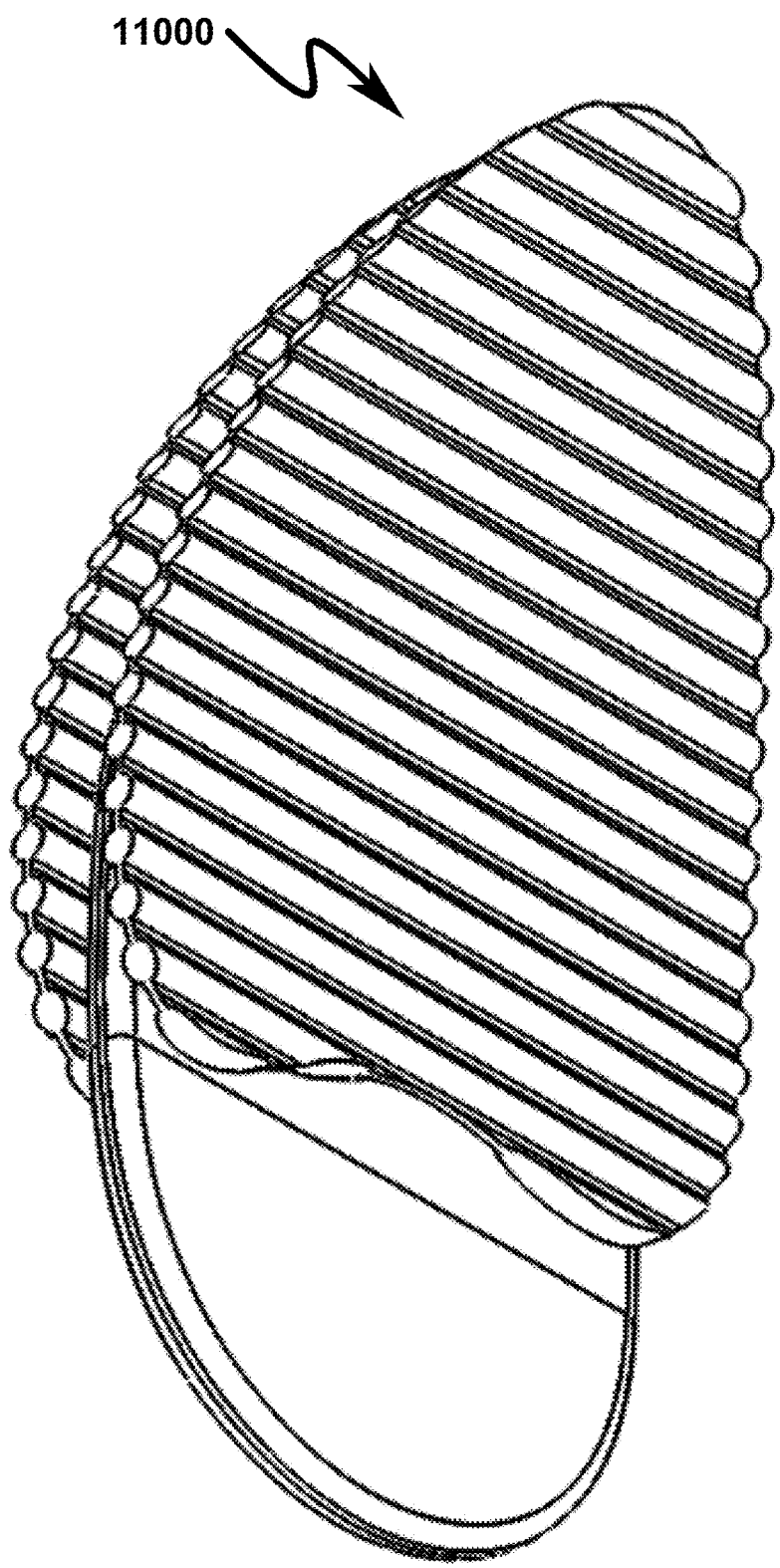
FIG. 110 illustrates a rear bottom right perspective view of a preferred exemplary embodiment of a ribbed primary plate (RPP) and ribbed secondary plate (RSP) useful in some preferred invention embodiments that are configured to retain a portion of an AEP.
Figure 111:
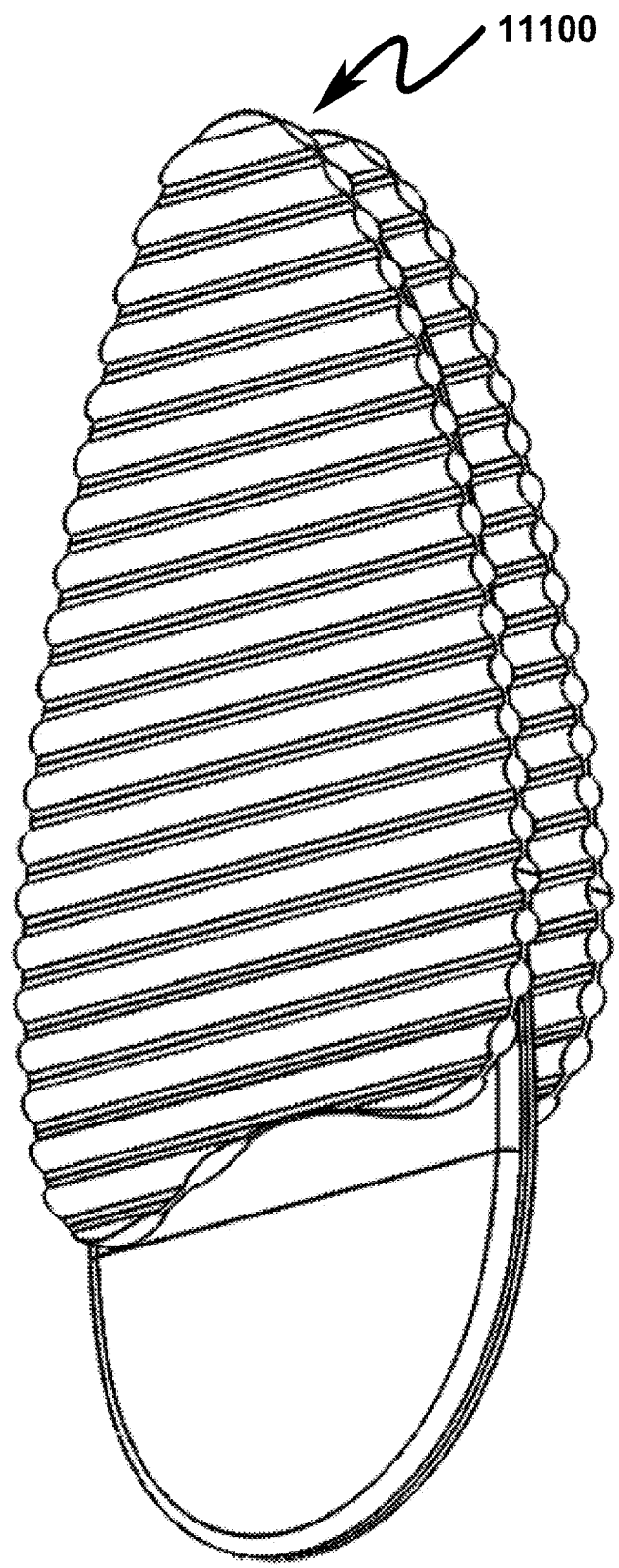
FIG. 111 illustrates a rear bottom left perspective view of a preferred exemplary embodiment of a ribbed primary plate (RPP) and ribbed secondary plate (RSP) useful in some preferred invention embodiments that are configured to retain a portion of an AEP.
Figure 112:
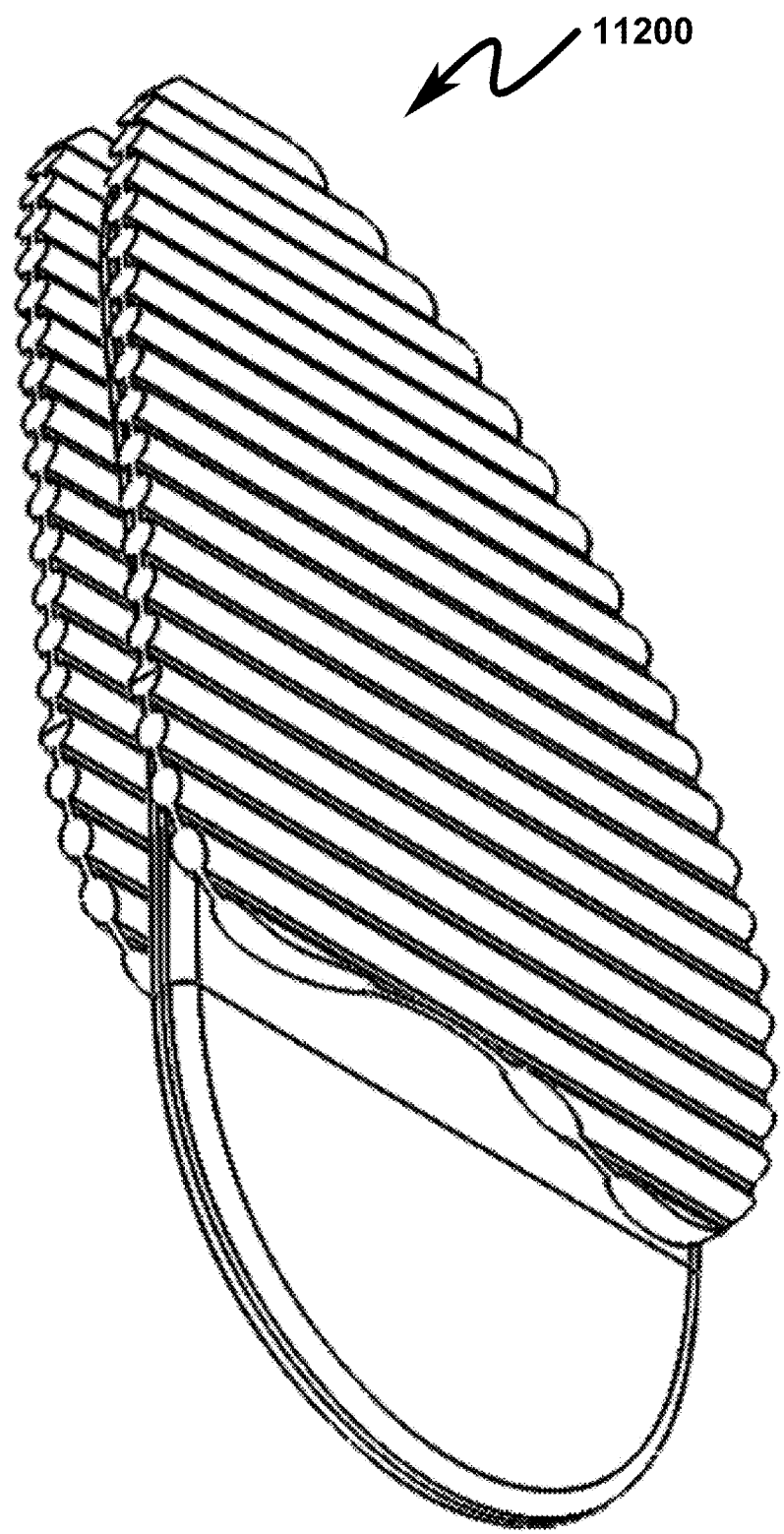
FIG. 112 illustrates a front bottom left perspective view of a preferred exemplary embodiment of a ribbed primary plate (RPP) and ribbed secondary plate (RSP) useful in some preferred invention embodiments that are configured to retain a portion of an AEP.

One preferred invention embodiment replaces the CPP/ASP configuration with a ribbed plate sandwich (RPS) comprising a ribbed primary plate (RPP) and ribbed secondary plate (RSP) as generally depicted in FIG. 97 (9700)-FIG. 112 (11200). In this configuration the AEP (9901) (only a portion of which is illustrated in the drawings) is sandwiched between the RPP (9902) and RSP (9903). The drawings show the relative positions of these components and additional spacing between these elements has been provided to show their relative position. Additionally, the ear pinna foundation (EPF) and ribbed plate attachment (RPA) (each of which comprise one or more cross strips and/or long straps detailed herein) used to wrap the AEP (9901) individually, and the RPP (9902) and RSP (9903) collectively around the AEP (9901) are omitted for visual clarity in these drawings.

The RPP (9902) and RSP (9903) are similarly constructed (and in some preferred embodiments may be identical) and ribbed along their transverse axis (9707) as illustrated with thinner webbing (9905) mechanically coupling the ribs (9906), allowing the RPP (9902) and RSP (9903) to curve (9904) to a desired curvature of the AEP (9901) along a longitudinal axis (9908) before the AEP (9901), RPP (9902), and RSP (9903) are taped together in a sandwich configuration to allow the AEP hematoma to heal. As illustrated herein, some forms of the CPP, ASP, RPP, and/or RSP may have perforations (10309, 10409) and/or access ports (10310, 10410) to allow air transfer to the AEP and/or access to the hematoma for treatment.

Generally speaking the RPP (9902) and RSP (9903) are configured to be larger than the AEP (9901) to allow encapsulating the AEP (9901) along its perimeter prior to taping the combination together. This allows the longitudinal curvature (9904) of the overall configuration to be set during the AEP taping process while maintaining straight transverse pressure application to the hematoma after taping with strips/straps is complete.

The strips/straps detailed herein may be used with this configuration with no loss of effectiveness in treating the AEP hematoma. This particular configuration is adapted well to situations in which the AEP is configured in a horizontal or downward pendant position rather that the upward vertical configuration as is the case with the CPP/ASP configuration detailed herein. Thus, animals having ears that "droop" and/or normally held horizontally are amenable to this embodiment of the claimed invention.

CPP/ASP System Summary

The present CPP/ASP invention system may be generally described as an aural hematoma splint (AHS) system for an animal ear pinna (AEP), the system comprising:
(a) ear pinna foundation (EPF);
(b) conical primary plate (CPP);
(c) angular secondary plate (ASP);
(d) long strap collar (LSC);
(e) primary plate attachment (PPA);
(f) secondary stabilizer attachment (SSA); and
wherein:
the EPF comprises non-elastic fabric tape (NFT);
the EPF comprises a first outer tape (OT1), second outer tape (OT2), first inner tape (IT1), second inner tape (IT2), a first long strap collar (LS1), and a first cross strip (CS1);
the OT1 is configured for attachment to an outer surface of the AEP;
the OT2 is configured for attachment to an outer surface of the AEP;
the IT1 is configured for attachment to an inner surface of the AEP;
the IT2 is configured for attachment to an inner surface of the AEP;
the LS1 is configured for attachment over the OT1, the OT2, the IT1, and the IT2;
the EPF is configured to position and stabilize the AEP via the OT1, the OT2, the IT1, the IT2, the LS1, and the CS1;
the CPP comprises an inner convex surface (ICS) conforming to an inner surface of the AEP;
the CPP comprises an outer concave surface (OCS) conforming to the ICS;
the CPP comprises an CPP outer perimeter (COP) comprising an CPP upper perimeter (CUP) conforming to an upper perimeter outline (UPO) of the AEP and a lower perimeter outline (LPO) comprising a curved raised portion (CRP);
the COP is configured to have a perimeter conforming to a perimeter shape of the AEP;
the ICS is in contact with the IT1, the IT2, the LS1, and the CS1;
the PPA comprises non-elastic fabric tape (NFT);
the PPA comprises a second cross strip (CS2), second long strap (LS2), third cross strip (CS3), fourth cross strip (CS4), third long strap (LS3), fifth cross strip (CS5), and AEP covering tape (ACT);
the PPA encapsulates at least a portion of the OT1, the OT2, the AEP, the IT1, the IT2, the LS1, the CS1, and the CPP;
the ASP comprises an angular base plate (ABP) and an angular vertical plate (AVP);

the ABP and the AVP are mechanically coupled at an angle ranging from 60 to 120 degrees;

the AVP is in contact with the PPA;

the SSA comprises non-elastic fabric tape (NFT);

the SSA comprises sixth cross strip (CS6), fourth long strap (LS4), and seventh cross strip (CS7);

the SSA encapsulates at least a portion of the PPA and the AVP;

the LSC comprises non-elastic fabric tape (NFT); and the LSC comprise the LS1, the LS2, the LS3, and the LS4.

The general system presented herein may be augmented by the various elements described herein to produce a wide variety of invention embodiments consistent with this overall design description.

CPP/ASP Method Summary

The present CPP/ASP invention method may be generally described as an aural hematoma splint (AHS) method for an animal ear pinna (AEP), the method comprising:
(1) isolating the AEP (0901) (1001);
(2) applying a first outer tape (OT1) (0902) to the AEP outer surface (1002);
(3) applying a second outer tape (OT2) (0903) to the AEP outer surface (1003);
(4) applying a first inner tape (IT1) (0904) to the AEP inner surface (1004);
(5) applying a second inner tape (IT2) (0905) to the AEP inner surface (1005);
(6) applying a first long strap (LS1) (0906) to the AEP over the OT1/OT2 and looped to cover the IT1/IT2 (1006);
(7) applying a first cross strip (CS1) (0907) to the AEP over the LS1 (1007);
(8) tucking the CS1 over the AEP to the inner surface of the LSC (1008);
(9) measuring width of AEP as covered by the OT1/OT2/IT1/IT2/LS1/CS1 (1109);
(10) measuring height of AEP as covered by the OT1/OT2/IT1/IT2/LS1/CS1 (1110);
(11) forming a conical primary plate (CPP) based on the AEP measurements and curvature (1111);
(12) applying the CPP (0908) over the inner surface of the IT1/IT2/LS1/CS1 layers (1112);
(13) applying a second cross strip (CS2) (0909) to the outside of the AEP (1113);
(14) folding the CS2 over the inner side of the AEP to secure sides of the CS2 (1114);
(15) applying a second long strap (LS2) (0910) to the AEP and looping it inside to cover the CPP (1115);
(16) applying a third cross strip (CS3) (0911) to the AEP and looping it inside of the AEP (1116);
(17) applying a fourth cross strip (CS4) (0912) to the AEP and looping it inside of the AEP (1217);
(18) applying a third long strap (LS3) (0913) to the AEP and looped inside to cover the CPP (1218);
(19) applying a fifth cross strip (CS5) (0914) to the AEP and looping it inside of the AEP (1219);
(20) applying AEP covering tape (ACT) (0915) to cover the AEP and attached strips/straps (1220);
(21) applying an angular secondary plate (ASP) (0916) to the outer surface of the AES (1221);
(22) applying a sixth cross strip (CS6) (0917) to secure the ASP to the AEP (1222);
(23) applying a fourth long strap (LS4) (0918) to the AEP and looping it inside to cover the CPP (1223);
(24) applying a seventh cross strip (CS7) (0919) to secure the LS4/ASP to the AEP (1224); and
(25) merging the long straps (LS1/LS2/LS3/LS4) (0920) to form a long strap collar (LSC) (1225).

This general method depicted herein may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

RPP/RSP System Summary

The present RPP/RSP invention system may be generally described as an aural hematoma splint (AHS) system for an animal ear pinna (AEP), the system comprising:
(a) ear pinna foundation (EPF);
(b) ribbed primary plate (RPP);
(c) ribbed secondary plate (RSP);
(d) long strap collar (LSC);
(e) primary plate attachment (PPA);
(f) secondary stabilizer attachment (SSA); and
wherein:

the EPF comprises non-elastic fabric tape (NFT);

the EPF comprises a first outer tape (OT1), second outer tape (OT2), first inner tape (IT1), second inner tape (IT2), a first long strap collar (LS1), and a first cross strip (CS1);

the OT1 is configured for attachment to an outer surface of the AEP;

the OT2 is configured for attachment to an outer surface of the AEP;

the IT1 is configured for attachment to an inner surface of the AEP;

the IT2 is configured for attachment to an inner surface of the AEP;

the LS1 is configured for attachment over the OT1, the OT2, the IT1, and the IT2;

the EPF is configured to position and stabilize the AEP via the OT1, the OT2, the IT1, the IT2, the LS1, and the CS1;

the RPP comprises a plurality of primary ribs (PPR) comprising tubular segments extending along a primary transverse axis (PTA);

the PPR are each mechanically coupled together along the PTA with an individual primary web coupling (PWC) that is thinner than each of the PPR;

the PWC allows the RPP to flex along a primary longitudinal axis (PLA) of the RPP while maintaining rigidity along the PTA;

the RSP comprises a plurality of secondary ribs (PSR) comprising tubular segments extending along a secondary transverse axis (STA);

the PSR are each mechanically coupled together along the STA with an individual secondary web coupling (SWC) that is thinner than each of the PSR;

the SWC allows the RSP to flex along a secondary longitudinal axis (SLA) of the RSP while maintaining rigidity along the STA;

the RPP comprises a perimeter outline configured to parallel a perimeter outline of the AEP;

the RSP comprises a perimeter outline configured to parallel a perimeter outline of the RPP;

the RPP comprises an inner convex surface (ICS) conforming to an inner surface of the AEP;

the RPP comprises an outer concave surface (OCS) conforming to the ICS;

the RPP comprises a RPP outer perimeter (ROP) comprising an RPP upper perimeter (RUP) conforming to an upper perimeter outline (UPO) of the AEP and a lower perimeter outline (LPO) comprising a curved raised portion (CRP);

the ROP is configured to have a perimeter conforming to a perimeter shape of the AEP;

the ICS is in contact with the IT1, the IT2, the LS1, and the CS1;

the PPA comprises non-elastic fabric tape (NFT);

the PPA comprises a second cross strip (CS2), second long strap (LS2), third cross strip (CS3), fourth cross strip (CS4), third long strap (LS3), fifth cross strip (CS5), and AEP covering tape (ACT);

the PPA encapsulates at least a portion of the OT1, the OT2, the AEP, the IT1, the IT2, the LS1, the CS1, and the RPP;

the SSA comprises non-elastic fabric tape (NFT);

the SSA comprises sixth cross strip (CS6), fourth long strap (LS4), and seventh cross strip (CS7);

the SSA encapsulates at least a portion of the PPA and the AVP;

the RPP and the RSP are configured to and positioned to sandwich the AEP and form a ribbed plate sandwich (RPS);

the SSA comprises one or more cross strips and/or long straps that sandwich the RPS;

the LSC comprises non-elastic fabric tape (NFT); and the LSC comprise the LS1, the LS2, the LS3, and the LS4.

The general system presented herein may be augmented by the various elements described herein to produce a wide variety of invention embodiments consistent with this overall design description.

RPP/RSP General System Summary

The present RPP/RSP invention general system may be generally described as an aural hematoma splint (AHS) system for an animal ear pinna (AEP), the system comprising:
(a) ribbed primary plate (RPP);
(b) ribbed secondary plate (RSP);
(c) ear pinna foundation (EPF); and
(d) ribbed plate attachment (RPA);
wherein:
the RPP comprises a plurality of primary ribs (PPR) comprising tubular segments extending along a primary transverse axis (PTA);
the PPR are each mechanically coupled together along the PTA with an individual primary web coupling (PWC) that is thinner than each of the PPR;
the PWC allows the RPP to flex along a primary longitudinal axis (PLA) of the RPP while maintaining rigidity along the PTA;
the RSP comprises a plurality of secondary ribs (PSR) comprising tubular segments extending along a secondary transverse axis (STA);
the PSR are each mechanically coupled together along the STA with an individual secondary web coupling (SWC) that is thinner than each of the PSR;
the SWC allows the RSP to flex along a secondary longitudinal axis (SLA) of the RSP while maintaining rigidity along the STA;
the RPP comprises a perimeter outline configured to parallel a perimeter outline of the AEP;

the RSP comprises a perimeter outline configured to parallel a perimeter outline of the RPP;

the EPF comprises one or more cross strips and/or long straps that sandwich the AEP;

the RPP and the RSP are configured to and positioned to sandwich the EPF and form a ribbed plate sandwich (RPS); and the RPA comprises one or more cross strips and/or long straps that sandwich the RPS.

The general system presented herein may be augmented by the various elements described herein to produce a wide variety of invention embodiments consistent with this overall design description.

RPP/RSP Method Summary

The present RPP/RSP invention method may be generally described as an aural hematoma splint (AHS) method for an animal ear pinna (AEP), the method comprising:
(1) isolating the AEP (1301) for which the AHS is to be applied (1401);
(2) applying a first outer tape (OT1) (1302) to the AEP outer surface (1402);
(3) applying a second outer tape (OT2) (1303) to the AEP outer surface (1403);
(4) applying a first inner tape (IT1) (1304) to the AEP inner surface (1404);
(5) applying a second inner tape (IT2) (1305) to the AEP inner surface (1405);
(6) applying a first long strap (LS1) (1306) to the AEP over the OT1/OT2 and looped to cover the IT1/IT2 (1406);
(7) applying a first cross strip (CS1) (1307) to the AEP over the LS1 (1407);
(8) tucking the CS1 over the AEP to the inner surface of the LSC (1408);
(9) measuring width of AEP as covered by the OT1/OT2/IT1/IT2/LS1/CS1 (1509);
(10) measuring height of AEP as covered by the OT1/OT2/IT1/IT2/LS1/CS1 (1510);
(11) forming a ribbed primary plate (RPP) based on the AEP measurements and curvature (1511);
(12) applying the RPP (1308) over the inner surface of the IT1/IT2/LS1/CS1 layers (1512);
(13) applying a second cross strip (CS2) (1309) to the outside of the AEP (1513);
(14) folding the CS2 over the inner side of the AEP to secure sides of the CS2 (1514);
(15) applying a second long strap (LS2) (1310) to the AEP and looping it inside to cover the RPP (1515);
(16) applying a third cross strip (CS3) (1311) to the AEP and looping it inside of the AEP (1516);
(17) applying a fourth cross strip (CS4) (1312) to the AEP and looping it inside of the AEP (1617);
(18) applying a third long strap (LS3) (1313) to the AEP and looped inside to cover the RPP (1618);
(19) applying a fifth cross strip (CS5) (1314) to the AEP and looping it inside of the AEP (1619);
(20) applying AEP covering tape (ACT) (1315) to cover the AEP and attached strips/straps (1620);
(21) applying a ribbed secondary plate (RSP) (1316) to the outer surface of the AES (1621);
(22) applying a sixth cross strip (CS6) (1317) to secure the RSP to the AEP (1622);
(23) applying a fourth long strap (LS4) (1318) to the AEP and looping it inside to cover the RPP (1623);

(24) applying a seventh cross strip (CS7) (1319) to secure the LS4/RSP to the AEP (1624); and

(25) merging the long straps (LS1/LS2/LS3/LS4) (1320) to form a long strap collar (LSC) (1625).

This general method depicted herein may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

System/Method Variations

The present invention anticipates the following system/method variations:

An embodiment wherein the CRP comprises an arching shape conforming to surface contact irregularities of an AEP.

An embodiment wherein the CPP further comprises a foam padding strip (FPS) mechanically coupled to the CRP.

An embodiment wherein the CPP further comprises a plurality of foam padding strips (FPS), the plurality of FPS mechanically coupled to more than one side of the CRP.

An embodiment wherein the CRP is molded into the CPP.

An embodiment wherein the CPP comprises a fabric covering.

An embodiment wherein the CPP comprises a fabric infused with anti-bacterial, anti-microbial, and/or anti-fungal agents, the fabric covering one or more surfaces of the CPP.

An embodiment wherein the CPP and/or the ASP are perforated.

An embodiment wherein the CPP and/or the ASP comprise one or more access ports.

An embodiment wherein the SSA comprises a harness configured to secure the AHS.

The present invention anticipates a wide variety of variations in the basic theme of construction. The examples presented previously do not represent the entire scope of possible usages. They are meant to cite a few of the almost limitless possibilities.

One skilled in the art will recognize that other embodiments are possible based on combinations of elements taught within the above invention description.

CONCLUSION

An aural hematoma splint (AHS) system/method providing for animal ear pinna (AEP) suspension and/or compression allowing non-surgical treatment of AEP auricular hematoma has been disclosed. The AHS promotes healing performance by including a conical primary plate (CPP) and angular secondary plate (ASP) that are used in conjunction with non-elastic fabric tape (NFT) to hold the AEP in suspension during treatment. The NFT includes a long strap collar (LSC) and cross support strips (CSS) for preparatory taping and application of the CPP/ASP to the AEP. This sandwich configuration of the CPP/ASP surrounding the AEP creates equilibrium in hematoma fluid pressures within the damaged area of the AEP, promotes a uniform thin layer of blood to clot in the entirety of the hematoma region, and allows regeneration of damaged tissues in a controlled environment while limiting structural and aesthetic damage to the healed AEP post treatment.

CLAIMS INTERPRETATION

The following rules apply when interpreting the CLAIMS of the present invention:

The CLAIM PREAMBLE should be considered as limiting the scope of the claimed invention.

"WHEREIN" clauses should be considered as limiting the scope of the claimed invention.

"WHEREBY" clauses should be considered as limiting the scope of the claimed invention.

"ADAPTED TO" clauses should be considered as limiting the scope of the claimed invention.

"ADAPTED FOR" clauses should be considered as limiting the scope of the claimed invention.

The term "MEANS" specifically invokes the means-plus-function claims limitation recited in 35 U.S.C. § 112(f) and such claim shall be construed to cover the corresponding structure, material, or acts described in the specification and equivalents thereof.

The phrase "MEANS FOR" specifically invokes the means-plus-function claims limitation recited in 35 U.S.C. § 112(f) and such claim shall be construed to cover the corresponding structure, material, or acts described in the specification and equivalents thereof.

The phrase "STEP FOR" specifically invokes the step-plus-function claims limitation recited in 35 U.S.C. § 112(f) and such claim shall be construed to cover the corresponding structure, material, or acts described in the specification and equivalents thereof.

The step-plus-function claims limitation recited in 35 U.S.C. § 112(f) shall be construed to cover the corresponding structure, material, or acts described in the specification and equivalents thereof ONLY for such claims including the phrases "MEANS FOR", "MEANS", or "STEP FOR".

The phrase "AND/OR" in the context of an expression "X and/or Y" should be interpreted to define the set of "(X and Y)" in union with the set "(X or Y)" as interpreted by Ex Parte Gross (USPTO Patent Trial and Appeal Board, Appeal 2011-004811, Ser. No. 11/565,411, ("'and/or' covers embodiments having element A alone, B alone, or elements A and B taken together").

The claims presented herein are to be interpreted in light of the specification and drawings presented herein with sufficiently narrow scope such as to not preempt any abstract idea.

The claims presented herein are to be interpreted in light of the specification and drawings presented herein with sufficiently narrow scope such as to not preclude every application of any idea.

The claims presented herein are to be interpreted in light of the specification and drawings presented herein with sufficiently narrow scope such as to preclude any basic mental process that could be performed entirely in the human mind.

The claims presented herein are to be interpreted in light of the specification and drawings presented herein with sufficiently narrow scope such as to preclude any process that could be performed entirely by human manual effort.

What is claimed is:

1. An aural hematoma splint (AHS) for an animal ear pinna (AEP), said system comprising:

(a) ear pinna foundation (EPF);

(b) conical primary plate (CPP);
(c) angular secondary plate (ASP);
(d) long strap collar (LSC);
(e) primary plate attachment (PPA);
(f) secondary stabilizer attachment (SSA); and
wherein:
said EPF comprises non-elastic fabric tape (NFT);
said EPF comprises a first outer tape (OT1), second outer tape (OT2), first inner tape (IT1), second inner tape (IT2), a first long strap collar (LS1), and a first cross strip (CS1);
said OT1 is configured for attachment to an outer surface of said AEP;
said OT2 is configured for attachment to an outer surface of said AEP;
said IT1 is configured for attachment to an inner surface of said AEP;
said IT2 is configured for attachment to an inner surface of said AEP;
said LS1 is configured for attachment over said OT1, said OT2, said IT1, and said IT2;
said EPF is configured to position and stabilize said AEP via said OT1, said OT2, said IT1, said IT2, said LS1, and said CS1;
said CPP comprises an inner convex surface (ICS) conforming to an inner surface of said AEP;
said CPP comprises an outer concave surface (OCS) conforming to said ICS;
said CPP comprises an CPP outer perimeter (COP) comprising an CPP upper perimeter (CUP) conforming to an upper perimeter outline (UPO) of said AEP and a lower perimeter outline (LPO) comprising a curved raised portion (CRP);
said COP is configured to have a perimeter conforming to a perimeter shape of said AEP;
said ICS is in contact with said IT1, said IT2, said LS1, and said CS1;
said PPA comprises non-elastic fabric tape (NFT);
said PPA comprises a second cross strip (CS2), second long strap (LS2), third cross strip (CS3), fourth cross strip (CS4), third long strap (LS3), fifth cross strip (CS5), and AEP covering tape (ACT);
said PPA encapsulates at least a portion of said OT1, said OT2, said AEP, said IT1, said IT2, said LS1, said CS1, and said CPP;
said ASP comprises an angular base plate (ABP) and an angular vertical plate (AVP);
said ABP and said AVP are mechanically coupled at an angle ranging from 60 to 120 degrees;
said AVP is in contact with said PPA;
said SSA comprises non-elastic fabric tape (NFT);
said SSA comprises sixth cross strip (CS6), fourth long strap (LS4), and seventh cross strip (CS7);
said SSA encapsulates at least a portion of said PPA and said AVP;
said LSC comprises non-elastic fabric tape (NFT); and
said LSC comprise said LS1, said LS2, said LS3, and said LS4.

2. The aural hematoma splint (AHS) system of claim 1, wherein said CPP comprises a fabric covering.

3. The aural hematoma splint (AHS) system of claim 2, wherein said CPP comprises a fabric infused with anti-bacterial, anti-microbial, and/or anti-fungal agents, said fabric covering one or more surfaces of said CPP.

4. The aural hematoma splint (AHS) system of claim 1, wherein said CRP comprises an arching shape conforming to surface contact irregularities of an AEP.

5. The aural hematoma splint (AHS) system of claim 1, wherein said CPP further comprises a foam padding strip (FPS) mechanically coupled to said CRP.

6. The aural hematoma splint (AHS) system of claim 1, wherein said CPP further comprises a plurality of foam padding strips (FPS), said plurality of FPS mechanically coupled to more than one side of said CRP.

7. The aural hematoma splint (AHS) system of claim 1, wherein said CRP is molded into said CPP.

8. The aural hematoma splint (AHS) system of claim 1, wherein said CPP and/or said ASP are perforated.

9. The aural hematoma splint (AHS) system of claim 1, wherein said CPP and/or said ASP comprise one or more access ports.

10. The aural hematoma splint (AHS) system of claim 1, wherein said SSA comprises a harness configured to secure said AHS.

* * * * *